(12) United States Patent
Lee et al.

(10) Patent No.: US 6,268,363 B1
(45) Date of Patent: Jul. 31, 2001

(54) IMIDAZOLE DERIVATIVES HAVING AN INHIBITORY ACTIVITY FOR FARNESYL TRANSFERASE AND PROCESS FOR PREPARATION THEREOF

(75) Inventors: Hyun Il Lee; Jong Sung Koh; Jin Ho Lee, all of Youseong-ku; Won Hee Jung, Seo-ku; You Seung Shin, Youseong-ku; Hyun Ho Chung, Youseong-ku; Jong Hyun Kim, Youseong-ku; Seong Gu Ro, Youseong-ku; Tae Saeng Choi, Youseong-ku; Shin Wu Jeong, Youseong-ku; Tae Hwan Kwak, Youseong-ku; In Ae Ahn, Youseong-ku; Hyun Sung Kim, Youseong-ku; Sun Hwa Lee, Youseong-ku; Kwi Hwa Kim, Youseong-ku; Jung Kwon Yoo, Seo-ku, all of (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/554,646

(22) PCT Filed: Nov. 25, 1998

(86) PCT No.: PCT/KR98/00377

§ 371 Date: May 17, 2000

§ 102(e) Date: May 17, 2000

(87) PCT Pub. No.: WO99/28315

PCT Pub. Date: Jun. 10, 1999

(30) Foreign Application Priority Data

Nov. 28, 1997 (KR) .................................................. 97/63858
Mar. 31, 1998 (KR) .................................................. 98/11359
Jun. 23, 1998 (KR) .................................................. 98/23698
Jun. 26, 1998 (KR) .................................................. 98/24423
Aug. 3, 1998 (KR) .................................................. 98/31512
Oct. 30, 1998 (KR) .................................................. 98/46457

(51) Int. Cl.$^7$ ..................... A61K 31/4178; C07D 403/06
(52) U.S. Cl. ..................... 514/235.8; 544/58.2; 544/58.4; 544/128; 544/130; 544/133; 544/139; 544/370; 546/205; 548/200; 548/236; 548/311.7; 548/312.1; 548/312.4; 548/314.7
(58) Field of Search ..................... 544/139; 548/314.7, 548/200; 514/235.8

(56) References Cited

FOREIGN PATENT DOCUMENTS

| | | |
|---|---|---|
| 0300688 | 1/1989 | (EP) . |
| WO 96/39137 | 12/1996 | (WO) . |
| WO 97/36581 | 10/1997 | (WO) . |
| WO 97/36585 | 10/1997 | (WO) . |
| WO 97/36876 | 10/1997 | (WO) . |
| WO 97/36891 | 10/1997 | (WO) . |
| WO 97/36896 | 10/1997 | (WO) . |
| WO 97/36901 | 10/1997 | (WO) . |

OTHER PUBLICATIONS

Chemical Abstracts, vol. 95, No. 23, p. 654, abstract 203671d (1981).
Chemical Abstracts, vol. 116, No. 9, p. 871, abstract 84129y (1992).
Chemical Abstracts, vol. 115, No. 13, p. 948, abstract 135775V (1991).
Chemical Abstracts, vol. 98, No. 17, p. 579, abstract 143394r (1983).
Chemical Abstracts, vol. 91, No. 21, p. 601, abstract 174606w (1979).
Chemical Abstracts, vol. 123, No. 21, p. 1109, abstract 284946u (1995).
Chemical Abstracts, vol. 77, No. 3, p. 496, abstract 19492y (1972).

Primary Examiner—Robert W. Ramsuer
(74) Attorney, Agent, or Firm—Peter F. Corless; Christine C. O'Day; Edwards & Angell, LLP

(57) ABSTRACT

The present invention relates to a novel imidazole derivative represented by formula (1) which shows an inhibitory activity against farnesyl transferase or pharmaceutically acceptable salts or isomers thereof, in which A, $n_1$ and Y are defined in the specification; to a process for preparation of the compound of formula (1); to intermediates which are used in the preparation of the compound of formula (1); and to a pharmaceutical composition comprising the compound of formula (1) as an active ingredient.

(1)

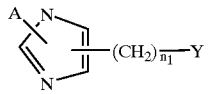

10 Claims, No Drawings

IMIDAZOLE DERIVATIVES HAVING AN INHIBITORY ACTIVITY FOR FARNESYL TRANSFERASE AND PROCESS FOR PREPARATION THEREOF

This application is a 371 of PCT/KR98/00377 filed Nov. 25, 1998.

TECHNICAL FIELD

The present invention relates to a novel imidazole derivative represented by the following formula (1) which shows an inhibitory activity against farnesyl transferase:

[Formula 1]

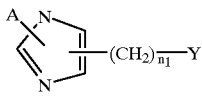

in which A, $n_1$ and Y are defined as described below, or pharmaceutically acceptable salts or isomers thereof.

The present invention also relates to a process for preparation of the compound of formula (1), to intermediates which are used in the preparation of the compound of formula (1), and to a pharmaceutical composition comprising the compound of formula (1) as an active ingredient.

BACKGROUND ART

Mammalian Ras proteins act as molecular switches in the signalling events associated with cell growth and differentiation. The ras proto-oncogene family consists of three members, N-, K-, and H-ras, which code for highly homologous 4 types of proteins; i.e., H, N-ras proteins of 189 residues and two isomorphic K-ras-4B and K-ras-4A proteins of 188 and 189 residues, respectively. The chemical basis for the switch mechanism involves cycling of the protein between the inactive (off) guanosine diphosphate (GDP) bound state and the active (on) guanosine triphosphate (GTP) bound state (Boune, H. R.; Sanders, D. A.; McCormick. F.; Nature, 1991, 349, 117). Biochemical and structural studies have shown that point mutations of the residues 12, 13 and 61, positioned in the neighborhood of phosphoryl ground of GTP, resulting in the decrease of guanosine triphosphatase activity are associated with many human cancers, particularly, pancreatic cancer, urinary bladder carcinoma, colon cancer, etc. (Bos, J. L., Cancer Res., 1989, 49, 4682).

Ras protein is synthesized as a cytosolic precursor that ultimately localized to the cytoplasmic face of the plasma membrane after a series of posttranslational modification (Gibbs, J. B., Cell 1991, 65, 1). These series of biochemical modifications, by changing the electrical charge state or spacial structure to increase the hydrophobicity allow Ras protein to attach to cell membrane more easily. The first and obligatory step in the series is the addition of a farnesyl moiety to the cysteine residue of the C-terminal CAAX motif (C, cysteine; A, usually aliphatic residue; X, any other amino acid) in a reaction catalyzed by farnesyl protein transferase (FTase). This modification is essential for Ras function, as demonstrated by the inability of Ras mutants lacking the C-terminal cysteine to be farnesylated, to localize to the plasma, and to transform mammalian cells in culture (Hancock, J. F., Magee, A. I., Childs, J. E., Marshall, C. J., Cell 1989, 57, 1167). The subsequent posttranslational modifications, cleavage of the AAX residues, carboxyl methylation of the the farnesylated cysteine, and palmitoylation of the cysteines located upstream of the CAAX motif in H- and N-ras proteins are not obligatory for Ras membrane association or cellular transforming activity. Interestingly, K-ras-4B, different from H- and N-ras, has a multiple lysine rich region named polybasic domain, instead of having cysteine required for palmitoylation, thereby facilitating the farnesylated ras protein to bind to anionic lipid layer of cell membrane. The inhibitors of FTase that catalyzes the obligatory modification have therefore been suggested as anticancer agents for tumors in which Ras oncogene contributes to transformation (Buses, J. E. et al., Chemistry & Biology, 1995, 2, 787). A number of FTase inhibitors recently identified demonstrated potent and specific ability to block Ras farnesylation, signalling and transformation in transformed cells and tumor cell lines both in vitro and in animal models (Kohl. N. E. et. al., Proc. Natl. Acad. Sci. USA. 1994, 91, 9141; Kohl, N. E. et al., Nature Medicine, 1995, 1 792).

However, most of the inhibitors are related to CAAX motif as Ras substrate mimic and peptidic in nature or contain a sulfhydryl group (U.S. Pat. No. 5,141,851; Kohl, N. E. et. al., Science, 1993, 260, 1934; PCT/US95/12224, Graham et al.; Sebti, S. M. et. al., J. Biol. Chem., 1995. 270, 26802; James, G. L. et al., Science, 1993, 260, 1937; Bishop, W. R. et al., J. Biol. Chem., 1995, 270, 30611). Recently, a new type of peptidomimetic inhibitor imitating catalytic step of FTase has been reported (Poulter, C. D. et al., J. Am. Chem. Soc., 1996, 118, 8761). The chemical basis of the inhibitor design relates to the reaction mechanism. This is, transferring prenyl group by the enzyme is electrophilic displacement and the reaction requires (+) charge in a transition state.

These inhibitors previously described, however, possess limited activity and selectivity for inhibition of the oncogenic function of Ras proteins, particularly K-ras-4B, which is found to be most common in human cancer. Therefore, new inhibitor having the ability of effectively inhibiting K-ras activity is required.

With regard to the restenosis and vascular proliferative diseases, it has been shown that inhibition of cellular ras prevents smooth muscle proliferation after vascular injury in vivo (Indolfi C. et al., Nature Med., 1995, 1(6), 541–545). This report definitively supports a role for farnesyl transferase inhibitors in this disease, showing inhibition of accumulation and proliferation of vascular smooth muscle.

DISCLOSURE OF INVENTION

The present inventors have performed studies for developing a compound having the structural characteristics imitating an intermediate state of catalytic reaction of FTase and as a result, found that imidazole derivatives according to the present invention can potently inhibit the enzyme.

Therefore, the object of the present invention is to provide an imidazole derivative of formula (1) which inhibits the activity of FTase, a process for preparation thereof, and an intermediate which can be used effectively for the preparation of the compound of formula (1).

It is another object of the present invention to provide a pharmaceutical composition comprising the compound of formula (1) as an active ingredient.

BEST MODE FOR CARRYING OUT THE INVENTION

It is the first object of the present invention to provide an imidazole derivative represented by the following formula (1) which inhibit the activity of farnesyl transferase:

[Formula 1]

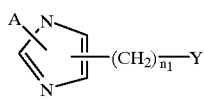

in which n$_1$ represents an integer of 1 to 4,

A represents hydrogen; straight-chain or branched C$_1$–C$_{10}$-alkyl which may be optionally substituted by C$_3$–C$_7$-cycloalkyl or lower alkoxy; or a radical selected from the following group:

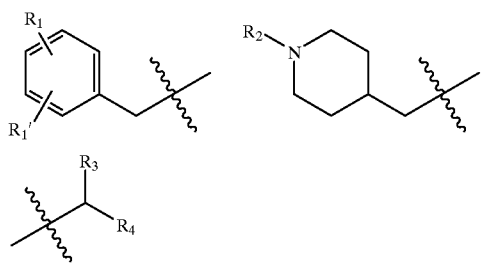

wherein

R$_1$ and R$_1$' independently of one another represent hydrogen, halogen, cyano, nitro, hydroxycarbonyl, aminocarbonyl, aminothiocarbonyl, lower alkoxy, phenoxy, phenyl, benzyloxy, or lower alkyl which may be optionally substituted by C$_3$–C$_6$-cycloalkyl, R$_2$ represents hydrogen or lower alkyl, or represents —E—F wherein E is —CH$_2$—, —C(O)— or —S(O)$_2$— and F is hydrogen; lower alkyl which may be optionally substituted by phenoxy or biphenyl; lower alkoxy which may be optionally substituted by aryl; phenyl; benzyl; benzyloxy; or amino which may be optionally substituted by lower alkyl, benzyl or C$_5$–C$_6$-cycloalkyl, R$_3$ represents hydrogen, lower alkyl or phenyl, R$_4$ represents a radical selected from the following group:

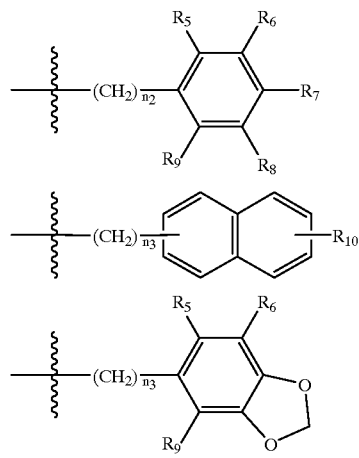

wherein n$_2$ and n$_3$ independently of one another denote 0, 1, 2, 3 or 4,

R$_5$ and R$_9$ independently of one another represent hydrogen, lower alkyl, lower alkoxy, phenoxy, phenyl, hydroxy or halogen, R$_6$ and R$_8$ independently of one another represent hydrogen, lower alkyl, lower alkoxy, phenoxy, phenyl, cyano, hydroxy or halogen, R$_7$ represents hydrogen; lower alkyl which may be optionally substituted by C$_3$–C$_6$-cycloalkyl; lower alkoxy; hydroxy; C$_3$–C$_6$-cycloalkyl; di(lower alkyl) amino; phenyl; phenoxy; or halogen, R$_{10}$ represents hydrogen, lower allyl or lower alkoxy, Y represents a radical selected from the following group:

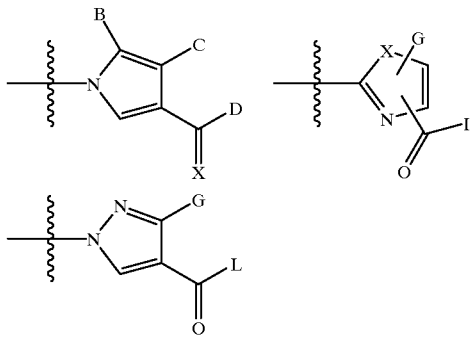

wherein

X represents O or S,

B represents hydrogen, or lower alkyl which may be optionally substituted by hydroxy, mercapto, lower alkoxy, lower alkylthio or aryl, C represents hydrogen, or lower alkyl which may be optionally substituted by aryl; or represents a radical selected from the following group:

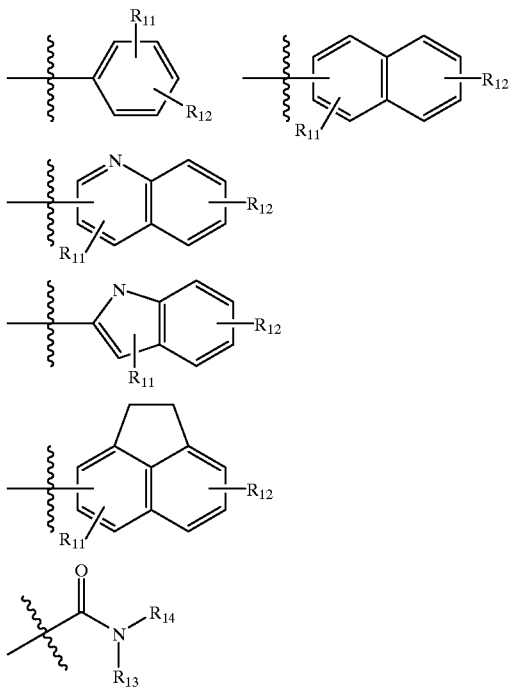

wherein

R$_{11}$ and R$_{12}$ independently of one another represent hydrogen, lower alkyl, lower alkoxy, halogen, cyano, hydroxycarbonyl, amino-carbonyl, aminothiocarbonyl, hydroxy phenyl or phenoxy, $R_{13}$ and $R_{14}$ independently of one another represent hydrogen, lower alkyl, aryl or

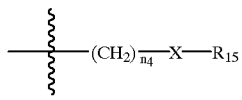

wherein X is defined as previously described, $n_4$ is an integer of 2 to 4 and $R_{15}$ is lower alkyl, D represents amino acid residue or lower alkyl ester of amino acid residue; or represents a radical selected from the following group:

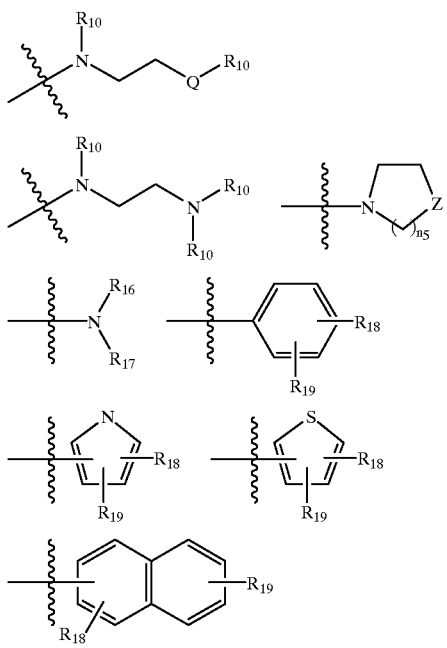

wherein $R_{10}$ is defined as previously described,

Q represents O, S, S=O or $SO_2$,

Z represents O, S, S=O, $SO_2$, C=O or C=S, or represents CH—$R_{20}$ or

N—$R_{20}$(wherein $R_{20}$ is hydrogen, lower alkyl or hydroxy), $n_5$ denotes an integer of 1 to 3, $R_{16}$ and $R_{17}$ independently of one another represents hydrogen; aryl; lower alkyl which may be optionally substituted by aryl or cyanoaryl; or

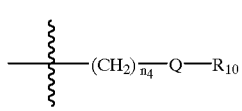

wherein $n_4$, Q and $R_{10}$ are defined as previously described, $R_{18}$ and $R_{19}$ independently of one another represents hydrogen; halogen; hydroxy; cyano; lower alkyl; lower alkoxy; alkoxyalkyl; alkylthio; hydroxycarbonyl; amninocarbonyl; aminothiocarbonyl; alkylsulfonyl; alkylthioalkyl; alkylthioalkyloxy; aryl; or oxy, thio, sulfonyl or lower alkyl substituted by aryl, G represents a radical selected by the following group:

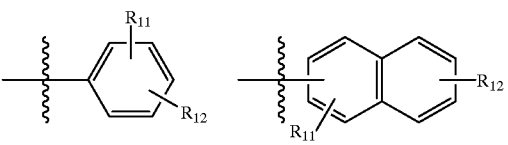

wherein $R_{11}$ and $R_{12}$ are defined as previously described,

I represents lower alkoxy, or represents a radical selected from the following group:

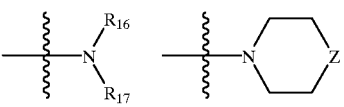

wherein $R_{16}$, $R_{17}$ and Z are defined as previously described,

L represents a radical selected from the following group:

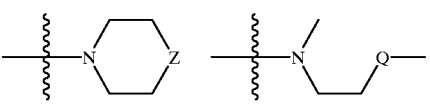

wherein Z and Q are defined as previously described, provided that (1) $n_2$ is other than 0 when $R_3$ is hydrogen, and (2) Y is other than

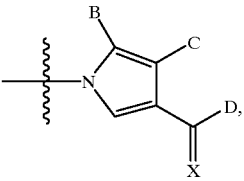

when A is

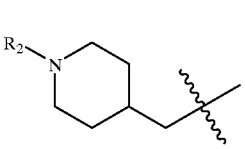

or pharmaceutically acceptable salts or isomers thereof.

Particularly, the compound according to the present invention has a quite different structure from the known inhibitors for farnesyl transferase, and furthermore it does never include the thiol moiety.

In the definitions for the substituents of the compound of formula (1), the term "lower alkyl" means a straight-chain or branched alkyl having 1 to 4 carbon atoms which includes methyl, ethyl, isopropyl, isobutyl and t-butyl.

Since the compound of formula (1) according to the present invention may have asymmetric carbon atoms depending on the substituents, it can be present in the form of R or S isomer, racemate, or mixtures thereof. Thus, the present invention also includes all of these stereoisomers and their mixtures.

Also, the compound of formula (1) according to the present invention can form a pharmaceutically acceptable salt. Such salt includes non-toxic acid addition salt containing pharmaceutically acceptable anion, for example a salt with inorganic acids such as hydrochloric acid, sulfuric acid, nitric acid, phosphoric acid, hydrobromic acid, hydriodic acid, etc., a salt with organic carboxylic acids such as tartaric acid, formic acid, citric acid, acetic acid, trichloroacetic acid, trofluoroacetic acid, gluconic acid, benzoic acid, lactic acid, fumaric acid, maleic acid, asparagic acid, etc., or a salt with sulfonic acids such as methanesulfonic acid, benzenesulfonic acid, p-toluenesulfonic acid, naphthalenesulfonic acid, etc.; base addition salt for example a salt with pyridine or ammonia; and metal addition salt, for example, a salt with alkali metal or alkaline earth metal such as lithium salt. Further, the present invention includes a solvate of the compound of formula (1) such as alcoholate or hydrate thereof. They can be produced by conventional conversion methods.

Among the compound of formula (1) according to the present invention, the preferred compounds include those wherein $n_1$ represents an integer of 1 to 3, A represents hydrogen; straight-chain or branched $C_1$–$C_{10}$-alkyl which may be optionally substituted by $C_3$–$C_7$-cycloalkyl or lower alkoxy; or a radical selected from the following group:

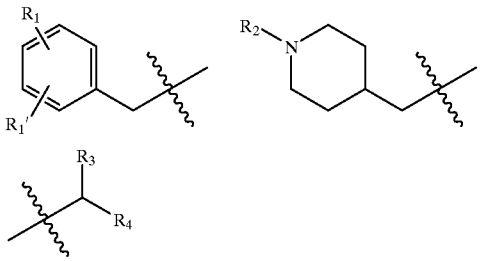

wherein $R_1$ and $R_1'$ independently of one another represent hydrogen, halogen, cyano, nitro, hydroxycarbonyl, aminocarbonyl, aminothiocarbonyl, lower alkoxy, phenoxy, phenyl, benzyloxy, or lower alkyl which may be optionally substituted by $C_3$–$C_6$-cycloalkyl, $R_2$ represents hydrogen or lower alkyl, or represents —E—F wherein E is —$CH_2$—, —C(O)— or —S(O)$_2$— and F is hydrogen; lower alkyl which may be optionally substituted by phenoxy or biphenyl; lower alkoxy which may be optionally substituted by aryl; phenyl; benzyl; benzyloxy; or amino which may be optionally substituted by lower alkyl, benzyl or $C_5$–$C_6$-cycloalkyl, $R_3$ represents hydrogen or lower alkyl, $R_4$ represents a radical selected from the following group:

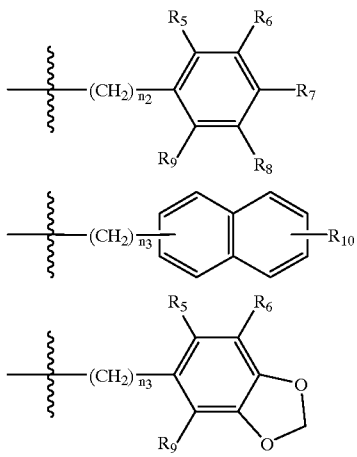

wherein $n_2$ and $n_3$ independently of one another denote 0, 1, 2, 3 or 4, $R_5$, $R_6$, $R_8$ and $R_9$ independently of one another represent hydrogen, lower alkyl, lower alkoxy, hydroxy or halogen, $R_7$ represents hydrogen; lower alkyl which may be optionally substituted by $C_3$–$C_6$-cycloalkyl; lower alkoxy; hydroxy; $C_3$–$C_6$-cycloalkyl; or halogen, $R_{10}$ represents hydrogen, methyl or methoxy, Y represents a radical selected from the following group:

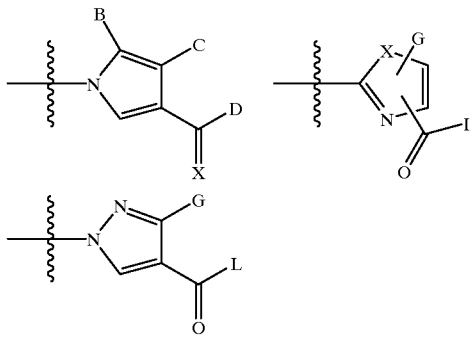

wherein

X represents O or S,

B represents hydrogen, or lower alkyl which may be optionally substituted by lower alkoxy or aryl, C represents hydrogen, or lower alkyl which may be optionally substituted by aryl; or represents a radical selected from the following group:

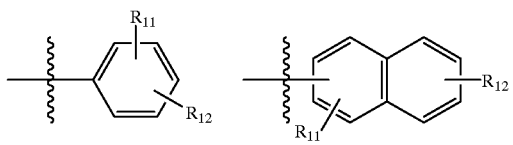

-continued

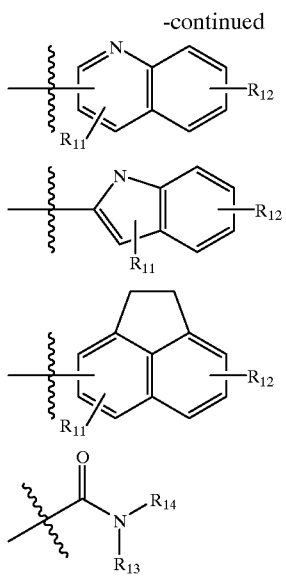

wherein

R$_{11}$ and R$_{12}$ independently of one another represent hydrogen, lower alkyl, lower alkoxy, halogen, cyano, aminocarbonyl, phenyl or phenoxy, R$_{13}$ and R$_{14}$ independently of one another represent hydrogen, lower alkyl, aryl or

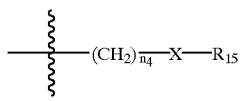

wherein X is defined as previously described, n$_4$ is 2 and R$_{15}$ is lower alkyl, D represents amino acid residue or lower alkyl ester of amino acid residue; or represents a radical selected from the following group:

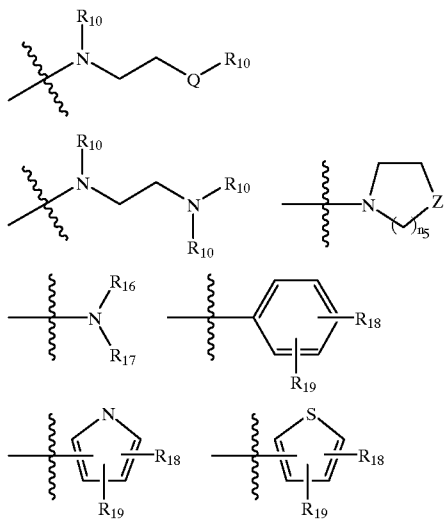

-continued

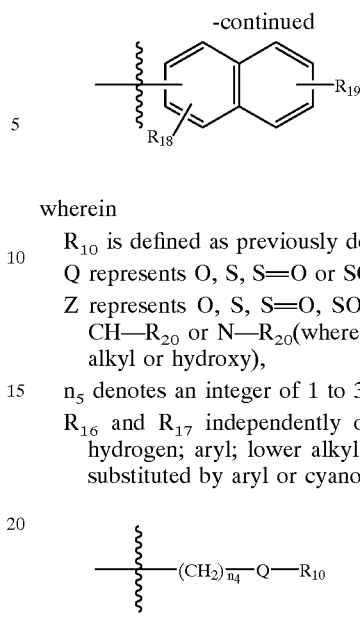

wherein

R$_{10}$ is defined as previously described,

Q represents O, S, S=O or SO$_2$,

Z represents O, S, S=O, SO$_2$ or C=O, or represents CH—R$_{20}$ or N—R$_{20}$ (wherein R$_{20}$ is hydrogen, lower alkyl or hydroxy), n$_5$ denotes an integer of 1 to 3, R$_{16}$ and R$_{17}$ independently of one another represents hydrogen; aryl; lower alkyl which may be optionally substituted by aryl or cyanoayl; or $$-\!\!\!\{\!\!-(CH_2)\overline{_{n_4}}\!-Q\!-\!R_{10}$$

wherein n$_4$, Q and R$_{10}$ are defined as previously described,

R$_{18}$ and R$_{19}$ independently of one another represents hydrogen; halogen; hydroxy; cyano; lower allyl; lower alkoxy; alkoxyalkyl; alkylthio; hydroxycarbonyl; aminocarbonyl; aminothiocarbonyl; alkylsulfonyl; alkylthioalkyl; alkylthioalkyloxy; aryl; or oxy, thio, sulfonyl or lower alkyl substituted by aryl, G represents a radical selected by the following group:

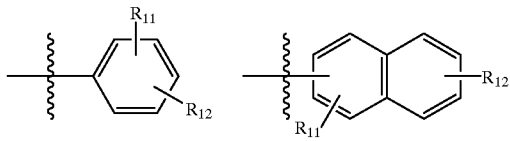

wherein

R$_{11}$ and R$_{12}$ are defined as previously described,

I represents lower alkoxy, or represents a radical selected from the following group:

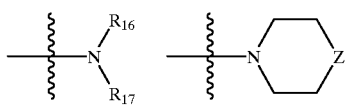

wherein

R$_{16}$, R$_{17}$ and Z are defined as previously described,

L represents a radical selected from the following group:

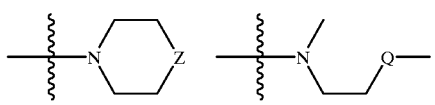

wherein Z and Q are defined as previously described, provided that (1) n$_2$ is other than 0 when R$_3$ is hydrogen, and (2) Y is other than
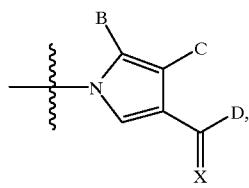
when A is
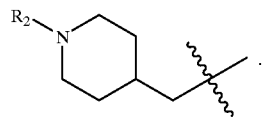
Particularly preferred compounds include those wherein Y represents
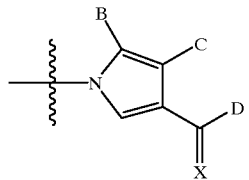
and C represents
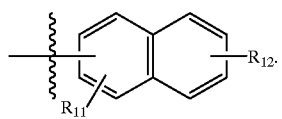
Typical examples of the compound of formula (1) according to the present invention are presented in the following Table 1.
TABLE 1-1
| COM. NO. | STRUCTURE |
| --- | --- |
| 1 | |
| 2 | 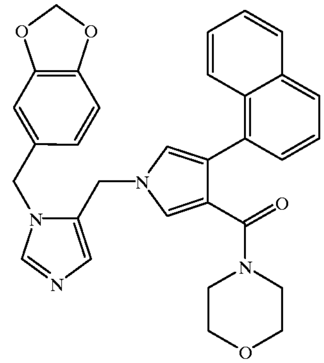 |
| 3 | 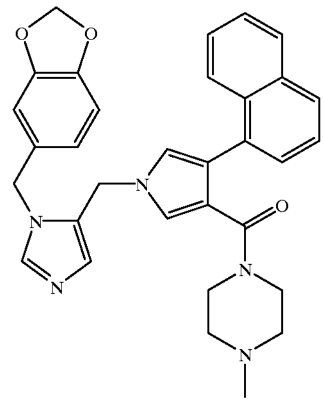 |
| 4 | 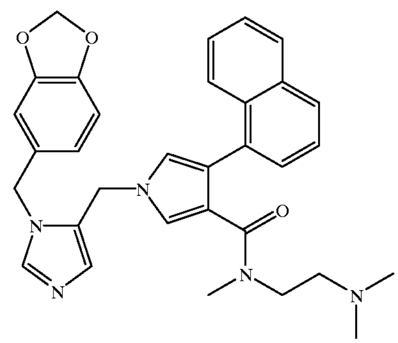 |
| 5 | 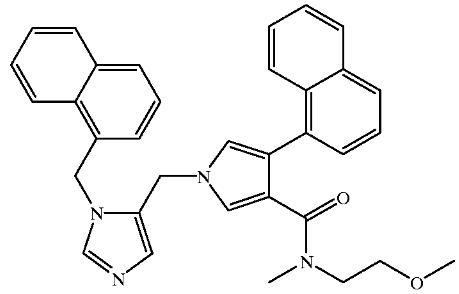 |

TABLE 1-1-continued
| COM. NO. | STRUCTURE |
|---|---|
| 6 | 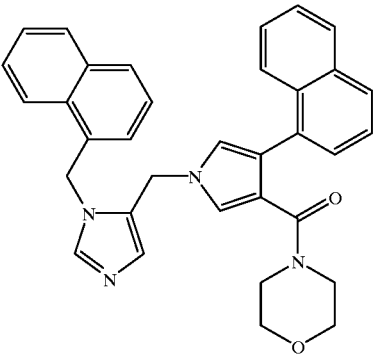 |
TABLE 1-2
| COM. NO. | STRUCTURE |
|---|---|
| 7 | 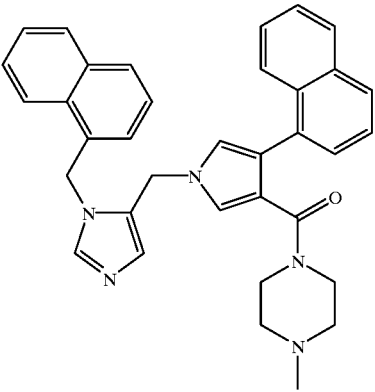 |
| 8 | 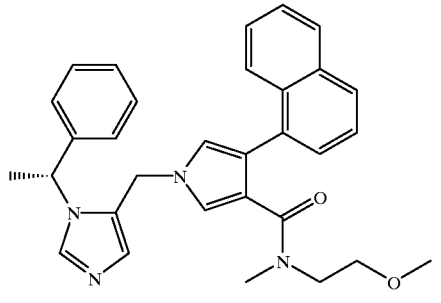 |
TABLE 1-2-continued
| COM. NO. | STRUCTURE |
|---|---|
| 9 | 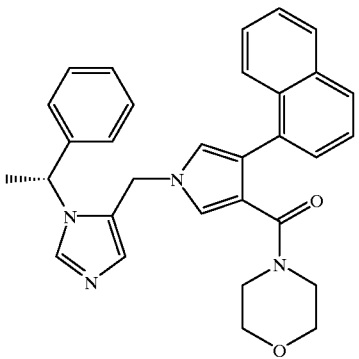 |
| 10 | 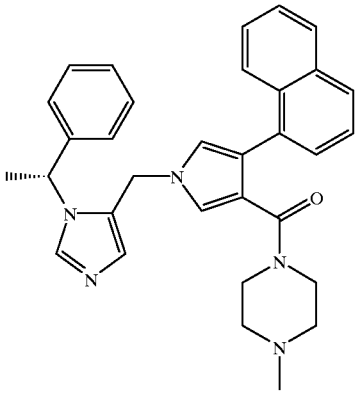 |
| 11 | 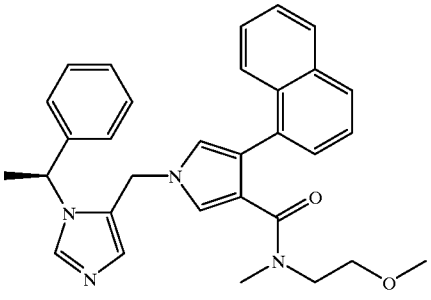 |
| 12 | 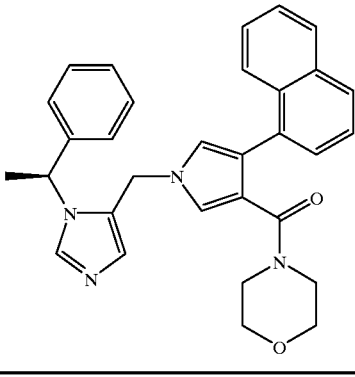 |

TABLE 1-3
| COM. NO. | STRUCTURE |
|---|---|
| 13 | 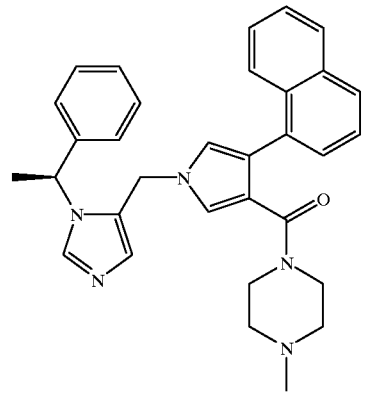 |
| 14 | 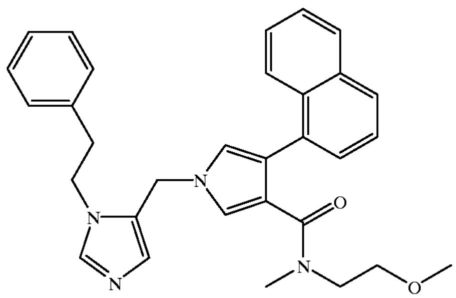 |
| 15 | 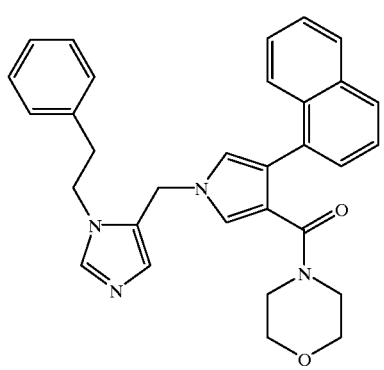 |
| 16 | 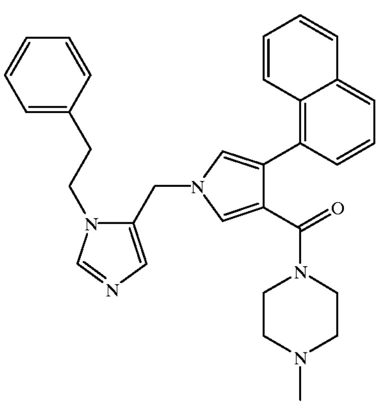 |
TABLE 1-3-continued
| COM. NO. | STRUCTURE |
|---|---|
| 17 | 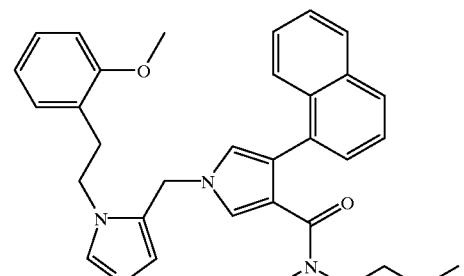 |
| 18 | 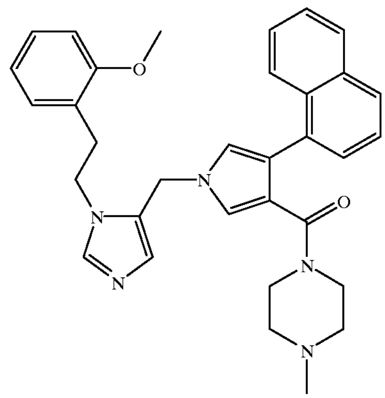 |
TABLE 1-4
| COM. NO. | STRUCTURE |
|---|---|
| 19 | 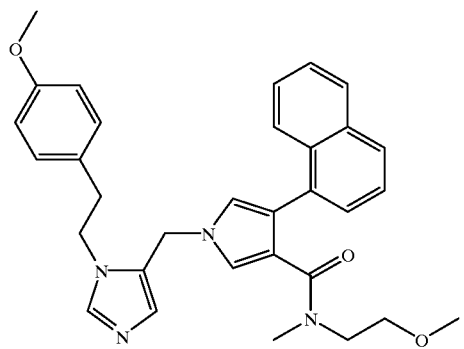 |

TABLE 1-4-continued

| COM. NO. | STRUCTURE |
|---|---|
| 20 | 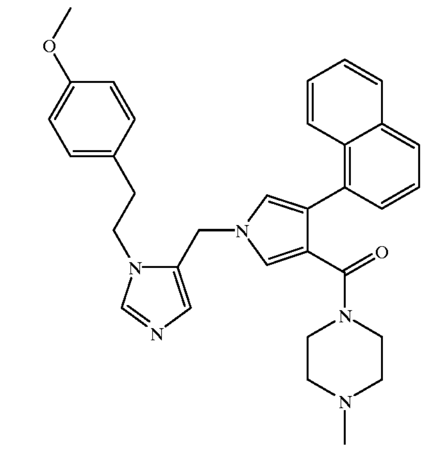 |
| 21 | 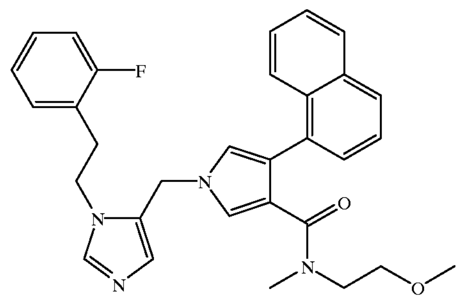 |
| 22 | 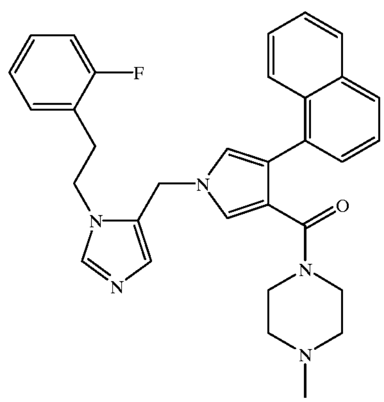 |
| 23 | 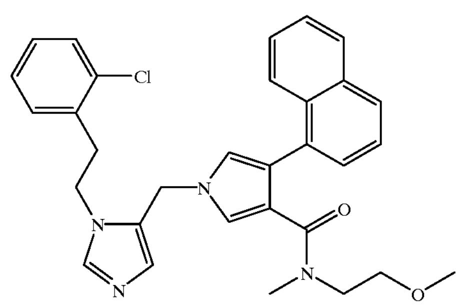 |

TABLE 1-4-continued

| COM. NO. | STRUCTURE |
|---|---|
| 24 | |

TABLE 1-5

| COM. NO. | STRUCTURE |
|---|---|
| 25 | 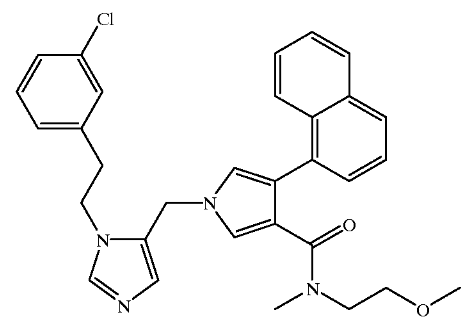 |
| 26 | 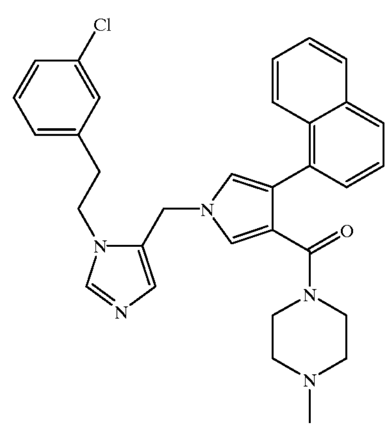 |

TABLE 1-5-continued

| COM. NO. | STRUCTURE |
|---|---|
| 27 | 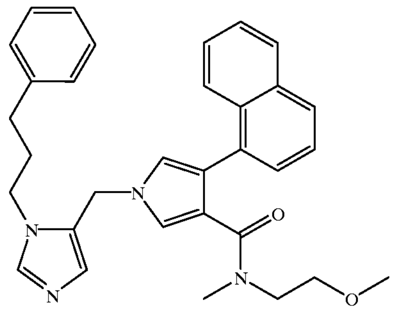 |
| 28 | 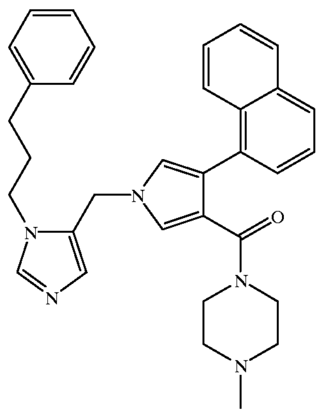 |
| 29 | 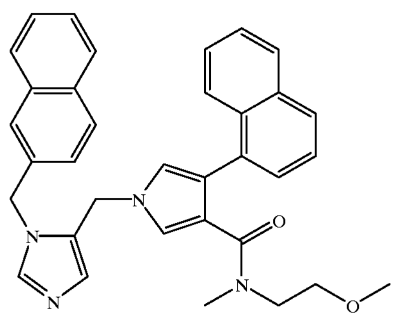 |
| 30 | 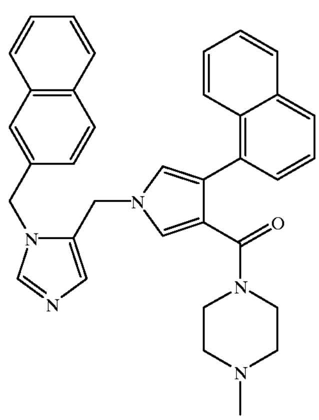 |

TABLE 1-6

| COM. NO. | STRUCTURE |
|---|---|
| 31 | 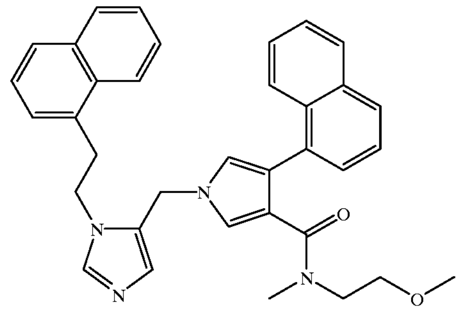 |
| 32 | 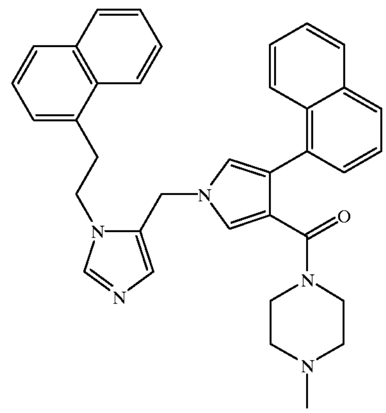 |
| 33 | 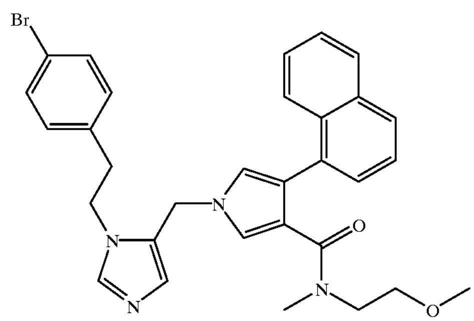 |
| 34 | 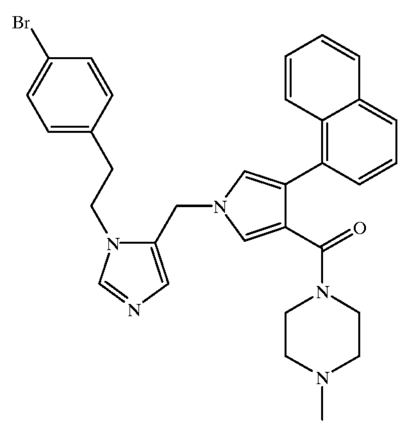 |

TABLE 1-6-continued
| COM. NO. | STRUCTURE |
|---|---|
| 35 | 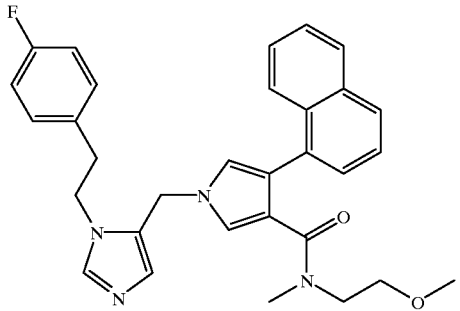 |
| 36 | 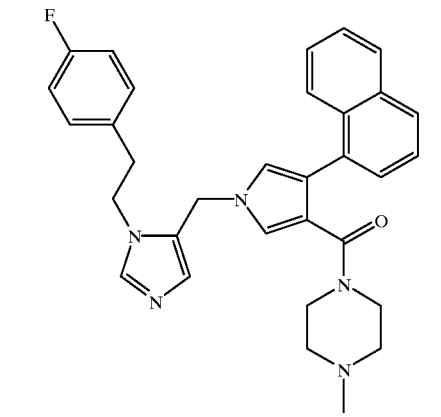 |
TABLE 1-7
| COM. NO. | STRUCTURE |
|---|---|
| 37 | 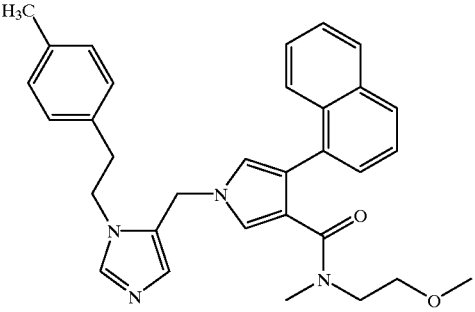 |
TABLE 1-7-continued
| COM. NO. | STRUCTURE |
|---|---|
| 38 | 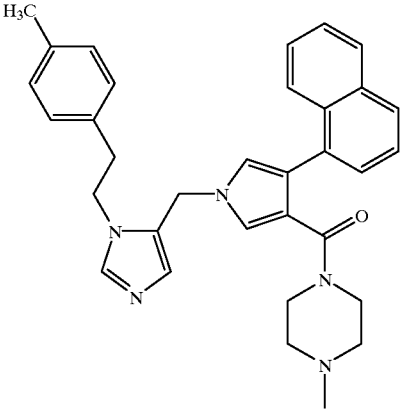 |
| 39 | 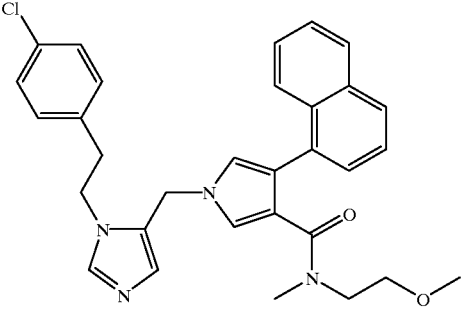 |
| 40 | 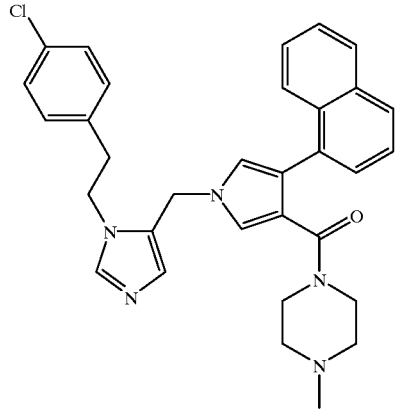 |
| 41 | 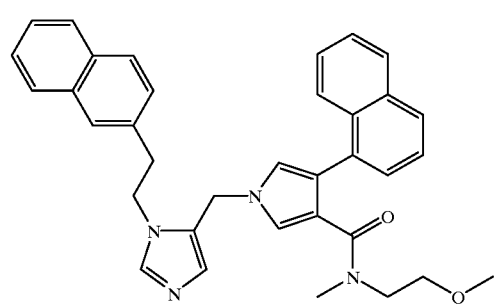 |

TABLE 1-7-continued
| COM. NO. | STRUCTURE |
|---|---|
| 42 | 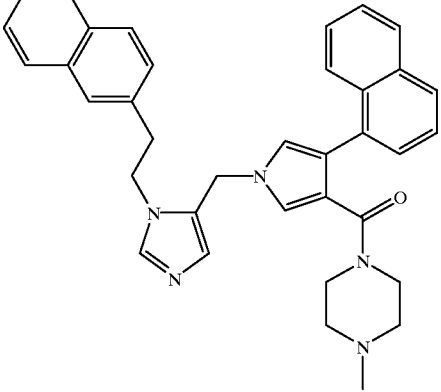 |
TABLE 1-8
| COM. NO. | STRUCTURE |
|---|---|
| 43 | 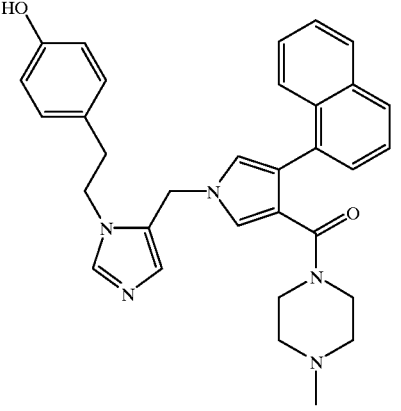 |
TABLE 1-9
| COM. NO. | STRUCTURE |
|---|---|
| 44 | 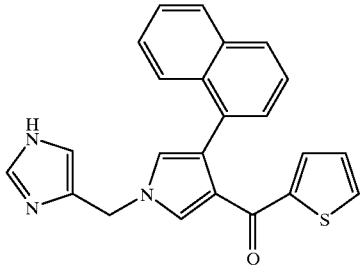 |
TABLE 1-9-continued
| COM. NO. | STRUCTURE |
|---|---|
| 45 | 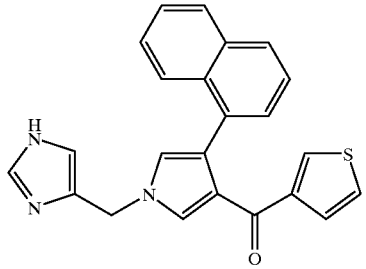 |
| 46 | 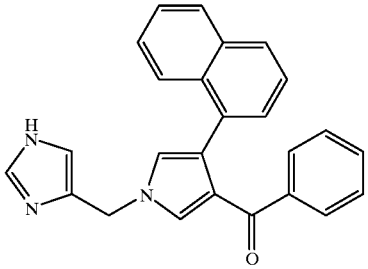 |
| 47 | 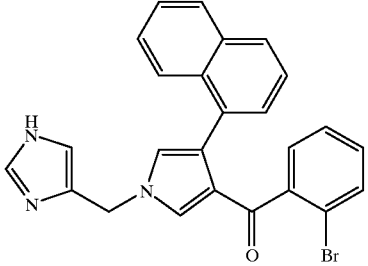 |
| 48 | 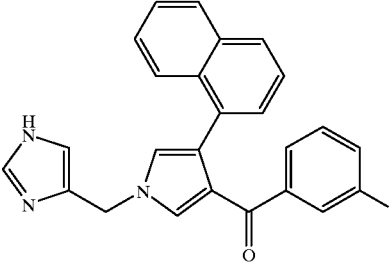 |
| 49 | 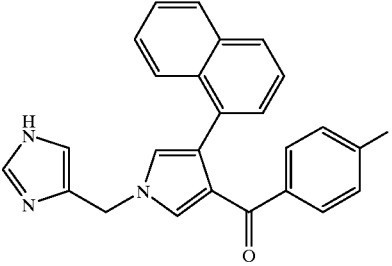 |

TABLE 1-9-continued

| COM. NO. | STRUCTURE |
|---|---|
| 50 | (1-naphthyl at pyrrole-4; imidazol-4-ylmethyl on pyrrole N; 2-methylbenzoyl at pyrrole-3) |
| 51 | (1-naphthyl at pyrrole-4; imidazol-4-ylmethyl on pyrrole N; 3-methylbenzoyl at pyrrole-3) |
| 52 | (1-naphthyl at pyrrole-4; imidazol-4-ylmethyl on pyrrole N; 4-methylbenzoyl at pyrrole-3) |
| 53 | (1-naphthyl at pyrrole-4; imidazol-4-ylmethyl on pyrrole N; 3-methoxybenzoyl at pyrrole-3) |

TABLE 1-10

| COM. NO. | STRUCTURE |
|---|---|
| 54 | (1-naphthyl at pyrrole-4; imidazol-4-ylmethyl on pyrrole N; 4-methoxybenzoyl at pyrrole-3) |
| 55 | (1-naphthyl at pyrrole-4; imidazol-4-ylmethyl on pyrrole N; 2-chlorobenzoyl at pyrrole-3) |
| 56 | (1-naphthyl at pyrrole-4; imidazol-4-ylmethyl on pyrrole N; 4-chlorobenzoyl at pyrrole-3) |
| 57 | (1-naphthyl at pyrrole-4; imidazol-4-ylmethyl on pyrrole N; 2,4-dichlorobenzoyl at pyrrole-3) |
| 58 | (1-naphthyl at pyrrole-4; imidazol-4-ylmethyl on pyrrole N; 4-fluorobenzoyl at pyrrole-3) |

TABLE 1-10-continued
| COM. NO. | STRUCTURE |
|---|---|
| 59 | 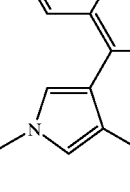 |
| 60 | 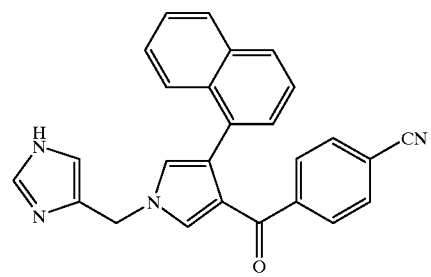 |
| 61 | 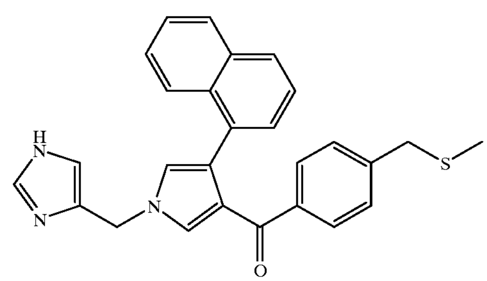 |
| 62 | 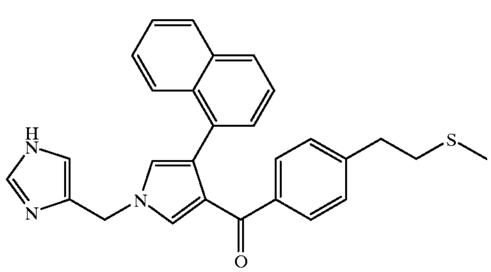 |
| 63 | 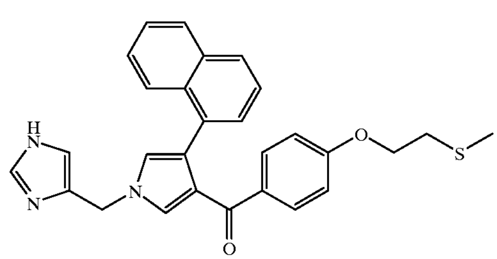 |
TABLE 1-11
| COM. NO. | STRUCTURE |
|---|---|
| 64 | 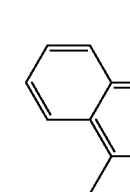 |
| 65 | 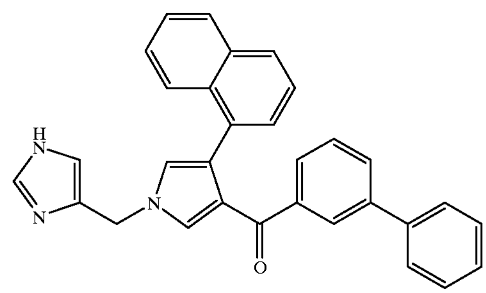 |
| 66 | 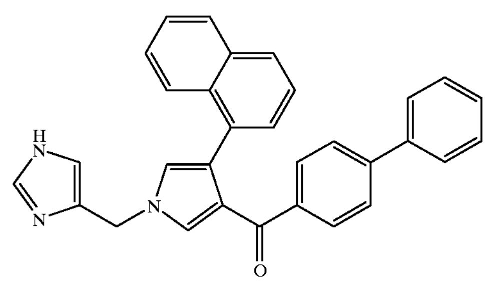 |
| 67 | 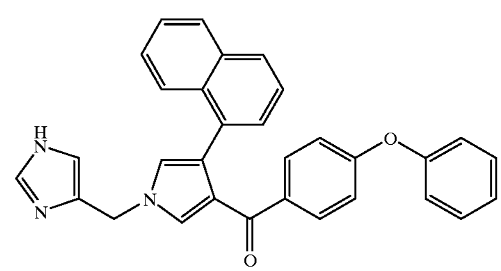 |
| 68 | 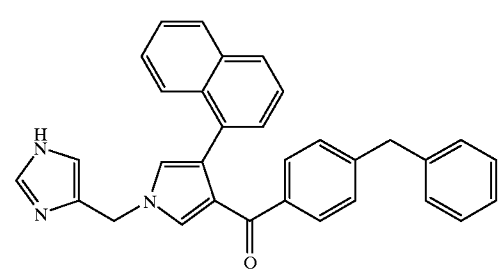 |

TABLE 1-11-continued
| COM. NO. | STRUCTURE |
|---|---|
| 69 | 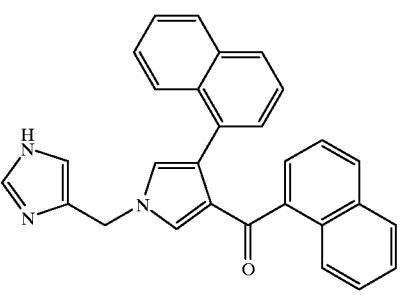 |
| 70 | 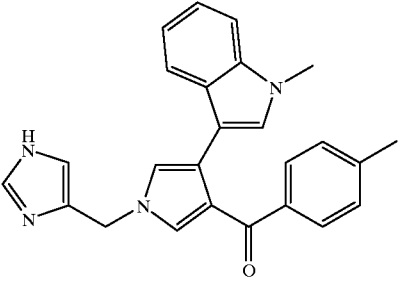 |
| 71 | 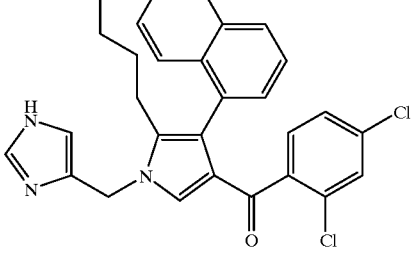 |
| 72 | 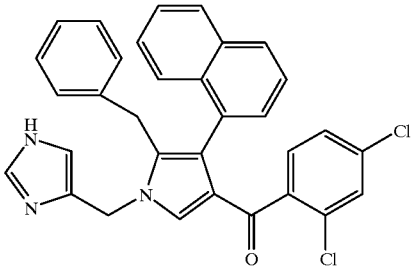 |
| 73 | 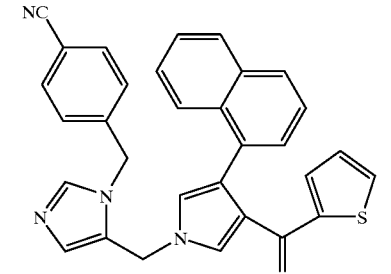 |
TABLE 1-12
| COM. NO. | STRUCTURE |
|---|---|
| 74 | 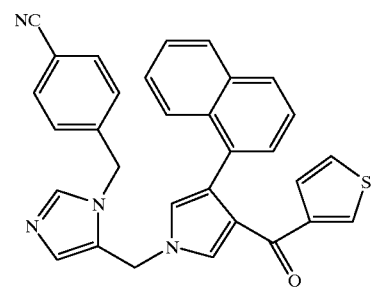 |
| 75 | 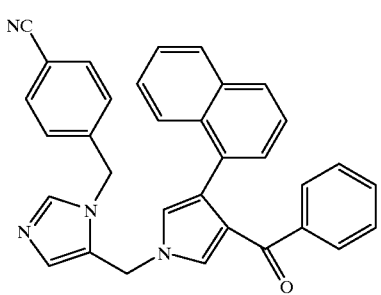 |
| 76 | 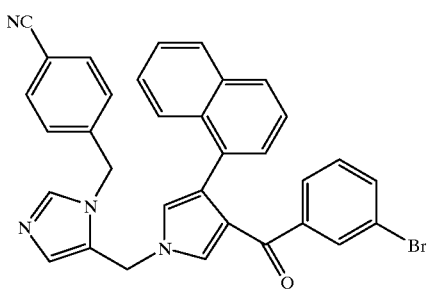 |
| 77 | 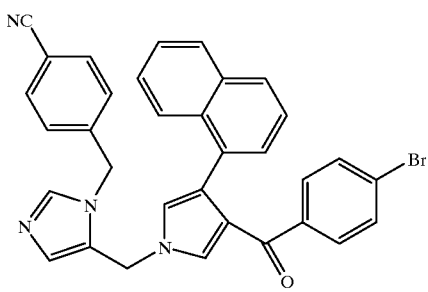 |
| 78 | 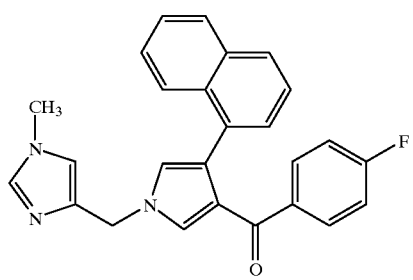 |

| 79 | 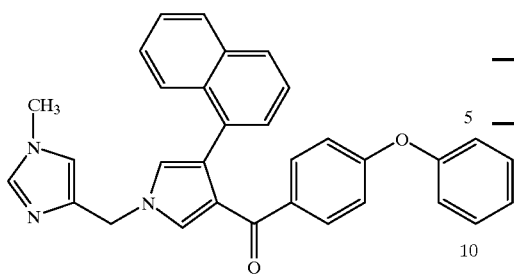 |
|---|---|
TABLE 1-13
| COM. NO. | STRUCTURE |
|---|---|
| 84 | 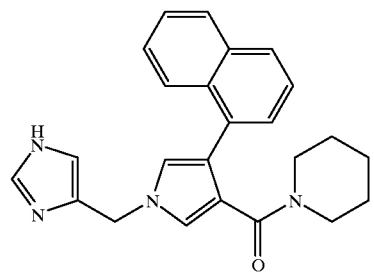 |
| 80 | 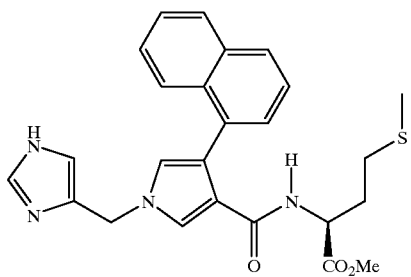 |
|---|---|
| 85 | 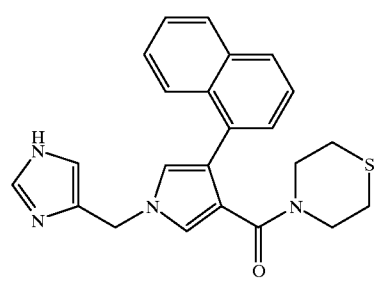 |
|---|---|
| 81 | 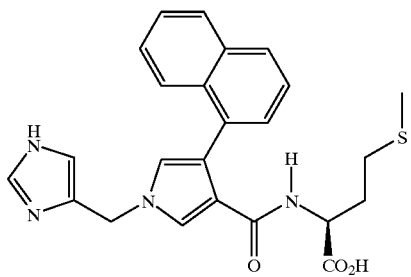 |
|---|---|
| 86 | 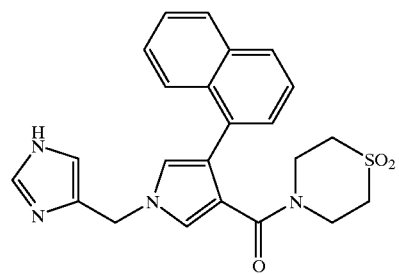 |
|---|---|
| 82 | 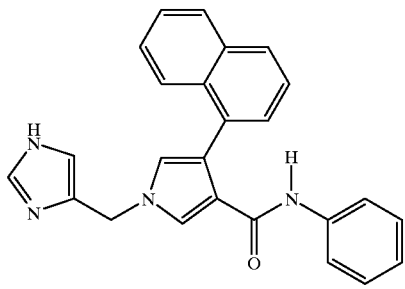 |
|---|---|
| 87 | 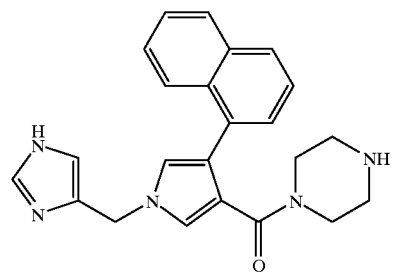 |
|---|---|
| 83 | 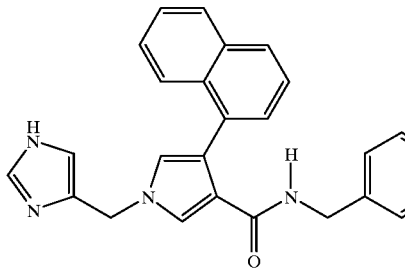 |
|---|---|
| 88 | |

TABLE 1-13-continued
| COM. NO. | STRUCTURE |
|---|---|
| 89 | 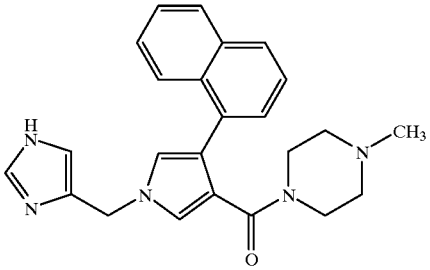 |
| 90 | 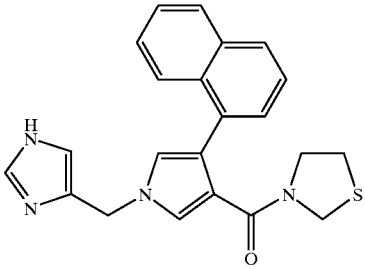 |
| 91 | 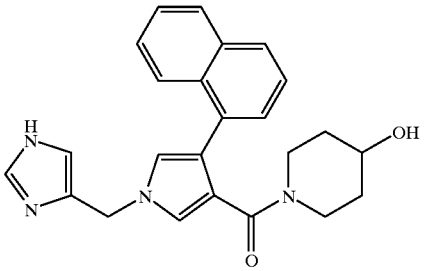 |
| 92 | 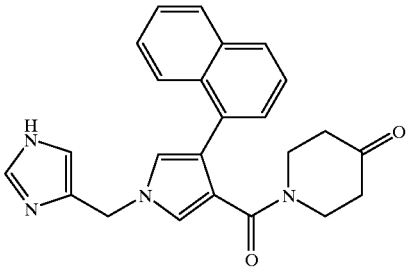 |
| 93 | 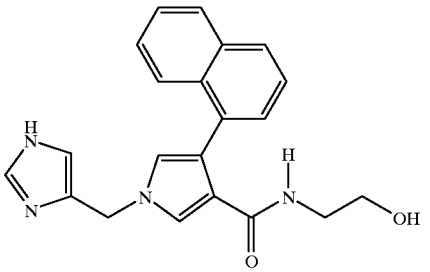 |
TABLE 1-14
| COM. NO. | STRUCTURE |
|---|---|
| 94 | 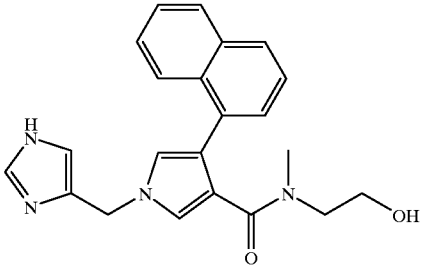 |
| 95 | 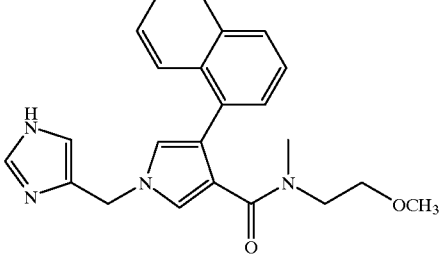 |
| 96 | 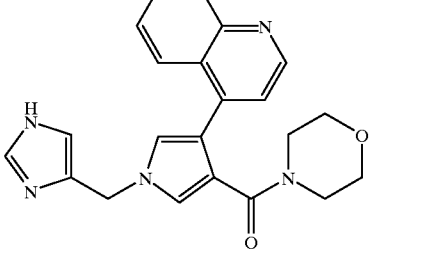 |
| 97 | 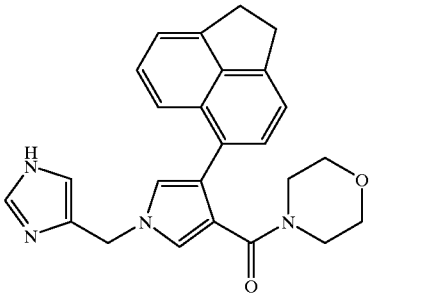 |
| 98 | 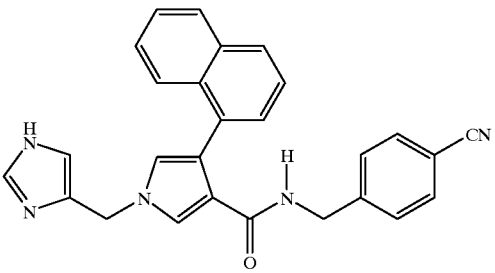 |

TABLE 1-14-continued
| COM. NO. | STRUCTURE |
|---|---|
| 99 | 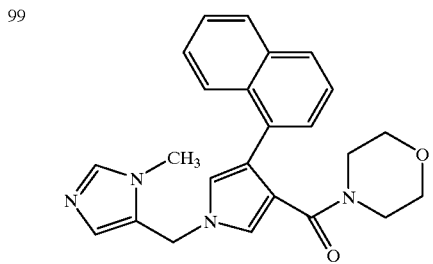 |
| 100 | 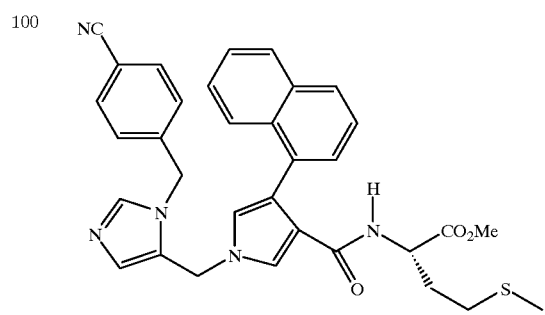 |
| 101 | 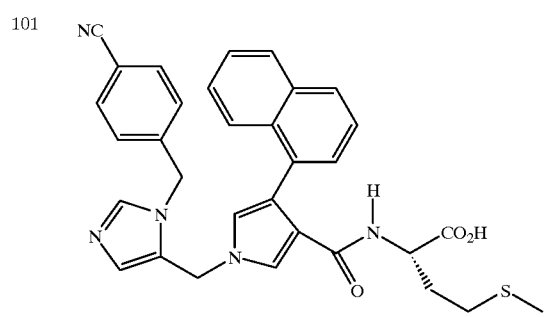 |
| 102 | 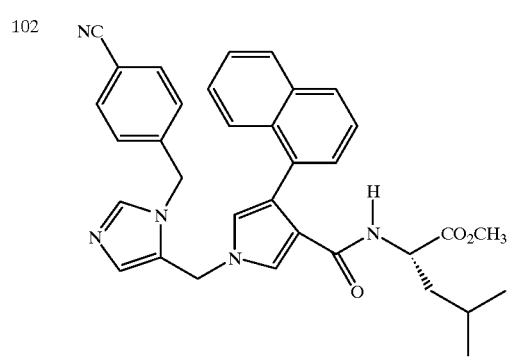 |
TABLE 1-14-continued
| COM. NO. | STRUCTURE |
|---|---|
| 103 | 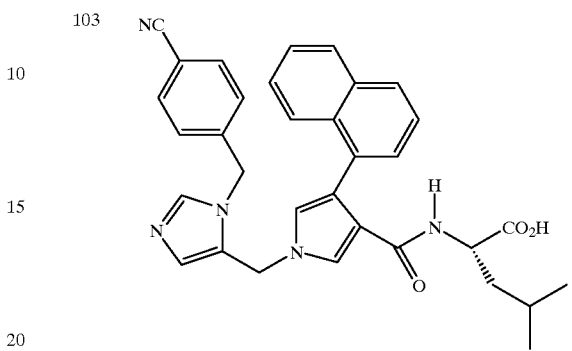 |
TABLE 1-15
| COM. NO. | STRUCTURE |
|---|---|
| 104 | 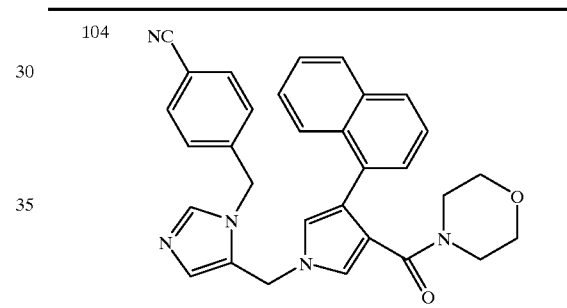 |
| 105 | 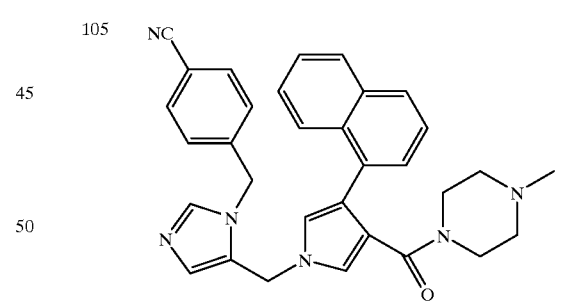 |
| 106 | 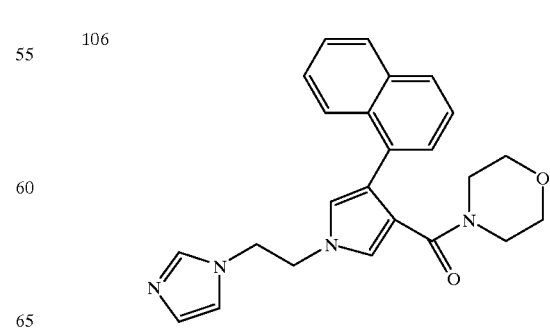 |

TABLE 1-15-continued
| COM. NO. | STRUCTURE |
|---|---|
| 107 | 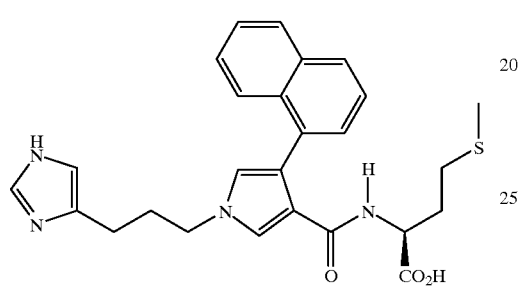 |
| 108 | 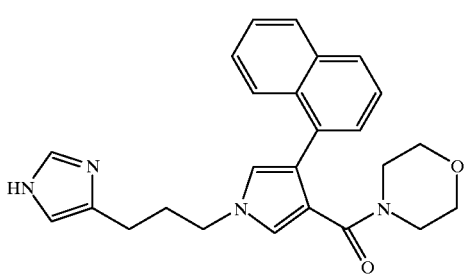 |
| 109 | 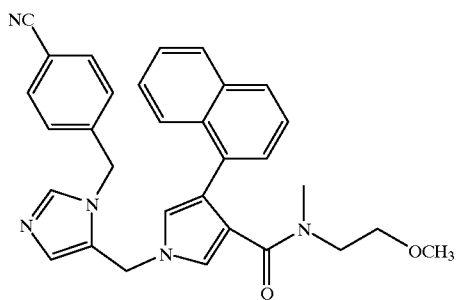 |
| 110 | 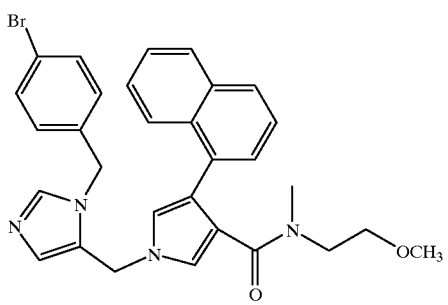 |
| 111 | 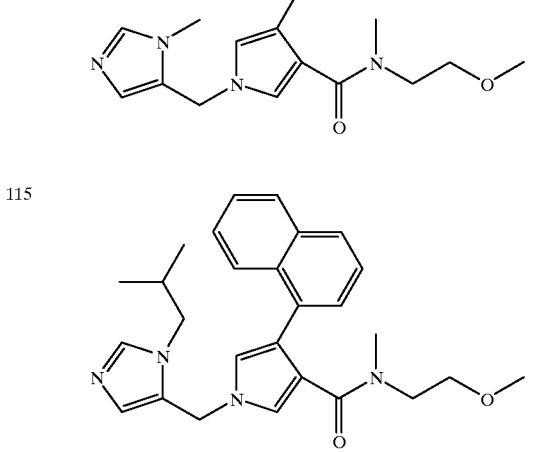 |
TABLE 1-15-continued
| COM. NO. | STRUCTURE |
|---|---|
| 112 | 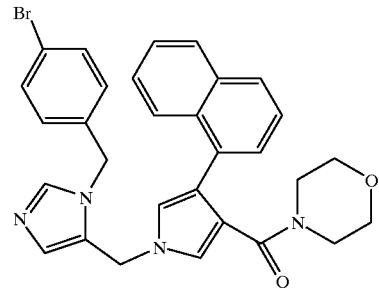 |
| 113 | 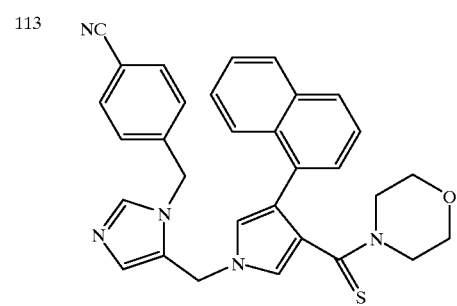 |
TABLE 1-16
| COM. NO. | STRUCTURE |
|---|---|
| 114 | 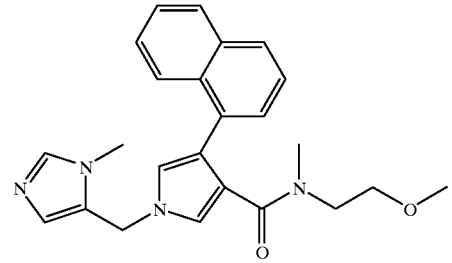 |
| 115 | 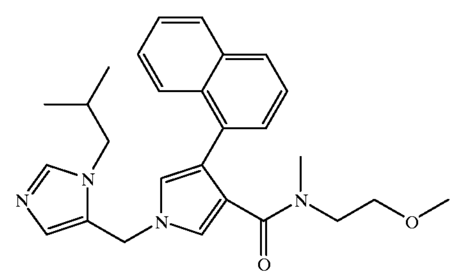 |

TABLE 1-16-continued

| COM. NO. | STRUCTURE |
|---|---|
| 116 | (structure) |
| 117 | (structure) |
| 118 | (structure) |
| 119 | (structure) |
| 120 | (structure) |
| 121 | (structure) |
| 122 | (structure) |
| 123 | (structure) |

TABLE 1-17

| COM. NO. | STRUCTURE |
|---|---|
| 124 | (structure) |

TABLE 1-17-continued

| COM. NO. | STRUCTURE |
|---|---|
| 125 | 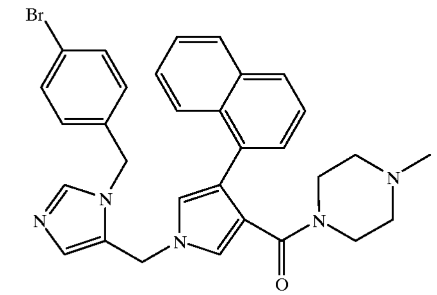 |
| 126 | 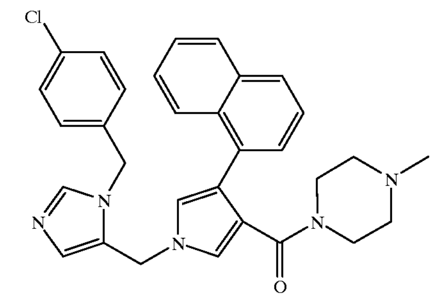 |
| 127 | 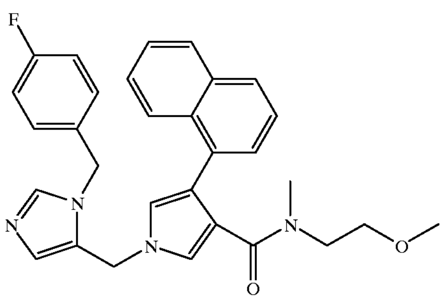 |
| 128 | 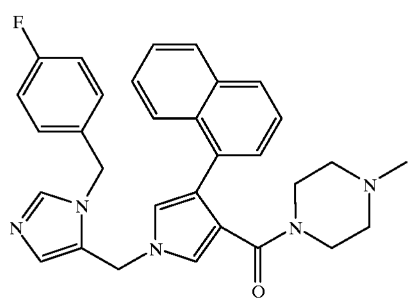 |
| 129 | 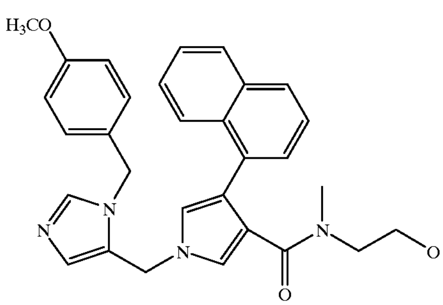 |
| 130 | |
| 131 | |
| 132 | |
| 133 | |

TABLE 1-18
| COM. NO. | STRUCTURE |
|---|---|
| 134 | 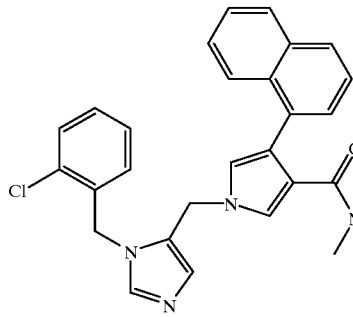 |
| 135 | 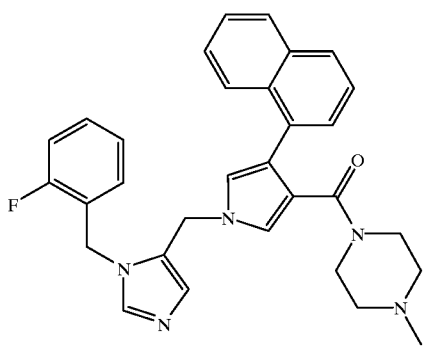 |
| 136 | 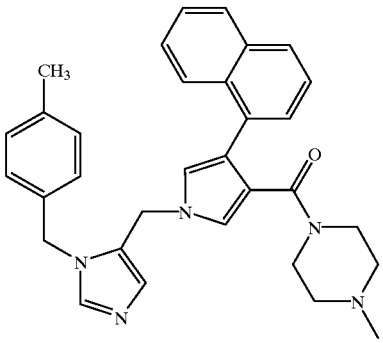 |
| 137 | 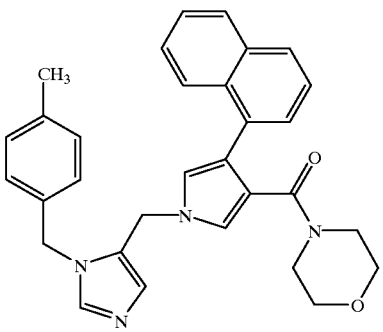 |
TABLE 1-18-continued
| COM. NO. | STRUCTURE |
|---|---|
| 138 | 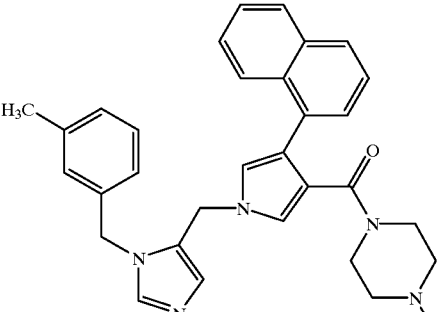 |
| 139 | 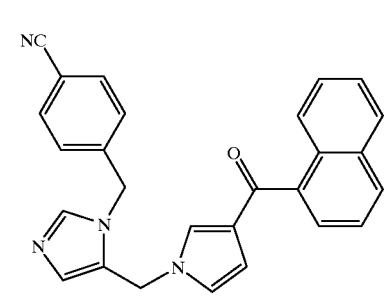 |
| 140 | 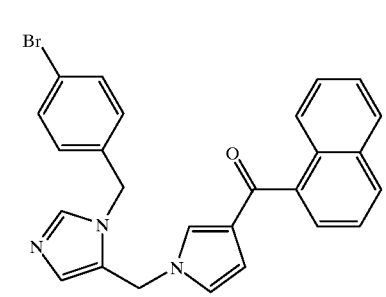 |
| 141 | 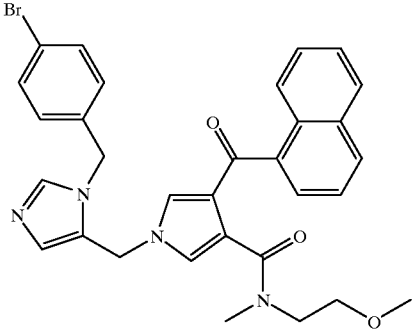 |

TABLE 1-19

| NO. | STRUCTURE |
| --- | --- |
| 142 | 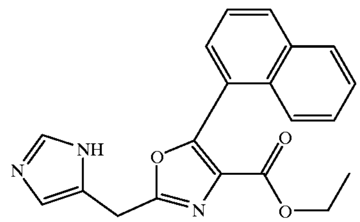 |
| 143 | 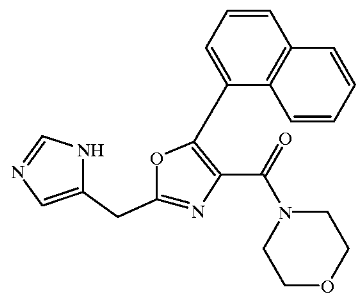 |
| 144 | 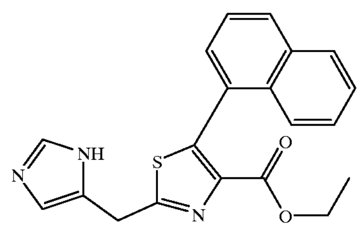 |
| 145 | 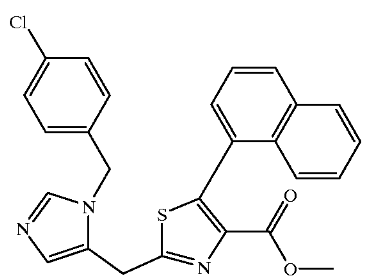 |
| 146 | 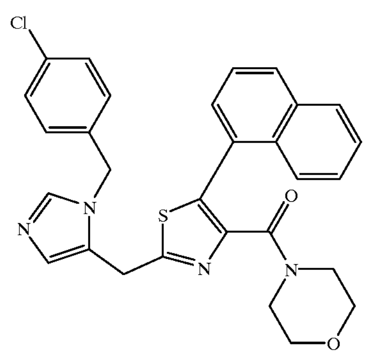 |

TABLE 1-19-continued

| NO. | STRUCTURE |
| --- | --- |
| 147 | 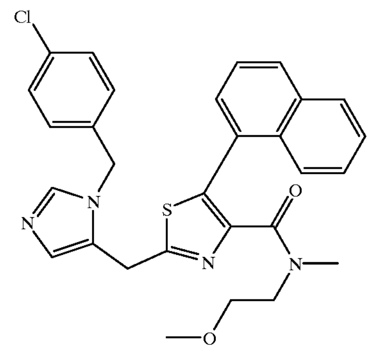 |
| 148 | 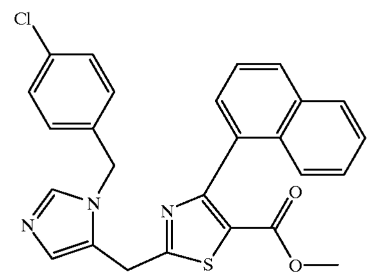 |
| 149 | 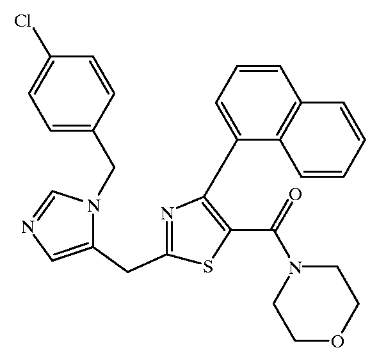 |

TABLE 1-20

| COM. NO. | STRUCTURE |
| --- | --- |
| 150 | 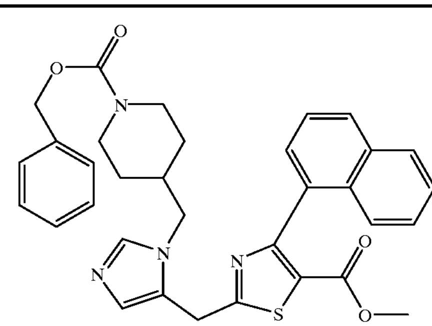 |

TABLE 1-20-continued

| COM. NO. | STRUCTURE |
|---|---|
| 151 | 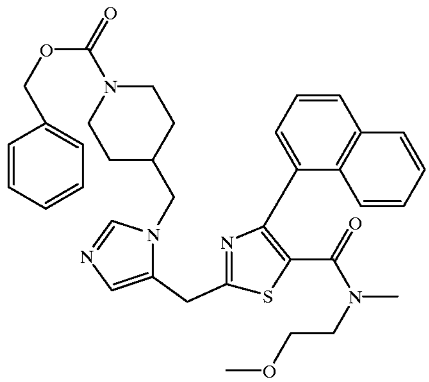 |
| 152 | 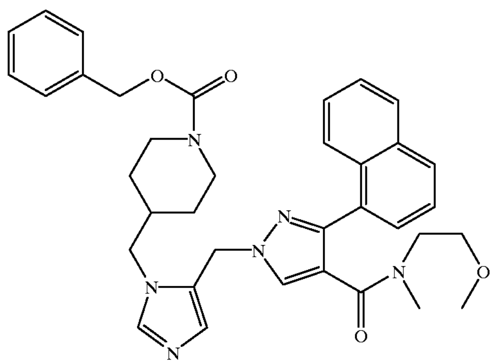 |
| 153 | 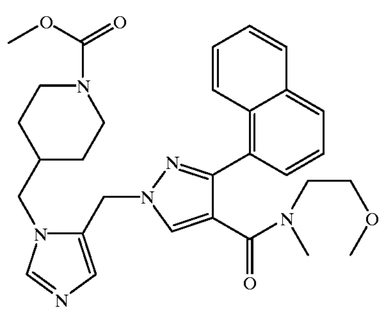 |
| 154 | 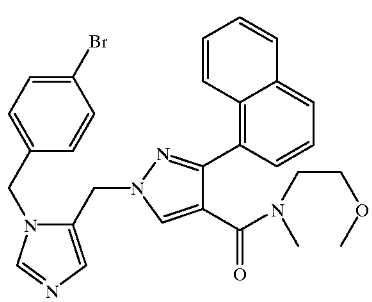 |

TABLE 1-20-continued

| COM. NO. | STRUCTURE |
|---|---|
| 155 | 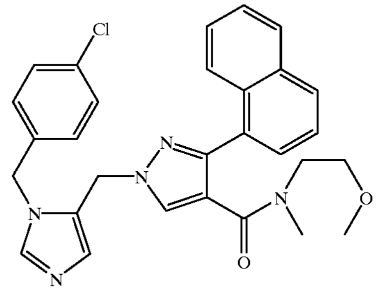 |
| 156 | 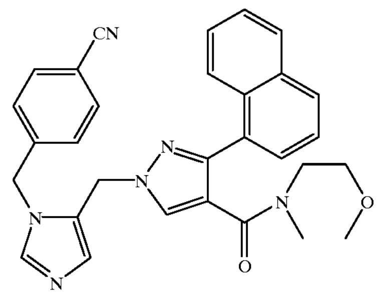 |
| 157 | 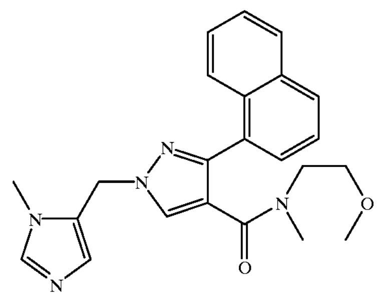 |

TABLE 1-21

| COM. NO. | STRUCTURE |
|---|---|
| 158 | 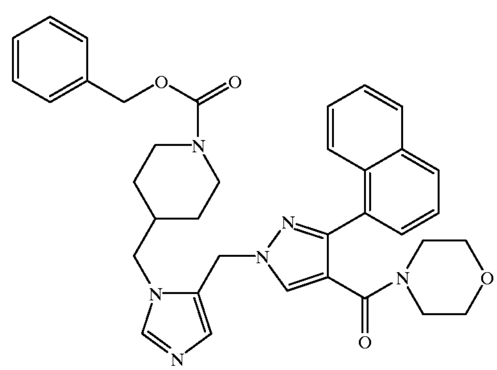 |

TABLE 1-21-continued

| COM. NO. | STRUCTURE |
|---|---|
| 159 | 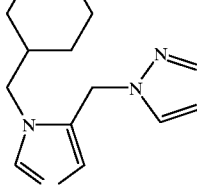 |
| 160 | 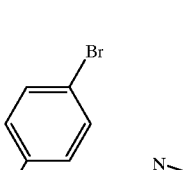 |
| 161 | 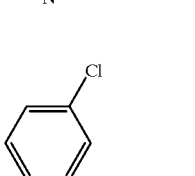 |
| 162 | 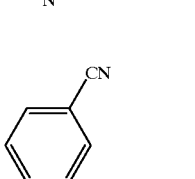 |
| 163 | 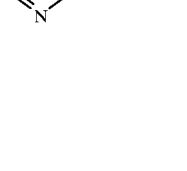 |

It is another object of the present invention to provide processes for preparing the imidazole derivative of formula (1) as defined above.

According to the present invention, the imidazole derivative of formula (1) can be prepared by processes characterized in that (a) a compound represented by the following formula (2) is reacted in a solvent in the presence of a base with a compound represented by the following formula (3), then the trityl group in the product thus obtained is eliminated in the presence of trifluoroacetic acid to produce a compound represented by the following formula (1a); or Reaction Scheme 1

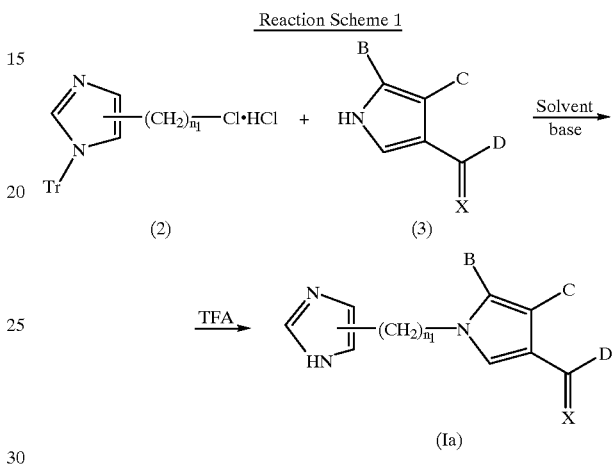

(b) a compound represented by the following formula (4) is reacted in a solvent in the presence of a base with the compound of formula (3) to produce a compound represented by the following formula (1b); or Reaction Scheme 2

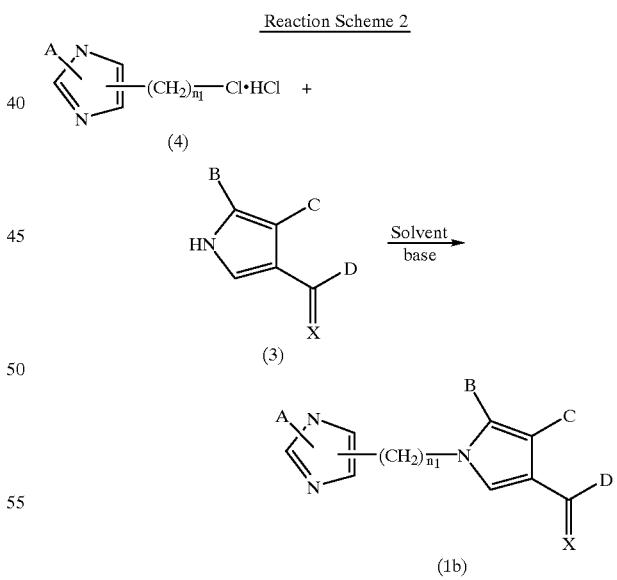

(c) a compound represented by the following formula (5) is reacted in a solvent in the presence of a base with the compound of formula (3), the trityl group in the product thus obtained is eliminated in the presence of trifluoroacetic acid to produce a compound represented by the following formula (6), and then hydrogenation reaction is carried out to produce a compound represented by the following formula (1c); or

Reaction Scheme 3

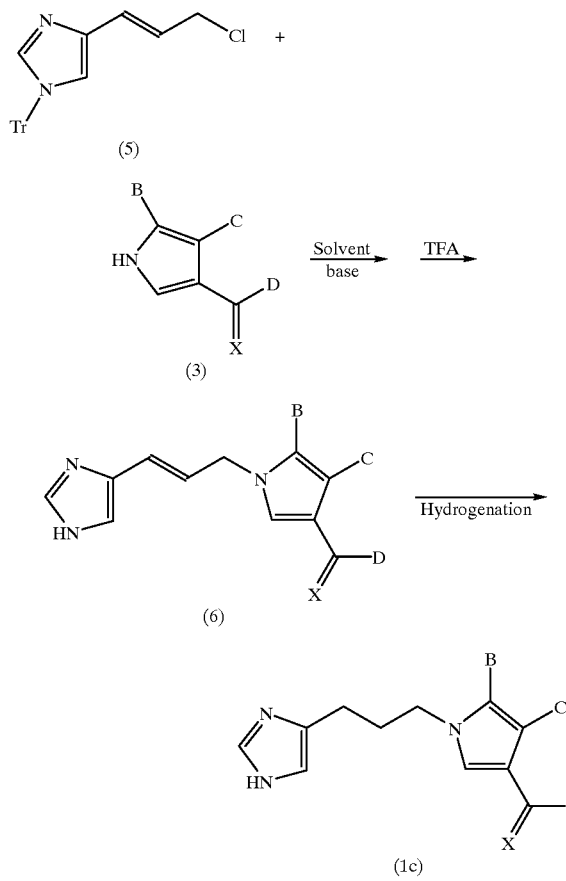

(d) a compound represented by the following formula (7) is hydrolyzed to produce a compound represented by the following formula (8) which is then reacted with a compound represented by the following formula (9) in the presence of a coupling agent to produce a compound represented by the following formula (1d); or

Reaction Scheme 4

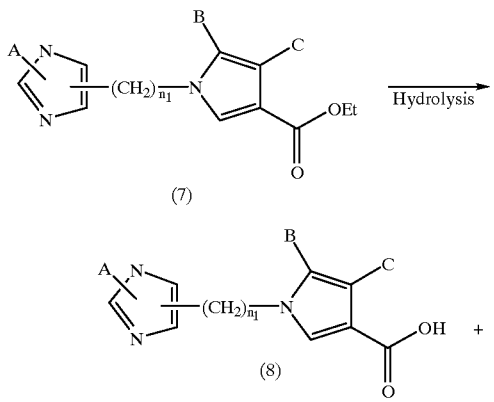

(e) the carbonyl group in a compound represented by the following formula (1e) is converted into the thiocarbonyl group in the presence of a sulfurizing agent to produce a compound represented by the following formula (1f); or

Reaction Scheme 5

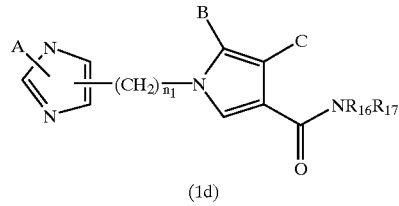

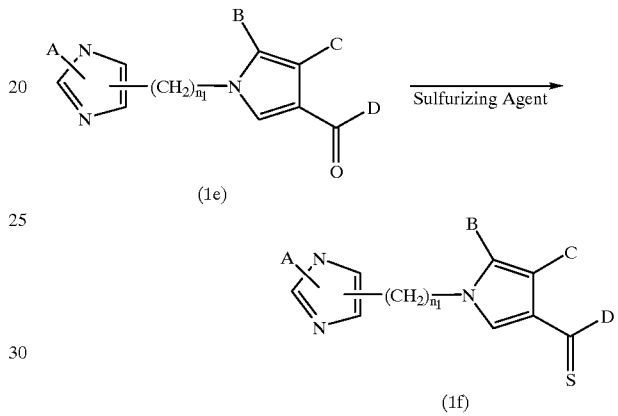

(f) a compound represented by the following formula (1 g) is coupled in a solvent with a compound represented by the following formula (10) to produce a compound represented by the following formula (1h); or

Reaction Scheme 6

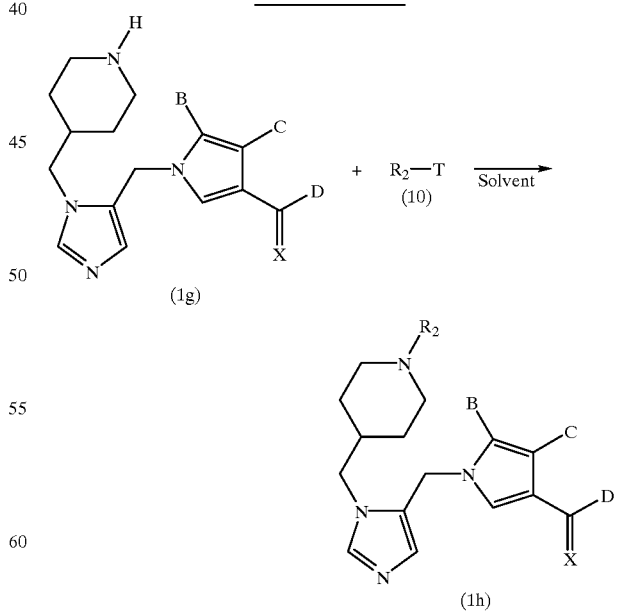

(g) a compound represented by the following formula (11) is cyclized in an inert solvent to produce a compound represented by the following formula (1i); or

Reaction Scheme 7

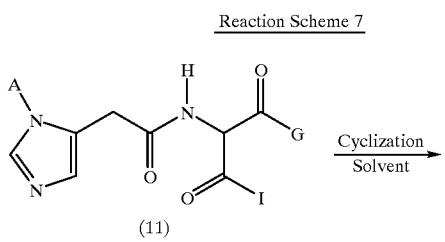

(11)

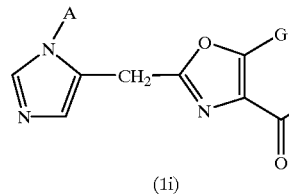

(1i)

(h) the amide group in the compound of formula (11) is converted into the thioamide group to produce a compound represented by the following formula (12) which is then cyclized in an inert solvent to produce a compound represented by the following formula (1j); or

Reaction Scheme 8

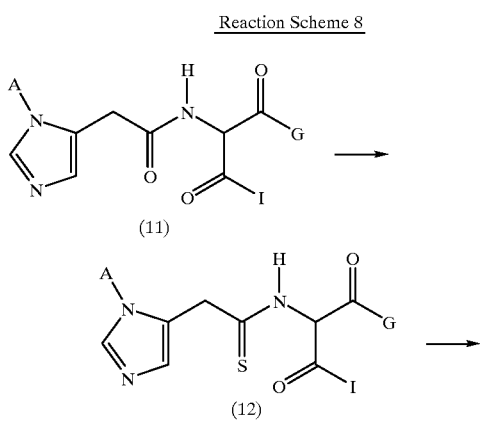

(i) a compound represented by the following formula (13) is reacted in a solvent with a compound represented by the following formula (14a) to produce the compound of formula (1j); or

Reaction Scheme 9

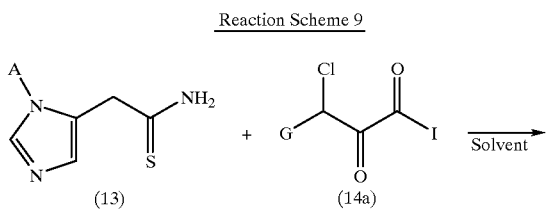

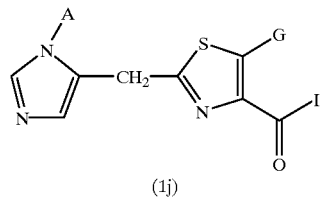

(1j)

(j) compound of formula (13) is reacted in a solvent with a compound represented by the following formula (14b) to produce a compound represented by the following formula (1k); or

Reaction Scheme 10

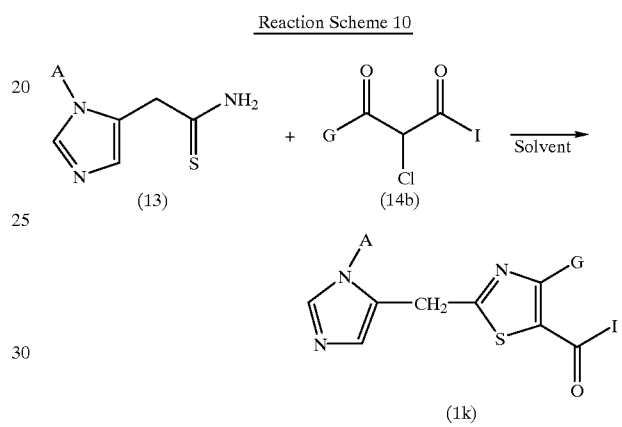

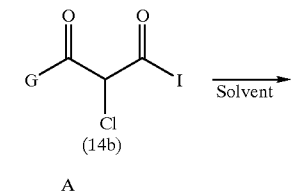

(1k)

(k) a compound represented by the following formula (1l) is hydrolyzed in the presence of a base and the product thus obtained is reacted in a solvent in the presence of a coupling agent with a compound represented by the following formula (15) to produce a compound represented by the following formula (1m); or

Reaction Scheme 11

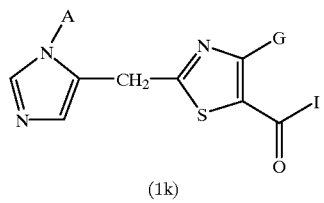

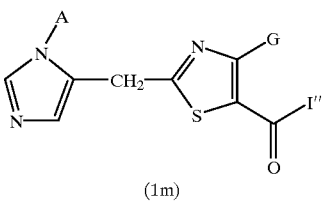

(1m)

(l) a compound represented by the following formula (16) is reacted in a solvent in the presence of a base with a compound represented by the following formula (17) to produce a compound represented by the following formula (1n); or

Reaction Scheme 12

(m) a compound represented by the following formula (18) is reacted in a solvent in the presence of a base with the compound of formula (17) and deprotected to produce a compound represented by the following formula (1o) which is then coupled with a compound represented by the following formula (19) to produce a compound represented by the following formula (1p):

Reaction Scheme 13 in the above reaction schemes

A, $n_1$, B, C, X, D, $R_{16}$, $R_{17}$, $R_2$, G, I, L, E and F are defined as previously described, I' represents lower alkoxy, I" is identical with I except that lower alkoxy is not included, T represents hydroxy or reactive leaving group, preferably halogen, Tr represents trityl, Cbz represents benzyloxycarbonyl and has the same meaning through the present specification.

However, the compound according to the present invention may be conveniently prepared by any methods designed by combining various synthetic ways known in the prior arts, and such combination can be easily performed by a person having ordinary skill in this art. The processes (a) to (m) will be more specifically explained in below.

In processes (a) to (e) for preparing the compound according to the present invention, any inert solvents which does not adversely affect to the reaction, preferably one or more selected from a group consisting of dimethylformamide, dimethylacetamide, ethanol, water, methylene chloride, chloroform, tetrahydrofuran and N-methylpyrrolidinone can be used. As the base, one or more selected from a group consisting of sodium hydride, potassium hydroxide, potassium carbonate, potassium t-butoxide, sodium amide, sodium bis(trimethylsilyl)amide and potassium bis(trimethylsilyl)amide, more preferably sodium hydride or potassium hydroxide can be mentioned. As the coupling agent used in the process for reacting the compound of formula (8) with the compound of formula (9), a mixture of 1-hydroxybenzotrizole and one or more substances selected from a group consisting of carbodiimides such as dicyclohexylcarbodiimide(DCC), 1-ethyl-3-(3-dimethylaminopropyl)carbodiimide(EDC), 1,1'-dicarbonyldiimidazole(CDI), etc., and inorganic dehydrating agent such as silicone tetrachloride can be mentioned. Among them, a mixture of 1-ethyl-3-(3-dimethylaminopropyl)carbodiimide(EDC) and 1-hydroxybenzotrizole hydrate is particularly preferred.

The sulfurizing agent used in preparing the compound of formula (1f) from the compound of formula (1e) includes 2,4-bis(phenylthio)-1,3-dithia-2,4-diphosphatane-2,4-disulfide, Lawesson's Reagent and $P_4S_{10}$. 2,4-bis(phenylthio)-1,3-dithia-2,4-diphosphatane-2,4-disulfide can be used most preferably The compound of formula (1 g) which is used as a starting material in process (f) can be prepared by deprotecting the corresponding compound which is protected by benzyloxycarbonyl group at position-1 of piperidine moiety. The deprotection reaction may be carried out by applying the conventional reaction conditions, preferably by using Pd(OH)$_2$/C or Pd/C in an alcohol solvent under hydrogen atmosphere. The compound of formula (1 g) thus obtained is coupled with the compound of formula (10) in an inert solvent as mentioned above optionally in the presence of a tertiary amine base to produce the compound of formula (1h). Alternatively, the compound of formula (1 g) can be reacted in the presence of a coupling agent as mentioned for process (d) with the carboxylic acid derivative(T=OH) to produce the compound of formula (1h) in the form of amide.

In the cyclization reactions of (g) and (h) for preparing the compounds (1i) and (1j), any inert solvents, preferably one or more selected from tetrahydrofuran and ethanol can be used. As the sulfurizing agent used in the conversion procedure of amide to thioamide group in process (h), 2,4-bis(phenylthio)-1,3-dithia-2,4-diphosphatane-2,4-disulfide, Lawesson's Reagent or P$_4$S$_{10}$, preferably Lawesson's Reagent can be mentioned.

In processes (i) and (j) for preparing the compounds (1j) and (1k) by reacting the compound of formula (13) with the compound of formula (14a) or (14b), one or more solvents selected from ethanol and isopropyl alcohol can be used. Also, ordinary inorganic base, such as for example, one or more selected from a group consisting of lithium hydroxide, sodium hydroxide and potassium hydroxide, preferably lithium hydroxide can be used in the process (k) wherein the compound of formula (1l) is hydrolyzed and then reacted with the compound of formula (15) to produce the compound of formula (1m). As the coupling agent, those mentioned for process (d) can be used.

In processes (l) and (m), any inert solvents, preferably one or more selected from dimethylformamide and dimethylacetamide are used as the solvent, and one or more selected from a group consisting of sodium hydride, sodium amide, sodium bis(trimethylsilyl)amide and potassium bis(trimethylsilyl)amide are used as the base. The deprotection reaction in process (m) may be carried out under the conventional reaction conditions for deprotection, preferably in the presence of Pd/C or Pd(OH)$_2$/C under hydrogen atmosphere. Further, the coupling agent used for the coupling of the compound of formula (1o) with the compound of formula (19) may be the same with those mentioned for process (d).

The compound of formula (3) used as the key intermediate in processes (a) to (c) for preparing the compound of formula (1) according to the present invention is itself a novel compound. Therefore, it is another object of the present invention to provide the compound of formula (3). As depicted in the following Reaction Schemes 14 to 16, the compound of formula (3) can be prepared by a process characterized in that a compound represented by the following formula (20) is reacted in a solvent in the presence of a coupling agent with a compound represented by the following formula (21); the compound of formula (20) is reacted in a solvent in the presence of dimethylformamide(DMF) with thionyl chloride to produce a compound represented by the following formula (20a) and then the compound of formula (20a) thus obtained is reacted in a solvent with the compound of formula (21); or a compound represented by the following formula (3a) is oxidized in a solvent to produce a compound represented by the following formula (3b).

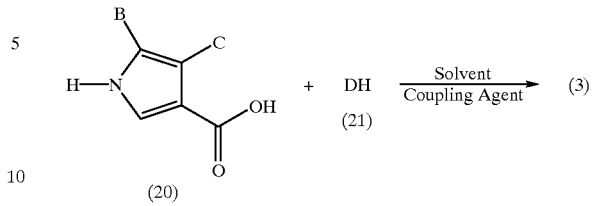

Reaction Scheme 14

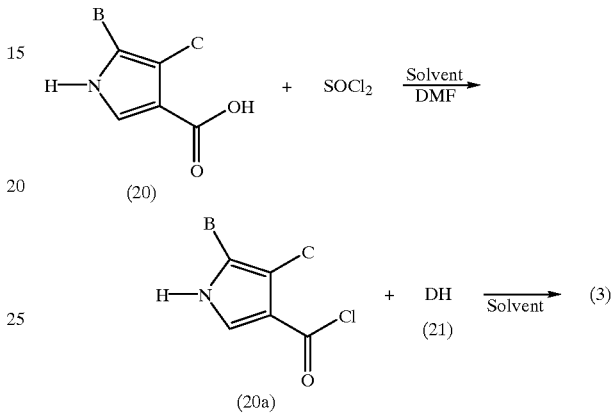

Reaction Scheme 15

Reaction Scheme 16

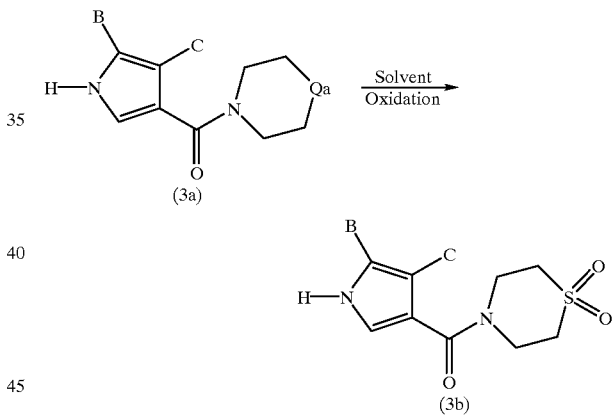

in the above Reaction Shemes 14, 15 and 16

B, C and D are defined as previously described,

Q$_a$ represents S or S=O.

In the above processes according to Reaction Scheme 14 to 16 for preparing the compound (3), any inert solvents, preferably one or more selected from dimethylformamide, dimethylacetamide, methylene chloride, tetrahydrofuran and 1,2-dichloroethane are used as the solvent. As the coupling agent in Reaction Scheme 14, a mixture of 1-hydroxybenzotrizole and one or more substances selected from a group consisting of carbodiimides such as dicyclohexylcarbodiimide(DCC), 1-ethyl-3-(3-dimethylaminopropyl)carbodiimide(EDC), etc. can be mentioned. Among them, a mixture of 1-ethyl-3-(3-dimethylaminopropyl) carbodiimide(EDC) and 1-hydroxybenzotrizole hydrate is particularly preferred. The dimethylformamide in the process of Reaction Scheme 15 is used in a catalytic amount. Also, excess metachloroperbenzoic acid is preferably used as the oxidant in the process according to the Reaction Scheme 16. However, the coupling agent, oxidant, solvent, catalyst, etc. may be appropriately selected beyond those as mentioned above as far as the purpose of the reaction can be accomplished. And the reaction conditions including the amount of reactants, reaction temperature, reaction time, etc. can easily be determined by a person skilled in this art depending on the specific reactants.

Since the compound of formula (8) which is used as an intermediate for preparing the compound of formula (1d) in process (d) is also a novel compound like the compound of formula (3), it is another object of the present invention to provide the intermediate compound of formula (8). It can be obtained by hydrolyzing the compound of formula (7).

On the other hand, the starting materials used in the above processes can be prepared according to the specific processes described in the following Reaction Schemes 17 to 29.

First, the compound of formula (2) can be obtained through protection and halogenation as depicted in the following Reaction Scheme 17.

Reaction Scheme 17

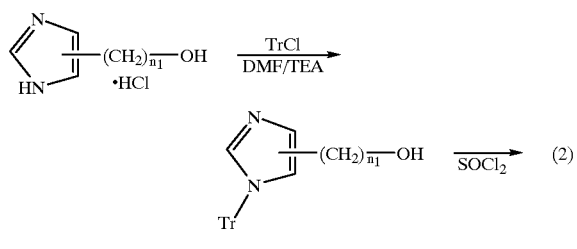

The compound of formula (4) wherein A is 4-cyanobenzyl may be synthesized through protection, acetylation, coupling, deprotection and halogenation as depicted in the following Reaction Scheme 18. More frequently, the compound (4) is prepared by a process wherein an amine compound is reacted with dihydroxyacetone to produce a mercaptoimidazole derivative, which is then desulfurized and halogenated as depicted in the following Reaction Scheme 19. *J. Med. Chem.*, 33, 1312–1329, 1990 in which a similar reaction is explained in detail can be referred to for the specific reaction conditions.

Reaction Scheme 18

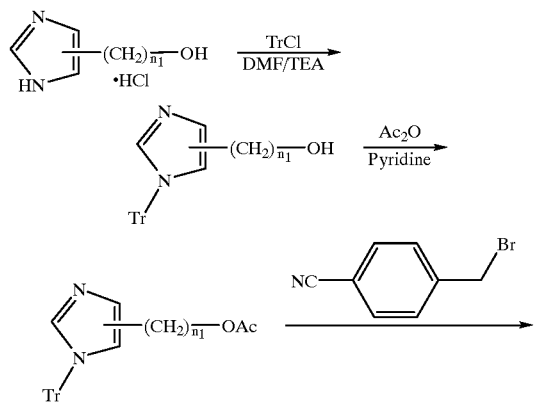

Reaction Scheme 19

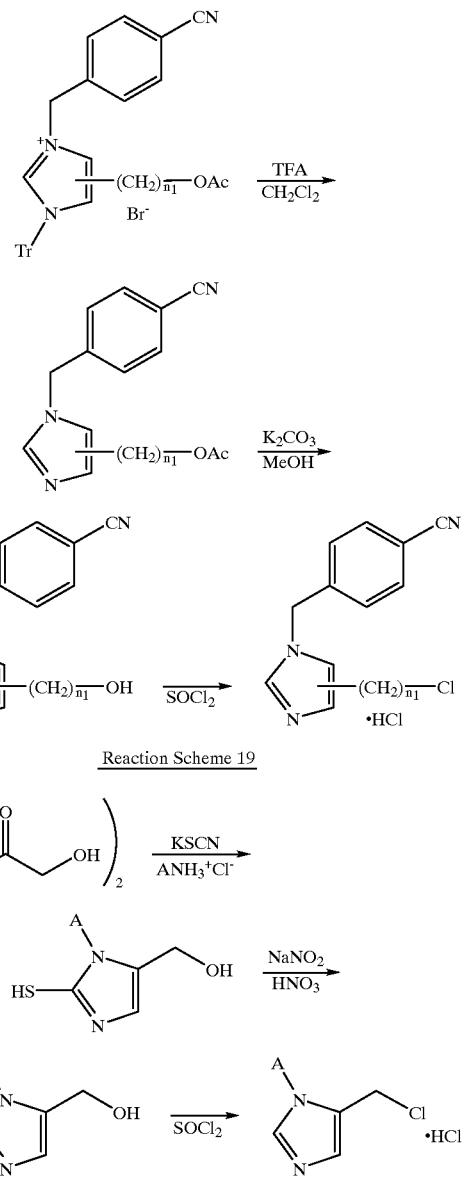

The amine compound used in the above Reaction Scheme 19 wherein A represents 1-(benzyloxycarbonyl)piperidine-4-ylmethyl may be synthesized from 4-aminomethylpiperidine through protection, benzyloxycarbonylation and deprotection as depicted in Reaction Scheme 20.

Reaction Scheme 20

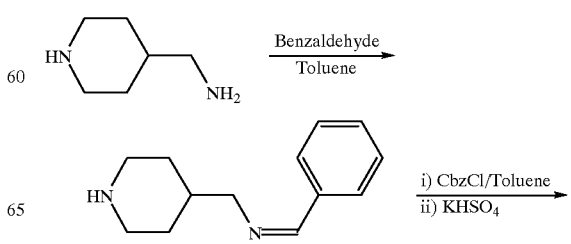

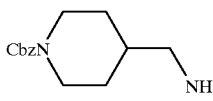

in the above Reaction Scheme 20

CbzCl represents benzylchloroformate and has the same meaning through the present specification.

The compound of formula (5) may be synthesized through esterification, protection, reduction and halogenation as depicted in the following Reaction Scheme 21.

Reaction Scheme 21

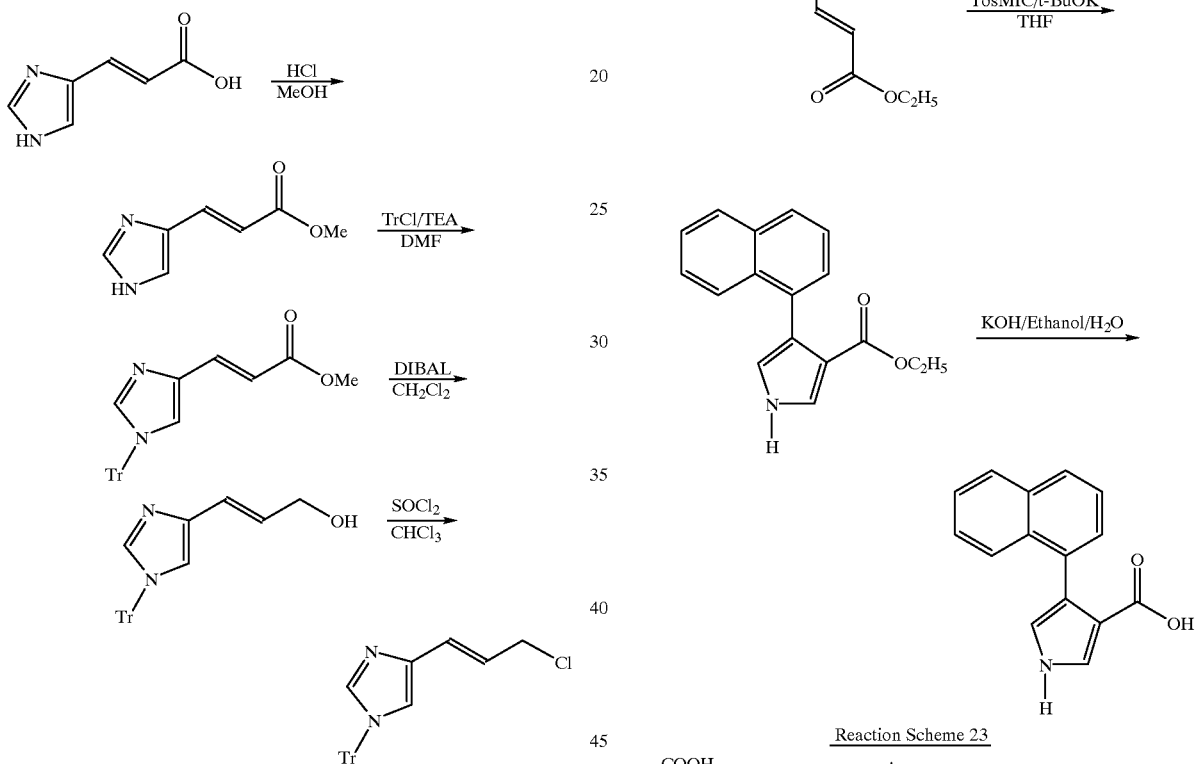

in the above Reaction Scheme 21

DIBAL represents diisobutylaluminumhydride.

Also, in the above Reaction Scheme 21, the alcohol compound obtained before preparing the final chloride compound may be reduced according to the conventional manner and then reacted with thionyl chloride to produce the compound of formula (2) wherein $n_1$ is 3.

The compound of formula (20) used as a starting material in preparing the intermediate of formula (3) may be prepared, for example, according to a process described in the following Reaction Scheme 22, a process starting from 1-naphthaldehyde. Particularly, the intermediate of formula (3) wherein D is 1-naphthyl can be conveniently synthesized according to the following reactions of Schemes 23 and 24.

Reaction Scheme 22

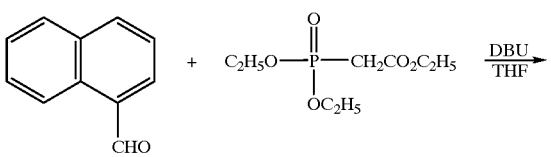

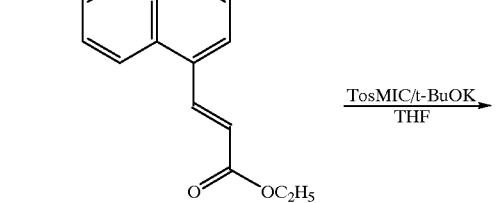

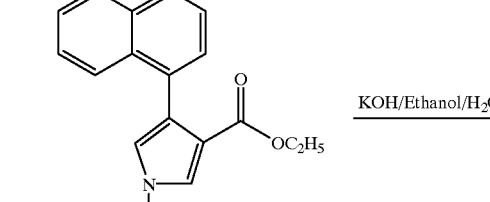

Reaction Scheme 23

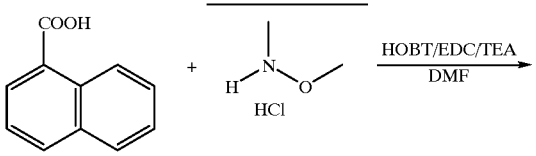

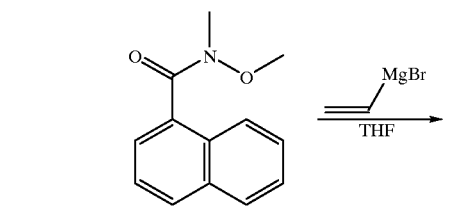

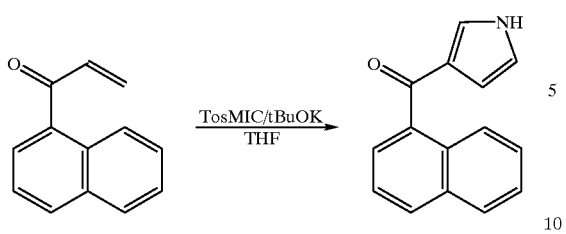

Reaction Scheme 24

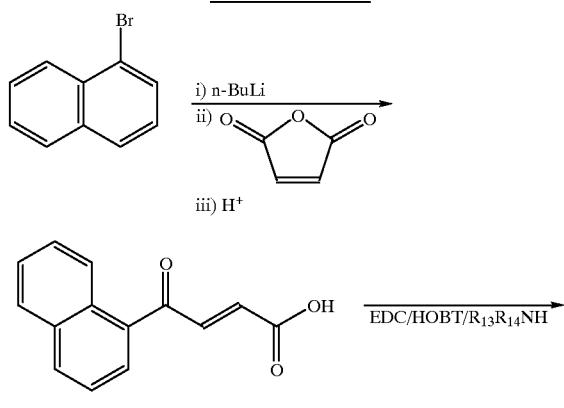

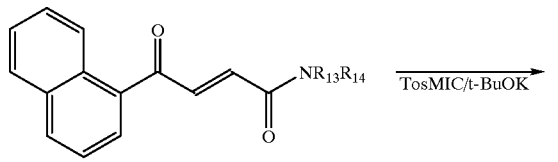

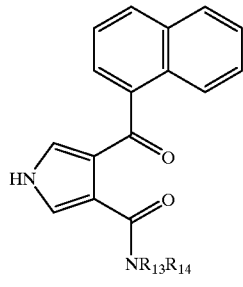

The compound of formula (11) used as a starting material in process (g) can be prepared by coupling a hydrochloride salt of glycinate derivative with a hydrochloride salt of 4-imidazoleacetic acid, as represented in the following Reaction Scheme 25. As the coupling agent, those mentioned in process (d) can be used. While, the compound of formula (13) used in process (i) may be prepared according to the procedure described in the following Reaction Scheme 26 in which the chloride derivative obtained in the process of Reaction Scheme 19 is used as a starting material.

Reaction Scheme 25

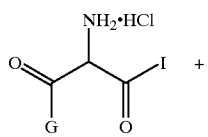

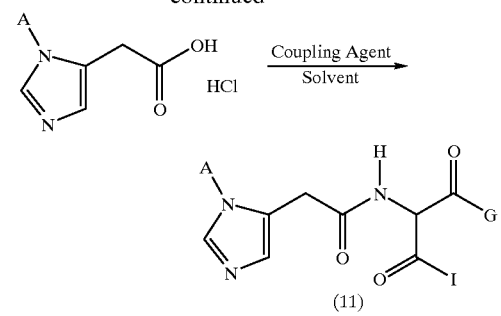

Reaction Scheme 26

The compounds (14a) and (14b) used in processes (i) and (j) can be prepared according to the following Reaction Schemes 27 and 28, respectively. First, the compound of formula 14a can be synthesized by reacting an aldehyde derivative with methyl dichloroacetate in the presence of potassium t-butoxide. The compound of formula (14b) wherein I is I' can be synthesized by reacting a ketone derivative with a dialkylcarbonate in the presence of sodium hydride, then by reacting the product thus obtained with sulfuryl chloride.

Reaction Scheme 27

Reaction Scheme 28

Finally, the reactant of formula (17) in processes (l) and (m) wherein G represents 1-naphthyl and L represents N-methyl-N-(2-methoxyethyl)amino may be prepared from 1-naphthaldehyde according to the following Reaction Scheme 29. The other compounds (17) having different substituents may also be prepared by referring to Reaction Scheme 29.

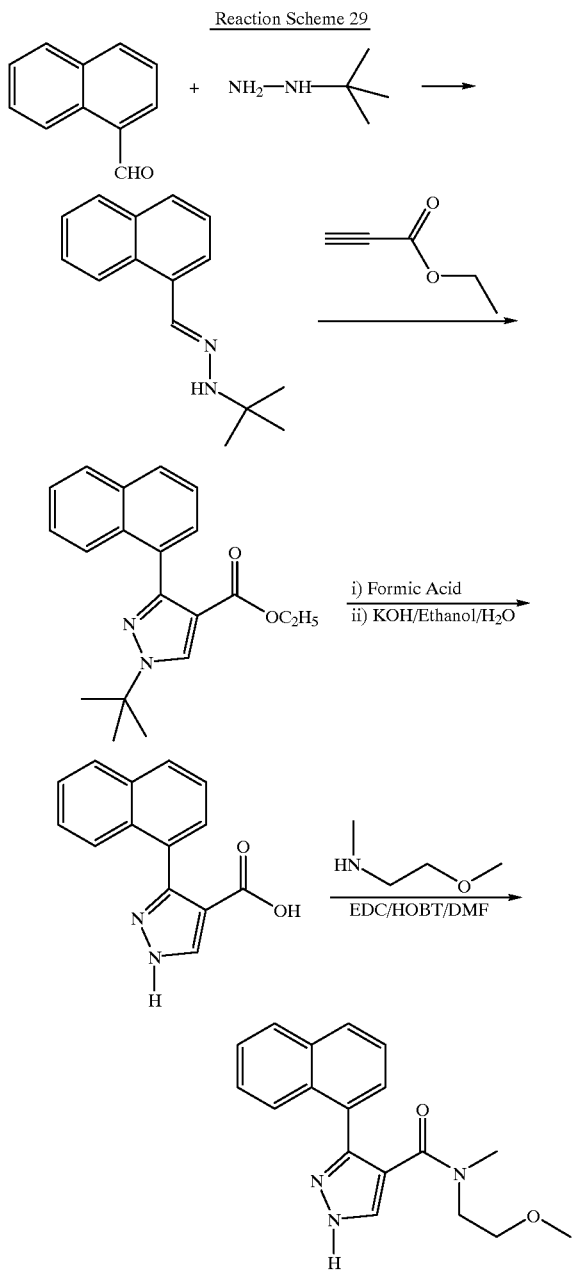

The compound of formula (1) prepared according to the processes above shows an inhibitory activity against farnesyl transferase, and thus can be effectively used as an anti-cancer agent. Therefore, the present invention also provides a pharmaceutical composition comprising the novel compound of formula (1), as defined above, or a pharmaceutically acceptable salt or an isomer thereof as an active ingredient together with a pharmaceutically acceptable carrier. Particularly, the compound of formula (1) can be used very effectively for treating cancer, restenosis, atherosclerosis and infections from hepatitis delta and related viruses.

When the active compound according to the present invention is used for clinical purpose, it is preferably administered in an amount ranging from 10 mg to 100 mg per kg of body weight a day. The total daily dosage may be administered in one time or over several times. However, the specific administration dosage for the patient can be varied with the specific compound used, body weight of the subject patient, sex, hygienic condition, diet, time or method of administration, excretion rate, mixing ratio of the agent, severity of the disease to be treated, etc.

The compound of the present invention may be administered in the form of injections or oral preparations. Injections, for example, sterilized aqueous or oily suspension for injection, can be prepared according to the known procedure using suitable dispersing agent, wetting agent, or suspending agent. Solvents which can be used for preparing injections include water, Ringer's fluid and NaCl solution, and also sterilized fixing oil may be conveniently used as the solvent or suspending media. Any non-stimulative fixing oil including mono-, di-glyceride may be used for this purpose. Fatty acid such as oleic acid may also be used for injections.

As the solid preparation for oral administration, capsules, tablets, pills, powders and granules, etc., preferably capsules and tablets can be mentioned. It is also desirable for tablets and pills to be formulated into enteric-coated preparation. The solid preparations may be prepared by mixing the active compound of formula (1) according to the present invention with at least one carrier selected from a group consisting of inactive diluents such as sucrose, lactose, starch, etc., lubricants such as magnesium stearate, disintegrating agent and binding agent.

The present invention will be more specifically explained in the following examples. However, it should be understood that the following examples are intended to illustrate the present invention but not in any manner to limit the scope of the present invention. Processes for preparing the starting substances used for obtaining the compound of formula (1) will be also explained in detail in the following Preparations.

Preparation 1

Synthesis of 1-(3,4-methylenedioxybenzyl)-5-chloromethyl-1H-imidazole hydrochloride 1-1) 1-(3,4-Methylenedioxybenzyl)-5-hydroxymethyl-1H-imidazole A modified method from J. Med Chem., 33, 1312–1329. 1990 was carried out using dihydroxyacetone dimer and piperonylamine as starting materials. 1.37 g(10 mmol) of piperonylamine, 1.08 g(5.5 mmol) of dihydroxyacetone dimer and 1.15 g(11 mmol) of potassium thiocyanide were introduced to 10 ml of isopropyl alcohol, and then 2 ml of acetic acid was added thereto and the mixture was reacted at room temperature for 48 hours. The reaction mixture was filtered and the residual solid thus obtained was washed with 5 ml of isopropyl alcohol(×2) and with 5 ml of water(×2). The filtered solid was introduced into 12.5 ml of 10% aqueous nitric acid solution and the resulting solution was cooled down to 0° C. After 10 mg of sodium nitrite was added portionwise to the reaction solution, the mixture was reacted at room temperature for 1 hour. The aqueous solution was washed with 10 ml of ethyl acetate, basified, and then recrystallized to obtain 1.16 g (Yield 50%) of the title compound.

¹H NMR(CDCl₃) δ4.45(s, 2H), 5.13(s, 2H), 5.97(s, 2H), 6.70(m, 2H), 6.78 (d, 1H), 6.95(s, 1H), 7.45(s, 1H)

FAB 233 (M+H), $C_{12}H_{12}N_2O_3$

1-2) 1-(3,4-Methylenedioxybenzyl)-5-chloromethyl-1H-imidazole hydrochloride 233 mg(1 mmol) of the compound prepared in Preparation 1-1) was dissolved in 3 ml of chloroform and then 355 mg(3 mmol) of thionyl chloride was slowly added dropwise thereto at 0° C. After stirring for 2 hours, the solvent was removed by distillation under reduced pressure and the remained hydrochloride was eliminated to obtain the title compound in a yield of 95%. The product thus obtained was directly used in the next reaction without purification.

Preparation 2

Synthesis of 1-(naphthalen-1-ylmethyl)-5-chloromethyl-1H-imidazole hydrochloride

2-1) 1-(Naphthalen-1-ylmethyl)-5-hydroxymethyl-1H-imidazole

The title compound was obtained in a yield of 65% according to the same procedure as Preparation 1-1) except that dihydroxyacetone dimer and (naphthalen-1-ylmethyl)amine were used as starting materials.

¹H NMR(CDCl₃) δ4.44(s, 2H), 5.42(s, 2H), 6.78(d, 1H), 6.85(s, 1H), 7.25(m, 1H), 7.35(s, 1H), 7.43(m, 2H), 7.65(d, 1H), 7.68(d, 1H), 8.02(d, 1H)

FAB 239 (M+H), $C_{15}H_{14}N_2O$

2-2) 1-(Naphthalen-1-ylmethyl)-5-chloromethyl-1H-imidazole hydrochloride

The title compound was obtained in a yield of 90% according to the same procedure as Preparation 1-2) using the compound prepared in Preparation 2-1). The product thus obtained was directly used in the next reaction without purification.

Preparation 3

Synthesis of 1-((R)-α-methylbenzyl)-5chloromethyl-1H-imidazole hydrochloride

3-1) 1-((R)-α-methylbenzyl)-5-hydroxymethyl-1H-imidazole

The title compound was obtained in a yield of 60% according to the same procedure as Preparation 1-1) except that dihydroxyacetone dimer and (R)-(+)-α-methylbenzylamine were used as starting materials.

¹H NMR(CDCl₃) δ1.73 (d, 3H), 4.28 (s, 1H), 4.43(d, 1H), 5.60(m, 1H), 6.75(s, 1H), 7.04(d, 2H), 7.23(m, 3H), 7.42(s, 1H)

FAB 203 (M+H), $C_{12}H_{14}N_2O$

3-2) 1-((R)-α-methylbenzyl)-5-chloromethyl-1H-imidazole hydrochloride

The title compound was obtained in a yield of 90% according to the same procedure as Preparation 1-2) using the compound prepared in Preparation 3-1). The product thus obtained was directly used in the next reaction without purification.

Preparation 4

Synthesis of 1-((S)-α-methylbenzyl)-5chloromethyl-1H-imidazole hydrochloride

4-1) 1-((S)-α-methylbenzyl)-5-hydroxymethyl-1H-imidazole

The title compound was obtained in a yield of 55% according to the same procedure as Preparation 1-1) except that dihydroxyacetone dimer and (S)-(+)-α-methylbenzylamine were used as starting materials.

¹H NMR(CDCl₃) δ1.73(d, 3H), 4.28(s, 1H), 4.43(d, 1H), 5.60(m, 1H), 6.75(s, 1H), 7.04(d, 2H), 7.23(m, 3H), 7.42(s, 1H)

FAB 203 (M+H), $C_{12}H_{14}N_2O$

4-2) 1-((S)-α-methylbenzyl)-5-chloromethyl-1H-imidazole hydrochloride

The title compound was obtained in a yield of 94% according to the same procedure as Preparation 1-2) using the compound prepared in Preparation 4-1). The product thus obtained was directly used in the next reaction without purification.

Preparation 5

Synthesis of 1-phenethyl-5-chloromethyl-1H-imidazole hydrochloride

5-1) 1-Phenethyl-5-hydroxymethyl-1H-imidazole

The title compound was obtained in a yield of 70% according to the same procedure as Preparation 1-1) except that dihydroxyacetone dimer and phenethylamine were used as starting materials.

¹H NMR(CDCl₃) δ3.08(t, 2H), 4.27(t, 2H), 4.47(s, 2H), 6.89(s, 1H), 7.05(d, 2H), 7.26(m, 3H), 7.44(s, 1H)

FAB 203 (M+H), $C_{12}H_{14}N_2O$

5-2) 1-Phenethyl-5-chloromethyl-1H-imidazole hydrochloride

The title compound was obtained in a yield of 90% according to the same procedure as Preparation 1-2) using the compound prepared in Preparation 5-1). The product thus obtained was directly used in the next reaction without purification.

Preparation 6

Synthesis of 3-[N-(2-methoxyethyl)-N-methyl]carbamoyl-4-(naphthalen-1-yl)-1H-pyrrole

6-1) 3-(Naphthalen-1-yl)-acrylic acid ethylester 22.4 g(0.10 mol) of triethylphosphonoacetate was dissolved in 500 ml of acetonitrile and 30.4 g(0.2 mol) of 1,8-diazabicyclo[5.4.0]undec-7-ene(1,5-5)(DBU) was slowly added thereto. To this solution was slowly added 15.6 g(0.10 mol) of 1-naphthaldehyde dissolved in 20 ml of tetrahydrofuran and the mixture was stirred for 8 hours. The organic solvent was removed by distillation under reduced pressure. The resulting residue was dissolved in ethyl acetate, washed twice with water, dried over magnesium sulfate, concentrated and then subjected to silica gel column chromatography (eluent: n-hexane/ethyl acetate=95/5, v/v) to obtain 20.3 g(0.090 mol, Yield 90%) of the title compound.

¹H NMR(CDCl₃) δ1.33(t, 3H), 4.10(q, 2H), 6.75(q, 1H), 7.50(m, 3H), 7.73(d, 1H), 7.85(m, 2H), 8.10(d, 1H), 8.21(d, 1H)

FAB 227 (M+H)

6-2) 3-(Ethoxycarbonyl)-4-(naphthalen-1-yl)-1H-pyrrole 4.3 g(18.9 mmol) of 3-(naphthalen-1-yl)-acrylic acid ethylester prepared in Preparation 6-1) and 3.68 g(18.9 mmol) of tosylmethylisocyanide were dissolved in 100 ml of tetrahydrofuran. 2.55 g(22.7 mmol) of potassium t-butoxide dissolved in 100 ml of tetrahydrofuran was slowly added thereto and the mixture was refluxed for 30 minutes. 100 ml of water was added to the reaction solution to stop the reaction and the solvent was removed under reduced pressure. The reaction solution was extracted with diethylether, washed with aqueous sodium chloride solution and then dried over magnesium sulfate. The solvent was removed under reduced pressure and the resulting residue was subjected to silica gel column chromatography(eluent: ethyl acetate/n-hexane=1/3, v/v) to obtain 3.85 g(14.5 mmol, Yield 77%) of the title compound.

$^1$H NMR(CDCl$_3$) δ1.27(t, 3H), 4.07(q, 2H), 6.76(s, 1H), 7.28–7.47(m, 5H), 7.59(s, 1H), 7.82(m, 2H), 9.99(s, 1H)

FAB 266 (M+H)

6-3) 3-Hydroxycarbonyl-4-(naphthalen-1-yl)-1H-pyrrole 2.64 g(10 mmol) of the compound prepared in Preparation 6-2) was dissolved in 50 ml of 50% ethanol and 2.24 g(40 mmol) of potassium hydroxide was added thereto. The reaction mixture was refluxed for 7 hours, cooled down to room temperature, adjusted to pH 4–5, extracted with ethyl acetate, dried over sodium sulfate. The solvent was removed under reduced pressure to obtain 1.90 g(8.1 mmol, Yield 81%) of the title comound. The product thus obtained was directly used in the next reaction without purification.

$^1$H NMR(CDCl$_3$) δ6.60(s, 1H), 7.32–7.49(m, 5H), 7.54(s, 1H), 7.84(m, 2H), 9.92(s, 1H)

FAB 238 (M+H)

6-4) 3-[N-(2-Methoxyethyl)-N-methyl]carbamoyl-4-(naphthalen-1-yl)-1H-pyrrole 234 mg(1 mmol) of the compound prepared in Preparation 6-3) was dissolved in 2 ml of dimethylformamide, and then 230 mg(1.2 mmol) of EDC, 101 mg(1 mmol) of triethylamine and 162 mg(1.2 mmol) of HOBT were added thereto. The resulting mixture was stirred at 0° C. for 5 minutes. To the reaction solution was added 124 mg(1 mmol) of N-(2-methoxyethyl)-N-methylamine hydrochloride, which was then stirred at room temperature for 5 hours. The solvent was removed under reduced pressure and then 10 ml of saturated potassium carbonate solution was added to the residue. The resulting solution was extracted with 20 ml of ethyl acetate, washed with 10 ml of 1N aqueous hydrochloric acid solution, washed with aqueous sodium chloride solution and water, dried over sodium sulfate and concentrated to give 246 mg(0.79 mmol, Yield 79%) of the title compound.

$^1$H NMR(CDCl$_3$) δ2.46(s, 2H), 2.80–3.40(m, 8H), 3.40(s, 1H), 6.80(s, 1H), 7.00(s, 1H), 7.42(m, 4H), 7.73(d, 1H), 7.81(d, 1H), 8.17(d, 1H), 10.66 (s, 1H)

FAB 309 (M+H)

Preparation 7

Synthesis of 3-(morpholin-4-yl)carbonyl-4-(naphthalen-1-yl)-1H-pyrrole 234 mg(1 mmol) of the compound prepared in Preparation 6-3) was dissolved in 2 ml of dimethylformamide, and then 230 mg(1.2 mmol) of EDC and 162 mg(1.2 mmol) of HOBT were added thereto. The resulting mixture was stirred at 0° C. for 5 minutes. To the reaction solution was added 87 mg(1 mmol) of morpholine, which was then stirred at room temperature for 5 hours. The solvent was removed under reduced pressure and then 10 ml of saturated potassium carbonate solution was added to the residue. The resulting solution was extracted with ethyl acetate, washed with 10 ml of 1N aqueous hydrochloric acid solution, washed with aqueous sodium chloride solution and water, dried over sodium sulfate and concentrated to give 243 mg(0.8 mmol, Yield 80%) of the title compound.

$^1$H NMR(CDCl$_3$) δ2.13–3.52(br, 8H), 6.54(s, 1H), 7.31–7.51(m, 5H), 7.53 (s, 1H), 7.81(m, 2H), 9.93(s, 1H)

FAB 307 (M+H)

Preparation 8

Synthesis of 3-(4-methylpiperazin-1-yl)carbonyl-4-(naphthalen-1-yl)-1H-pyrrole The title compound was obtained in a yield of 75% according to the same procedure as Preparation 6-4) except that the compound prepared in Preparation 6-3) and 4-methylpiperazine were used.

$^1$H NMR(CDCl$_3$) δ1.15(br, 2H), 1.87(br, 2H), 1.92(s, 3H), 2.96(br, 2H), 3.41(br, 2H), 6.83(s, 1H), 7.09(s, 1H), 7.36–7.42(m, 4H). 7.73(d, 1H), 7.75 (d, 1H), 8.10(d, 1H), 10.52(s, 1H)

FAB (M+H): 320

Preparation 9

Synthesis of 3-{N-[2(N,N-dimethylamino)ethyl]-N-methyl}carbamoyl-4-(naphthalen-1-yl)-1H-pyrrole The title compound was obtained in a yield of 82% according to the same procedure as Preparation 6-4) except that the compound prepared in Preparation 6-3) and N,N,N'-trimethyl-ethylenediamine were used.

$^1$H NMR(CDCl$_3$) δ1 .89(br, 3H), 2.18(br, 4H), 2.44(br, 2H), 2.75(s, 1H), 2.98(br, 1H), 3.36(br, 2H), 6.84(s, 1H), 7.07(s, 1H), 7.38–7.43(m, 4H), 7.74 (d, 1H), 7.83(d, 1H), 8.13(b, 1H), 10.14(br, 1H)

FAB (M+H): 322

Preparation 10

Synthesis of 4-(naphthalen-1-yl)-3-(thiomorpholin-4-yl) carbonyl-1H-pyrrole 234 mg(1 mmol) of the compound prepared in Preparation 6-3) was dissolved in 2 ml of dimethylformamide, and then 230 mg(1.2 mmol) of EDC and 162 mg(1.2 mmol) of HOBT were added thereto. The resulting mixture was stirred at 0° C. for 5 minutes. To the reaction solution was added 87 mg(1 mmol) of thiomorpholine, which was then stirred at room temperature for 5 hours. The solvent was removed under reduced pressure and then 10 ml of saturated potassium carbonate solution was added to the residue. The resulting solution was extracted with ethyl acetate, washed with 10 ml of 1N aqueous hydrochloric acid solution, washed with saturated sodium chloride solution and water, dried over sodium sulfate and concentrated to give 258 mg(0.8 mmol, Yield 80%) of the title compound.

$^1$H NMR(CDCl$_3$) δ1.35 (br, 2H), 2.14 (br, 2H), 3.21(br, 2H), 3.41(br, 2H), 6.91 (s, 1H), 7.21 (s, 1H), 7.31–7.51 (m, 4H), 7.80 (d, 1H), 7.87 (d, 1H), 8.11(d, 1H), 10.69(s, 1H)

FAB 323 (M+H)

Preparation 11

Synthesis of 3-(1,1-dioxothiomorpholin-4-yl)carbonyl-4-(naphthalen-1-yl)-1H-pyrrole 323 mg(1 mmol) of the compound prepared in Preparation 10 was dissolved in 5 ml of dichloromethane, 430 mg(1.5 mmol) of 60% 3-chloroperbenzoic acid(MCPBA)

was added thereto, and then the mixture was stirred at room temperature for 1 hour. 3 ml of 10% sodium thiosulfite was added to the mixture in order to remove the excess 3-chloroperbenzoic acid and the resulting mixture was stirred at room temperature for 30 minutes. After adding 10 ml of saturated potassium carbonate solution thereto, the mixture was extracted with dichloromethane, washed with saturated sodium chloride solution and water, dried over sodium sulfate and concentrated to give 264 mg(0.75 mmol, Yield 75%) of the title compound.

$^1$H NMR(CDCl$_3$) δ1.50–2.30(br, 4H), 3.65 (br, 4H), 6.92 (s, 1H), 7.20 (s, 1H), 7.32–7.54 (m, 4H), 7.81 (d, 1H), 7.88 (d, 1H), 8.12(d, 1H), 10.69(s, 1H)

FAB 355 (M+H)

Preparation 12

Synthesis of 3-[N-(2-methylthioethyl)-N-methyl] carbamoyl-4-(naphthalen-1-yl)-1H-pyrrole 234 mg(1 mmol) of the compound prepared in Preparation 6-3) was dissolved in 2 ml of dimethylformamide, and then 230 mg(1.2 mmol) of EDC, 101 mg(1 mmol) of triethylamine and 162 mg(1.2 mmol) of HOBT were added thereto. The resulting mixture was stirred at 0° C. for 5 minutes. To the reaction solution was added 140 mg(1 mmol) of N-(2-methylthioethyl)-N-methylamine hydrochloride, which was then stirred at room temperature for 5 hours. The solvent was removed under reduced pressure and then 10 ml of saturated potassium carbonate solution was added to the residue. The resulting solution was extracted with 20 ml of ethyl acetate, washed with 10 ml of 1N aqueous hydrochloric acid solution, washed with saturated sodium chloride solution and water, dried over sodium sulfate and concentrated to give 243 mg(0.75 mmol, Yield 75%) of the title compound.

$^1$H NMR(CDCl$_3$) δ1.98 (s, 3H), 2.13 (br, 2H), 2.46 (br, 2H), 2.65 (br, 1H), 2.95 (br, 1H), 3.29 (br, 1H), 6.81 (s, 1H), 7.02 (s, 1H), 7.43 (m, 4H), 7.72 (d, 1H), 7.82 (d, 1H), 8.18 (d, 1H), 10.65 (s, 1H)

FAB 325 (M+H)

Preparation 13

Synthesis of 3-hydroxycarbonyl-5-methyl-4-(naphthalen-1-yl)-1H-pyrrole 13-1) 3-ethoxycarbonyl-5-methyl-4-(naphthalen-1-yl)-1H-pyrrole 4.3 g(18.9 mmol) of 3-(naphthalen-1-yl)-acrylic acid ethylester prepared in Preparation 6-1) and 3.95 g(18.9 mmol) of α-methyltosylmethylisocyanide disclosed in A. M. van Leusen, et al., *Tetrahedron Letter*, 1975, 40, 3487 were dissoved in 100 ml of tetrahydrofuran. 2.55 g(22.7 mmol) of potassium t-butoxide dissolved in 100 ml of tetrahydrofuran was slowly added thereto, which was then refluxed for 30 minutes. To the reaction solution was added 100 ml of water to stop the reaction and the solvent was removed under reduced pressure. The residue was extracted with diethylether, washed with saturated sodium chloride solution and dried over magnesium sulfate. The solvent was removed under reduced pressure and the residue was subjected to silica gel column chromatography using a solvent mixture of ethyl acetate/n-hexane(1/3, v/v) as an eluent to give 3.50 g(12.5 mmol, Yield 66%) of the title compound.

FAB 280 (M+H)

13-2) 3-Hydroxycarbonyl-5-methyl-4-naphthalen-1-yl)-1H-pyrrole 2.80 g(10 mmol) of the compound prepared in Preparation 13-1) was dissolved in 50 ml of 50% ethanol, 2.24 g(40 mmol) of potassium hydroxide was added thereto, and the mixture was refluxed for 7 hours. The reaction solution was cooled down to room temperature, adjusted to pH 4–5, extracted with ethyl acetate and dried over sodium sulfate. The solvent was eliminated under reduced pressure to obtain 2.02 g(8.1 mmol, Yield 81%) of the title compound.

FAB 252 (M+H)

Preparation 14

Synthesis of 5-methyl-3-(morpholin-4-yl)carbonyl-4-(naphthalen-1-yl)-1H-pyrrole 248 mg(1 mmol) of the compound prepared in Preparation 13-2) was dissolved in 2 ml of dimethylformamide, and then 230 mg(1.2 mmol) of EDC and 162 mg(1.2 mmol) of HOBT were added thereto. The resulting mixture was stirred at 0° C. for 5 minutes. To the reaction solution was added 87 mg(1 mmol) of morpholine, which was then stirred at room temperature for 5 hours. The solvent was removed under reduced pressure and then 10 ml of saturated potassium carbonate solution was added to the residue. The resulting solution was extracted with ethyl acetate, washed with 10 ml of 1N aqueous hydrochloric acid solution, washed with saturated sodium chloride solution and water, dried over sodium sulfate and concentrated to give 224 mg(0.7 mmol, Yield 70%) of the title compound.

$^1$H NMR(CDCl$_3$) δ2.12 (s, 3H), 2.80–3.40 (br, 8H), 7.01 (s, 1H), 7.30–7.50 (m, 4H), 7.75–7.95 (m, 3H), 10.60 (br, 1H)

FAB 321 (M+H)

EXAMPLE 1

Synthesis of 3-[N-(2-methoxyethyl)-N-methyl] carbamoyl-1-[1-(3,4-methylenedioxybenzyl)-1H-imidazol-5-ylmethyl]-4-(naphthalen-1-yl)-1H-pyrrole(1)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 1 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 78 mg(Yield 75%) of the title compound.

$^1$H NMR(CDCl$_3$) δ2.40(m, 2H), 2.72(m, 1H), 2.91(s, 3H), 3.09(m, 2H), 3.32(br, 1H), 4.09(br, 1H), 4.89(s, 2H), 4.95(s, 2H), 5.89(s, 2H), 6.45(s, 1H), 6.62(d, 1H), 6.63(s, 1H), 6.70(d, 1H), 7.0(s, 1H), 7.16(s, 1H), 7.31(t, 1H), 7.41(m, 3H), 7.66(s, 1H), 7.73(d, 1H), 7.81(d, 1H), 8.03(d, 1H)

FAB (M+H) 523, $C_{31}H_{30}N_4O_2$

EXAMPLE 2

Synthesis of 1-[1-(3,4-methylenedioxybenzyl)-1H-imidazol-5-ylmethyl]-3-(morpholin-4-yl)carbonyl-4-(naphthalen-1-yl)-1H-pyrrole(2)

62 mg(0.2 mmol) of the compound prepared in Preparation 7 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 1 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 70 mg(Yield 67%) of the title compound.

$^1$H NMR(CDCl$_3$) δ2.36(br, 2H), 3.06(br, 4H), 3.33(br, 2H), 5.23(s, 2H), 5.33(s, 2H), 5.96(s, 2H), 6.65(s, 1H), 6.70–6.85(m, 3H), 7.18–7.50(m, 7H), 7.79(d, 1H), 7.81(d, 1H), 7.94(d, 1H)

FAB (M+H) 521, $C_{31}H_{28}N_4O_4$

EXAMPLE 3

Synthesis of 1-[1-(3,4-methylenedioxybenzyl)-1H-imidazol-5-ylmethyl]-3-(4methylpiperazin-1-yl) carbonyl-4(naphthalen-1-yl)-1H-pyrrole(3)

64 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 1 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=90/10, v/v) to obtain 73 mg(Yield 67%) of the title compound.

$^1$H NMR(CDCl$_3$) δ2.18(s, 3H), 2.30–2.60(br, 4H), 3.10–3.30(br, 4H), 4.98 (s, 2H), 5.05(s, 2H), 5.95(s, 2H), 6.44(s, 1H), 6.53(d, 1H), 6.70(d, 1H), 6.73(d, 1H), 7.14(d, 1H), 7.20–7.40(m, 3H), 7.50(m, 3H), 7.81(d, 1H), 7.83(d, 1H), 7.88(d, 1H)

FAB (M+H) 534, $C_{32}H_{31}N_5O_3$

EXAMPLE 4

Synthesis of 3-{N-[2-(N,N-dimethylamino)ethyl]-N-methyl}carbamoyl-1-[1-(3,4-methylendioxybenzyl)-1H-imidazol-5ylmethyl]-4-(naphthalen-1-yl)-1H-pyrrole(4)

64 mg(0.2 mmol) of the compound prepared in Preparation 9 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 1 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=90/10, v/v) to obtain 78 mg(Yield 71%) of the title compound.

$^1$H NMR(CDCl$_3$) δ1.87(m, 1H), 2.01(m, 2H), 2.14(br, 6H), 2.36(br, 2H), 2.50–3.00(br, 1H), 3.29(br, 2H), 4.87(s, 2H), 4.95(s, 2H), 5.89(s, 2H), 6.45 (s, 1H), 6.50(d, 1H), 6.63(d, 1H), 6.72(d, 1H), 7.00(s, 1H), 7.18(s, 1H), 7.31(br, 1H), 7.35–7.47(m. 3H), 7.54(s, 1H), 7.73(d, 1H), 7.81(d, 1H), 8.01(br, 1H)

FAB (M+H) 536, $C_{32}H_{33}N_5O_3$

EXAMPLE 5

Synthesis of 3-[N-(2-methoxyethyl)-N-methyl] carbamoyl-4-naphthalen-1-yl)-1-[1-naphthalen-1-ylmethyl)-1H-imidazol-5-ylmethyl]-1H-pyrrole(5)

62 mg(0.2 mmol) of the compound prepared Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 58 mg(2.2 mmol) of the compound prepared in Preparation 2 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 79 mg(Yield 75%) of the title compound.

$^1$H NMR(CDCl$_3$) δ2.37(br, 2H), 2.72(br, 1H), 2.99(br, 3H), 3.00(br, 2H), 3.31(br, 1H), 3.71(br, 1H), 5.06(s, 2H), 5.48(s, 2H), 6.62(d, 1H), 6.91(d, 1H0, 7.03(d, 1H), 7.27(d, 2H), 7.28–7.55(m, 6H), 7.58(s, 1H), 7.69(d, 1H), 7.75(d, 1H), 7.81(d, 2H), 7.87(d, 1H), 8.00(d, 1H)

FAB (M+H) 529, $C_{34}H_{32}N_4O_2$

EXAMPLE 6

Synthesis of 3-(morpholin-4-yl)carbonyl-4-(naphthalen-1-yl)-1-[1-naphthalen-1-ylmethyl)-1H-imidazol-5-ylmethyl]-1H-pyrrole(6)

62 mg(0.2 mmol) of the compound prepared in Preparation 7 was dissolved in 2 ml of dimethylformamide, 26.4 mg(0.66 mmol) of sodium hydride(60%) was added thereto at 0° C. and then the mixture was stirred for 5 minutes. To the mixture was added 58 mg(2.2 mmol) of the compound prepared in Preparation 2 and the whole mixture was stirred at room temperature for 3 hours. The solvent was removed by distillation under reduced pressure and 3ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 76 mg(Yield 72%) of the title compound.

$^1$H NMR(CDCl$_3$) δ2.38(br, 2H), 3.06(br, 4H), 3.30(br, 2H), 4.99(s, 2H), 5.42(s, 2H), 6.58(d, 1H), 6.80(d, 1H), 7.00(s, 1H), 7.17(d, 1H), 7.25(s, 1H), 7.26–7.54(m, 6H), 7.69(d, 1H), 7.71–7.81(m, 3H), 7.85(d, 1H), 7.91(d, 1H)

FAB (M+H) 527, $C_{34}H_{30}N_4O_2$

EXAMPLE 7

Synthesis of 3-(4-methylpiperazin-1-yl)carbonyl-4-(naphthalen-1-yl)-1-[1-(naphthalen-1-ylmethyl)-1H-imidazol-5-ylmethyl]-1H-pyrrole(7)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 58 mg(2.2 mmol) of the compound prepared in Preparation 2 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=90/10, v/v) to obtain 75 mg(Yield 69%) of the title compound.

$^1$H NMR(CDCl$_3$) δ1.07(br, 2H), 1.77(d, 2H), 1.85(s, 3H), 2.84(br, 2H), 3.27(br, 2H), 4.99(s, 2H), 5.42(s, 2H), 6.58(d, 1H), 6.80(d, 1H), 7.01(d, 1H), 7.16(d, 1H), 7.25(s, 1H), 7.31–7.60(m, 6H), 7.68(d, 1H), 7.69–7.83(m, 3H), 7.85(d, 1H), 7.94(d, 1H)

FAB (M+H) 540, C$_{35}$H$_{33}$N$_5$O

EXAMPLE 8

Synthesis of 3-[N-(2-methoxyethyl)-N-methyl] carbamoyl-1-[1-((R)-α-methylbenzyl)-1H-imidazol-5ylmethyl]-4-(naphthalen-1-yl)-1H--pyrrole(8)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 3 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 70 mg(Yield 71%) of the title compound.

$^1$H NMR(CDCl$_3$) δ1.78(d, 3H), 2.28(s, 1H), 2.40(br, 2H), 3.02(br, 3H), 3.09(br, 2H), 3.32(br, 2H), 4.71(d, 2H), 4.92(d, 2H), 5.12(q, 1H), 6.59(d, 1H), 7.00(m, 3H), 7.18(s, 1H), 7.20–7.39(m, 4H), 7.40–7.62(m, 3H), 7.74(m, 2H), 7.82(d, 1H), 8.04(d, 1H)

FAB (M+H) 493, C$_{31}$H$_{32}$N$_4$O$_2$

EXAMPLE 9

Synthesis of 1-[1-((R)-α-methylbenzyl)-1H-imidazol-5-ylmethyl]-3-(morpholin-4yl)carbonyl-4-(naphthalen-1-yl)-1H-pyrrole(9)

62 mg(0.2 mmol) of the compound prepared in Preparation 7 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 3 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 71 mg(Yield 72%) of the title compound.

$^1$H NMR(CDCl$_3$) δ1.81(d, 3H), 2.28(br, 2H), 3.06(br, 4H), 3.29(br, 2H), 4.65(d, 1H), 4.96(d, 1H), 5.14(q, 1H), 6.62(d, 1H), 7.01(d, 2H), 7.04(s, 1H), 7.20(s, 1H), 7.23–7.36 (m, 5H), 7.39–7.50(m, 3H), 7.76(s, 1H), 7.78(d, 1H), 7.84(d, 1H), 8.00(d, 1H)

FAB (M+H) 491, C$_{31}$H$_{30}$N$_4$O$_2$

EXAMPLE 10

Synthesis of 1-[1-((R)-α-methylbenzyl)-1H-imidazol-5-ylmethyl]-3-(4-methylpiperazin-1-yl) carbonyl-4-(naphthalen-1-yl)-1H-pyrrole(10)

64 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 3 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=90/10, v/v) to obtain 73 mg(Yield 73%) of the title compound.

$^1$H NMR(CDCl$_3$) δ1.09(br, 2H), 1.77(d, 3H), 1.83(s, 3H), 1.70–1.90(br, 2H), 2.90(br, 2H), 3.31(br, 2H), 4.73(d, 1H), 4.92(d, 1H), 5.14(q, 1H), 6.60(d, 1H), 7.01(m, 3H), 7.17(s, 1H), 7.20–7.35(m, 4H), 7.45(m, 3H), 7.73(m, 2H), 7.80(d, 1H), 8.00(d, 1H)

FAB (M+H) 504, C$_{32}$H$_{33}$N$_5$O

EXAMPLE 11

Synthesis of 3-[N-(2-methoxyethyl)-N-methyl] carbamoyl-1-[1-((S)-α-methylbenzyl)-1H-imidazol-5ylmethyl]-4(naphthalen-1-yl)-1H-pyrrole(11)

62 mg(0.2 mmol) of the compound prepared in Preparation 6 was dissolved in 2 ml of dimethylformamide, 26.4 mg(0.66 mmol) of sodium hydride(60%) was added thereto at 0 ° C. and then the mixture was stirred for 5 minutes. To the mixture was added 50 mg(2.2 mmol) of the compound prepared in Preparation 4 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 75 mg(Yield 75%) of the title compound.

$^1$H NMR(CDCl$_3$) δ1.78(d, 3H), 2.28(s, 1H), 2.40(br, 2H), 3.02(br, 3H), 3.09(br, 2H), 3.32(br, 2H), 4.72(d, 2H), 4.93(d, 2H), 5.12(q, 1H), 6.59(d, 1H), 7.00(m, 3H), 7.18(s, 1H), 7.20–7.39(m, 4H), 7.40–7.62(m, 3H), 7.74(m, 2H), 7.82(d, 1H), 8.04(d, 1H)

FAB (M+H) 493, C$_{31}$H$_{32}$N$_4$O$_2$

EXAMPLE 12

Synthesis of 1-[1-((S)-α-methylbenzyl)-1H-imidazol-5-ylmethyl]-3-(morpholin-4-yl)carbonyl-4-(naphthalen-1-yl)-1H-pyrrole(12)

62 mg(0.2 mmol) of the compound prepared in Preparation 7 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 4 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 73 mg(Yield 73%) of the title compound.

$^1$H NMR(CDCl$_3$) δ1.81(d, 3H), 2.28(br, 2H), 3.06(br, 4H), 3.29(br, 2H), 4.64(d, 1H), 4.95(d, 1H), 5.14(q, 1H), 6.62(d, 1H), 7.01(d, 2H), 7.04(s, 1H), 7.20(s, 1H), 7.23–7.36 (m, 5H), 7.39–7.50(m, 3H), 7.76(s, 1H), 7.78(d, 1H), 7.84(d, 1H), 8.00(d, 1H)

FAB (M+H) 491, $C_{31}H_{30}N_4O_2$

EXAMPLE 13

Synthesis of 1-[1-((S)-α-methylbenzyl)-1H-imidazol-5-ylmethyl]-3-(4-methylpiperazin-1-yl)carbonyl-4-(naphthalen-1-yl)-1H-pyrrole(13)

64 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 4 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=90/10, v/v) to obtain 75 mg(Yield 75%) of the title compound.

$^1$H NMR(CDCl$_3$) δ1.09(br, 2H), 1.77(d, 3H), 1.83(s, 3H), 1.70–1.90(br, 2H), 2.90(br, 2H), 3.31(br, 2H), 4.74(d, 1H), 4.93(d, 1H), 5.14(q, 1H), 6.60(d, 1H), 7.01(m, 3H), 7.17(s, 1H), 7.20–7.35(m, 4H), 7.45(m, 3H), 7.73(m, 2H), 7.80(d, 1H), 8.00(d, 1H)

FAB (M+H) 504, $C_{32}H_{33}N_5O$

EXAMPLE 14

Synthesis of 3-[N-(2-methoxyethyl)-N-methyl]carbamoyl-4-(naphthalen-1-yl)-1-[1-(phenethyl)-1H-imidazol-5-ylmethyl]-1H-pyrrole (14)

62 mg (0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 5 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 77 mg(Yield 78%) of the title compound.

$^1$H NMR(CDCl$_3$) δ2.38(br, 2H), 2.70(m, 1H0, 2.80(t, 2H), 2.90(m, 3H), 3.00(br, 2H), 3.31(br, 1H), 3.41(br, 1H), 4.03(t, 2H), 4.77(s, 2H), 6.66(d, 1H), 6.97(d, 1H), 7.06(d, 1H), 7.22(m, 3H), 7.30–7.60(m, 5H), 7.75(d, 1H), 7.80(d, 1H), 8.04(d, 1H)

FAB (M+H) 493, $C_{31}H_{32}N_4O_2$

EXAMPLE 15

Synthesis of 3-(morpholin-4-yl)carbonyl-4-(naphthalen-1-yl)-1-[1-(phenethyl)-1H-imidazol-5-ylmethyl]-1H-pyrrole(15)

62 mg(0.2 mmol) of the compound prepared in Preparation 7 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 5 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 79 mg(Yield 80%) of the title compound.

$^1$H NMR(CDCl$_3$) δ2.28(br, 2H), 2.81(t, 2H0, 2.83(br, 4H), 3.21(br, 2H), 4.07(t, 2H), 4.78(s, 2H), 6.68(d, 1H), 6.99(d, 1H), 7.10(d, 2H), 7.10(d, 2H), 7.23(m, 3H), 7.30(d, 1H), 7.50(m, 3H), 7.67(s, 1H), 7.77(d, 1H), 7.82(d, 1H), 8.00(d, 1H)

FAB (M+H) 491, $C_{31}H_{30}N_4O_2$

EXAMPLE 16

Synthesis of 3-(4-methylpiperazin-1-yl)carbonyl-4-(naphthalen-1-yl)-1-[1-(phenethyl)-1H-imidazol-5-ylmethyl)-1H-pyrrole (16)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 50 mg(2.2 mmol) of the compound prepared in Preparation 5 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=90/10, v/v) to obtain 75 mg(Yield 75%) of the title compound.

$^1$H NMR(CDCl$_3$) δ1.06(br, 2H), 1.90–2.00(br, 2H), 2.05 (s, 3H), 2.80(t, 2H), 3.37(br, 4H), 4.04(t, 2H), 4.77(s, 2H), 6.69(d, 1H), 6.99(m, 2H), 7.09 (d, 2H), 7.20–7.56(m, 8H), 7.78(d, 1H), 7.83(d, 1H), 8.00(d, 1H)

FAB (M+H) 504, $C_{32}H_{33}N_5O$

Preparation 15

Synthesis of 1-(2-methoxy)phenethyl-5-chloromethyl-1H-imidazole hydrochloride 15-1) 1-(2-Methoxy)phenethyl-5-hydroxymethyl-1H-imidazole The title compound was obtained in a yield of 65% according to the same procedure as Preparation 1-1) except that dihydroxyacetone dimer and 2-methoxyphenethylamine were used as starting materials.

$^1$H NMR(CDCl$_3$) δ3.03(t, 2H), 3.75(s, 3H), 4.16(t, 2H), 4.47(s, 2H), 4.75(s, 1H), 6.74(s, 1H), 6.75–7.00(m, 3H), 7.13–7.30(m, 1H)

FAB 233 (M+H), $C_{13}H_{16}N_2O_2$(M)

15-2) 1-(2-Methoxy)phenethyl-5-chloromethyl-1H-imidazole hydrochloride

The title compound was obtained in a yield of 89% according to the same procedure as Preparation 1-2) using the compound prepared in Preparation 15-1). The product thus obtained was directly used in the next reaction without purification.

Preparation 16

Synthesis of 1-(4-methoxy)phenethyl-5chloromethyl-1H-imidazole hydrochloride 16-1) 1-(4-Methoxy)phenethyl-5-hydroxymethyl-1H-imidazole The title compound was obtained in a yield of 60% according to the same procedure as Preparation 1-1) except that dihydroxyacetone dimer and 4-methoxyphenethylamine were used as starting materials.

$^1$H NMR(CDCl$_3$) δ2.91(t, 2H), 3.68(s, 3H), 4.09(t, 2H), 4.36(s, 2H), 6.70(d, 2H), 6.77(s, 1H), 6.87(d, 2H), 7.13 (s, 1H)

FAB 233 (M+H), C$_{13}$H$_{16}$N$_2$O$_2$(M)

16-2) 1-(4-Methoxy)phenethyl-5-chloromethyl-1H-imidazole hydrochloride

The title compound was obtained in a yield of 89% according to the same procedure as Preparation 1-2) using the compound prepared in Preparation 16-1). The product thus obtained was directly used in the next reaction without purification.

Preparation 17

Synthesis of 1-(2-fluoro)phenethyl-5-chloromethyl-1H-imidazole hydrochloride 17-1) 1-(2-Fluoro)phenethyl-5-hydroxymethyl-1H-imidazole The title compound was obtained in a yield of 68% according to the same procedure as Preparation 1-1) except that dihydroxyacetone dimer and 2-fluorophenethylamine were used as starting materials.

$^1$H NMR(CDCl$_3$) δ3.12(t, 2H), 3.50(br, 1H), 4.23 (t, 2H), 4.52(s, 2H), 6.82(s, 1H), 7.02(m, 3H), 7.20(m, 2H)

FAB 221 (M+H), C$_{12}$H$_{13}$N$_2$OF(M)

17-2) 1-(2-Fluoro)phenethyl-5-chloromethyl-1H-imidazole hydrochloride

The title compound was obtained in a yield of 89% according to the same procedure as Preparation 1-2) using the compound prepared in Preparation 17-1). The product thus obtained was directly used in the next reaction without purification.

Preparation 18

Synthesis of 1-(2-chloro)phenethyl-5chloromethyl-1H-imidazole hydrochloride 18-1) 1-(2-Chloro)phenethyl-5-hydroxymethyl-1H-imidazole The title compound was obtained in a yield of 71% according to the same procedure as Preparation 1-1) except that dihydroxyacetone dimer and 2-chlorophenethylamine were used as starting materials.

$^1$H NMR(CDCl$_3$) δ3.13(t, 2H), 3.34(br, 1H), 4.18 (t, 2H), 4.42(s, 2H), 6.79(s, 1H), 6.94(d, 1H), 7.03–7.20(m, 3H), 7.29(d, 1H)

FAB 237 (M+H), C$_{12}$H$_{13}$N$_2$OCl(M)

18-2) 1-(2-Chloro)phenethyl-5-chloromethyl-1H-imidazole hydrochloride

The title compound was obtained in a yield of 89% according to the same procedure as Preparation 1-2) using the compound prepared in Preparation 18-1). The product thus obtained was directly used in the next reaction without purification.

Preparation 19

Synthesis of 1-(3-chloro)phenethyl-5chloromethyl-1H-imidazole hydrochloride 19-1) 1-(3-Chloro)phenethyl-5-hydroxymethyl-1H-imidazole The title compound was obtained in a yield of 72% according to the same procedure as Preparation 1-1) except that dihydroxyacetone dimer and 3-chlorophenethylamine were used as starting materials.

$^1$H NMR(CDCl$_3$) δ2.95(t, 2H), 3.90(br, 1H), 4.10 (t, 2H), 4.37(s, 2H), 6.74(s, 1H), 6.85(m, 1H), 6.98(s, 1H), 7.10(m, 3H)

FAB 237 (M+H), C$_{12}$H$_{13}$N$_2$OCl(M)

19-2) 1-(3-Chloro)phenethyl-5-chloromethyl-1H-imidazole hydrochloride

The title compound was obtained in a yield of 91% according to the same procedure as Preparation 1-2) using the compound prepared in Preparation 19-1). The product thus obtained was directly used in the next reaction without purification.

Preparation 20

Synthesis of 1-(3-phenyl)propyl-5-chloromethyl-1H-imidazole hydrochloride 20-1) 1-(3-Phenyl)propyl-5-hydroxymethyl-1H-imidazole The title compound was obtained in a yield of 73% according to the same procedure as Preparation 1-1) except that dihydroxyacetone dimer and 3-phenylpropylamine were used as starting materials.

$^1$H NMR(CDCl$_3$) δ2.11(m, 2H), 2.61(t, 2H), 3.98(t, 2H), 4.25(br, 1H), 4.53(s, 1H), 6.76(s, 1H), 7.10–7.60(m, 6H)

FAB 217 (M+H), C$_{13}$H$_{16}$N$_2$O (M)

20-2) 1-(3-Phenyl)propyl-5-chloromethyl-1H-imidazole hydrochloride

The title compound was obtained in a yield of 91% according to the same procedure as Preparation 1-2) using the compound prepared in Preparation 20-1). The product thus obtained was directly used in the next reaction without purification.

Preparation 21

Synthesis of 1-(naphthalen-2-yl)methyl-5-chloromethyl-1H-imidazole hydrochloride 21-1) 1-(Naphthalen-2-yl)methyl-5-hydroxymethyl-1H-imidazole The title compound was obtained in a yield of 58% according to the same procedure as Preparation 1-1) except that dihydroxyacetone dimer and (naphthalen-2-yl)methylamine were used as starting materials.

$^1$H NMR(CDCl$_3$) δ4.36(s, 2H), 5.28(s, 2H), 6.89(s, 1H), 7.17(d, 1H), 7.35(m, 2H), 7.41(s, 1H), 7.50(s, 1H), 7.65(m, 1H), 7.69(m, 2H)

FAB 239 (M+H), C$_{15}$H$_{14}$N$_2$O (M)

21-2) 1-(Naphthalen-2-yl)methyl-5chloromethyl-1H-imidazole hydrochloride

The title compound was obtained in a yield of 87% according to the same procedure as Preparation 1-2) using the compound prepared in Preparation 21-1). The product thus obtained was directly used in the next reaction without purification.

Preparation 22

Synthesis of 1-[2-naphthalen-1-yl)ethyl]-5-chloromethyl-1H-imidazole hydrochloride 22-1) 1-[2-(Naphthalen-1-yl)ethyl]-5-hydroxymethyl-1H-imidazole The title compound was obtained in a yield of 58% according to the same procedure as Preparation 1-1) except that dihydroxyacetone dimer and (naphthalen-1-yl) ethylamine were used as starting materials.

$^1$H NMR(CDCl$_3$) δ3.44(t, 2H), 4.23(t, 2H), 4.38(s, 2H), 6.79(s, 1H), 7.07(d, 1H), 7.17(s, 1H), 7.24(t, 1H), 7.32–7.48 (m, 2H), 7.62(d, 1H), 7.74(d, 1H), 7.92(d, 1H)

FAB 253 (M+H), C$_{16}$H$_{16}$N$_2$O (M)

22-2) 1-[2-(Naphthalen-1-yl)ethyl]-5-chloromethyl-1H-imidazole hydrochloride

The title compound was obtained in a yield of 87% according to the same procedure as Preparation 1-2) using the compound prepared in Preparation 22-1). The product thus obtained was directly used in the next reaction without purification.

Preparation 23

Synthesis of 1-(4-bromo)phenethyl-5-chloromethyl-1H-imidazole hydrochloride 23-1) 1-(4-Bromo)phenethyl-5-hydroxymethyl-1H-imidazole The title compound was obtained in a yield of 72% according to the same procedure as Preparation 1-1) except that dihydroxyacetone dimer and 4-bromophenethylamine were used as starting materials.

$^1$H NMR(CDCl$_3$) δ2.94(t, 2H), 3.76(br, 1H), 4.11 (t, 2H), 4.37(s, 2H), 6.74(s, 1H), 6.85(d, 2H), 6.84(d, 2H), 7.12(s, 1H), 7.29(d, 2H)

FAB 281 (M+H), C$_{12}$H$_{13}$N$_2$OBr(M)

23-2) 1-(4-Bromo)phenethyl-5-chloromethyl-1H-imidazole hydrochloride

The title compound was obtained in a yield of 91% according to the same procedure as Preparation 1-2) using the compound prepared in Preparation 23-1). The product thus obtained was directly used in the next reaction without purification.

Preparation 24

Synthesis of 1-(4fluoro)phenethyl-5-chloromethyl-1H-imidazole hydrochloride 24-1) 1-(4-Fluoro)phenethyl-5-hydroxymethyl-1H-imidazole The title compound was obtained in a yield of 72% according to the same procedure as Preparation 1-1) except that dihydroxyacetone dimer and 4-fluorophenethylamine were used as starting materials.

$^1$H NMR(CDCl$_3$) δ2.99(t, 2H), 3.76(br, 1H), 4.15(t, 2H), 4.45(s, 2H), 6.80–7.20(m, 5H), 7.26(s, 1H)

FAB 221 (M+H), C$_{12}$H$_{13}$N$_2$OF(M)

24-2) 1-(4-Fluoro)phenethyl-5-chloromethyl-1H-imidazole hydrochloride

The title compound was obtained in a yield of 91% according to the same procedure as Preparation 1-2) using the compound prepared in Preparation 24-1). The product thus obtained was directly used in the next reaction without purification.

Preparation 25

Synthesis of 1-(4-methyl)phenethyl-5-chloromethyl-1H-imidazole hydrochloride 25-1) 1-(4-Methyl)phenethyl-5-hydroxymethyl-1H-imidazole The title compound was obtained in a yield of 72% according to the same procedure as Preparation 1-1) except that dihydroxyacetone dimer and 4-methylphenethylamine were used as starting materials.

$^1$H NMR(CDCl$_3$) δ3.02(t, 2H), 2.99(t, 2H), 3.76(br, 1H), 4.19(t, 2H), 4.47(s, 2H), 6.83(s, 1H), 6.94(d, 2H), 7.06(d, 2H), 7.28(s, 1H)

FAB 217 (M+H), C$_{13}$H$_{16}$N$_2$O (M)

25-2) 1-(4-Methyl)phenethyl-5-chloromethyl-1H-imidazole hydrochloride

The title compound was obtained in a yield of 91% according to the same procedure as Preparation 1-2) using the compound prepared in Preparation 25-1). The product thus obtained was directly used in the next reaction without purification.

Preparation 26

Synthesis of 1-(4chloro)phenethyl-5-chloromethyl-1H-imidazole hydrochloride 26-1) 1-(4-Chloro)phenethyl-5-hydroxymethyl-1H-imidazole The title compound was obtained in a yield of 73% according to the same procedure as Preparation 1-1) except that dihydroxyacetone dimer and 4-chlorophenethylamine were used as starting materials.

$^1$H NMR(CDCl$_3$) δ3.04(t, 2H), 4.18(t, 2H), 4.48(s, 2H), 6.79(s, 1H), 6.96(d, 2H), 7.20–7.40(m, 3H)

FAB 237 (M+H), C$_{12}$H$_{13}$N$_2$OCl(M)

26-2) 1-(4-Chloro)phenethyl-5-chloromethyl-1H-imidazole hydrochloride

The title compound was obtained in a yield of 91% according to the same procedure as Preparation 1-2) using the compound prepared in Preparation 26-1). The product thus obtained was directly used in the next reaction without purification.

Preparation 27

Synthesis of 1-[2-(naphthalen-2-yl)ethyl]-5-chloromethyl-1H-imidazole hydrochloride 27-1) 1-[2-(Naphthalen-2-yl)ethyl]-5-hydroxymethyl-1H-imidazole The title compound was obtained in a yield of 58% according to the same procedure as Preparation 1-1) except that dihydroxyacetone dimer and 2-(naphthalen-2-yl) ethylamine were used as starting materials.

$^1$H NMR(CDCl$_3$) δ3.22(t, 2H), 4.28(t, 2H), 4.48(s, 2H), 6.84(s, 1H), 7.19(d, 1H), 7.24(d, 2H), 7.44(m, 2H), 7.52(s, 1H), 7.76(m, 3H)

FAB 253 (M+H), C$_{16}$H$_{16}$N$_2$O (M)

27-2) 1-[2-(Naphthalen-2-yl)ethyl]-5-chloromethyl-1H-imidazole hydrochloride

The title compound was obtained in a yield of 88% according to the same procedure as Preparation 1-2) using the compound prepared in Preparation 27-1). The product thus obtained was directly used in the next reaction without purification.

EXAMPLE 17

Synthesis of 3-[N-(2-methoxyethyl)-N-methyl] carbamoyl-1-[1-(2-methoxy)phenethyl-1H-imidazol-5-yl]methyl-4-(naphthalen-1-yl)-1H-pyrrole(17)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 63 mg(2.2 mmol) of the compound prepared in Preparation 15 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 78 mg(Yield 75%) of the title compound.

$^1$H NMR(CDCl$_3$) δ2.39(s, 2H), 2.71(br, 1H), 2.90(t, 2H), 2.95–3.15(m, 5H), 3.31(br, 1H), 3.52(br, 1H), 3.76(s, 3H), 4.06(t, 2H), 4.83(s, 2H), 6.68(s, 1H), 6.75–6.95(m, 3H), 7.23(s, 1H), 7.25(s, 1H), 7.21(t, 1H), 7.30–7.48(m, 4H), 7.50(s, 1H), 7.75(d, 1H), 7.81(d, 1H), 8.06(d, 1H)

FAB 523 (M+H), C$_{32}$H$_{34}$N$_4$O$_3$ (M)

EXAMPLE 18

Synthesis of 1-[1-(2-methoxy)phenethyl-1H-imidazol-5-yl]methyl-3-[4-methylpiperazin-1-yl]carbonyl-4-(naphthalen-1-yl)-1H-pyrrole(18)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 63 mg(2.2 mmol) of the compound prepared in Preparation 15 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 75 mg(Yield 70%) of the tide compound.

$^1$H NMR(CDCl$_3$) δ1.09(br, 2H), 1.70–2.10(br+s, 5H), 2.85(t, 2H), 2.99 (br, 2H), 3.40(br, 2H), 3.76(s, 3H), 4.04(t, 2H), 4.85(s, 2H), 6.69(d, 1H), 6.80–6.92(m, 3H), 7.04(s, 1H), 7.08(s, 1H), 7.25(t, 1H), 7.30(d, 1H), 7.35–7.50(m, 4H), 7.77(d, 1H), 7.80(d, 1H), 8.02(d, 1H)

FAB 534 (M+H), C$_{33}$H$_{34}$N$_5$O$_2$ (M)

EXAMPLE 19

Synthesis of 3-[N-(2-methoxyethyl)-N-methyl]carbamoyl-1-[1-(4-methoxy)phenethyl-1H-imidazol-5-yl]methyl-4-(naphthalen-1-yl)-1H-pyrrole(19)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 63 mg(2.2 mmol) of the compound prepared in Preparation 16 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 83 mg(Yield 80%) of the title compound.

$^1$H NMR(CDCl$_3$) δ2.38(br, 2H), 2.72(t, 2H), 2.85–3.15 (m, 7H), 3.31(br, 1H), 3.72(s, 3H), 3.97(t, 2H), 4.78(s, 2H), 6.69(d, 1H), 6,77 (d, 2H), 6.85(d, 2H), 7.03(s, 1H), 7.06(s, 1H), 7.24–7.50(m, 5H), 7.73(d, 1H), 7.82(d, 1H), 8.05(d, 1H)

FAB 523 (M+H), C$_{32}$H$_{34}$N$_4$O$_3$ (M)

EXAMPLE 20

Synthesis of 1-[1-(4-methoxy)phenethyl-1H-imidazol-5-yl]methyl-3-[4-methylpiperazin-1-yl]carbonyl-4-(naphthalen-1-yl)-1H-pyrrole(20)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 63 mg(2.2 mmol) of the compound prepared in Preparation 16 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 83 mg(Yield 78%) of the title compound.

$^1$H NMR(CDCl$_3$) δ1.05(br, 2H), 1.70–2.10(br+s, 4H), 2.24(br, 1H), 2.72(t, 2H), 2.89(br, 2H), 3.30(br, 1H), 3.73(s, 3H), 3.98(t, 2H), 4.79(s, 2H), 6.69(d, 1H), 6.76(d, 2H), 6.86(d, 2H), 7.08(m, 2H), 7.30–7.50(m, 5H), 7.74(d, 1H), 7.80(d, 1H), 8.00(d, 1H)

FAB 534 (M+H), C$_{33}$H$_{35}$N$_5$O$_2$ (M)

EXAMPLE 21

Synthesis of 1-[1-(2-fluoro)phenethyl-1H-imidazol-5-yl]methyl-3-[N-(2-methoxyethyl)-N-methyl]carbamoyl-4-(naphthalen-1-yl)-1H-pyrrole(21)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 61 mg(2.2 mmol) of the compound prepared in Preparation 17 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 78 mg(Yield 77%) of the title compound.

$^1$H NMR(CDCl$_3$) δ2.38(br, 2H), 2.70(br, 1H), 2.81(t, 2H), 2.90–3.38(m, 7H), 4.03(t, 2H), 4.91(s, 2H), 6.71(d, 2H0, 6.92(m, 1H), 6.95–7.12(m, 4H), 7.19(m, 1H), 7.30–7.65(m, 4H), 7.73(d, 1H), 7.80(d, 1H), 8.05(d, 1H)

FAB 511 (M+H), C$_{31}$H$_{31}$N$_4$O$_2$F (M)

EXAMPLE 22

Synthesis of 1-[1-(2-fluoro)phenethyl-1H-imidazol-5-yl]methyl-3-[4-methylpiperazin-1-yl]carbonyl-4-(naphthalen-1-yl)-1H-pyrrole(22)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 61 mg(2.2 mmol) of the compound prepared in Preparation 17 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 78 mg(Yield 75%) of the title compound.

$^1$H NMR(CDCl$_3$) δ1.04(br, 2H), 1.70–2.10(br+s, 5H), 2.81(m, 2H), 3.90 (br, 2H), 3.32 (br, 2H), 4.05(t, 2H), 4.93(s, 2H), 6.72(d, 1H), 6.90(t, 1H), 6.95–7.05(m, 2H), 7.10(d, 2H), 7.20(m, 1H), 7.25–7.50(m, 4H), 7.75(d, 1H), 7.82(d, 2H), 8.00(d, 1H)

FAB 522 (M+H), C$_{32}$H$_{32}$N$_5$OF (M)

EXAMPLE 23

Synthesis of 1-[1-(2-chloro)phenethyl-1H-imidazol-5-yl]methyl-3-[N-(2-methoxyethyl)-N-methyl] carbamoyl-4-(naphthalen-1-yl)-1H-pyrrole(23)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 64 mg(2.2 mmol) of the compound prepared in Preparation 18 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 75 mg(Yield 71%) of the title compound.

$^1$H NMR(CDCl$_3$) δ2.39(br, 2H), 2.71(br, 1H), 2.90–3.38 (m, 9H), 4.06(t, 2H), 4.87(s, 2H), 6.71(s, 1H), 6.87(m, 1H), 7.00–7.20(m, 4H), 7.30–7.60(m, 6H), 7.73(d, 1H), 7.89(d, 1H), 8.06(d, 1H)

FAB 527 (M+H), C$_{31}$H$_{31}$N$_4$O$_2$Cl (M)

EXAMPLE 24

Synthesis of 1-[1-(2-chloro)phenethyl-1H-imidazol-5-yl]methyl-3-[4-methylpiperazin-1-yl]carbonyl-4-naphthalen-1-yl)-1H-pyrrole(24)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 64 mg(2.2 mmol) of the compound prepared in Preparation 18 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 84 mg(Yield 78%) of the title compound.

$^1$H NMR(CDCl$_3$) δ1.04(br, 1H), 1.70–2.10(br+s, 5H), 2.35(br, 1H), 2.92 (t+br, 4H), 3.32(br, 2H), 4.08(t, 2H), 4.88(s, 2H), 6.71(s, 1H), 6.87(m, 1H), 7.09(m, 3H), 7.18(m, 1H), 7.30–7.55(m, 6H), 7.75(d, 1H), 7.81(d, 1H), 8.01(d, 1H)

FAB 538 (M+H), C$_{32}$H$_{32}$N$_5$OCl (M)

EXAMPLE 25

Synthesis of 1-[1-(3-chloro)phenethyl-1H-imidazol-5-yl]methyl-3-[N-(2-methoxyethyl)-N-methyl] carbamoyl-4-(naphthalen-1-yl)-1H-pyrrole(25)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 64 mg(2.2 mmol) of the compound prepared in Preparation 19 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 80 mg(Yield 76%) of the title compound.

$^1$H NMR(CDCl$_3$) δ2.37(br, 2H), 2.71(m, 3H), 2.90–3.20 (m, 6H), 3.30(br, 1H), 3.99(t, 2H), 4.86(s, 2H), 6.69(d, 1H), 6.81(d, 1H), 7.00(s, 1H), 7.05–7.20(m, 5H), 7.30–7.50(m, 4H), 7.74(d, 1H), 7.81(d, 1H), 8.04(d, 1H)

FAB 527 (M+H), C$_{31}$H$_{31}$N$_4$O$_2$Cl (M)

EXAMPLE 26

Synthesis of 1-[1-(3-chloro)phenethyl-1H-imidazol-5-yl]methyl-3-[4-methylpiperazin-1-yl]carbonyl-4-(naphthalen-1-yl)-1H-pyrrole(26)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 64 mg(2.2 mmol) of the compound prepared in Preparation 19 and the whole mixture was stirred at room temperature for 2 hours. The solvent was removed by distillation under reduced pressure and 3 ml, of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 85 mg(Yield 79%) of the title compound.

$^1$H NMR(CDCl$_3$) δ1.05(br, 2H), 1.70–2.10(br+s, 5H), 2.69(t, 2H) 2.90 (br, 2H), 3.32(br, 2H), 3.98(t, 2H), 4.87(s, 2H), 6.70(d, 1H), 6.79(d, 1H), 6.98(s, 1H), 7.05–7.21(m, 3H), 7.30–7.50(m, 6H), 7.74(d, 1H), 7.82(d, 1H), 7.99(d, 1H)

FAB 538 (M+H), C$_{32}$H$_{32}$N$_5$OCl (M)

EXAMPLE 27

Synthesis of 3-[N-(2-methoxyethyl)-N-methyl] carbamoyl-4-(naphthalen-1-yl)-1-[1-(3-phenyl) propyl-1H-imidazol-5-yl]methyl-1H-pyrrole(27)

62 mg(0.2 mmol) of the compound prepared in Preparation 6 was dissolved in 2 ml of dimethylformamide, 26.4 mg(0.66 mmol) of sodium hydride(60%/) was added thereto at 0° C. and then the mixture was stirred for 5 minutes. To the mixture was added 62 mg(2.2 mmol) of the compound prepared in Preparation 20 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 76 mg(Yield 75%) of the title compound.

$^1$H NMR(CDCl$_3$) δ1.91(m, 2H), 2.24(t, 2H), 2.56(m, 5H), 2.90–3.07(m, 4H), 3.18(br, 1H), 4.03(t, 2H), 5.12(s, 2H), 6.57(s, 1H), 6.90–7.20(m, 8H), 7.21–7.52(m, 3H), 7.66(d, 1H), 7.72(d, 1H), 7.89(d, 1H), 8.06(br, 1H)

FAB 507 (M+H), $C_{32}H_{34}N_4O_2$ (M)

EXAMPLE 28

Synthesis of 3-[4-methylpiperazin-1-yl]carbonyl-4-naphthalen-1-yl)-1-[1-(3-phenyl)propyl-1H-imidazol-5-yl]methyl-1H-pyrrole(28)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 62 mg(2.2 mmol) of the compound prepared in Preparation 20 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 77 mg(Yield 74%) of the title compound.

$^1$H NMR(CDCl$_3$) δ1.01(br, 2H), 2.80–2.01(s+br+m, 6H), 2.30(br, 1H), 2.55 (t, 2H), 2.86(br, 2H), 3.30(br, 2H), 3.79(t, 2H), 5.00(s, 2H), 6.58(s, 1H), 7.00–7.20(m, 8H), 7.36(m, 1H), 7.41(m, 2H), 7.50(s, 1H), 7.74(d, 1H), 7.80(d, 1H), 8.00(d, 1H)

FAB 518(M+H), $C_{33}H_{35}N_5O$ (M)

EXAMPLE 29

Synthesis of 3-[N-(2-methoxyethyl)-N-methyl]carbamoyl-4-(naphthalen-1-yl)-1-[1-(naphthalen-2-yl)methyl-1H-imidazol-5-yl]methyl-1H-pyrrole(29)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 65 mg(2.2 mmol) of the compound prepared in Preparation 21 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 85 mg(Yield 80%) of the title compound.

$^1$H NMR(CDCl$_3$) δ2.36(br, 2H), 2.72(br, 1H), 2.98(br, 3H), 3.02(br, 2H), 3.31(br, 1H), 3.73(br, 1H), 5.10(s, 2H), 5.47(s, 2H), 6.58(s, 1H), 7.03(s, 1H), 7.08(d, 1H), 7.15(d, 1H), 7.21(s, 1H), 7.34–7.53(m, 7H), 7.60(s, 1H), 7.70–7.83 (m, 4H), 7.97(d, 1H)

FAB 529 (M+H), $C_{34}H_{30}N_4O_2$ (M)

EXAMPLE 30

Synthesis of 3-[4-methylpiperazin-1-yl]carbonyl-4-(naphthalen-1-yl)-1-[1-naphthalen-2-yl)methyl-1H-imidazol-5-yl]methyl-1H-pyrrole(30)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 65 mg(2.2 mmol) of the compound prepared in Preparation 21 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 74 mg(Yield 69%) of the title compound.

$^1$H NMR(CDCl$_3$) δ0.98(br, 2H), 1.70–2.00(s+br, 5H), 2.81(br, 2H), 3.37 (br, 1H), 4.88(s, 2H), 5.10(s, 2H), 6.57(s, 1H), 7.02(s, 1H), 7.08(d, 1H), 7.16(d, 1H), 7.21(s, 1H), 7.34–7.52(m, 7H), 7.60(s, 1H), 7.70–7.83(m, 4H), 7.97(d, 1H)

FAB 540(M+H), $C_{35}H_{33}N_5O$ (M)

EXAMPLE 31

Synthesis of 3-[N-(2-methoxyethyl)N-methyl]carbamoyl-4-(naphthalen-1-yl)-1-{1-[2-(naphthalen-1-yl)ethyl]-1H-imidazol-5-yl}methyl-1H-pyrrole(31)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 68 mg(2.2 mmol) of the compound prepared in Preparation 22 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 77 mg(Yield 71%) of the title compound.

$^1$H NMR(CDCl$_3$) δ2.34(br, 2H), 2.68(br, 1H), 2.80–3.20 (m, 5H), 3.23(t, 2H), 3.29(br, 2H), 4.12(t, 2H), 4.45(s, 2H), 6.43(d, 1H), 6.84(d, 1H), 6.97 (m, 2H), 7.21–7.52(m, 10H), 7.72(d, 1H), 7.78–7.85(m, 2H), 8.01(d, 1H)

FAB 543 (M+H), $C_{35}H_{34}N_4O_2$ (M)

EXAMPLE 32

Synthesis of 3-[4-methylpiperazin-1-yl]carbonyl-4-(naphthalen-1-yl)-1-{1-[2-(naphthalen-1-yl)ethyl]-1H-imidazol-5-yl}methyl-1H-pyrrole(32)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 68 mg(2.2 mmol) of the compound prepared in Preparation 22 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 83 mg(Yield 75%) of the title compound.

$^1$H NMR(CDCl$_3$) δ1.01(br, 2H), 1.70–2.00(br+s, 5H), 2.89(br, 2H), 3.27 (t, 2H), 3.40(br, 2H), 4.16(t, 2H), 4.50(s, 2H), 6.45(d, 1H), 6.90(d, 1H), 6.97(d, 1H), 6.99(s, 1H), 7.25–7.55(m, 8H), 7.73–7.95(m, 5H), 8.00(d, 1H)

FAB 554(M+H), $C_{36}H_{35}N_5O$ (M)

EXAMPLE 33

Synthesis of 1-[1-(4-bromo)phenethyl-1H-imidazol-5-yl]methyl-3-[N-(2-methoxyethyl)-N-methyl] carbamoyl-4-(naphthalen-1-yl)-1H-pyrrole(33)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 74 mg(2.2 mmol) of the compound prepared in Preparation 23 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 88 mg(Yield 77%) of the title compound.

$^1$H NMR(CDCl$_3$) δ2.38(br, 3H), 2.67(t, 2H), 2.90–3.23 (m, 7H), 3.30(br, 1H), 3.97(t, 2H), 4.88(s, 1H), 6.69(d, 1H), 6.82(d, 2H), 7.08(d, 2H), 7.27–7.53(m, 7H), 7.73(d, 1H), 7.80(d, 1H), 8.02(d, 1H)

FAB 571 (M+H), $C_{31}H_{31}N_4O_2Br$ (M)

EXAMPLE 34

Synthesis of 1-[1-(4bromo)phenethyl-1H-imidazol-5-yl]methyl-3-[4-methylpiperazin-1-yl]carbonyl-4-(naphthalen-1-yl)-1H-pyrrole(34)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 74 mg(2.2 mmol) of the compound prepared in Preparation 23 and the whole mixture was stirred at room temperature for 2 hours. The solvent was removed by distillation under reduced pressure and 3 mg of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 82 mg(Yield 70%) of the title compound.

$^1$H NMR(CDCl$_3$) δ1.04(br, 2H), 1.80–2.00(br+s, 4H), 2.48(br, 1H), 2.66 (t, 2H), 2.90(br, 2H), 3.31(br, 1H), 2.96(t, 2H), 4.88(s, 2H), 6.70(s, 1H), 6.82(d, 2H), 7.10(d, 2H), 7.25–7.60(m, 7H), 7.75(d, 1H), 7.82(d, 1H), 8.01(d, 1H)

FAB 582(M+H), $C_{32}H_{32}N_5OBr$ (M)

EXAMPLE 35

Synthesis of 1-[1-(4fluoro)phenethyl-1H-imidazol-5-yl]methyl-3-[N-(2-methoxyethyl)-N-methyl] carbamoyl-4-(naphthalen-1-yl)-1H-pyrrole(35)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 60 mg(2.2 mmol) of the compound prepared in Preparation 24 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 77 mg(Yield 76%) of the title compound.

$^1$H NMR(CDCl$_3$) δ2.34(br, 3H), 2.70(t, 2H), 2.90–3.20 (br, 6H), 3.30(br, 1H), 3.96(t, 2H), 4.86(s, 1H), 6.68(d, 1H), 6.90(m, 4H), 7.05(s, 1H), 7.09(s, 1H), 7.25–7.52(m, 5H), 7.73(d, 1H), 8.05(d, 1H)

FAB 511 (M+H), $C_{31}H_{31}N_4O_2F$ (M)

EXAMPLE 36

Synthesis of 1-[1-(4-fluoro)phenethyl-1H-imidazol-5-yl]methyl-3-[4-methylpiperazin-1-yl]carbonyl-4-(naphthalen-1-yl)-1H-pyrrole(36)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 60 mg(2.2 mmol) of the compound prepared in Preparation 24 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 78 mg(Yield 75%) of the title compound.

$^1$H NMR(CDCl$_3$) δ1.05(br, 2H), 1.70–2.00(br+s, 4H), 2.25(br, 1H), 2.70 (t, 2H), 2.90(br, 2H), 3.30(br, 2H), 3.88(t, 2H), 4.87(s, 2H), 6.69(s, 1H), 6.90(m, 4H), 7.10(m, 2H), 7.29(m, 2H), 7.35–7.50(m, 3H), 7.74(d, 1H), 7.82(d, 1H), 8.00(d, 1H)

FAB 522(M+H), $C_{32}H_{32}N_5OF$ (M)

EXAMPLE 37

Synthesis of 3-[N-(2-methoxyethyl)-N-methyl] carbamoyl-1-[1-(4-methyl)phenethyl-1H-imidazol-5-yl]methyl-4-(naphthalen-1-yl)-1H-pyrrole(37)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 60 mg(2.2 mmol) of the compound prepared in Preparation 25 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 78 mg(Yield 80%) of the title compound.

$^1$H NMR(CDCl$_3$) δ2.02(br, 1H), 2.28(s, 3H), 2.38(br, 2H), 2.70(br, 1H), 2.75(t, 2H), 2.95–3.20(m, 5H), 3.31(br, 1H), 3.99(t, 2H), 4.77(s, 2H), 6.67(s, 1H), 6.85(d, 2H), 7.06(m, 4H), 7.25–7.50(m, 5H), 7.74(d, 1H), 7.81(d, 1H), 8.07(d, 1H)

FAB 507 (M+H), $C_{32}H_{34}N_4O_2$ (M)

EXAMPLE 38

Synthesis of 1-[1-(4-methyl)phenethyl-1H-imidazol-5-yl]methyl-3-[4-methylpiperazin-1-yl]carbonyl-4-(naphthalen-1-yl)-1H-pyrrole(38)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 60 mg(2.2 mmol) of the compound prepared in Preparation 25 and the whole mixture was stirred at room temperature for 3 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 81 mg(Yield 78%) of the title compound.

$^1$H NMR(CDCl$_3$) δ1.07(br, 1H), 1.70–2.10(br+s, 6H), 2.28(s, 3H), 2.75(t, 2H), 2.90(br, 2H), 3.33(br, 2H), 4.00(t, 2H), 4.78(s, 2H), 6.72(s, 1H), 6.86(m, 2H), 7.04–7.23(m, 4H), 7.25–7.60(m, 5H), 7.75(d, 1H), 7.82(d, 1H), 8.01(d, 1H)

FAB 518 (M+H), $C_{33}H_{35}N_5O$ (M)

EXAMPLE 39

Synthesis of 1-[1-(4-chloro)phenethyl-1H-imidazol-5-yl]methyl-3-[N-(2-methoxyethyl)-N-methyl] carbamoyl-4-(naphthalen-1-yl)-1H-pyrrole(39)

62 mg(0.2 mmol) of the compound prepared in Preparation 6 was dissolved in 2 ml of dimethylformamide, 26.4 mg(0.66 mmol) of sodium hydride(60%) was added thereto at 0° C. and then the mixture was stirred for 5 minutes. To the mixture was added 64 mg(2.2 mmol) of the compound prepared in Preparation 26 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 74 mg(Yield 70%) of the title compound.

$^1$H NMR(CDCl$_3$) δ2.38(br, 2H), 2.70(t, 2H), 2.90–3.20 (m, 7H), 3.30(br, 1H), 3.97(t,2H), 4.88(s, 2H), 6.69(d, 1H), 6.88(d, 2H), 7.04(s, 1H), 7.09(s, 1H), 7.19(d, 1H), 7.24–7.50 (m, 5H), 7.75(d, 1H), 7.81(d, 1H), 8.02(d, 1H)

FAB 527 (M+H), $C_{31}H_{31}N_4O_2Cl$ (M)

EXAMPLE 40

Synthesis of 1-[1-(4-chloro)phenethyl-1H-imidazol-5-yl]methyl-3-[4-methylpiperazin-1-yl]carbonyl-4-(naphthalen-1-yl)-1H-pyrrole(40)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 64 mg(2.2 mmol) of the compound prepared in Preparation 26 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 84 mg(Yield 78%) of the title compound.

$^1$H NMR(CDCl$_3$) δ1.08(br, 2H), 1.80(br, 2H), 1.95(s, 3H), 2.73(t, 2H), 2.93(br, 2H), 3.35(br, 2H), 4.00(t, 2H), 4.90(s, 2H), 6.71(d, 1H), 6.91(d, 2H), 7.13–7.60(m, 9H), 7.78(d, 1H), 7.82(d, 1H), 8.01(d, 1H)

FAB 538 (M+H), $C_{32}H_{32}N_5OCl$ (M)

EXAMPLE 41

Synthesis of 3-[N-(2-methoxyethyl)-N-methyl] carbamoyl-4-(naphthalen-1-yl)-1-{1-[2-(naphthalen-2-yl)ethyl]-1H-imidazol-5-yl}methyl-1H-pyrrole(41)

62 mg(0.2 mmol) of the compound prepared in Preparation 6 was dissolved in 2 ml of dimethylformamide, 26 mg(0.66 mmol) of sodium hydride(60%) was added thereto at 0° C. and then the mixture was stirred for 5 minutes. To the mixture was added 67 mg(2.2 mmol) of the compound prepared in Preparation 27 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 79 mg(Yield 71%) of the title compound.

$^1$H NMR(CDCl$_3$) δ2.96(br, 1H), 2.39(br, 2H), 2.71(br, 1H), 2.80–3.15(m, 7H), 3.32(br, 1H), 4.10(t, 2H), 4.78(s, 1H), 6.66(s, 1H), 7.09(m, 3H), 7.42(m, 8H), 7.63(m, 1H), 7.75(m, 3H), 7.82(d, 1H), 8.06(d, 1H)

FAB 543 (M+H), $C_{35}H_{34}N_4O_2$ (M)

EXAMPLE 42

Synthesis of 3-[4-methylpiperazin-1-yl]carbonyl-4-(naphthalen-1-yl)-1-{1-[2-(naphthalen-2-yl)ethyl]-1H-imidazol-5-yl}methyl-1H-pyrrole(42)

62 mg(0.2 mmol) of the compound prepared in Preparation 8 was dissolved in 2 ml of dimethylformamide, 26.4 mg(0.66 mmol) of sodium hydride(60%) was added thereto at 0° C. and then the mixture was stirred for 5 minutes. To the mixture was added 67 mg(2.2 mmol) of the compound prepared in Preparation 27 and the whole mixture was stirred at room temperature for 2 hours. The solvent was removed by distillation under reduced pressure and 3 ml of water was added to the residue. The mixture was then extracted twice with 10 ml of ethyl acetate, dried over anhydrous sodium sulfate, concentrated, and subjected to silica gel column chromatography (eluent: dichloromethane/methanol=95/5, v/v) to obtain 82 mg(Yield 74%) of the title compound.

$^1$H NMR(CDCl$_3$) δ1.05(br, 2H), 1.70–2.00(s+br, 4H), 2.34(br, 1H), 2.90 (t, 2H), 3.01(br, 2H), 3.32(br, 2H), 4.08(t, 2H), 4.78(s, 2H), 6.65(d, 2H), 7.10(m, 3H), 7.21–7.42(m, 7H), 7.64(m, 1H), 7.75(m, 3H), 7.82(d, 1H), 8.01(d, 1H)

FAB 554(M+H), $C_{36}H_{35}N_5O$ (M)

EXAMPLE 43

Synthesis of 1-[1-(4-hydroxy)phenethyl-1H-imidazol-5-yl]methyl-3-[4-methylpiperazin-1-yl] carbonyl-4-(naphthalen-1-yl)-1H-pyrrole(43)

53 mg(0.1 mmol) of the compound prepared in Example 20 was dissolved in 1 ml of dichloromethane, 75 mg(0.3 mmol) of borontribromide (BBr$_3$) was added thereto, and the mixture was stirred for 3 hours. 1 ml of methanol was added to stop the reaction and the solvent was removed by distillation under reduced pressure. The residue was subjected to silica gel column chromatography(eluent: dichloromethane/methanol=20/80, v/v) to obtain 26 mg(Yield 50%) of the title compound.

¹H NMR(CDCl₃) δ1.20(br, 2H), 1.80–2.05(br+s, 4H), 2.65(t, 2H), 3.00–3.60(br, 5H), 3.98(t, 2H), 4.88(s, 2H), 6.72(m, 5H), 7.09(s, 1H), 7.14(d, 1H), 7.23(s, 1H), 7.27(s, 1H), 7.33(d, 1H), 7.40–7.53(m, 3H), 7.77(d, 1H), 7.82(d, 1H), 7.93(d, 1H)

FAB 520(M+H), $C_{32}H_{33}O_2N_5$ (M)

Preparation 28

Synthesis of 4-chloromethyl-1-trityl-1H-imidazole hydrochloride 28-1) 4-Hydroxymethyl-1-trityl-1H-imidazole 3.99 g(29.6 mmol) of hydroxymethylimidazole hydrochloride was dissolved in a mixture of 30 ml of dimethylformamide and 10 ml triethylamine, and then a solution of 9.35 g(33.5 mmol) of triphenylmethyl chloride in 110 ml of dimethylformamide was added slowly thereto. After 2 hours, 500 ml of ice water was added to the reaction mixture to obtain a solid. This solid was recrystallized from dioxane to give 8.82 g(Yield 87%) of the title compound.

m.p.: 227–229° C.

28-2) 4-Chloromethyl-1-trityl-1H-imidazole hydrochloride 1.50 g(4.41 mmol) of the compound prepared in Preparation 28-1) was dissolved in 50 ml of chloroform, 0.94 ml(13.2 mmol) of thionyl chloride was slowly added thereto at 0° C., and the mixture was stirred at room temperature for 2 hours. The organic solvent was removed under reduced pressure to give 1.66 g(4.20 mmol, Yield 95%) of the title compound, which was directly used in the next reaction without purification.

Preparation 29

Synthesis of 4-(5-chloromethyl-1H-imidazol-1-ylmethyl)benzonitrile hydrochloride 29-1) 4-Acetoxymethyl-1-trityl-1H-imidazole To 100 ml of pyridine were added 5.00 g(14.7 mmol) of the compound prepared in Preparation 28-1) and 1.65 g(16.2 mmol) of acetic anhydride, and the mixture was stirred at room temperature for 24 hours. The reaction solution was distilled under reduced pressure to remove the pyridine and then the residue was dissolved in 200 ml of ethyl acetate and washed with 100 ml of aqueous sodium chloride solution. The organic solvent was eliminated by distillation under reduced pressure and the residue was subjected to column chromatography (eluent: dichloromethane/methanol=20/1, v/v) to give 5.22 g(13.7 mmol, Yield 93%) of the title compound.

¹H NMR(CDCl₃) δ2.01(s, 3H), 4.95(s, 2H), 6.88(s, 1H) 7.08(s, 5H), 7.27(s, 10H), 7.45 (s, 1H)

29-2) 4-(4-Acetoxymethyl-1-trityl-1H-imidazol-3-ylmethyl)benzonitrile bromide 5.00 g(13.1 mmol) of the compound prepared in Preparation 29-1) was dissolved in 20 ml of dichloromethane, 2.82 g(14.4 mmol) of 4-cyanobenzyl bromide was added thereto, and the mixture was stirred at room temperature for 60 hours. The organic solvent was removed by distillation under reduced pressure and the residue was subjected to column chromatography(eluent: dichloromethane/methanol=5/1, v/v) to give 5.31 g(9.17 mmol, Yield 70%) of the title compound.

¹H NMR(CDCl₃+CD₃OD) δ1.95(s, 3H), 4.95(s, 2H), 5.45(s, 2H), 7.11–7.40(m, 18H), 7.65(d, 2H), 8.21(s, 1H)

29-3) 4-(5-Acetoxymethyl-1H-imidazol-1-ylmethyl)benzonitrile 9.10 g(15.7 mmol) of the compound prepared in Preparation 29-2) was dissolved in 500 ml of dichloromethane, 6.06 ml(78.7 mmol) of trifluoroacetic acid and 12.5 ml(78.7 mmol) of triethylsilane were slowly added thereto at 0° C., and the mixture was stirred at room temperature for 1 hour. The organic solvent was removed by distillation under reduced pressure, and then the residue was adjusted to pH 10 with saturated $K_2CO_3$ aqueous solution and extracted with 300 ml of ethyl acetate. The organic solvent was removed by distillation under reduced pressure and the residue was subjected to column chromatography using ethyl acetate as an eluent to give 3.60 g(14.1 mmol, Yield 90%) of the title compound.

¹H NMR(CDCl₃) δ1.90(s, 3H), 4.97(s, 2H), 5.25(s, 2H), 7.14(d, 2H), 7.21(d, 1H), 7.67(s, 1H), 7.75(d, 2H)

29-4) 4-(5-Hydroxymethyl-1H-imidazol-1-ylmethyl)benzonitrile 4.20 g(16.5 mmol) of the compound prepared in Preparation 29-3) was dissolved in 200 ml of methanol, 4.50 g(32.9 mmol) of $K_2CO_3$ was added thereto, and the mixture was stirred at room temperature for 20 minutes. The organic solvent was removed by distillation under reduced pressure at room temperature. The residue was then extracted with 300 ml of ethyl acetate and the extract was subjected to column chromatography(eluent: dichloromethane/methanol=10/1, v/v) to give 3.19 g (15.0 mmol, Yield 91%) of the title compound.

¹H NMR(CDCl₃+CD₃OD) δ4.28(s, 2H), 5.18(s, 2H), 6.84(s, 1H), 7.12(d, 2H), 7.42(s, 1H), 7.55(d, 2H)

29-5) 4-(5-Chloromethyl-1H-imidazol-1-ylmethyl)benzonitrile hydrochloride 3.00 g(14.1 mmol) of the compound prepared in Preparation 29-4) was dissolved in 40 ml of chloroform, 5.02 ml(70.5 mmol) of thionyl chloride was added slowly thereto at 0° C., and the mixture was stirred at room temperature for 2 hours. The organic solvent was removed under reduced pressure to obtain 3.50 g(13.1 mmol, Yield 93%) of the title compound. This compound was directly used in the next reaction without purification.

Preparation 30

Synthesis of 4-(3-chloro-1-propenyl)-1-trityl-1H-imidazole 30-1) Methyl 3-(1H-imidazol4-yl)acrylate 500 mg(3.62 mmol) of 3-(1H-imidazol4-yl)acrylic acid was added to 20 ml of methanolic HCl and the mixture was stirred at room temperature for 10 hours. The solvent was removed under reduced pressure and then 30 ml of dichloromethane was added to the residue. The mixture was washed sequentially with saturated $NaHCO_3$ solution, aqueous sodium chloride solution and water. The organic layer was dried over anhydrous magnesium sulfate and concentrated to give 510 mg(3.35 mmol, Yield 93%) of the title compound. This compound was used directly in the next reaction without purification.

30-2) Methyl 3-(1-trityl-1H-imidazol-4-yl)acrylate 350 mg(2.30 mmol) of the compound prepared in Preparation 30-1) and 705 mg(2.53 mmol) of triphenylmethylchloride were dissolved in 10 ml of dimethylformamide, and 350 μl(2.53 mmol) of triethylamine was added thereto. After 2 hours, 100 ml of ice water was added to the reaction mixture to obtain a solid. This solid was filtered, washed with diethylether and hexane, and then dried to give 810 mg(2.05 mmol, Yield 87%) of the title compound.

$^1$H NMR(CDCl$_3$) δ3.75(s, 3H), 6.35(d, 1H), 7.05–7.50(m, 18H)

30-3) 1-(1-Trityl-1H-imidazol4-yl)propen-3-ol 800 mg(2.03 mmol) of the compound prepared in Preparation 30-2) was added to 20 ml of dry dichloromethane. After the mixture was cooled down to −78° C., 6.1 ml(1M solution in hexane) of diisobutylaluminum hydride was added thereto. Temperature was raised slowly to room temperature and then 2 ml of water was added to the mixture to stop the reaction. 3 ml of 1N NaOH was added and then 2 ml of water was added, and the mixture was filtered through cellite. The organic layer of the filtrate was separated and combined with the dichloromethane-extract from the aqueous layer. The mixture was dried over anhydrous magnesium sulfate. The organic solvent was removed under reduced pressure and the residue was subjected to column chromatography(eluent: dichloromethane/methanol=20/1, v/v) to give 671 mg(1.83 mmol, Yield 90%) of the title compound.

$^1$H NMR(CDCl$_3$) δ4.25(s, 2H), 6.45(s, 2H), 6.78(s, 1H), 7.10–7.50(m, 16H)

30-4) 4-(3-Chloropropenyl)1-trityl-1H-imidazole 650 mg(1.77 mmol) of the compound prepared in Preparation 30-3) was added to 10 ml of chloroform. 135 μl(1.9 mmol) of thionyl chloride was added thereto at 0° C. and the mixture was stirred at room temperature for 2 hours. The organic solvent was removed by distillation under reduced pressure and the residue was dissolved in 10 ml of ethyl acetate. The solution was washed with saturated NaHCO$_3$ aqueous solution and the organic solvent was distilled under reduced pressure to give 647 mg(1.68 mmol, Yield 95%) of the title compound.

$^1$H NMR(CDCl$_3$) δ4.22(d, 2H), 6.40–6.55(m, 2H), 6.81(s, 1H), 7.10–7.50 (m, 16H)

Preparation 31

Synthesis of 5-chloromethyl-1-methylimidazole hydrochloride

31-1) 5-Hydroxymethyl-1-methylimidazole

The title compound was obtained in a yield of 32% according to the procedure described in J. M. Dener, L-H Zhang, H. Rapoport, *J. Org. Chem.*, 1993, 58, 1159 using dihydroxyacetone and methylamine hydrochloride as starting materials.

$^1$H NMR(CDCl$_3$) δ3.67(s, 3H), 4.58(s, 2H), 5.37(brs, 1H), 6.76(s, 1H), 7.32(s, 1H)

31-2) 5-Chloromethyl-1-methylimidazole hydrochloride

The title compound was obtained in a yield of 95% according to the same procedure as Preparation 28-2) except that the compound prepared in Preparation 31-1) was used as a starting material.

Preparation 32

Synthesis of 1-(4bromobenzyl)-5chloromethyl-1H-imidazole hydrochloride

32-1) 1-(4-Bromobenzyl)-5-hydroxymethyl-1H-imidazole

The title compound was obtained in a yield of 50% according to the procedure described in J. M. Dener, L-H Zhang, H. Rapoport, *J. Org Chem.*, 1993, 58, 1159 using dihydroxyacetone dimer and 4-bromobenzylamine hydrochloride as starting materials.

$^1$H NMR (CDCl$_3$+CD$_3$OD) δ4.46(s, 2H), 5.26(s, 2H), 7.00(s, 1H), 7.07(d, 2H), 7.50(d, 2H), 7.65(s, 1H)

32-2) 1-(4-Bromobenzyl)-5-chloromethyl-1H-imidazole hydrochloride

The title compound was obtained in a yield of 96% according to the same procedure as Preparation 28-2) except that the compound prepared in Preparation 32-1) was used as a starting material. The product thus obtained was directly used in the next reaction without purification.

Preparation 33

Synthesis of 5-chloromethyl-1-isobutylimidazole hydrochloride

33-1) 5-Hydroxymethyl-1-isobutylimidazole

The title compound was obtained in a yield of 45% according to the same procedure as Preparation 31-1) using dihydroxyacetone and isobutylamine hydrochloride as starting materials.

$^1$H NMR(CDCl$_3$) δ0.90(d, 6H), 1.76(m, 1H), 3.62(d, 2H), 4.24(brs, 1H), 4.60(s, 2H), 6.85(s, 1H), 7.45(s, 1H)

FAB (M+H): 155

33-2) 5-Chloromethyl-1-isobutylimidazole hydrochloride

The title compound was obtained in a yield of 95% according to the same procedure as Preparation 28-2) except that the compound prepared in Preparation 33-1) was used as a starting material.

Preparation 34

Synthesis of 5-chloromethyl-1-cyclohexylmethylimidazole hydrochloride

34-1) 5-Hydroxymethyl-1-cyclohexylmethylimidazole

The title compound was obtained in a yield of 45% according to the same procedure as Preparation 31-1) using dihydroxyacetone and cyclohexylmethylamine hydrochloride as starting materials.

$^1$H NMR(CDCl$_3$) δ0.94(m, 2H), 1.16(m, 3H), 1.50–1.70 (m, 6H), 3.65(d, 2H), 4.24(brs, 1H), 4.60(s, 2H), 6.85(s, 1H), 7.45(s, 1H)

FAB (M+H): 195

34-2) 5-Chloromethyl-1-cyclohexylmethylimidazole hydrochloride

The title compound was obtained in a yield of 95% according to the same procedure as Preparation 28-2) except that the compound prepared in Preparation 34-1) was used as a starting material.

Preparation 35

Synthesis of 5-chloromethyl-1-pentylimidazole hydrochloride

35-1) 5-Hydroxymethyl-1-pentylimidazole

The title compound was obtained in a yield of 50% according to the same procedure as Preparation 31-1) using dihydroxyacetone and pentylamine hydrochloride as starting materials.

¹H NMR(CDCl₃) δ0.90(t, 3H), 1.08(brs, 2H), 1.30(m, 4H), 1.45(m, 2H), 3.64(t, 2H), 4.24(brs, 1H), 4.60(s, 2H), 6.84(s, 1H), 7.44(s, 1H)

FAB (M+H): 169

35-2) 5-Chloromethyl-1-pentylimidazole hydrochloride

The title compound was obtained in a yield of 90% according to the same procedure as Preparation 28-2) except that the compound prepared in Preparation 35-1) was used as a starting material.

Preparation 36

Synthesis of 5-chloromethyl-1-octylimidazole hydrochloride

36-1) 5-Hydroxymethyl-1-octylimidazole

The title compound was obtained in a yield of 52% according to the same procedure as Preparation 31-1) using dihydroxyacetone and octylamine hydrochloride as starting materials.

¹H NMR(CDCl₃) δ0.88(t, 3H), 1.18(brs, 2H), 1.30(brs, 10H), 1.42(m, 2H), 3.67(t, 2H), 4.23(brs, 1H), 4.60(s, 2H), 6.84(s, 1H), 7.44(s, 1H)

FAB (M+H): 211

36-2) 5-Chloromethyl-1-octylimidazole hydrochloride

The title compound was obtained in a yield of 93% according to the same procedure as Preparation 28-2) except that the compound prepared in Preparation 36-1) was used as a starting material.

Preparation 37

Synthesis of 5-chloromethyl-1-decylimidazole hydrochloride

37-1) 5-Hydroxymethyl-1-decylimidazole

The title compound was obtained in a yield of 52% according to the same procedure as Preparation 31-1) using dihydroxyacetone and decylamine hydrochloride as starting materials.

¹H NMR(CDCl₃) δ0.88(t, 3H), 1.04(brs, 2H), 1.30(brs, 14H), 1.42(m, 2H), 3.68(t, 2H), 4.23(brs, 1H), 4.60(s, 2H), 6.84(s, 1H), 7.44(s, 1H)

FAB (M+H): 239

37-2) 5-Chloromethyl-1-decylimidazole hydrochloride

The title compound was obtained in a yield of 93% according to the same procedure as Preparation 28-2) except that the compound prepared in Preparation 37-1) was used as a starting material.

Preparation 38

Synthesis of 5-chloromethyl-1-(3-methyl) butylimidazole hydrochloride

38-1) 5-Hydroxymethyl-1-(3-methyl)butylimidazole

The title compound was obtained in a yield of 52% according to the same procedure as Preparation 31-1) using dihydroxyacetone and isoamylamine hydrochloride as starting materials.

¹H NMR(CDCl₃) δ0.90(d, 6H), 1.32(m, 2H), 1.65(m, 1H), 3.67(t, 2H), 4.23(brs, 1H), 4.60(s, 2H), 6.84(s, 1H), 7.44(s, 1H)

FAB (M+H): 169

38-2) 5-Chloromethyl-1-(3-methyl)butylimidazole hydrochloride

The title compound was obtained in a yield of 93% according to the same procedure as Preparation 28-2) except that the compound prepared in Preparation 38-1) was used as a starting material.

Preparation 39

Synthesis of 5chloromethyl-1-(2-methoxy) ethylimidazole hydrochloride

39-1) 5-Hydroxymethyl-1-(2-methoxy) ethylimidazole

The title compound was obtained in a yield of 60% according to the same procedure as Preparation 31-1) using dihydroxyacetone and 2-methoxyethylamine hydrochloride as starting materials.

¹H NMR(CDCl₃) δ3.38(s, 3H), 3.42(t, 2H), 3.65(t, 2H), 4.23(brs, 1H), 4.60(s, 2H), 6.84(s, 1H), 7.44(s, 1H)

FAB (M+H): 157

39-2) 5-Chloromethyl-1-(2-methoxy)ethylimidazole hydrochloride

The title compound was obtained in a yield of 93% according to the same procedure as Preparation 28-2) except that the compound prepared in Preparation 39-1) was used as a starting material.

Preparation 40

Synthesis of 5-chloromethyl-1-(3methoxy) propylimidazole hydrochloride

40-1) 5-Hydroxymethyl-1-(3-methoxy) propylimidazole

The title compound was obtained in a yield of 61% according to the same procedure as Preparation 31-1) using dihydroxyacetone and 3-methoxypropylamine hydrochloride as starting materials.

¹H NMR(CDCl₃) δ1.72(m, 2H), 3.32(s, 3H), 3.46(t, 2H), 3.63(t, 2H), 4.23(brs, 1H), 4.60(s, 2H), 6.84(s, 1H), 7.44(s, 1H)

FAB (M+H): 171

40-2) 5-Chloromethyl-1-(3-methoxy) propylimidazole hydrochloride

The title compound was obtained in a yield of 90% according to the same procedure as Preparation 28-2) except that the compound prepared in Preparation 40-1) was used as a starting material.

Preparation 41

Synthesis of 5-chloromethyl-1-(3-ethoxy) propylimidazole hydrochloride 41-1) 5-Hydroxymethyl-1-(3-ethoxy) propylimidazole The title compound was obtained in a yield of 61% according to the same procedure as Preparation 31-1) using dihydroxyacetone and 3-ethoxypropylamine hydrochloride as starting materials.

$^1$H NMR(CDCl$_3$) δ1.20(t, 3H), 1.72(m, 2H), 3.50(s, 4H), 3.63(t, 2H), 4.23(brs, 1H), 4.60(s, 2H), 6.84(s, 1H), 7.44(s, 1H)

FAB (M+H): 185

41-2) 5-Chloromethyl-1-(3-ethoxy)propylimidazole hydrochloride

The title compound was obtained in a yield of 90% according to the same procedure as Preparation 28-2) except that the compound prepared in Preparation 41-1) was used as a starting material.

Preparation 42

Synthesis of 5-chloromethyl-1-(3-isopropoxy) propylimidazole hydrochloride 42-1) 5-Hydroxymethyl-1-(3-isopropoxy) propylimidazole The tide compound was obtained in a yield of 61% according to the same procedure as Preparation 31-1) using dihydroxyacetone and 3-isopropoxypropylamine hydrochloride as starting materials.

$^1$H NMR(CDCl$_3$) δ1.15(d, 6H), 1.71(m, 2H), 3.45–3.55 (m, 3H), 3.63(t, 2H), 4.23(brs, 1H), 4.60(s, 2H), 6.84(s, 1H), 7.44(s, 1H)

FAB (M+H): 199

42-2) 5-Chloromethyl-1-(3-isopropoxy) propylimidazole hydrochloride

The title compound was obtained in a yield of 90% according to the same procedure as Preparation 28-2) except that the compound prepared in Preparation 42-1) was used as a starting material.

EXAMPLE 44

Synthesis of 1-(1H-imidazol-4-yl)methyl-4-(naphthalen-1-yl)-3-(thiophen-2-yl)carbonyl-1H-pyrrole(44)

44-1) 3-(Naphthalen-1-yl)-1-(thiophen-2-yl)-prop2-en-1-one 3.12 g(20 mmol) of 1-naphthaldehyde and 2.52 g(20 mmol) of 2-acetylthiophene were dissolved in 20 ml of methanol and 800 mg(20 mmol) of sodium hydroxide was slowly added thereto. The mixture was reacted at room temperature for 8 hours and then the solid thus produced was filtered and dried. The filtrate was adjusted to pH 4–6 using 1N hydrochloric acid solution and extracted with ethyl acetate. The organic solvent was removed under reduced pressure and the residue was subjected to column chromatography(eluent: hexane/ethyl acetate=4/1, v/v) to give 4.23 g(16 mmol, Yield 80%) of the title compound together with the filtered solid.

$^1$H NMR(CDCl$_3$) δ7.13–7.31(m, 2H), 7.55–7.70(m, 3H), 7.70(d, 1H), 7.85–7.90(m, 4H), 8.28(d, 1H), 8.70(d, 1H)

44-2) 4-(Naphthalen-1-yl)-3-(thiophen-2-yl) carbonyl-1H-pyrrole 2.64 g(9.99 mmol) of the compound prepared in Example 44-1) and 2.35 g(12.0 mmol) of tosylmethylisocyanide were dissolved in 30 ml of tetrahydrofuran. 1.35 g(12.0 mmol) of potassium t-butoxide was slowly added thereto and the mixture was refluxed for 30 minutes. The solvent was removed under reduced pressure and then 15 ml of water and 20 ml of ethyl acetate was added to the residue. The mixture was shaken thoroughly and filtered to obtain the resulting solid. This solid was washed with diethylether and dried to give, 1.97 g(6.48 mmol, Yield 65%) of the title compound.

$^1$H NMR(CDCl$_3$) δ6.90(s, 1H), 7.12(s, 1H), 7.20–7.45(m, 4H), 7.55(s, 1H), 7.61(s, 1H), 7.70–8.00(m, 4H), 11.4(s, 1H)

44-3) 4-(Naphthalen-1-yl)-3-(thiophen-2-yl) carbonyl-1-(1-trityl-1H-imidazol-4-yl)methyl-1H-pyrrole 200 mg(0.99 mmol) of the compound prepared in Example 44-2) was dissolved in 5 ml of dimethylformamide, 95 mg(4.0 mmol) of sodium hydride (50%) was added thereto at 0° C., and the mixture was stirred for 5 minutes. 391 mg(0.99 mmol) of the compound prepared in Preparation 28-2) was added to the reaction solution and stirred at room temperature for 5 hours. The solvent was removed by distillation under reduced pressure and the residue was extracted with ethyl acetate. The extract was dried over anhydrous magnesium sulfate, concentrated and subjected to column chromatography(eluent: hexane/ethyl acetate=1/3, v/v) to give 205 mg(0.33 mmol, Yield 33%) of the title compound.

$^1$H NMR(CDCl$_3$) δ5.02(s, 2H), 6.75(s, 1H), 6.79(s, 1H), 6.86(t, 1H), 7.10–7.52(m, 23H), 7.71(d, 1H), 7.78(d, 1H), 7.89(d, 1H)

44-4) 1-(1H-Imidazol-4-yl)methyl4-(naphthalen-1-yl)-3thiophen-2-yl)carbonyl-1H-pyrrole 190 mg(0.304 mmol) of the compound prepared in Example 44-3) was dissolved in a solvent mixture of trifluoroacetic acid/dichloromethane(0.5 ml/0.5 ml) and the solution was stirred at room temperature for 2 hours. The organic solvent was removed under reduced pressure. The residue was dissolved in 10 ml of ethyl acetate, washed with saturated Na$_2$CO$_3$ solution and water, dried over anhydrous magnesium sulfate, concentrated and subjected to column chromatography(eluent:ethyl acetate) to give 103 mg(0.269 mmol, Yield 88%) of the title compound.

$^1$H NMR(CDCl$_3$) δ4.87(s, 2H), 6.55(s, 1H), 6.72(s, 1H), 6.88(t, 1H), 7.11–7.34(m, 7H), 7.50–7.67(m, 3H), 7.83(d, 1H)

FAB MS: 384(M+1)

EXAMPLES 45 to 72

The compounds represented in the following Tables 2-1 to 2-3 were obtained according to the similar procedure as Example 44.

TABLE 2-1

| COM. NO. | $^1$H NMR (CDCl$_3$) δ | FAB MS (M + 1) |
|---|---|---|
| 45 | 4.85(s, 2H), 6.51(s, 1H), 6.67(s, 1H), 7.06(s, 1H), 7.14(s, 1H), 7.21–7.32(m, 7H), 7.61–7.74(m, 3H), 7.82(d, 1H) | 384 |
| 46 | 4.95(s, 2H), 6.58(s, 1H), 6.76(s, 1H), 7.13–7.35(m, 9H), 7.61–7.68(m, 4H), 7.91(d, 1H) | 378 |
| 47 | 4.92(s, 2H), 6.61(s, 1H), 6.70(s, 1H), 7.02(d, 2H), 7.17–7.35(m, 9H), 7.62(d, 1H), 7.70(d, 1H), 7.95(d, 1H) | 456 |
| 48 | 5.03(s, 2H), 6.76(s, 1H), 6.85(s, 1H), 7.07(t, 1H), 7.34–7.54(m, 9H), 7.72–7.79(m, 3H), 7.94(d, 1H) | 456 |
| 49 | 5.00(s, 2H), 6.72(s, 1H), 6.77(s, 1H), 7.21–7.38(m, 11H), 7.62(d, 1H), 7.70(d, 1H), 7.78(d, 1H) | 456 |
| 50 | 2.23(s, 3H), 5.02(s, 2H), 6.74–7.10(m, 5H), 7.17–7.50 (m, 8H), 7.65(d, 1H), 7.71(d, 1H), 7.86(d, 1H) | 392 |
| 51 | (CDCl$_3$ + CD$_3$OD) 2.05(s, 3H), 5.09(s, 2H), 6.84(s, 1H), 6.99–7.05(m, 8H), 7.23–7.36(m, 3H), 7.70(d, 1H), 7.86(d, 1H) | 392 |

TABLE 2-2

| COM. NO. | $^1$H NMR (CDCl$_3$) δ | FAB MS (M + 1) |
|---|---|---|
| 52 | 2.21(s, 3H), 4.92(s, 2H), 6.62(s, 1H), 6.83(s, 1H), 7.14–7.35(m, 8H), 7.61–7.73(m, 5H), 7.88(d, 1H) | 392 |
| 53 | 3.66(s, 3H), 5.04(s, 2H), 6.85(s, 1H), 6.82(d, 1H), 6.90(m, 1H), 7.12–7.17(m, 2H), 7.26–7.36(m, 8H), 7.67(t, 1H), 7.74(d, 1H), 7.93(d, 1H) | 408 |
| 54 | 3.75(s, 3H), 5.02(s, 2H), 6.71(m, 3H), 6.80(t, 1H), 7.20–7.35(m, 6H), 7.60–7.75(m, 4H), 7.91(d, 1H) | 408 |
| 55 | 4.83(s, 2H), 6.51(s, 1H), 6.63(s, 1H), 6.85(m, 1H), 7.03–7.29(m, 10H), 7.61–7.69(m, 2H), 7.83(d, 1H) | 412 |
| 56 | 5.01(s, 2H), 6.72(s, 1H), 6.77(s, 1H), 7.22–7.35(m, 11H), 7.61–7.80(m, 3H) | 412 |
| 57 | 4.82(s, 2H), 6.63(s, 1H), 6.72(s, 1H), 7.02–7.24(m, 10H), 7.56–7.70(m, 3H) | 446 |
| 58 | 4.91(s, 2H), 6.65(s, 1H), 6.77(m, 1H), 7.20–7.31(m, 7H), 7.61(m, 3H), 7.81(d, 1H) | 396 |
| 59 | 4.92(s, 2H), 6.45(m, 1H), 6.71(m, 2H), 7.20–7.32(m, 9H), 7.63–7.77(m, 3H) | 414 |
| 60 | 5.09(s, 2H), 6.80–7.20(m, 4H), 7.15–7.35(m, 4H), 7.40(d, 1H), 7.45–7.50(m, 3H), 7.60(m, 1H), 7.65(d, 1H), 7.75(d, 1H) | 403 |
| 61 | 1.87(s, 3H), 3.55(s, 2H), 5.07(s, 2H), 6.84(s, 2H), 7.08(d, 2H), 7.28–7.48(m, 6H), 7.57(d, 2H), 7.63(t, 1H), 7.71(d, 1H), 7.90(d, 1H) | 438 |
| 62 | 2.03(s, 3H), 2.74(m, 2H), 2.91(m, 2H), 5.00(s, 2H), 6.67(s, 1H), 7.02(d, 2H), 7.14–7.43(m, 11H), 7.72–7.89(m, 3H) | 452 |
| 63 | 1.98(s, 3H), 2.75(t, 2H), 3.90(t, 2H), 4.85(s, 2H), 6.60–6.72(m, 4H), 7.11–7.45(m, 9H), 7.68–7.82(m, 3H) | 468 |
| 64 | 2.01(s, 3H), 3.61(s, 2H), 4.98(s, 2H), 6.61(s, 2H), 6.74(m, 2H), 7.10–7.48(m, 10H), 7.71–7.88(m, 3H) | 438 |

TABLE 2-3

| COM. NO. | $^1$H NMR (CDCl$_3$) δ | FAB MS (M + 1) |
|---|---|---|
| 65 | 4.92(s, 2H), 6.62(s, 1H), 6.70(s, 1H), 7.12–7.27(m, 14H), 7.53–7.62(m, 4H), 7.81(d, 1H) | 454 |
| 66 | 4.97(s, 2H), 6.87(d, 1H), 7.15–7.46(m, 15H), 7.55–7.73(m, 4H), 7.86(m, 1H) | 454 |
| 67 | 5.10(s, 2H), 6.70(t, 2H), 6.80–6.95(m, 4H), 7.15(t, 1H), 7.21–7.45(m, 7H), 7.50(t, 1H), 7.60(d, 2H), 7.71(d, 1H), 7.75–7.80(m, 2H), 7.91(m, 1H) | 470 |

TABLE 2-3-continued

| COM. NO. | $^1$H NMR (CDCl$_3$) δ | FAB MS (M + 1) |
|---|---|---|
| 68 | 3.82(s, 2H), 4.95(s, 2H), 6.57(s, 1H), 6.63(s, 1H), 6.92(d, 2H), 7.04(d, 2H), 7.20–7.32(m, 10H), 7.51–7.68(m, 4H), 7.82(d, 1H) | 468 |
| 69 | 4.82(s, 2H), 6.41(s, 1H), 6.70(s, 1H), 6.95(s, 1H), 7.16–7.32(m, 9H), 7.51(d, 1H), 7.59(d, 1H), 7.67(m, 3H), 7.90(d, 1H), 8.05(d, 1H) | 428 |
| 70 | 2.38(s, 3H), 3.65(s, 3H), 4.91(s, 2H), 6.69(s, 1H), 6.97(d, 1H), 7.00(t, 1H), 7.04(d, 1H), 7.10–7.16(m, 3H), 7.19(d, 1H), 7.34(s, 1H), 7.42(s, 1H), 7.57(d, 1H), 7.67(s, 2H) | 395 |
| 71 | 0.61(t, 3H), 1.02(m, 2H), 1.25(m, 2H), 2.31(m, 1H), 2.47(m, 1H), 5.05(s, 2H), 6.57(s, 1H), 6.63(s, 1H), 6.80(d, 1H), 6.87(s, 1H), 7.22–7.35(m, 7H), 7.61–7.72(m, 3H) | 502 |
| 72 | 3.71(d, 1H), 3.85(d, 1H), 4.85(s, 2H), 6.61(s, 1H), 6.73(d, 1H), 6.92–7.41(m, 14H), 7.62–7.73(m, 3H) | 536 |

Example 73

Synthesis of 1-[1-(4-cyanobenzyl)-1H-imidazol-5-yl]methyl-4-(naphthalen-1-yl)-3-(thiophen-2-yl)carbonyl-1H-pyrrole(73)

80 mg(0.3 mmol) of the compound prepared in Preparation 29-5) 90 mg(0.3 mmol) of the compound prepared in Example 44-2) were dissolved in 2 ml of dimethylformamide, 36 mg of sodium hydride(60%) was added thereto, and the mixture was stirred for 2 hours. The solvent was removed by distillation under reduced pressure and the residue was subjected to column chromatography (eluent: dichloromethane/methanol=10/1, v/v) to give 83 mg(0.17 mmol, Yield 56%) of the title compound.

$^1$H NMR(CDCl$_3$) δ5.02(s, 2H), 5.08(s, 1H), 6.73(s, 1H), 6.85(s, 1H), 7.03(t, 1H), 7.32–7.45(m, 1H), 7.63(s, 1H), 7.75(d, 1H), 7.82(d, 1H), 8.02 (d, 1H)

FAB MS: 499 (M+1)

EXAMPLE 74 내지 77

The compounds represented in the following Table 3 were obtained according to the similar procedure as Example 73.

TABLE 3

| COM. NO. | $^1$H NMR (CDCl$_3$) δ | FAB MS (M + 1) |
|---|---|---|
| 74 | 4.82(s, 2H), 5.12(s, 1H), 6.30(s, 1H), 6.41(s, 1H), 6.77–7.08(m, 12H), 7.31–7.46(m, 3H), 7.68(d, 1H) | 499 |
| 75 | 5.00(s, 2H), 5.05(s, 2H), 6.76(s, 1H), 6.82(s, 1H), 7.23–7.40(m, 12H), 7.63(s, 2H), 7.72(d, 1H), 7.90(d, 1H) | 493 |
| 76 | 5.02(s, 2H), 5.08(s, 2H), 6.65(s, 1H), 6.78(s, 1H), 6.98(t, 1H), 7.23–7.42(m, 12H), 7.65–7.73(m, 3H), 7.82(d, 1H) | 571 |
| 77 | 5.03(s, 2H), 5.10(s, 2H), 6.78(s, 1H), 6.87(s, 1H), 7.32–7.45(m, 12H), 7.74(d, 3H), 7.81(d, 1H), 7.88(d, 1H) | 571 |

EXAMPLE 78

Synthesis of 3-(4fluorobenzoyl)-1-(1-methyl-1H-imidazol-4-yl)methyl-4-(naphthalen-1-yl)1H-pyrrole (78)

The title compound was obtained in a yield of 75% according to the same procedure as Example 44-3) except that 3-(4-fluorobenzoyl)-4-(naphthalen-1-yl)1H-pyrrole and the compound prepared in Preparation 31-2) were used.

$^1$H NMR(CDCl$_3$) δ3.42(s, 3H), 5.01(s, 2H), 6.73(m, 3H), 7.11 (s, 1H), 7.24–7.57(m, 8H), 7.67–7.75(m, 2H)

FAB MS (M+1): 410

EXAMPLE 79

Synthesis of 1-(1-methyl-1H-imidazol-4-yl)methyl-4-(naphthalen-1-yl)3-(4-phenoxybenzoyl)1H-pyrrole (79)

The title compound was obtained in a yield of 70% according to the same procedure as Example 44-3) except that 4-(naphthalen-1-yl)-3-(4-phenoxybenzoyl)-1H-pyrrole and the compound prepared in Preparation 31-2) were used.

$^1$H NMR(CDCl$_3$) δ3.52(s, 3H), 5.12(s, 2H), 6.63(d, 2H), 6.76(d, 1H), 6.85(d, 2H), 7.12(t, 1H), 7.20(s, 1H), 7.28–7.40 (m, 7H), 7.51(d, 2H), 7.68(d, 2H), 7.74(d, 1H), 7.83(d, 1H)

FAB MS (M+1): 484

EXAMPLE 80

Synthesis of (S)-1-(1H-imidazol4-yl)methyl-3-[N-(1-methoxycarbonyl-3methylthio)propyl]carbamoyl-4-(naphthalen-1-yl)-1H-pyrrole(80)

80-1) Ethyl3-(naphthalen-1-yl)acrylate 22.4 g(0.10 mol) of triethylphosphonoacetate was dissolved in 500 ml of tetrahydrofuran and 12.4 g(1.1 mol) of potassium t-butoxide was slowly added thereto. To this solution was slowly added 15.6 g(0.10 mol) of 1-naphtaldehyde dissolved in 20 ml of tetrahydrofuran and the mixture was stirred for 8 hours. The organic solvent was removed by distillation under reduced pressure. The residue was dissolved in ethyl acetate, washed twice with water, dried over anhydrous magnesium sulfate, concentrated and subjected to column chromatography(eluent: hexane/ethyl acetate=95/5, v/v) to give 20.3 g(0.090 mol, Yield 90%) of the title compound.

$^1$H NMR(CDCl$_3$) δ1.42(t, 3H), 4.30(q, 2H), 6.50(d, 1H), 7.40–7.60(m, 3H), 7.73(d, 2H), 7.82(m, 2H), 8.20(d, 1H), 8.50(d, 1H)

80-2) 3-Ethoxycarbonyl-4-naphthalen-1-yl)-1H-pyrrole 500 mg(1.89 mmol) of ethyl 3-(naphthalen-1-yl)acrylate prepared in Example 80-1) and 368 mg(1.89 mmol) of tosylmethylisocyanide were dissolved in 10 ml of tetrahydrofuran. 255 mg(2.27 mmol) of potassium t-butoxide dissolved in tetrahydrofuran(10 ml) was slowly added thereto and the mixture was refluxed for 30 minutes. 10 ml of water was added to the reaction solution to stop the reaction and the solvent was removed under reduced pressure. The residue was extracted with diethylether, washed with aqueous sodium chloride solution and dried over anhydrous magnesium sulfate. The solvent was removed under reduced pressure and the residue was subjected to column chromatography(eluent: ethyl acetate/hexane=1/3, v/v) to give 385 mg(1.45 mmol, Yield 77%) of the title compound.

$^1$H NMR(CDCl$_3$) δ0.86(t, 3H), 4.02(q, 2H), 6.81(s, 1H), 7.48–7.61(m, 5H), 7.90–7.97(m, 3H), 8.92(s, 1H)

80-3) 3-Ethoxycarbonyl-1(1H-imidazol4-yl)methyl-4-(napbthalen-1-yl)-1H-pyrrole

The title compound was obtained in a yield of 39% by applying the procedure described in Examples 44-3) and 44-4) from the compounds prepared in Example 80-2) and Preparation 28-2).

$^1$H NMR(CDCl$_3$) δ1.11(t, 3H), 4.20(q, 2l), 5.05(s, 2H), 6.78(s, 1H), 6.89(s, 1H), 7.38–7.49(m, 6H), 7.85–7.97(m, 3H)

80-4) 3-Hydroxycarbonyl-1-(1H-imidazol-4-yl)methyl-4-(naphthalen-1-yl)-1H-pyrrole 220 mg(0.64 mmol) of the compound prepared in Example 80-3) was dissolved in 5 ml of 50% ethanol, 216 mg(3.8 mmol) of potassium hydroxide was added dropwise thereto, and the mixture was refluxed for 7 hours. The reaction solution was cooled down to room temperature, adjusted to pH 4–5, extracted with ethyl acetate and dried over anhydrous sodium sulfate. The solvent therein was removed under reduced pressure to give 162 mg(0.51 mmol, Yield 80%) of the title compound. This compound was directly used in the next reaction without purification.

$^1$H NMR(CD$_3$OD+CDCl$_3$) δ5.01(s, 2H), 6.82(s, 1H), 6.87(s, 1H), 7.42–7.70(m, 7H), 7.82–7.89(m, 3H)

80-5) (S)-1H-Imidazol4-yl)methyl-3-[N-(1-methoxycarbonyl-3-methylthio)propyl]carbamoyl-4-(naphthalen-1-yl)-1H-pyrrole 200 mg(0.60 mmol) of the compound prepared in Example 80-4) was dissolved in 2 ml of dimethylformamide, and then 150 mg(0.78 mmol) of EDC and 105 mg(0.78 mmol) of HOBT were added thereto. The resulting mixture was stirred at 0° C. for 5 minutes. To the reaction solution was added 120 mg(0.60 mmol) of L-methionine methylester, which was then stirred at room temperature for 5 hours. The solvent was removed under reduced pressure and then 10 ml of saturated NaHCO$_3$ solution was added to the residue. The resulting solution was extracted with ethyl acetate, washed with aqueous sodium chloride solution and water, dried over anhydrous sodium sulfate and concentrated. The residue was subject to column chromatography(eluent: dichloromethane/methanol=20/1, v/v) to give 104 mg(0.225 mmol, Yield 37%) of the title compound.

$^1$H NMR(CDCl$_3$) δ1.21(m, 1H), 1.55(m, 3H), 1.80(s, 3H), 3.42(s, 3H), 4.43(m, 1H), 5.05(s, 2H), 5.60(d, 1H), 6.71(s, 1H), 6.95(s, 1H), 7.21–7.45(m, 7H), 7.75–7.87(m, 3H)

FAB MS: 463 (M+1)

EXAMPLE 81

Synthesis of (S)-3-[N-(1-hydroxycarbonyl-3-methylthio)propyl]carbamoyl-1-(1H-imidazol-4-yl)methyl4(naphthalen-1-yl)1H-pyrrole(81)

70 mg(0.15 mmol) of the compound prepared in Example 80-5) was dissolved in 2 ml of a solvent mixture of tetrahydrofuran/methanol/water(3/2/1, v/v/v), 10 mg(0.18 mmol) of lithium hydroxide was added thereto, and the mixture was stirred at room temperature for 4 hours. The solvent was removed under reduced pressure to give 68 mg(0.15 mmol, Yield 99.7%) of the lithium salt of the title compound.

$^1$H NMR(CD$_3$OD+CDCl$_3$) δ1.25(m, 1H), 1.49(m, 3H), 1.85(s, 3H), 4.41 (m, 1H), 5.11(s, 2H), 5.58(d, 1H), 6.70(s, 1H), 6.89(s, 1H), 7.15–7.38(m, 7H), 7.7–7.81(m, 3H)

FAB MS: 449 (M+1)

EXAMPLES 82 to 98

The compounds represented in the following Tables 4-1 and 4-2 were obtained according to the similar procedure as Example 80.

TABLE 4-1

| COM. NO. | $^1$H NMR (CDCl$_3$) δ | FAB MS (M + 1) |
|---|---|---|
| 82 | 5.02(s, 2H), 6.69(d, 2H), 6.77(s, 1H), 6.92–7.18(m, 5H), 7.40–7.58(m, 6H), 7.75–7.87(m, 4H) | 393 |
| 83 | 4.06(d, 2H), 5.01(s, 2H), 5.57(t, 1H), 6.46(d, 1H), 6.71(s, 1H), 6.83(s, 1H), 6.92–7.05(m, 3H), 7.42–7.55(m, 7H), 7.74–7.81(m, 3H) | 407 |
| 84 | 0.45(brs, 2H), 1.22(brs, 4H), 2.95(brs, 2H), 3.37(brs, 2H), 5.04(s, 2H), 6.65(s, 1H), 6.92(s, 1H), 7.08(s, 1H), 7.31–7.45(m, 6H), 7.72(d, 1H), 7.82(d, 1H), 8.12(d, 1H) | 385 |
| 85 | 2.32(brs, 2H), 2.22(brs, 2H), 3.23(brs, 2H), 3.65(brs, 2H), 5.06(s, 2H), 6.72(s, 1H), 6.95(s, 1H), 7.12(s, 1H), 7.31–7.48(m, 6H), 7.81(d, 1H), 7.85(d, 1H), 8.11(d, 1H) | 387 |
| 86 | 1.41(brs, 2H), 2.86–3.25(m, 6H), 4.97(s, 2H), 6.68(s, 1H), 6.85(s, 1H), 7.06(s, 1H), 7.21–7.35(m, 6H), 7.72(d, 1H), 7.78(d, 1H), 7.95(d, 1H) | 403 |
| 87 | 2.04(brs, 4H), 3.62(brs, 4H), 5.03(s, 2H), 6.91(d, 2H), 7.22–7.48(m, 7H), 7.81–7.88(m, 2H), 8.02(m, 1H) | 435 |
| 88 | 1.46(brs, 2H), 2.21(brs, 2H), 3.14(brs, 4H), 5.11(s, 2H), 6.88(s, 1H), 7.02(s, 1H), 7.11(s, 1H), 7.32–7.51(m, 5H), 7.62(s, 1H), 7.72–7.80(m, 2H), 8.05(d, 1H) | 386 |
| 89 | (CDCl$_3$ + CD$_3$OD) 2.05(s, 3H), 3.33(brs, 8H), 5.13(s, 2H), 6.90(s, 1H), 7.06(s, 1H), 7.21(s, 1H), 7.30–7.55(m, 4H), 7.64(s, 1H), 7.81(s, 1H), 7.88(d, 1H), 8.06(d, 1H) | 400 |
| 90 | 2.62(brs, 2H), 3.15(brs, 2H), 3.86(brs, 1H), 4.35(brs, 1H), 5.06(s, 2H), 6.83(s, 1H), 6.90(s, 1H), 7.15–7.60(m, 6H), 7.73(d, 1H), 7.82(d, 1H), 8.06(d, 1H) | 389 |
| 91 | 0.22(m, 1H), 0.63(m, 1H), 0.83(m, 1H), 1.24(m, 1H), 2.61(brs, 2H), 3.24(brs, 2H), 3.65(brs, 1H), 4.94(s, 2H), 6.71(s, 1H), 6.84(s, 1H), 6.94(s, 1H), 7.24–7.42(m, 6H), 7.62–7.70(m, 2H), 7.94(d, 1H) | 401 |

TABLE 4-2

| COM. NO. | $^1$H NMR (CDCl$_3$) δ | FAB MS (M + 1) |
|---|---|---|
| 92 | 1.37(brs, 2H), 1.96(brs, 2H), 3.52(brs, 4H), 5.21(s, 2H), 7.08(s, 1H), 7.20(s, 1H), 7.37(s, 1H), 7.54(m, 5H), 7.70(s, 1H), 7.94(m, 2H), 8.23(d, 1H) | 399 |
| 93 | 2.12(brs, 2H), 3.02(brs, 2H), 4.98(s, 2H), 5.24(m, 1H), 6.82(s, 1H), 7.03(s, 1H), 7.20–7.34(m, 6H), 7.62–7.71(m, 3H), 7.93(d, 1H) | 361 |
| 94 | 2.24(brs, 2H), 3.04(brs, 4H), 3.11(s, 3H), 5.03(s, 2H), 6.77(s, 1H), 6.89(s, 1H), 7.14–7.31(m, 6H), 7.56–7.63(m, 3H), 7.87(d, 1H) | 375 |
| 95 | 2.51(m, 2H), 3.10(s, 3H), 3.21(m, 2H), 3.47(s, 3H), 5.05(s, 2H), 6.68(s, 1H), 7.05–7.48(m, 7H), 7.74–7.85(m, 2H), 8.09(d, 1H) | 389 |
| 96 | 2.58–3.50(brs, 8H), 5.16(s, 2H), 6.98(d, 1H), 7.08(s, 1H), 7.20–7.27(m, 2H), 7.47(t, 1H), 7.67(s, 1H), 7.71(t, 1H), 8.08(d, 1H), 8.15(d, 1H), 8.80(d, 1H) | 388 |
| 97 | 3.40(m, 4H), 3.70–4.45(brs, 8H), 3.11(s, 3H), 5.18(s, 2H), 6.98(d, 1H), 7.12(s, 1H), 7.17–7.22(m, 2H), 7.25(d, 1H), 7.30(d, 1H), 7.35(t, 1H), 7.62(d, 1H), 7.90(s, 1H) | 413 |
| 98 | (CD$_3$OD) 3.86(s, 2H), 4.83(s, 2H), 5.58(t, 1H), 6.37(d, 1H), 6.52(s, 1H), 6.81(s, 1H), 7.05–7.35(m, 9H), 7.51(d, 1H), 7.54(d, 1H), 7.58(d, 1H) | 432 |

EXAMPLE 99

Synthesis of 1-(1-methyl-1H-imidazol-5-yl)methyl-3-(morpholin-4-yl)carbonyl-4-(naphthalen-1-yl)-1H-pyrrole(99)

To the compound prepared in Example 85 was introduced trityl protecting group according to the same procedure as Preparation 28-1), and then the title compound was obtained in a yield of 55% by applying the procedures described in Preparation 29-2) and 29-3) using methyliodide.

$^1$H NMR(CDCl$_3$) δ2.80–3.45(m, 8H), 3.58(s, 3H), 5.19(s, 2H), 6.75(d, 1H), 7.18(d, 1H), 7.21(s, 1H), 7.35(d, 1H), 7.40–7.50(m, 3H), 7.72(d, 1H), 8.03(d, 1H)

FAB MS: 401 (M+1)

EXAMPLE 100

Synthesis of (S)-1-[1-(4-cyanobenzyl)-1H-imidazol-5yl]methyl-3-[N-(1-methoxycarbonyl-3-methylthio) propyl]carbamoyl-4-(naphthalen-1-yl)-1H-pyrrole (100)

100-1) 1-[1-(4-Cyanobenzyl)1H-imidazol-5-ylmethyl]-3-hydroxycarbonyl-4-(naphthalen-1-yl)-1H-pyrrole The title compound was obtained in a yield of 75% from the compounds prepared in Example 80-2) and Preparation 29-5) by sequentially applying the procedures of Example 73 and Example 80-4).

$^1$H NMR(CDCl$_3$+CD$_3$OD) δ5.02(s, 2H), 5.10(s, 2H), 6.76(s, 1H), 7.07(m, 2H), 7.25–7.82(m, 12H)

100-2) (S)-1-[1-(4-Cyanobenzyl)-1H-imidazol-5-yl] methyl-3-[N-(1-methoxycarbonyl-3-methylthio) propyl]carbamoyl-4-(naphthalen-1yl)-1H-pyrrole The title compound was obtained in a yield of 35% according to the same procedure as Example 80-5) except that the compound prepared in Example 100-1) was used.

$^1$H NMR(CDCl$_3$) δ1.85(s, 3H), 2.04(m, 1H), 2.13(m, 1H), 2.42(t, 2H), 3.61(s, 3H), 4.83(m, 1H), 5.02(s, 2H), 5.11(s, 2H), 6.63(s, 1H), 7.01(d, 2H), 7.13(d, 1H), 7.22–7.43 (m, 7H), 7.65–7.92(m, 4H)

FAB MS: 578 (M+1)

EXAMPLE 101

Synthesis of (S)-1-[1-(4-cyanobenzyl)-1H-imidazol-5-yl]methyl-3-[N-(1-hydroxycarbonyl-3-methylthio) propyl]carbamoyl-4-(naphthalen-1-yl)-1H-pyrrole (101)

Lithium salt of the title compound was obtained in a yield of 96% according to the similar procedure as Example 81 from the compound prepared in Example 100-2).

$^1$H NMR(CDCl$_3$+CD$_3$OD) δ1.82(s, 3H), 2.00(m, 1H), 2.11(m, 1H), 2.36(t, 2H), 4.82(m, 1H), 4.89(s, 2H), 5.02(s, 2H), 6.49(s, 1H), 6.88(d, 2H), 7.11(d, 1H), 7.17–7.32(m, 7H), 7.62–7.83(m, 4H)

FAB MS: 564(M+1)

EXAMPLES 102 and 103

The compounds represented in the following Table 5 were obtained according to the similar procedure as Examples 100 and 101.

TABLE 5

| COM. NO. | ¹H NMR δ | FAB MS (M + 1) |
|---|---|---|
| 102 | (CDCl₃) 0.67(d, 3H), 0.78(d, 3H), 0.82(m, 1H), 0.90(m, 1H), 1.10(m, 1H), 3.52(s, 3H), 4.32(m, 1H), 5.02(s, 2H), 5.17(s, 2H), 6.72(s, 1H), 6.83(s, 1H), 7.23–7.34(m, 3H), 7.41–7.92(m, 10H) | 560 |
| 103 | (CDCl₃ + CD₃OD) 0.62(d, 3H), 0.71(d, 3H), 0.79(m, 1H), 0.88(m, 1H), 0.98(m, 1H), 4.12(m, 1H), 4.97(s, 2H), 5.08(s, 2H), 6.77(s, 1H), 6.82(s, 1H), 7.14–7.30(m, 4H), 7.38–7.48(m, 9H) | 546 |

EXAMPLES 104 and 105

The compounds represented in the following Table 6 were obtained according to the similar procedure as Example 101.

TABLE 6

| COM. NO. | ¹H NMR (CDCl₃) δ | FAB MS (M + 1) |
|---|---|---|
| 104 | 1.95(brs, 2H), 2.33(brs, 1H), 2.95(brs, 5H), 4.93(s, 2H), 5.05(s, 2H), 6.62(s, 1H), 7.05(s, 1H), 7.11(d, 2H), 7.28(m, 2H), 7.51(m, 3H), 7.63(m, 3H), 7.81–7.88(m, 2H), 7.95(d, 1H) | 502 |
| 105 | 1.12(brs, 2H), 1.88(brs, 2H), 1.90(s, 3H), 2.95(brs, 2H), 3.34(brs, 2H), 4.97(s, 2H), 5.07(s, 2H), 6.60(s, 1H), 7.02(s, 1H), 7.10(d, 2H), 7.29(m, 2H), 7.46(m, 3H), 7.60(m, 3H), 7.80(d, 1H), 7.85(d, 1H), 7.97(d, 1H) | 515 |

EXAMPLE 106

Synthesis of 1-[2-(1H-imidazol-1-yl)ethyl]-3-(morpholin-4-yl)carbonyl-4(naphthalen-1-yl)-1H-pyrrole(106)

106-1) 2-(1H-Imidazol-1-yl)ethyl p-tosylate 0.24 g(2.41 mmol) of 2-(1H-imidazol-1-yl)ethanol and 0.55 g(2.88 mmol) of tosylchloride were dissolved in 20 ml of dichloromethane, 0.67 ml of triethylamine was slowly added thereto at 0° C., and the mixture was stirred at room temperature for 4 hours. The organic solvent was removed under reduced pressure. The residue was dissolved in 10 ml of ethyl acetate, washed sequencially with 1N hydrochloric acid solution, saturated sodium bicarbonate solution and aqueous sodium chloride solution, dried over magnesium sulfate and then concentrated. The residue was subjected to column chromatography(eluent: dichloromethane/methanol=20/1, v/v) to give 0.30 g(1.13 mmol, Yield 47%) of the title compound.

¹H NMR(CDCl₃) δ2.42(s, 3H), 4.17–4.28(m, 4H), 6.88(s, 1H), 6.99(s, 1H), 7.29(d, 2H), 7.45(s, 1H), 7.64(d, 2H)

106-2) 3-Hydroxycarbonyl-4-(naphthalen-1-yl)-1H-pyrrole

The title compound was obtained in a yield of 80% by hydrolyzing the compound prepared in Example 80-2) according to the same procedure as Example 80-4).

¹H NMR (CDCl₃+CD₃OD) δ7.12(m, 3H), 7.20–7.31(m, 3H), 7.50(d, 1H), 7.68(d, 1H), 7.76(d, 1H)

106-3) 3-(Morpholin-4-yl)carbonyl-4-(naphthalen-1-yl)-1H-pyrrole

The title compound was obtained in a yield of 99% according to the same procedure as Example 80-5) from the compound prepared in Example 106-2) and morpholine.

¹H NMR (CDCl₃) δ2.68–3.62(brs, 8H), 6.88(s, 1H), 7.20 (s, 1H), 7.30–7.62(m, 4H), 7.78(d, 1H), 7.85(d, 1H), 8.08(d, 1H), 10.34(s, 1H)

106-4) 1-[2-(1H-Imidazol-1-yl)ethyl]-3-(morpholin-4-yl)carbonyl-4-(naphthalen-1-yl)-1H-pyrrole The title compound was obtained in a yield of 51% by reacting the compound prepared in Example 106-1) with the compound prepared in Example 106-3) according to the same procedure as Example 44-3).

¹H NNR (CDCl₃) δ2.20–3.72(brs, 12H), 7.20(s, 1H), 7.40–7.55(m, 8H), 7.82(d, 1H), 7.88(d, 1H), 8.05(d, 1H)

FAB MS: 401 (M+1)

EXAMPLE 107

Synthesis of (S)-1-[3-(1H-imidazol-4-yl)propyl[-3-[N-(1-methoxycarbonyl-3-methylthio)propyl)] carbamoyl-4-(naphthalen-1-yl)-1H-pyrrole(107)

107-1) 3-Ethoxycarboxyl-4-(naphthalen-1-yl)-1-[3-(1-trityl-1H-imidazol-4-yl)allyl]-1H-pyrrole The title compound was obtained in a yield of 85% by reacting the compound prepared in Example 80-2) with the compound prepared in Preparation 30-4) according to the same procedure as Example 44-3).

¹H NMR (CDCl₃) δ0.82(t, 3H), 3.95(q, 2H), 4.67(s, 2H), 6.23(d, 1H), 6.47(m, 1H), 6.63(s, 1H), 7.02(s, 1H), 7.25–7.81(m, 24H)

107-2) 3-Ethoxycarbonyl-4-(naphthalen-1-yl)-1-[3-(1-trityl-1H-imidazol-4-yl)propyl]-1H-pyrrole 300 mg(0.49 mmol) of the compound prepared in Example 107-1) was dissolved in 2 ml of methanol, catalytic amount of Pd/C was added thereto, and the mixture was stirred for 1 hour under hydrogen atmosphere. The mixture was filtered to remove the catalyst and the solvent therein was removed under reduced pressure. The residue was subject to column chromatography(eluent: dichloromethane/methanol=98/2, v/v) to give 246 mg(0.40 mmol, Yield 82%) of the title compound.

¹H NMR (CDCl₃) δ0.92(t, 3H), 2.22(m, 2H), 2.73(t, 2H), 4.01(m, 4H), 6.70(s, 1H), 6.82(s, 1H), 7.32–7.73(m, 21H), 7.91(m, 3H)

107-3) (S)-1-[3-(1H-Imidazol-4-yl)propyl]-3-[N-(1-methoxycarbonyl-3-methylthio)propyl]carbamoyl-4-(naphthalen-1-yl)-1H-pyrrole The compound prepared in Example 107-2) was treated according to the procedures of Example 44-4) and 80-4) to eliminate the trityl group and hydrolyze. Then, the product thus obtained was reacted with (L)-methionine methylester according to the same procedure as Example 80-5) to give the title compound in a yield of 29%.

¹H NMR (CDCl₃) δ1.65(m, 2H), 1.90(s, 3H), 2.12(m, 2H), 2.31(m, 2H), 2.73(m, 2H), 3.54(s, 3H), 4.02(m, 2H), 4.56(m, 1H), 5.77(d, 1H), 6.72(s, 1H), 6.90(s, 1H), 7.42–7.67(m, 7H), 7.82–8.01(m, 5H)

FAB MS: 491(M+1)

EXAMPLE 108

Synthesis of (S)-3-[N-(1-hydroxycarbonyl-3-methylthio)propyl]carbamoyl-1-[3-(1H-imidazol-4-yl)propyl]-4-naphthalen-1-yl)-1H-pyrrole(108)

The title compound was obtained in a yield of 95% according to the same procedure as Example 81 except that the compound prepared in Example 107-3) was used.

¹H NMR (CDCl₃) δ1.57(m, 2H), 1.88(s, 3H), 2.08(m, 2H), 2.29(m, 2H), 2.77(m, 2H), 4.12(m, 2H), 4.49(m, 1H), 5.69(d, 1H), 6.77(s, 1H), 6.92(s, 1H), 7.34–7.58(m, 7H), 7.80–7.89(m, 5H)

FAB MS: 477(M+1)

EXAMPLE 109

Synthesis of 1-[3-(1H-imidazol-4-yl)propyl]-3-(morpholin-4-yl)carbonyl-4-(naphthalen-1-yl)-1H-pyrrole(109)

The title compound was obtained in a yield of 42% according to the same procedure as Example 107-3) except that morpholine was used to the compound prepared in Example 107-2).

¹H NMR (CDCl₃) δ2.16(m, 2H), 2.35(brs, 2H), 2.63(m, 2H), 2.80–3.50(brs, 6H), 3.54(s, 3H), 3.96(m, 2H), 6.74(d, 1H), 6.76(s, 1H), 7.07(s, 1H), 7.33(t, 1H), 7.36–7.50(m, 4H), 7.76(d, 1H), 7.84(d, 1H), 8.08(d, 1H)

FAB MS: 415(M+1)

EXAMPLE 110

Synthesis of 1-[1-4-cyanobenzyl)1H-imidazol-5-yl]methyl-3-[N-(2-methoxyethyl)-N-methyl]carbamoyl-4-(naphthalen-1-yl)-1H-pyrrole(110)

110-1) 3-[N-(2-Methoxyethyl)-N-methyl]carbamoyl-4-(naphthalen-1-yl)-1 H-pyrrole 100 mg(0.42 mmol) of the compound prepared in Example 106-2) and 38 mg (0.4 mmol) of N-(2-methoxyethyl)-N-methylamine were reacted according to the similar procedure as Example 80-5) to give 110 mg(0.35 mmol, Yield 85%) of the title compound.

¹H NMR (CDCl₃) δ2.21(s, 3H), 2.64(brs, 1H), 2.75(brs, 1H), 3.02(s, 3H), 3.13(brs, 1H), 3.32(brs, 1H), 6.72(s, 1H), 7.05(m, 2H), 7.21(m, 2H), 7.54(m, 1H), 7.78(m, 2H), 8.04 (d, 1H), 8.78(brs, 1H)

110-2) 1-[1-(4-Cyanobenzyl)-1H-imidazol-5-yl]methyl-3-[N-(2-methoxyethyl)-N-methyl]carbamoyl-4-(naphthalen-1-yl)-1H-pyrrole 98 mg(0.32 mmol) of the compound prepared in Example 110-1) and 85 mg(0.32 mmol) of the compound prepared in Preparation 29-5) were reacted according to the similar procedure as Example 44-3) to give 115 mg(0.23 mmol, Yield 72%) of the title compound.

¹H NMR (CDCl₃) δ2.41(s, 3H), 2.75(brs, 2H), 3.07(s, 3H), 3.17(brs, 1H), 3.32(brs, 1H), 4.91(s, 2H), 5.11(s, 2H), 6.71(s, 1H), 7.05(s, 1H), 7.17(d, 1H), 7.40–7.68(m, 9H), 7.78(d, 1H), 7.88(d, 1H), 8.06(d, 1H)

FAB MS: 504 (M+1)

EXAMPLE 111

Synthesis of 1-[1-(4-bromobenzyl)-1H-imidazol-5-yl]methyl-3-[N-(2-methoxyethyl)-N-methyl]carbamoyl-4-(naphthalen-1-yl)-1H-pyrrole(111)

105 mg(0.29 mmol) of the compound prepared in Example 110-1) and 78 mg(0.29 mmol) of the compound prepared in Preparation 32-2) were reacted according to the similar procedure as Example 44-3) to give 121 mg(0.21 mmol, Yield 75%) of the title compound.

¹H NMR (CDCl₃) δ2.37(s, 3H), 2.72(brs, 2H), 3.04(s, 3H), 3.15(brs, 1H), 3.31(brs, 1H), 4.95(s, 2H), 5.10(s, 2H), 6.67(s, 1H), 7.11(s, 1H), 7.23–7.65(m, 10H), 7.81(d, 1H), 7.89(d, 1H), 8.02(d, 1H)

FAB MS: 557 (M+1)

EXAMPLE 112

Synthesis of 1-[1-(4-bromobenzyl)-1H-imidazol-5-yl]methyl-3-(morpholin-4-yl)carbonyl-4-(naphthalen-1-yl)-1H-pyrrole(112)

100 mg(0.33mmol) of the compound prepared in Example 106-3) and 105 mg(33 mmol) of the compound prepared in Preparation 32-2) were reacted according to the similar procedure as Example 44-3) to give 130 mg(0.23 mmol, Yield 71%) of the title compound.

¹H NMR (CDCl₃) δ2.04(brs, 2H), 2.25(brs, 1H), 3.03(brs, 5H), 4.93(s, 2H), 5.07(s, 2H), 6.62(s, 1H), 7.10(m, 3H), 7.29(m, 2H), 7.41(m, 3H), 7.60(m, 3H), 7.81(d, 1H), 7.89(d, 1H), 8.01(d, 1H)

FAB MS: 555 (M+1)

EXAMPLE 113

Synthesis of 1-[1-(4-cyanobenzyl)-1H-imidazol-5-yl]methyl-3-(morpholin-4-yl)thiocarbonyl-4-(naphthalen-1-yl)-1H-pyrrole (113)

20 mg(0.04 mmol) of the compound prepared in Example 104 and 18 mg of 2,4-bis(phenylthio)-1,3-dithia-2,4-diphosphatan-2,4-disulfide were dissolved in 1 ml of tetrahydrofuran, and the mixture was stirred at room temperature for 3 hours. To the reaction solution was added 2 ml of saturated sodium bicarbonate solution. The resulting mixture was extracted with ethyl acetate and dried over anhydrous sodium sulfate. The organic solvent was removed under reduced pressure and the residue was subjected to column chromatography(eluent: dichloromethane/methanol =9/1, v/v) to give 9 mg(0.017 mmol, Yield 43%) of the title compound.

¹H NMR ((CDCl₃) δ1.88(brs, 2H), 2.64(brs, 6H), 4.86(s, 2H), 5.01(s, 2H), 6.67(s, 1H), 7.14(m, 3H), 7.26–7.58(m, 8H), 7.81(m, 2H), 8.03(d, 1H)

FAB MS: 518 (M+1)

EXAMPLE 114

Synthesis of 3-[N-2-methoxyethyl)-N-methyl[carbamoyl-1-(1-methyl-1H-imidazol-5-yl]methyl-4-(naphthalen-1-yl)-1H-pyrrole(114) 114-1) 4-(Naphthalen-1-yl)-1H-pyrrole-3-carboxylic acid 2.64 g(10 mmol) of the compound prepared in Example 80-2) was dissolved in 50 ml of 50% ethanol, and 2.24 g(40 mmol) of potassium hydroxide was added thereto. The reaction mixture was refluxed for 7 hours, cooled down to room temperature, adjusted to pH 4–5, extracted with ethyl acetate, dried over anhydrous sodium sulfate. The solvent was removed under reduced pressure to obtain 1.62 g(8.1 mmol, Yield 81%) of the title compound. The product thus obtained was directly used in the next reaction without purification.

¹H NMR(CDCl₃) δ6.60(s, 1H), 7.32–7.49(m, 5H), 7.54(s, 1H), 7.84(m, 2H), 9.92(s, 1H)

FAB (M+H): 236

114-2) 3-[N-(2-Methoxyethyl)-N-methyl]carbamoyl-4-(naphthalen-1-yl)-1H-pyrrole 234 mg(1 mmol) of the compound prepared in Example 114-1) was dissolved in 2 ml of dimethylformamide, and then 230 mg(1.2 mmol) of EDC, 101 mg (1 mmol) of triethylamine and 162 mg(1.2 mmol) of HOBT were added thereto. The resulting mixture was stirred at 0° C. for 5 minutes. To the reaction solution was added 124 mg(1 mmol) of N-(2-methoxyethyl)-N-methylamine hydrochloride, which was then stirred at room temperature for 5 hours. The solvent was removed under reduced pressure and then 10 ml of saturated potassium carbonate solution was added to the residue. The resulting solution was extracted with 20 ml of ethyl acetate, washed with 10 ml of 1N aqueous hydrochloric acid solution, washed with aqueous sodium chloride solution and water, dried over anhydrous sodium sulfate and concentrated to give 246 mg(0.8 mmol) of the title compound.

$^1$H NMR(CDCl$_3$) δ2.46(s, 2H), 2.80–3.40(m, 7H), 3.40(s, 1H), 6.80(s, 1H), 7.00(s, 1H), 7.42(m, 4H), 7.73(d, 1H), 7.81(d, 1H), 8.17(d, 1H), 10.66 (s, 1H)

FAB (M+H): 309

114-3) 1-(1-Methyl-1H-imidazol-5-yl)methyl-3-[N-(2-methoxyethyl)-N-methyl]carbamoyl-4-(naphthalen-1-yl)-1H-pyrrole 618 mg(2.0 mmol) of the compound prepared in Example 114-2) was dissolved in 10 ml of dimethylformamide, 264 mg(6.6 mmol) of sodium hydride(60%) was added thereto at 0° C. and then the mixture was stirred for 5 minutes. To the mixture was added 367 mg(2.2 mmol) of 5-chloromethyl-1-methylimidazole hydrochloride and the whole mixture was stirred at room temperature for 5 hours. The solvent was removed by distillation under reduced pressure and 10 ml of water was added to the residue. The mixture was then extracted twice with 20 ml of ethyl acetate, dried over anhydrous sodium sulfate, concentrated, and subjected to silica gel column chromatography(eluent: dichloromethane/methanol=90/10, v/v) to obtain 644 mg(Yield 80%) of the title compound.

$^1$H NMR((CDCl$_3$) δ2.42(s, 2H), 2.71(m, 1H), 3.10(brs, 6H), 3.30(brs, 1H), 3.50(s, 3H), 5.09(s, 2H), 6.70(s, 1H), 7.05(s, 1H), 7.15(s, 1H), 7.30–7.49 (m, 4H), 7.72(d, 1H), 7.84(d, 2H), 8.08(d, 1H)

FAB (M+H): 403

EXAMPLE 115

Synthesis of 1-(1-isobutyl-1H-imidazol-5-yl)methyl-3-[N-(2-methoxyethyl)-N-methyl]carbamoyl-4-(naphthalen-1-yl)-1H-pyrrole (115)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 459 mg(2.2 mmol) of the compound prepared in Preparation 33-2) was added to the mixture, which was then stirred at room temperature for 5 hours. The solvent was removed by distillation under reduced pressure and 10 ml of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 667 mg(Yield 75%) of the title compound.

$^1$H NMR(CDCl$_3$) δ0.90(d, 6H), 1.75(m, 1H), 2.41(brs, 2H), 2.72(brs, 1H), 3.01(brs, 6H), 3.32(brs, 1H), 3.62(d, 2H), 5.13(s, 2H), 6.72(s, 1H), 7.09(s, 1H), 7.19(s, 1H), 7.30–7.49(m, 4H), 7.78(d, 1H), 7.84(d, 2H), 8.08 d, 1H)

FAB (M+H): 445

EXAMPLE 116

Synthesis of 1-(1-cyclohexylmethyl-1H-imidazol-5-yl)methyl-3-[N-(2-methoxyethyl)-N-methyl] carbamoyl-4-(naphthalen-1-yl)-1H-pyrrole (116)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 647 mg(2.2 mmol) of the compound prepared in Preparation 34-2) was added to the mixture, which was then stirred at room temperature for 5 hours. The solvent was removed by distillation under reduced pressure and 10 ml of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 726 mg(Yield 75%) of the title compound.

$^1$H NMR(CDCl$_3$) δ0.87(m, 2H), 1.12(m, 3H), 1.30(brs, 1H), 1.40–1.80(m, 5H), 2.41(brs, 2H), 2.72(brs, 1H), 3.01 (brs, 6H), 3.32(brs, 1H), 3.63(d, 2H), 5.09(s, 2H), 6.72(s, 1H), 7.09(s, 1H), 7.19(s, 1H), 7.25(s, 1H), 7.30–7.49 (m, 3H), 7.78(d, 1H), 7.83(d, 2H), 8.08(d, 1H)

FAB (M+H): 485

EXAMPLE 117

Synthesis of 3-[N-(2-methoxyethyl)-N-methyl] carbamoyl-4-(naphthalen-1-yl)-1-(1-pentyl-1H-imidazol-5-yl)methyl-1H-pyrrole (117)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 429 mg(2.2 mmol) of the compound prepared in Preparation 35-2) was added to the mixture, which was then stirred at room temperature for 5 hours. The solvent was removed by distillation under reduced pressure and 10 ml of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 714 mg(Yield 78%) of the title compound.

$^1$H NMR((CDCl$_3$) δ0.90(t, 3H), 1.08(brs, 2H), 1.30(m, 2H), 1.45(m, 2H), 2.41(brs, 2H), 2.72(brs, 1H), 3.01(brs, 6H), 3.32(brs, 1H), 3.63(t, 2H), 5.09 (s, 2H), 6.72(s, 1H), 7.09(s, 1H), 7.19(s, 1H), 7.25(s, 1H), 7.30–7.49(m, 3H), 7.78(d, 1H), 7.83(d, 2H), 8.08(d, 1H)

FAB (M+H): 459

EXAMPLE 118

Synthesis of 3-[N-(2-methoxyethyl)-N-methyl] carbamoyl-4-(naphthalen-1-yl)-1-(1-octyl-1H-imidazol-5-yl)methyl-1H-pyrrole(118)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 508 mg(2.2 mmol) of the compound prepared in Preparation 36-2) was added to the mixture, which was then stirred at room temperature for 5 hours. The solvent was removed by distillation under reduced pressure and 10 ml of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 760 mg(Yield 76%) of the title compound.

$^1$H NMR((CDCl$_3$) δ0.87(t, 3H), 1.17(brs, 2H), 1.30(brs, 10H), 1.44(m, 2H), 2.41(brs, 2H), 2.72(brs, 1H), 3.01(brs, 6H), 3.32(brs, 1H), 3.62(t, 2H), 5.09(s, 2H), 6.72(s, 1H), 7.09(s, 1H), 7.19(s, 1H), 7.25(s, 1H), 7.30–7.49 (m, 3H), 7.78(d, 1H), 7.83(d, 2H), 8.08(d, 1H)

FAB (M+H): 501

EXAMPLE 119

Synthesis of 1-(1-decyl-1H-imidazol-5-yl)methyl-3-[N-(2-methoxyethyl)-N-methyl]carbamoyl-4-(naphthalen-1-yl)-1H-pyrrole (119)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 567 mg(2.2 mmol) of the compound prepared in Preparation 37-2) was added to the mixture, which was then stirred at room temperature for 5 hours. The solvent was removed by distillation under reduced pressure and 10 ml of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 667 mg(Yield 75%) of the title compound.

$^1$H NMR(CDCl$_3$) δ0.87(t, 3H), 1.17(brs, 2H), 1.30(brs, 14H), 1.44(m, 2H), 2.41(brs, 2H), 2.72(brs, 1H), 3.01(brs, 6H), 3.32(brs, 1H), 3.62(t, 2H), 5.09(s, 2H), 6.72(s, 1H), 7.09(s, 1H), 7.19(s, 1H), 7.25(s, 1H), 7.30–7.49 (m, 3H), 7.78(d, 1H), 7.83(d, 2H), 8.08(d, 1H)

FAB (M+H): 529

EXAMPLE 120

Synthesis of 3-[N-(2-methoxyethyl)-N-methyl]carbamoyl-1-[1-(3-methylbutyl)-1H-imidazol-5-yl]methyl-4-(naphthalen-1-yl)-1H-pyrrole(120)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 429 mg(2.2 mmol) of the compound prepared in Preparation 38-2) was added to the mixture, which was then stirred at room temperature for 5 hours. The solvent was removed by distillation under reduced pressure and 10 ml of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 667 mg(Yield 75%) of the title compound.

$^1$H NMR((CDCl$_3$) δ0.91(d, 6H), 1.31(q, 2H), 1.67(m, 1H), 2.41(brs, 2H), 2.72(brs, 1H), 3.01(brs, 6H), 3.32(brs, 1H), 3.62(t, 2H), 5.09(s, 2H), 6.72 (s, 1H), 7.09(s, 1H), 7.19(s, 1H), 7.25(s, 1H), 7.30–7.49(m, 3H), 7.78(d, 1H), 7.83(d, 2H), 8.08(d, 1H)

FAB (M+H): 459

EXAMPLE 121

Synthesis of 1-[1-(2-methoxyethyl)-1H-imidazol-5-yl]methyl-3-[N-(2-methoxyethyl)-N-methyl]carbamoyl-4-(naphthalen-1-yl)-1H-pyrrole (121)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 429 mg(2.2 mmol) of the compound prepared in Preparation 39-2) was added to the mixture, which was then stirred at room temperature for 5 hours. The solvent was removed by distillation under reduced pressure and 10 ml, of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 667 mg(Yield 75%) of the title compound.

$^1$H NMR(CDCl$_3$) δ2.41(brs, 2H), 2.72(brs, 1H), 3.01(brs, 6H), 3.32(brs, 1H), 3.37(s, 3H), 3.45(t, 2H), 3.63(t, 2H), 5.09(s, 2H), 6.72(s, 1H), 7.09 (s, 1H), 7.19(s, 1H), 7.25(s, 1H), 7.30–7.49(m, 3H), 7.78(d, 1H), 7.83(d, 2H), 8.08(d, 1H)

FAB (M+H): 447

EXAMPLE 122

Synthesis of 3-[N-(2-methoxyethyl)-N-methyl]carbamoyl-1-[1-(3-methoxypropyl)-1H-imidazol-5-yl]methyl-4-(naphthalen-1-yl)-1H-pyrrole (122)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 459 mg(2.2 mmol) of the compound prepared in Preparation 40-2) was added to the mixture, which was then stirred at room temperature for 5 hours The solvent was removed by distillation under reduced pressure and 10 ml of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 683 mg(Yield 70%) of the title compound.

$^1$H NMR(CDCl$_3$) δ1.71(m, 2H), 2.41(brs, 2H), 2.72(brs, 1H), 3.01(brs, 6H), 3.31(s, 3H), 3.32(brs, 1H), 3.48(t, 2H), 3.63(t, 2H), 5.09(s, 2H), 6.72 (s, 1H), 7.09(s, 1H), 7.19(s, 1H), 7.25(s, 1H), 7.30–7.49(m, 3H), 7.78(d, 1H), 7.83(d, 2H), 8.08(d, 1H)

FAB (M+H): 461

EXAMPLE 123

Synthesis of 1-[1-(3-ethoxypropyl)-1H-imidazol-5-yl]methyl-3-[N-(2-methoxyethyl)-N-methyl]carbamoyl-4-(naphthalen-1-yl)-1H-pyrrole (123)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 459 mg(2.2 mmol) of the compound prepared in Preparation 41-2) was added to the mixture, which was then stirred at room temperature for 5 hours. The solvent was removed by distillation under reduced pressure and 10 ml of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 712 mg(Yield 71%) of the title compound.

$^1$H NMR(CDCl$_3$) δ1.20(t, 3H), 1.70(m, 2H), 2.41(brs, 2H), 2.72(brs, 1H), 3.01(brs, 6H), 3.32(brs, 1H), 3.50(m, 4H), 3.63(t, 2H), 5.09(s, 2H), 6.72(s, 1H), 7.09(s, 1H), 719(s, 1H), 7.25(s, 1H), 7.30–7.49(m, 3H), 7.78(d, 1H), 7.83(d, 2H), 8.08(d, 1H)

FAB (M+H): 475

EXAMPLE 124

Synthesis of 1-[1-(3-isopropoxypropyl)-1H-imidazol-5-yl]methyl-3-[N-(2-methoxyethyl)-N-methyl]carbamoyl-4-(naphthalen-1-yl)-1H-pyrrole (124)

618 mg(2.0 mmol) of the compound prepared in Example 114-2) was dissolved in 10 ml of dimethylformamide, 264 mg(6.6 mmol) of sodium hydride(60%) was added thereto at 0° C., and the mixture was stirred for 5 minutes. 459 mg(2.2 mmol) of the compound prepared in Preparation 42-2) was added to the mixture, which was then stirred at room temperature for 5 hours. The solvent was removed by distillation under reduced pressure and 10 ml of water was added to the residue. The resulting mixture was extracted twice with 20 ml of ethyl acetate, dried over anhydrous sodium sulfate, concentrated and subjected to silica gel column chromatography(eluent: dichloromethane/methanol=90/10, v/v) to obtain 751 mg(Yield 73%) of the title compound.

$^1$H NMR(CDCl$_3$) δ1.16(d, 6H), 1.70(m, 2H), 2.41(brs, 2H), 2.72(brs, 1H), 3.01(brs, 6H), 3.32(brs, 1H), 3.45–3.55 (m, 3H), 3.63(t, 2H), 5.09(s, 2H), 6.72(s, 1H), 7.09(s, 1H), 7.19(s, 1H), 7.25(s, 1H), 7.30–7.49(m, 3H), 7.78 (d, 1H), 7.83(d, 2H), 8.08(d, 1H)

FAB (M+H): 489

EXAMPLE 125

Synthesis of 1-[1-(4-bromobenzyl)-1H-imidazol-5-yl]methyl-3-[4-methylpiperazin-1-yl]carbonyl-4-(naphthalen-1-yl)-1H-pyrrole(125)

125-1) 3-[4-Methylpiperazin-1-yl]carbonyl-4-(naphthalen-1-yl)-1H-pyrrole

The title compound was obtained in a yield of 90% according to the same procedure as Example 80-5) from the compound prepared in Example 106-2) and 4-methylpiperazine.

$^1$H NMR (CDCl$_3$) δ1.15(br, 2H), 1.87(br, 2H), 1.92(s, 3H), 2.96(br, 2H), 3.41(br, 2H), 6.83(s, 1H), 7.09(s, 1H), 7.36–7.42(m, 4H), 7.73(d, 1H), 7.75 (d, 1H), 8.10(d, 1H), 10.52(s, 1H)

FAB(M+H): 320

125-2) 1-[1-(4-Bromobenzyl)-1H-imidazol-5-yl]methyl-3-[4-methylpiperazin-1-yl]carbonyl-4-(naphthalen-1-yl)-1H-pyrrole 64 mg(0.2 mmol) of the compound prepared in Example 125-1) was dissolved in 2 ml of dimethylformamide, 26 mg(0.66 mmol) of sodium hydride was added thereto at 0° C., and the mixture was stirred for 5 minutes. 66 mg(0.22 mmol) of the compound prepared in Preparation 32-2) was added to the mixture, which was then stirred at room temperature for 5 hours. The solvent was removed by distillation under reduced pressure and 10 ml of water was added to the residue. The resulting mixture was extracted twice with 10 mg of ethyl acetate, dried over anhydrous sodium sulfate, concentrated and subjected to silica gel column chromatography(eluent: dichloromethane/methanol=90/10, v/v) to obtain 91 mg(Yield 80%) of the title compound.

$^1$H NMR (CDCl$_3$) δ1.15(br, 2H), 1.77(br, 2H), 1.86(s, 3H), 2.82(br, 2H), 3.28(br, 2H), 4.87(s, 2H), 3.88(s, 2H), 6.55(s, 1H), 6.79(d, 2H), 6.97(s, 1H), 7.16(s, 1H), 7.36(d, 1H), 7.36–7.39(m, 5H), 7.50(s, 1H), 7.71(d, 1H), 7.79(d, 1H), 7.93(d, 1H)

FAB(M+H): 568

EXAMPLE 126

Synthesis of 1-[1-(4-chlorobenzyl)-1H-imidazol-5-yl]methyl-3-[4-methylpiperazin-1-yl]carbonyl-4-(naphthalen-1-yl)-1H-pyrrole(126)

64 mg(0.2 mmol) of the compound prepared in Example 125-1) was dissolved in 2 ml of dimethylformamide, 26 mg(0.66 mmol) of sodium hydride was added thereto at 0° C., and the mixture was stirred for 5 minutes. 55 mg(0.22 mmol) of 1-(4-chlorobenzyl)-5-chloromethylimidazole hydrochloride prepared according to the similar procedure as Preparation 32 was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=90/10, v/v) to obtain 77 mg(Yield 57%) of the title compound.

$^1$H NMR (CDCl$_3$) δ1.15(br, 2H), 1.77(br, 2H), 1.86(s, 3H), 2.82(br, 2H), 3.28(br, 2H), 4.92(s, 2H), 4.95(s, 2H), 6.60(s, 1H), 6.91(d, 2H), 6.01(s 1H), 7.22(s, 1H), 7.26–7.36 (m, 3H), 7.36–7.48(m, 2H), 7.56(s, 1H), 7.77(d, 1H), 7.82(d, 1H), 7.93(d, 1H)

FAB(M+H): 524

EXAMPLE 127

Synthesis of 1-[1-(4-fluorobenzyl)-1H-imidazol-5-yl]methyl-3-[N-(2-methoxyethyl)-N-methyl]carbamoyl-4-(naphthalen-1-yl)-1H-pyrrole(127)

62 mg(0.2 mmol) of the compound prepared in Example 114-2) was dissolved in 2 ml of dimethylformamide, 26 mg(0.66 mmol) of sodium hydride was added thereto at 0° C., and the mixture was stirred for 5 minutes. 51 mg(0.22 mmol) of 1-(4-fluorobenzyl)-5-chloromethylimidazole hydrochloride prepared according to the similar procedure as Preparation 32 was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=90/10, v/v) to obtain 77 mg(Yield 80%) of the title compound.

$^1$H NMR(CDCl$_3$) δ2.12(br, 3H), 2.72(br, 1H), 3.00–3.20 (m, 5H), 3.32(s, 1H), 4.97(s, 2H), 3.98(s, 2H), 6.64(s, 1H), 6.95–7.10(m, 5H), 7.21(s, 1H), 7.33(m, 1H), 7.40–7.51(m, 3H), 7.66(s, 1H), 7.74(d, 1H), 7.81(d, 1H), 8.08(d, 1H)

FAB(M+H):497

EXAMPLE 128

Synthesis of 1-[1-(4-fluorobenzyl)-1H-imidazol-5-yl]methyl-3-[4-methylpiperazin-1-yl]carbonyl-4-(naphthalen-1-yl)-1H-pyrrole(128)

64 mg(0.2 mmol) of the compound prepared in Example 125-1) was dissolved in 2 ml of dimethylformamide, 26 mg(0.66 mmol) of sodium hydride was added thereto at 0° C., and the mixture was stirred for 5 minutes. 51 mg(0.22 mmol) of 1-(4-fluorobenzyl)-5-chloromethylimidazole hydrochloride prepared according to the similar procedure as Preparation 32 was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/ methanol=90/10, v/v) to obtain 79 mg(Yield 80%) of the title compound.

$^1$H NMR (CDCl$_3$) δ1.15(br, 2H), 1.77(br, 2H), 1.86(s, 3H), 2.82(br, 2H), 3.28(br, 2H), 4.92(s, 2H), 4.97(s, 2H), 6.60(s, 1H), 6.93(d, 2H), 6.01(s, 1H), 7.22(s, 1H), 7.25–736 (m, 3H), 7.36–7.47(m, 2H), 7.57(s, 1H), 7.78(d, 1H), 7.82(d, 1H), 7.93(d, 1H)

FAB (M+H) 508

Preparation 43

Synthesis of 5-chloromethyl-1-(4-methoxybenzyl)-imidazole hydrochloride 43-1) 5-Hydroxymethyl-1-(4-methoxybenzyl) imidazole The title compound was obtained in a yield of 30% according to the same procedure as Preparation 31-1) using dihydroxyacetone and 4-methoxybenzylamine hydrochloride as starting materials.

$^1$H NMR(CDCl$_3$+CD$_3$OD) δ3.75(s, 3H), 4.50(s, 2H), 5.15(s, 2H), 6.86(m, 3H), 7.08(d, 2H), 7.42(s, 1H)

FAB(M+H):219

43-2) 5-Chloromethyl-1-(4-methoxybenzyl) imidazole hydrochloride

The title compound was obtained in a yield of 95% according to the same procedure as Preparation 28-2) except that the compound prepared in Preparation 43-1) was used as a starting material.

Preparation 44

Synthesis of 5-chloromethyl-1-(3-chlorobenzyl) imidazole hydrochloride 44-1) 5-Hydroxymethyl-1-(3-chlorobenzyl) imidazole The title compound was obtained in a yield of 60% according to the same procedure as Preparation 31-1) using dihydroxyacetone and 3-chlorobenzylamine hydrochloride as starting materials.

$^1$H NMR(CDCl$_3$+CD$_3$OD) δ3.81(s, 3H), 4.47(s, 2H), 5.25(s, 2H), 6.99(s, 1H), 7.05(m, 1H), 7.14(s, 1H), 7.30(d, 2H), 7.61(s, 1H)

FAB(M+H):239.5

44-2) 5-Chloromethyl-1-(3-chlorobenzyl)imidazole hydrochloride

The title compound was obtained in a yield of 92% according to the same procedure as Preparation 28-2) except that the compound prepared in Preparation 44-1) was used as a starting material.

Preparation 45

Synthesis of 5-chloromethyl-1-(2-chlorobenzyl) imidazole hydrochloride 45-1) 5-Hydroxymethyl-1-(2-chlorobenzyl) imidazole The title compound was obtained in a yield of 60% according to the same procedure as Preparation 31-1) using dihydroxyacetone and 2-chlorobenzylamine hydrochloride as sting materials.

$^1$H NMR(CDCl$_3$) δ3.24(s, 2H), 4.44(s, 2H), 5.26(s, 2H), 6.78(d, 1H), 6.90(s, 1H), 7.15(m, 1H), 7.21(m, 1H), 7.34(d, 1H), 7.38(s, 1H)

FAB(M+H):239.5

45-2) 5-Chloromethyl-1-(2-chlorobenzyl)imidazole hydrochloride

The title compound was obtained in a yield of 92% according to the same procedure as Preparation 28-2) except that the compound prepared in Preparation 45-1) was used as a starting material.

Preparation 46

Synthesis of 5-chloromethyl-1-(2-fluorobenzyl) imidazole hydrochloride 46-1) 5-Hydroxymethyl-1-(2-fluorobenzyl)imidazole The title compound was obtained in a yield of 71% according to the same procedure as Preparation 31-1) using dihydroxyacetone and 2-fluorobenzylamine hydrochloride as starting materials.

$^1$H NMR(CDCl$_3$) δ3.25(s, 2H), 4.45(s, 2H), 5.27(s, 2H), 6.79(d, 1H), 7.17(m, 1H), 7.26(m, 1H), 7.35(d, 1H), 7.38(s, 1H)

FAB(M+H): 223

46-2) 5-Chloromethyl-1-(2-fluorobenzyl)imidazole hydrochloride

The title, compound was obtained in a yield of 93% according to the same procedure as Preparation 28-2) except that the compound prepared in Preparation 46-1) was used as a starting material.

Preparation 47

Synthesis of 5-chloromethyl-1-(4-methylbenzyl) imidazole hydrochloride 47-1) 5-Hydroxymethyl-1(4-methylbenzyl) imidazole The title compound was obtained in a yield of 65% according to the same procedure as Preparation 31-1) using dihydroxyacetone and 4-methylbenzylamine hydrochloride as starting materials.

$^1$H NMR(CDCl$_3$) δ2.32(s, 3H), 4.50(s, 2H), 5.19(s, 2H), 6.95(s, 1H), 7.05(d, 2H), 7.15(d, 2H), 7.59(s, 1H)

FAB(M+H): 219

47-2) 5-Chloromethyl-1-(4-methylbenzyl)imidazole hydrochloride

The title compound was obtained in a yield of 91% according to the same procedure as Preparation 28-2) except that the compound prepared in Preparation 47-1) was used as a starting material.

Preparation 48

Synthesis of 5-chloromethyl-1-(3-methylbenzyl) imidazole hydrochloride 48-1) 5-Hydroxymethyl-1-(3-methylbenzyl) imidazole The title compound was obtained in a yield of 60% according to the same procedure as Preparation 31-1) using dihydroxyacetone and 3-methylbenzylamine hydrochloride as starting materials.

$^1$H NMR(CDCl$_3$) δ2.27(s, 3H), 4.45(s, 2H), 4.52(br, 1H), 5.13(s, 2H), 6.80(d, 1H), 6.90(m, 2H), 7.08(m, 1H), 7.17(m, 1H), 7.34(s, 1H)

FAB(M+H): 219

48-2) 5-Chloromethyl-1-(3-methylbenzyl)imidazole hydrochloride

The title compound was obtained in a yield of 92% according to the same procedure as Preparation 28-2) except that the compound prepared in Preparation 48-1) was used as a starting material.

EXAMPLE 129

Synthesis of 1-[1-(4 methoxybenzyl)1H-imidazol-5-yl]methyl-3-[N-(2-methoxyethyl)-N-methyl]carbamoyl-4-(naphthalen-1-yl)-1H-pyrrole(129)

62 mg(0.2 mmol) of the compound prepared in Example 114-2) was dissolved in 2 ml of dimethylformamide, 26 mg(0.66 mmol) of sodium hydride was added thereto at 0° C., and the mixture was stirred for 5 minutes. 60 mg(0.22 mmol) of the compound prepared in Preparation 43-2) was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=95/5, v/v) to obtain 77 mg(Yield 76%) of the title compound.

$^1$HNMR(CDCl$_3$) δ2.41(m, 2H), 2.75(m, 1H), 3.03(m, 5H), 3.10(m, 1H), 3.34(m, 1H), 3.76(m, 3), 4.91(s, 2H), 4.93(s, 2H), 6.62(d, 1H), 6.82(d, 2H), 6.90–7.07(m, 3H), 7.21(s, 1H), 7.32(m, 1H), 7.43(m, 2H), 7.60(s, 1H), 7.74(d, 1H), 7.82(d, 1H), 8.08(d, 1H)

FAB (M+H): 509, C31H32N4O3

EXAMPLE 130

Synthesis of 1-[1-(4 methoxybenzyl)-1H-imidazol-5-yl]methyl-3(4-methylpiperazin-1-yl)carbonyl-4-(naphthalen-1-yl)-1H-pyrrole(130)

64 mg(0.2 mmol) of the compound prepared in Example 125-1) was dissolved in 2 ml of dimethylformamide, 26 mg(0.66 mmol) of sodium hydride was added thereto at 0° C., and the mixture was stirred for 5 minutes. 60 mg(0.22 mmol) of the compound prepared in Preparation 43-2) was added to the mixture, which was then stirred at room temperature for 5 hours. The solvent was removed by distillation under reduced pressure and 10 mg of water was added to the residue. The resulting mixture was extracted twice with 10 ml of ethyl acetate, dried over anhydrous sodium sulfate, concentrated and subjected to silica gel column chromatography(eluent: dichloromethane/methanol=90/10, v/v) to obtain 79 mg(Yield 80%) of the title compound.

$^1$H NMR(CDCl$_3$) δ1.06(br, 2H), 1.72(m, 2H), 1.82(s, 3H), 2.86(br, 2H), 3.28(br, 2H), 3.75(s, 3H), 4.91(s, 2H), 4.93(s, 2H), 6.63(d, 1H), 6.82(d, 2H), 6.90–7.07(m, 3H), 7.23(s, 1H), 7.33(m, 1H), 7.44(m, 2H), 7.61(s, 1H), 7.75(d, 1H), 7.82(d, 1H), 8.08(d, 1H)

FAB (M+H): 520, C32H33N5O2

EXAMPLE 131

Synthesis of 1-[1-(3-chlorobenzyl)-1H-imidazol-5-yl]methyl-3-(4-methylpiperazin-1-yl)carbonyl-4-(naphthalen-1-yl)-1H-pyrrole(131)

64 mg(0.2 mmol) of the compound prepared in Example 125-1) was dissolved in 2 ml of dimethylformamide, 26 mg(0.66 mmol) of sodium hydride was added thereto at 0° C., and the mixture was stirred for 5 minutes. 61 mg(0.22 mmol) of the compound prepared in Preparation 44-2) was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=90/10, v/v) to obtain 75 mg(Yield 71%) of the title compound.

$^1$H NMR(CDCl$_3$) δ1.02(br, 2H), 1.78(br, 2H), 1.87(s, 3H), 2.84(br, 2H), 3.30(br, 2H), 6.64(m, 2H), 7.01(s, 1H), 7.10–7.30(m, 4H), 7.31–7.47(m, 4H), 7.53(s, 1H), 7.73(d, 1H), 7.81(d, 1H), 7.96(d, 1H)

FAB (M+H): 524, C31H30N5OCl

EXAMPLE 132

Synthesis of 1-[1-(3-chlorobenzyl)-1H-imidazol-5-yl]methyl-3-[N-(2-methoxyethyl)-N-methyl]carbamoyl-4-(naphthalen-1-yl)-1H-pyrrole(132)

62 mg(0.2 mmol) of the compound prepared in Example 114-2) was dissolved in 2 ml of dimethylformamide, 26 mg(0.66 mmol) of sodium hydride was added thereto at 0° C., and the mixture was stirred for 5 minutes. 61 mg(0.22 mmol) of the compound prepared in Preparation 44-2) was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=95/5, v/v) to obtain 80 mg(Yield 78%) of the title compound.

$^1$H NMR(CDCl$_3$) δ2.39(br, 2H), 2.71(m, 1H), 3.02(br, 4H), 3.09(br, 1H), 3.32(br, 1H), 4.09(br, 1H), 4.97(s, 2H), 5.04(s, 2H), 6.64(d, 1H), 6.90(m, 1H), 7.02(d, 2H), 7.20–7.40(m, 4H), 7.40–7.60(m, 3H), 7.74(d, 1H), 7.76(d, 1H), 7.85(s, 1), 8.04(d, 1H)

FAB (M+H): 513, C30H29N4O2Cl

EXAMPLE 133

Synthesis of 1-[1-(2-chlorobenzyl)-1H-imidazol-5-yl]methyl-3-(4-methylpiperazin-1-yl)carbonyl-4-naphthalen-1-yl)-1H-pyrrole(133)

64 mg(0.2 mmol) of the compound prepared in Example 125-1) was dissolved in 2 ml of dimethylformamide, 26 mg(0.66 mmol) of sodium hydride was added thereto at 0° C., and the mixture was stirred for 5 minutes. 61 mg(0.22 mmol) of the compound prepared in Preparation 45-2) was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=90/10, v/v) to obtain 80 mg(Yield 76%) of the title compound.

$^1$H NMR(CDCl$_3$) δ1.06(br, 2H), 1.80(br, 2H), 1.86(s, 3H), 2.84(br, 2H), 3.30(br, 2H), 4.98(s, 2H), 5.11(s, 2H), 6.63(m, 2H), 7.01(s, 1H), 7.12–7.30 (m, 4H), 7.32–7.46(m, 4H), 7.53(s, 1H), 7.73(d, 1H), 7.81(d, 1H), 7.97(d, 1H)

FAB (M+H): 524, C31H30N5OCl

EXAMPLE 134

Synthesis of 1-[1-(2-chlorobenzyl)-1H-imidazol-5-yl]methyl-3-[N-(2-methoxyethyl)-N-methyl]carbamoyl-4-(naphthalen-1-yl)-1H-pyrrole(134)

62 mg(0.2 mmol) of the compound prepared in Example 114-2) was dissolved in 2 ml of dimethylformamide, 26 mg(0.66 mmol) of sodium hydride was added thereto at 0° C., and the mixture was stirred for 5 minutes. 61 mg(0.22 mmol) of the compound prepared in Preparation 45-2) was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=95/5, v/v) to obtain 77 mg(Yield 75%) of the title compound.

$^1$H NMR(CDCl$_3$) δ2.37(br, 2H), 2.72(m, 1H), 3.01(br, 4H), 3.10(br, 1H), 3.32(br, 1H), 4.18(br, 1H), 5.04(s, 2H), 5.17(s, 2H), 6.65(d, 1H), 6.76(d, 2H), 7.04(d, 1H), 7.13–7.35(m, 4H), 7.36–7.50(m, 4H), 7.71(s, 1H), 7.75(d, 1H), 7.82(d, 1H), 8.01(d, 1H)

FAB (M+H): 513, C30H29N4O2Cl

EXAMPLE 135

Synthesis of 1-[1-(2-fluorobenzyl)-1H-imidazol-5-yl]methyl-3-(4-methylpiperazin-1-yl)carbonyl-4-naphthalen-1-yl)-1H-pyrrole(135)

64 mg(0.2 mmol) of the compound prepared in Example 125-1) was dissolved in 2 ml of dimethylformamide, 26 mg(0.66 mmol) of sodium hydride was added thereto at 0° C., and the mixture was stirred for 5 minutes. 51 mg(0.22 mmol) of the compound prepared in Preparation 46-2) was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=90/10, v/v) to obtain 79 mg(Yield 77%) of the title compound.

$^1$H NMR(CDCl$_3$) δ1.06(br, 2H), 1.80(br, 2H), 1.86(s, 3H), 2.93(br, 2H), 3.35(br, 2H), 5.03(s, 2H), 5.06(s, 2H), 6.66(m, 2H), 6.87(m, 1H), 7.12–7.30 (m, 4H), 7.32–7.46(m, 4H), 7.58(s, 1H), 7.77(d, 1H), 7.82(d, 1H), 7.97(d, 1H)

FAB (M+H): 508, C31H30N5OF

EXAMPLE 136

Synthesis of 1-[1-(4-methylbenzyl)-1H-imidazol-5-yl]methyl-3-(4-methylpiperazin-1-yl)carbonyl-4-(naphthalen-1-yl)-1H-pyrrole(136)

64 mg(0.2 mmol) of the compound prepared in Example 125-1) was dissolved in 2 mg of dimethylformamide, 26 mg(0.66 mmol) of sodium hydride was added thereto at 0° C., and the mixture was stirred for 5 minutes. 57 mg(0.22 mmol) of the compound prepared in Preparation 47-2) was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=90/10, v/v) to obtain 81 mg(Yield 80%) of the title compound.

$^1$H NMR(CDCl$_3$) δ1.09(br, 2H), 1.83(br, 2H), 1.86(s, 3H), 2.24(s, 3H), 2.93(br, 2H), 3.30(br, 2H), 4.86(s, 2H), 4.91(s, 2H), 6.59(d, 1H), 6.87(m, 2H), 7.01(s, 1H), 7.07(d, 2H), 7.15(s, 1H), 7.25(m, 1H), 7.50(m, 3H), 7.53(s, 1H), 7.73(d, 1H), 7.78(d, 1H), 7.97(d, 1H)

FAB (M+H): 504, C32H33N5O

EXAMPLE 137

Synthesis of 1-[1-(4-methylbenzyl)-1H-imidazol-5-yl]methyl-3-(morpholin-4yl)carbonyl-4-(naphthalen-1-yl)-1H-pyrrole(137)

62 mg(0.2 mmol) of the compound prepared in Example 106-3) was dissolved in 2 ml of dimethylformamide, 26 mg(0.66 mmol) of sodium hydride was added thereto at 0° C., and the mixture was stirred for 5 minutes. 57 mg(0.22 mmol) of the compound prepared in Preparation 47-2) was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=95/5, v/v) to obtain 80 mg(Yield 81%) of the title compound.

$^1$H NMR(CDCl$_3$) δ2.29(s, 3H), 2.30–3.60(br, 8H), 4.94(s, 1H), 4.99(s, 2H), 6.61(d, 1H), 6.91(d, 1H), 7.07(d, 1H), 7.12(d, 2H), 7.21(s, 1H), 7.32(d, 1H), 7.35–7.50(m, 4H), 7.71(s, 1H), 7.77(d, 1H), 7.84(d, 1H), 7.98(d, 1H)

FAB (M+H): 491, C31H30N4O2

EXAMPLE 138

Synthesis of 1-[1-(3-methylbenzyl)-1H-imidazol-5yl]methyl-3-(4methylpiperazin-1-yl)carbonyl-4-(naphthalen-1-yl)-1H-pyrrole(138)

64 mg(0.2 mmol) of the compound prepared in Example 125-1) was dissolved in 2 ml of dimethylformamide, 26 mg(0.66 mmol) of sodium hydride was added thereto at 0° C., and the mixture was stirred for 5 minutes. 57 mg(0.22 mmol) of the compound prepared in Preparation 48-2) was added to the mixture, which was then stirred at room temperature for 5 hours. The solvent was removed by distillation under reduced pressure and 10 ml of water was added to the residue. The resulting mixture was extracted twice with 10 ml of ethyl acetate, dried over anhydrous sodium sulfate, concentrated and subjected to silica gel column chromatography(eluent: dichloromethane/methanol=90/10, v/v) to obtain 74 mg(Yield 73%) of the title compound.

$^1$H NMR(CDCl$_3$) δ1.06(br, 2H), 1.80(br, 2H), 1.84(s, 3H), 2.91(br, 2H), 3.27(br, 2H), 4.86(s, 2H), 4.89(s, 2H), 6.57(d, 1H), 6.71(d, 1H), 6.77 (s, 1H), 6.97(s, 1H), 7.01(d,

1H), 7.15(m, 2H), 7.25(d, 1H), 7.37(m, 3H), 7.51(s, 1H), 7.70(d, 1H), 7.72(d, 1H), 7.98(d, 1H)

FAB (M+H): 504, C32H33N5O

Preparation 49

Synthesis of 3-(naphthalen-1-yl)carbonyl-1H-pyrrole

49-1) Methyl N-methyl-1-naphthalen hydroxamate 3.44 g(20 mmol) of 1-naphthoic acid was dissolved in 20 ml of dimethylformamide, and then 4.6 g(24 mmol) of EDC, 2.02 g(20 mmol) of triethylamine and 3.24 g(24 mmol) of HOBT were added thereto. The resulting mixture was stirred at 0° C. for 5 minutes. To the reaction solution was added 1.85 g(20 mmol) of N,O-dimethylhydroxylamine hydrochloride, which was then stirred at room temperature for 5 hours. The solvent was removed under reduced pressure and then 100 ml of saturated potassium carbonate solution was added to the residue. The resulting solution was extracted with ethyl acetate. Then, the organic layer was washed sequencially with 1N aqueous hydrochloric acid solution, aqueous sodium chloride solution and water, dried over anhydrous sodium sulfate and concentrated to give 3.04 g(1.50 mmol) of the title compound.

$^1$H NMR(CDCl$_3$) δ2.42(s, 3H), 3.24(s, 3H), 7.47(m, 4H), 7.67(d, 1H), 7.74(m, 2H),

FAB 216 (M+H)

49-2) 1-(Naphthalen-1-yl)-prop-2-en-1-one 2.03 g(9.4 mmol) of the compound prepared in Preparation 49-1) was dissolved in 20 ml of dry tetrahydrofuran and then 20 ml of 1N vinylmagnesiumbromide-tetrahydrofuran solution was added slowly thereto at 0° C. The mixture was stirred at room temperature for 30 minutes and 20 ml of 1N hydrochloric acid was added thereto, and then the resulting solution was extracted with 50 ml of ethyl acetate. The organic layer was dried over anhydrous magnesium sulfate and the solvent was removed under reduced pressure to give 1.63 g(9 mmol; Yield 96%) of the title compound.

$^1$H NMR(CDCl$_3$) δ6.92(m, 1H), 7.51(m, 4H), 7.74(d, 1H), 7.85(m, 2H), 7.98(d, 1H), 8.31(d, 1H)

49-3) 3-(Naphthalen-1-yl)carbonyl-1H-pyrrole 901 mg(5 mmol) of the compound prepared in Preparation 49-2) and 1.01 g(5.5 mmol) of tosylmethylisocyanide were dissolved in 10 ml of tetrahydrofuran. 555 mg(5.5 mmol) of potassium t-butoxide dissolved in 10 ml of tetrahydrofuran was slowly added thereto and the mixture was stirred for 30 minutes. 10 ml of water was added to the reaction solution to stop the reaction and the solvent was removed under reduced pressure. 20 ml of water was added to the residue and the resulting mixture was extracted with ethyl acetate, washed with aqueous sodium chloride solution and then dried over anhydrous magnesium sulfate. The solvent was removed under reduced pressure and the residue was subjected to silica gel column chromatography(eluent: ethyl acetate/hexane=1/3, v/v) to obtain 884 mg(4 mmol, Yield 80%) of the title compound.

$^1$H NMR(CDCl$_3$) δ6.57(s, 1H), 6.66(s, 1H), 6.79(s, 1H), 7.36(m, 3H), 7.48(d, 1H), 7.77(d, 1H), 7.82(d, 1H), 8.04(d, 1H), 9.91(s, 1H)

Preparation 50

Synthesis of 4-(naphthalen-1-yl)carbonyl-3[N-(2-methoxyethyl)-N-methylcarbamoyl]-1H-pyrrole

50-1) 4-(Naphthalen-1-yl)-4-oxo-2-butenoic acid 5.88 g(60 mmol) of dry maleic acid was dissolved in 100 ml of dry tetrahydrofuran and the mixture was cooled down to 78° C. 4.14 g(20 mmol) of 1-bromonaphthalene was dissolved in 100 ml of dry tetrahydrofuran and 13.8 ml of 1.6N n-butyllithium-hexane solution was added thereto at 78° C. This reaction solution was stirred for 5 minutes and then it was added to the dry maleic acid solution prepared in advance using cannula. The resulting mixture was stirred for 10 minutes, and water was added thereto to stop the reaction. The solvent was removed under reduced pressure, and the residue was acidified by 1N aqueous hydrochloric acid solution and extracted with ethyl acetate. The organic layer was washed with water and aqueous sodium chloride solution, dried over anhydrous magnesium sulfate, concentrated under reduced pressure and subjected to column chromatography(eluent: ethyl acetate/hexane=2/1, v/v) to give 1.35 g(6.0 mmol; Yield 30%) of the title compound.

$^1$H NMR(CDCl$_3$) δ6.81(d, 1H), 7.52–7.65(m, 3H), 7.85 (d, 1H), 7.89(d, 1H), 7.92(d, 1H), 8.06(d, 1H), 8.56(d, 1H)

50-2)N-(2-methoxyethyl)-N-methyl-4-(naphthalen-1-yl)-4-oxo-2-butenoamide 1.3 g(5.9 mmol) of the compound prepared in Preparation 50-1) was dissolved in 10 ml of dimethylformamide, and then 1.7 g(8.9 mmol) of EDC and 1.2 g(8.9 mmol) of HOBT were added thereto at 0° C. The resulting mixture was stirred for 5 minutes. To the reaction solution were added 530 mg(5.9 mmol) of N-(2-methoxyethyl)-N-methylamine and 1.2 ml(8.9 mmol) of triethylamine, the mixture of which was then stirred at room temperature for 2 hours. The solvent was removed under reduced pressure and then 50 ml of water was added to the residue. The resulting solution was extracted with ethyl acetate. The organic layer was washed with aqueous sodium chloride solution, dried over anhydrous magnesium sulfate and concentrated under reduced pressure. The residue was subjected to column chromatography(eluent: ethyl acetate/hexane=1/1, v/v) to give 1.4 g(4.7 mmol; Yield 80%) of the title compound.

$^1$H NMR(CDCl$_3$) δ3.05(s, 3H), 3.32(s, 3H), 3.54(m, 2H), 3.65(m, 2H), 7.40–7.58(m, 4H), 7.71(t, 1H), 7.89(m, 2H), 8.03(d, 1H), 8.54(d, 1H)

50-3) 3-[N-(2-methoxyethyl)-N-methyl]carbamoyl-4-(naphthalen-1-yl)carbonyl-1H-pyrrole 1.4 g(4.7 mmol) of the compound prepared in Preparation 50-2) and 1.0 g(5.1 mmol) of tosylmethylisocyanide were dissolved in 20 ml of tetrahydrofuran. 790 mg(7.0 mmol) of potassium t-butoxide was added thereto and the mixture was stirred at room temperature for 3 hours. 2 ml of water was added to the reaction solution to stop the reaction and the solvent was removed under reduced pressure. The residue was extracted with ethyl acetate, washed with aqueous sodium chloride solution and dried over anhydrous magnesium sulfate. The solvent was removed under reduced pressure and the residue was subjected to column chromatography(eluent: ethyl acetate/hexane=2/3, v/v) to give 1.2 g(3.6 mmol, Yield 76%) of the title compound.

$^1$H NMR(CDCl$_3$) δ3.04(s, 3H), 3.35(s, 3H), 3.47(m, 2H), 3.64(m, 2H), 6.55(d, 1H), 6.63(m, 1H), 7.21–7.40(m, 4H), 7.74(m, 2H), 8.00(m, 1H), 11.4(br, 1H)

EXAMPLE 139

Synthesis of 1-[1-(4-cyanobenzyl)-1H-imidazol-5-yl]methyl-3-(naphthalen-1-yl)carbonyl-1H-pyrrole (139)

The title compound was obtained in a yield of 35% according to the same procedure as Example 1 except that the compound prepared in Preparation 29-5) and the compound prepared in Preparation 49-3) were used.

$^1$H NMR(CDCl$_3$) δ4.86(s, 2H), 4.95(s, 2H), 6.52(s, 1H), 6.61(s, 1H), 6.89(m, 3H), 7.20(s, 1H), 7.49(m, 6H), 7.75(s, 1H), 7.87(d, 1H), 7.95(d, 1H), 8.11(d, 1H)

FAB: 417 (M+1)

EXAMPLE 140

Synthesis of 1-[1-(4-bromobenzyl)-1H-imidazol-5yl]methyl-3-(naphthalen-1-yl)carbonyl-1H-pyrrole (140)

The title compound was obtained in a yield of 20% according to the same procedure as Example 1 except that the compound prepared in Preparation 32-2) and the compound prepared in Preparation 49-3) were used.

$^1$H NMR(CDCl$_3$) δ4.84(s, 2H), 4.92(s, 2H), 6.54(s, 1H), 6.67(s, 1H), 6.78(d, 2H), 6.93(s, 1H), 7.22(s, 1H), 7.38(d, 2H), 7.50(m, 3H), 7.58(d, 1H), 7.89(d, 1H), 7.95(d, 1H), 8.13(d, 1H), 8.16(s, 1H)

FAB: 470 (M+1)

EXAMPLE 141

Synthesis of 1-[1-(4-bromobenzyl)-1H-imidazol-5-yl]methyl-3-[N-(2-methoxyethyl)-N-methyl]carbamoyl-4-(naphthalen-1-yl)carbonyl-1H-pyrrole (141)

The title compound was obtained in a yield of 81% according to the same procedure as Example 1 except that the compound prepared in Preparation 32-2) and the compound prepared in Preparation 50-3) were used.

$^1$H NMR(CDCl$_3$) δ2.94(s, 3H), 3.25(s,3H), 3.42(m, 2H), 3.48(m, 2H), 4.72 (s, 2H), 4.78(s, 2H), 6.64(m, 4H), 7.28–7.48(m, 8H), 7.81(m, 2H), 8.14(m, 1H)

FAB: 585 (M+1)

Preparation 51

Synthesis of ethyl 1-naphthoylglycinate hydrochloride

51-1) Ethyl N-(diphenylmethylene)glycinate

Glycine ethylester hydrochloride salt and diphenylketimine were reacted according to the procedure described in M. J. O'Donnell, R. L. Polt, *J. Org. Chem* 47, 2663, 1982 to give the title compound in a yield of 90%.

$^1$H NMR(CDCl$_3$) δ1.20(t,3H), 4.12(m,4H), 7.10–7.40(m, 8H), 7.59(d,2H)

51-2) Ethyl 1-naphthoylglycinate hydrochloride

1-Naphthoylchloride and the compound prepared in Preparation 51-1) were reacted according to the procedure described in J. Singh, et. al. *Tetrahedron Lett.*, 34(2), 211, 1993 to give the title compound in a yield of 48%.

$^1$H NMR(DMSO-d6) δ1.78(s,3H), 3.65(q,1H), 3.95–4.15 (m,2H), 6.33(s, 1H), 7.58–7.85(m,3H), 8.15(d,1H), 8.31(d, 1H), 8.38(d,2H), 8.42(d,2H)

Preparation 52

Synthesis of 2-[1-(4-chlorobenzyl)-1H-imidazol-5-yl]thioacetamide

52-1) 1-(4-Chlorobenzyl)-5-hydroxymethyl-1H-imidazole

The title compound was obtained in a yield of 50% according to the similar procedure descrbied in J. M. Dener, L-H Zhang, H. Rapoport, *J. Org. Chem.*, 1993, 58, 1159 using dihydroxyacetone dimer and 4-chlorobenzylamine hydrochloride as starting materials.

$^1$H NMR(CDCl$_3$+CD$_3$OD) δ4.50(s,2H), 5.20(s,2H), 6.94 (s,1H), 7.06(d,2H), 7.32(d,2H), 7.46(s,1H)

52-2) 1-(4-Chlorobenzyl)-5-chloromethyl-1H-imidazole hydrochloride 3.00 g(13.5 mmol) of the compound prepared in Preparation 52-1) was dissolved in 40 ml of chloroform, 2.88 ml(40.5 mmol) of thionylchloride was slowly added thereto at 0° C., and the mixture was stirred at room temperature for 2 hours. The organic solvent was removed under reduced pressure to give 3.64 g(13.1 mmol, Yield 97%) of the title compound. This compound was used directly in the next reaction without purification.

52-3) [1-(4-Chlorobenzyl)-1H-imidazol-5-yl]acetonitrile 1.2 g(4.3 mmol) of the compound prepared in Preparation 52-2) was dissolved in 10 ml of dimethylsulfoxide and 1.3 g(26 mmol) of sodiumcyanide was added thereto. The mixture was stirred at room temperature for 6 hours. 30 ml of water was added thereto and the resulting mixture was extracted with ethyl acetate(20 ml×3). The organic layer was dried over anhydrous sodium sulfate and concentrated to give 0.96 g(4.1 mmol, Yield 96%) of the title compound. This compound was used in the next reaction without purification.

$^1$H NMR(CDCl$_3$) δ3.70(s,2H), 5.12(s,2H), 6.88(s, 1H), 7.34(d,2H), 7.62(d, 2H), 7.71(s,1H)

52-4) 2-[1-(4-Chlorobenzyl)-1H-imidazol-5-yl]thioacetamide 150 mg(0.64 mmol) of the compound prepared in Preparation 52-3) was dissolved in a solvent mixture of 1ml of pyridine and 0.3 ml of triethylamine and then saturated by bubbling hydrogen sulfide gas through the solution for 30 minutes. The reaction solution was stirred at room temperature for 12 hours. The solvent was removed under reduced pressure and 10 ml of water was added thereto. The mixture was extracted with 10 ml of ethyl acetate. The organic layer was dried over anhydrous sodium sulfate, concentrated and subjected to silica gel column chromatography (eluent: methylene chloride/methanol=20/1, v/v) to give 110 mg(0.41 mmol, Yield 64%) of the tide compound.

$^1$H NMR(CDCl$_3$+CD$_3$OD) δ3.21(s,2H), 5.05(s,2H), 6.76 (s,1H), 7.24(d,2H), 7.61(d,2H), 7.67(s,1H)

FAB: 266(M+1)

Preparation 53

Synthesis of 2-{1-[1-(benzyloxycarbonyl)piperidin-4yl]methyl-1H-imidazol-5-yl}thioacetamide

53-1) 4-Aminomethyl-1-(benzyloxycarbonyl) piperidine 22.2 g(0.2 mol) of 4-aminomethylpiperidine was dissolved in 250 ml of toluene and 21.2 g(0.2 mol) of benzaldehyde was added thereto. The reaction mixture was refluxed for 3 hours with Dean-stack to remove water, and then cooled down to 0° C. 34.2 g(0.2 mol) of benzylchloroformate was added slowly thereto while stirring. The mixture was stirred at room temperature for 3 hours and 220 ml of 1N aqueous KHSO$_4$ solution was added thereto. The mixture was extracted three times with 200 ml of diethylether, and the aqueous layer was basified with 1N aqueous sodium hydroxide solution. The aqueous solution was saturated with sodium chloride. The aqueous layer was extracted three times with 100 ml of dichloromethane, dried over anhydrous magnesium sulfate and distilled under reduced pressure to give 38 g(Yield 91%, Molecular weight 248) of the title compound.

$^1$H NMR(CDCl$_3$) δ1.11(s,2H), 1.49(s,3H), 1.70(d,2H), 2.57(d,2H), 2.78(s, 2H), 4.20(s,2H), 5.12(s,2H), 7.34–7.35 (m, 5H)

53-2) 1-[1-(Benzyloxycarbonyl)piperidin-4-yl] methyl-5-hydroxymethyl-2-mercapto-1H-imidazole 24.8 g(0.1 mol) of the compound prepared in Preparation 53-1) and 6.0 g(0.1 mol) of acetic acid were dissolved in 50 ml of n-butanol, a solution wherein 12.6 g(0.13 mol) of potassium thiocyanate, 15 g(0.1 mol) of 1,3-dihydroxyacetone dimer and 10.0 g(0.17 mol) of acetic acid were dissolved in 50 ml of n-butanol was added thereto, and the whole mixture was stirred at room temperature. After 48 hours, the solvent was removed by distillation under reduced pressure, and then the residue was dissolved in 200 ml of ethyl acetate and washed three times with 100 ml of water. The organic layer was dried over anhydrous magnesium sulfate and concentrated to give 27 g(75 mmol, Yield 75%) of the title compound.

$^1$H NMR(CDCl$_3$) δ1.22(d,2H), 1.57(d,2H), 2.30(s,1H), 2.72(s,2H), 3.96(s, 2H), 4.15(d,2H), 4.46(s,2H), 5.10(s,2H), 6.62(s,1H), 7.26–7.37(m,5H)

53-3) 1-[1-Benzyloxycarbonyl)piperidin-4-yl] methyl-5-hydroxymethyl-1H-imidazole 18.05 g(50 mmol) of the compound prepared in Preparation 53-2) was added to a mixture of 100 ml of 10% nitric acid and 10 ml of ethyl acetate, the reaction mixture was cooled with cold ice water and then stirred at room temperature for 3 hours. The mixture was basified using 4N aqueous sodium hydroxide solution and extracted twice with 100 ml of ethyl acetate. The extracted organic solution was dried over magnesium sulfate and distilled under reduced pressure to give 12.3 g(38 mmol, Yield 75%) of the title compound.

$^1$H NMR(CDCl$_3$) δ1.16(d,2H), 1.56(d,2H), 1.98(s,1H), 2.70(s,2H), 3.88(d, 2H), 4.18(s,2H), 4.49(s,1H), 4.56(s,3H), 5.10(s,2H), 6.82(s,1H), 7.27–7.40(m, 6H)

53-4) 1-[1-(Benzyloxycarbonyl)piperidin-4-yl] methyl-5-chloromethyl-1H-imidazole hydrochloride 9.9 g(30 mmol) of the compound prepared in Preparation 53-3) was dissolved in 50 ml of chloroform, and 7.1 g(60 mmol) of thionylchloride was slowly added thereto at 0° C. The reaction solution was stirred for 2 hours and the solvent was removed by distillation under reduced pressure to give 9.9 g(Yield 95%, Molecular weight 347.5) of hydrochloride salt of the title compound. This compound was used directly in the next reaction without purification.

53-5) {1-[1-(Benzyloxycarbonyl)piperidin-4-yl] methyl-1H-imidazol-5-yl}acetonitrile The title compound was obtained in a yield of 39% according to the similar procedure as Preparation 52-3) using the compound prepared in Preparation 53-4).

$^1$H NMR(CDCl$_3$) δ1.19(br,2H), 1.60(br,2H), 1.90(m,1H), 2.72(br,2H), 3.71(s,2H), 3.81(d,2H), 4.22(br,2H), 5.11(s, 2H), 7.03(s,1H), 7.29–7.36(m, 5H), 7.51(s,1H)

53-6) 2-{1-[1-(Benzyloxycarbonyl)piperidin-4-yl] methyl-1H-imidazol-5-yl}thioacetamide The title compound was obtained in a yield of 74% according to the similar procedure as Preparation 52-4) using the compound prepared in Preparation 53-5).

$^1$H NMR(CDCl$_3$) δ1.21(br,2H), 1.63(br,2H ), 1.87(m, 1H), 2.71(br,2H), 3.31 (s,2H), 3.84(d,2H), 4.25(br,2H), 5.12 (s,2H), 7.10(s,1H), 7.33–7.41(m,5H), 7.62(s,1H)

FAB: 373 (M+1)

Preparation 54

Synthesis of methyl 3-chloro-3-(naphthalen-1-yl)-2-oxopropionate 7.80 g(49.9 mmol) of 1-naphthaldehyde and 7.15 g(49.9 mmol) of methyl dichloroacetate were dissolved in 100 ml of t-butanol, and 6.15 g(54.8 mmol) of potassium t-butoxide was added thereto at 0° C. The mixture was stirred at room temperature for 24 hours and then 50 ml of water was added to stop the reaction. The solvent was removed under reduced pressure and the residue was extracted with ethyl acetate. The organic layer was dried over magnesium sulfate, concentrated and subjected to silica gel column chromatography (eluent: n-hexane/ethyl acetate=90/10, v/v) to give 2.5 g(9.52 mmol, Yield 19%) of the title compound.

$^1$H NMR(CDCl$_3$) δ3.78(s,3H), 6.92(s,1H), 7.45–7.73(m, 4H), 7.95(m,2H), 8.12(d,1H)

Preparation 55

Synthesis of methyl 2-chloro-3-(naphthalen-1-yl)-3-oxopropionate

55-1) Methyl 3-(naphthalen-1-yl)-3-oxopropionate 10.2 g(59.9 mmol) of 1-acetonaphthone and 4.8 g(60% in mineral oi, 120 mmol) of sodium hydride were added to 100 mg of dimethylcarbonate and the mixture was refluxed for 24 hours. The solvent was removed under reduced pressure, 100 ml of 1N aqueous HCl solution was added to the residue, and the resulting mixtrue was extracted with 100 ml of ethyl acetate. The organic layer was washed with water (100 ml×3), dried over anhydrous magnesium sulfate and concentrated. The residue was subjected to silica gel column chromatography(eluent: n-hexane/ethyl acetate=90/10, v/v) to give 10.0 g (43.8 mmol, Yield 73%) of the title compound.

$^1$H NMR(CDCl$_3$) δ3.75(s,3H), 4.14(s,2H), 7.45–7.68(m, 3H), 7.82–8.08(m, 3H), 8.77(d,1H)

55-2) Methyl 2-chloro-3-(naphthalen-1-yl)-3-oxopropionate 4.56 g(20.0 mmol) of the compound prepared in Preparation 55-1) was dissolved in 50 ml of 1,2-dichloroethane, and 2.70 g(20.0 mmol) of sulfuryl chloride was slowly added thereto at 0° C. The mixture was stirred at room temperature for 3 hours. The solvent was removed by distillation under reduced pressure to give 4.70 g(17.9 mmol, Yield 89%) of the title compound.

$^1$H NMR(CDCl$_3$) δ3.75(s,3H), 5.82(s,2H), 7.50–7.72(m, 3H), 7.85–8.15(m, 3H), 8.65(d,1H)

EXAMPLE 142

Synthesis of 4-ethoxycarbonyl-2-(1H-imidazol-5-ylmethyl)-5-(naphthalen-1-yl)oxazole(142)

142-1) Ethyl 2-[(1H-imidazol-5-yl)acetylamino]-3-(naphthalen-1-yl)-3-oxopropionate 293 mg(0.997 mmol) of the compound prepared in Preparation 51-2), 162 mg(0.996 mmol) of 4-imidazoleacetic acid hydrochloride, 135 mg(0.999 mmol) of HOBT and 191 mg(0.996 mmol) of EDC were added to 10 ml of dimethylformamide, and then 202 mg(1.99 mmol) of triethylamine was slowly added thereto while stirring. The mixture was stirred at room temperature for 5 hours and then the solvent therein was removed under reduced pressure. To the residue was added 30 ml of ethyl acetate, which was then washed with saturated sodium bicarbonate solution and water. The organic layer was dried over anhydrous magnesium sulfate, concentrated and subjected to silica gel column chromatography(eluent: dichloromethane/methanol=95/5, v/v) to give 200 mg(0.547 mmol, Yield 55%) of the title compound.

$^1$H NMR(CDCl$_3$) δ0.92(t,3H), 3.70(s,2H), 3.98–4.15(m, 2H), 6.20(d,1H), 6.92(s,1H), 7.55(m,4H), 7.65(s,1H), 7.89 (d,1H), 8.06(d,1H), 8.12(br,1H), 8.21(d,1H), 8.45(d,1H)

142-2) 4-Ethoxycarbonyl-2-(1H-imidazol-5-ylmethyl)-5-(naphthalen-1-yl)oxazole 100 mg(0.27 mmol) of the compound prepared in Example 142-1) was dissolved in 5 ml of THF and then refluxed for 6 hours. The solvent was removed by distillation under reduced pressure and the residue was subjected to silica gel column chromatography(eluent: dichloromethane/methanol=95/5, v/v) to give 40 mg(0.12 mmol, Yield 44%) of the title compound.

$^1$H NMR(CDCl$_3$) δ0.98(t,3H), 4.13(q,2H), 4.27(s,2H), 6.92(s,1H), 7.45–7.58(m,4H), 7.65–7.75(m,2H), 7.89(d, 1H), 7.97(d,1H)

FAB: 348 (M+1)

EXAMPLE 143

Synthesis of 2-(1H-imidazol-5-ylmethyl)-4-(morpholin-4-yl)carbonyl-5-(naphthalen-1-yl)oxazole(143)

31 mg(0.09 mmol) of the compound prepared in Example 142-2) was dissolved in a solvent mixture of tetrahydrofuran/methanol/water(0.6 ml/0.3 ml/1 ml), and 6 mg(0.13 mmol) of lithium hydroxide was added thereto. The reaction solution was stirred at room temperature for 3 hours, and the solvent was removed under reduced pressure. The residue was adjusted to pH 6 using 0.1N aqueous hydrochloric acid solution and then extracted with ethyl acetate. The organic layer was dried over anhydrous sodium sulfate and concentrated. The concentrate was dissolved in 1 ml of dimethylformamide, 18 mg(0.13 mmol) of HOBT and 26 mg(0.13 mmol) of EDC were added thereto at 0° C., and the mixture was stirred for 10 minutes. 9 μl (0.09 mmol) of morpholine and 18 μl (0.13 mmol) of triethylamine were added thereto and the mixture was sitrred at room temperature for 2 hours. The reaction solution was treated according to the same procedure as Example 142-1) to give 14 mg(0.04 mmol, Yield 45%) of the title compound.

$^1$H NMR(CDCl$_3$) δ2.97(br,2H), 3.24(br,2H), 3.43(br,2H), 3.57(br,2H), 4.27(s,2H), 6.95(s,1H), 7.52–7.67(m,6H), 7.81–7.95(m,3H)

FAB: 389 (M+1)

EXAMPLE 144

Synthesis of 4-ethoxycarbonyl-2-(1H-imidazol-5-ylmethyl)-5-(naphthalen-1-yl)thiazole(144)

105 mg(0.287 mmol) of the compound prepared in Example 142-1) and 116 mg(0.287 mmol) of Lawesson's Reagent were dissolved in 10 ml of tetrahydrofuran, and the mixture was refluxed for 6 hours. The solvent was removed under reduced pressure, 10 ml of saturated sodium bicarbonate solution was added to the residue, and then the resulting mixture was extracted with ethyl acetate. The organic layer was dried over anhydrous magnesium sulfate, concentrated and subjected to silica gel column chromatography(eluent: dichloromethane/methanol=95/5, v/v) to give 26 mg(0.075 mmol, Yield 26%) of the compound of Example 142-2) and 24 mg(0.066 mmol, Yield 23%) of the title compound.

$^1$H NMR(CDCl$_3$) δ0.63(t,3H), 3.92(q,2H), 4.42(s,2H), 6.97(s,1H), 7.405–7.75(m,6H), 7.85–7.95(m,2H)

FAB: 364 (M+1)

EXAMPLE 145

Synthesis of 2-[1-(4-chlorobenzyl)-1H-imidazol-5-ylmethyl]-4-methoxycarbonyl-5-(naphthalen-1-yl)thiazole(145)

130 mg(0.49 mmol) of the compound prepared in Preparation 52-4) and 129 mg(0.49 mmol) of the compound prepared in Preparation 54 were dissolved in 5 ml of ethanol, and the mixture was refluxed for 5 hours. The solvent was removed by distillation under reduced pressure and the residue was subjected to silica gel column chromatography (eluent: dichloromethane/methanol=40/1, v/v) to give 45 mg(0.095 mmol, Yield 19%) of the title compound.

$^1$H NMR(CDCl$_3$) δ3.50(s,3H), 4.26(s,2H), 5.11(s,2H), 6.92(d,2H), 7.07(s, 1H), 7.21–7.43(m,7H), 7.53(s,1H), 7.83 (m,2H)

FAB: 474 (M+1)

EXAMPLE 146

Synthesis of 2-[1-(4-chlorobenzyl)-1H-imidazol-5-ylmethyl]-4-(morpholin-4-yl)carbonyl-5-(naphthalen-1-yl)thiazole(146)

The title compound was obtained in a yield of 23% according to the similar procedure as Example 143 using the compound prepared in Example 145.

$^1$H NMR(CDCl$_3$) δ2.63(br,2H), 3.02(br,2H), 3.24(br,2H), 3.42(br,2H), 4.26(s,2H), 5.21(s,2H), 7.02(m,2H), 7.18(s, 1H), 7.31(m,2H), 7.43–7.60(m,5H), 7.78–7.96(m,3H)

FAB: 529 (M+1)

EXAMPLE 147

Synthesis of 2-[1-(4-chlorobenzyl)-1H-imidazol-5-ylmethyl]-4-[N-(2-methoxy)ethyl-N-methylcarbamoyl]-5-(naphthalen-1-yl)thiazole (147)

The title compound was obtained in a yield of 41% according to the similar procedure as Example 143 using the compound prepared in Example 145 except that N-(2-methoxyethyl)methylamine was used instead of morpholine $^1$H NMR(CDCl$_3$) δ2.68(br,3H), 2.89–3.39(m,7H), 4.22(s, 2H), 5.17(s,2H), 7.01(m,2H), 7.15(s,1H), 7.33(m,2H), 7.40–7.61(m,5H), 7.71–7.82(m,3H)

FAB: 531 (M+1)

EXAMPLE 148

Synthesis of 2-[1-(4-chlorobenzyl)-1H-imidazol-5-ylmethyl]-5-methoxycarbonyl-4-(naphthalen-1-yl)thiazole(148)

250 mg(0.95 mmol) of the compound prepared in Preparation 52–4) and 249 mg(0.95 mmol) of the compound prepared in Preparation 55–2) were dissolved in 10 ml of ethanol, and the mixture was refluxed for 24 hours. The solvent was removed by distillation under reduced pressure and the residue was subjected to silica gel column chromatography (eluent: dichloromethane/methanol=40/1, v/v) to give 180 mg(0.38 mmol, Yield 40%) of the title compound.

$^1$H NMR(CDCl$_3$) δ3.53(s,3H), 4.22(s,2H), 5.12(s,2H), 6.91(m,2H), 7.11(s, 1H), 7.21–7.54(m,7H), 7.83(m,3H)

FAB: 474 (M+1)

EXAMPLE 149

Synthesis of 2-[1-(4-chlorobenzyl)-1H-imidazol-5-ylmethyl]-5-(morpholin-4-yl)carbonyl-4-(naphthalen-1-yl)thiazole(149)

The title compound was obtained in a yield of 39% according to the similar procedure as Example 143 using the compound prepared in Example 148.

$^1$H NMR(CDCl$_3$) δ2.38(br,2H), 2.82(br,2H), 3.21(br,2H), 3.42(br,2H), 4.27(s,2H), 5.21(s,2H), 6.98(m,2H), 7.25(m, 3H), 7.50–7.61(m,5H), 7.89–7.99 (m,3H)

FAB: 529 (M+1)

EXAMPLE 150

Synthesis of 2-{1-[1-(benzyloxycarbonyl)piperidin-4-ylmethyl]-1H-imidazol-5-ylmethyl}-5-methoxycarbonyl-4-(naphthalen-1-yl)thiazole(150)

124 mg(0.33 mmol) of the compound prepared in Preparation 53-6) and 87 mg(0.33 mmol) of the compound prepared in Preparation 55-2) were dissovedin 10 ml of ethanol, and the mixture was refluxed for 20 hours. The solvent was removed by distllation under reduced pressure and the residue was subjected to silica gel column chromatography (eluent: dichloromethane/methanol=95/5, v/v) to give 95 mg(0.16 mmol, Yield 48%) of the title compound.

$^1$H NMR(CDCl$_3$) δ1.10(br,2H), 1.53(br,3H), 2.50(br,2H), 3,62(s,3H), 3.81(d,2H), 4.19(br,2H), 4.41(s,2H), 5.14(d, 2H), 7.16(s, 1H), 7.27–7.61(m, 10H), 7.78(s,1H), 7.91(d, 1H), 7.96(d,1H)

FAB: 595 (M+1)

EXAMPLE 151

Synthesis of 2-{1-[1-(benzyloxycarbonyl)piperidin-4-ylmethyl]-1H-imidazol-5-ylmethyl}-5-[N-(2-methoxy)ethyl-N-methylcarbamoyl]-4-(naphthalen-1-yl)thiazole(151)

The title compound was obtained in a yield of 36% according to the similar procedure as Example 143 using the compound prepared in Example 150 except that N-(2-methoxyethyl)methylamine was used instead of morpholine.

$^1$H NMR(CDCl$_3$) δ2.68(br,3H), 2.89–3.39(m,7H), 4.22(s, 2H), 5.17(s,2H), 7.01(m,2H), 7.15(s,1H), 7.33(m,2H), 7.40–7.61(m,5H), 7.71–7.82(m,3H)

FAB: 638 (M+1)

Preparation 56

Synthesis of 4-(5-chloromethyl-1H-imidazol-1-ylmethyl)-piperidine-1-carboxylic acid benzylester 56-1) 4-Aminomethyl-piperidine-1-carboxylic acid benzylester 22.2 g(0.2 mol) of 4-aminomethyl-piperidine was dissolved in 250 ml of toluene and then 21.2 g(0.2 mol) of benzaldehyde was added thereto. The mixture was refluxed for 3 hours with Dean-stack and cooled down to 0° C., and then 34.2 g(0.2 mol) of benzylchloroformate was added thereto while stirring. After the mixture was stirred for 3 hours, 1N aqueous potassium hydrosulfate solution(220 ml) was added thereto at room temperature. The mixture was extracted three times with 200 ml of diethylether, and then the aqueous layer was basified with sodium hydroxide. The aqueous solution was saturated with sodium chloride and extracted three times with 100 ml of dichloromethane. The organic solution was dried over magnesium sulfate and distilled under reduced pressure to obtain 38 g(Yield 91%, Molecular weight 248) of the title compound $^1$H NMR(CDCl$_3$) δ1.11(s,2H), 1.49(s,3H), 1.70(d,2H), 2.57(d,2H), 2.78(s, 2H), 4.20(s,2H), 5.12(s,2H), 7.34–7.35 (m,5H)

FAB(M+H): 249

56-2) 4-(5-Hydroxymethyl-2-mercapto-1H-imidazol-1-ylmethyl)piperidine-1-carboxylic acid benzylester 24.8 g(0.1 mol) of the compound prepared in Preparation 56-1) and 6.0 g(0.1 mol) of acetic acid were dissolved in 50 ml of n-buthanol, and then the resulting solution was added to a solution wherein 12.6 g(0.13 mol) of potassium thiocyanate, 15.2 g(0.1 mol) of 1,3-dihydroxyacetone dimer and 10.0 g(0.17 mol) of acetic acid were dissolved in 50 ml, of n-butanol. The whole mixture was stirred for 48 hours. The solvent was removed by distillation under reduced pressure, 200 ml of ethyl acetate was added thereto, and the mixture was washed three times with 100 ml of water. The organic layer was dried over magnesium sulfate, and the solvent was removed by distillation under reduced pressure to obtain 27 g(75 mmol, Yield 75%, Molecular weight 361) of the title compound.

$^1$H NMR(CDCl$_3$) δ1.22(d,2H), 1.57(d,2H), 2.30(s,1H), 2.72(s,2H), 3,96 (s,2H), 4.15(d,2H), 4.46(s,2H), 5.10(s,2H), 6.62(s,1H), 7.26–7.37(m,5H)

FAB(M+H): 362

56-3) 4-(5-Hydroxymethyl-1H-imidazol-1-ylmethyl)-piperidine-1-carboxylic acid benzylester 18.05 g(50 mmol) of the compound prepared in Preparation 56-2) was added to a mixture of 100 ml of nitric acid(10%) and 10 ml of ethyl acetate. The whole mixture was soaked in cold ice water for 5 minutes, and stirred at room temperature for 3 hours. The mixture was basified with 4N aqueous sodium hydroxide solution, and then extracted twice with 100 ml of ethyl acetate. The organic extract was dried over magnesium sulfate and distilled under reduced pressure to obtain 12.3 g (38 mmol, Yield 75%, Molecular weight 329) of the title compound.

$^1$H NMR(CDCl$_3$) δ1.16(d,2H), 1.56(d,2H), 1.98(s,1H), 2.70(s,2H), 3,88 (d,2H), 4.18(s,2H), 4.49(s,1H), 4.56(s,3H), 5.10(s,2H), 6.82(s,1H), 7.27–7.40 (m,5H)

FAB(M+H): 330

56-4) 4-(5-Chloromethyl-1H-imidazol-1-ylmethyl)-piperidine-1-carboxylic acid benzylester 9.9 g(30 mmol) of the compound prepared in Preparation 56-3) was dissolved in 50 ml of chloroform, and 7.1 g(60 mmol) of thionyl chloride was slowly added thereto at 0° C. The mixture was stirred for 2 hours, the solvent was removed by distillation under reduced pressure, and the residual hydrochloric acid was removed under vacuum to obtain 9.9 g(Yield 95%, Molecular weight 347.5) of hydrochloric acid salt of the title compound.

¹H NMR(CDCl₃) δ1.12(d,2H), 1.53(d,2H), 2.65(s,2H), 3.82(d,2H), 4.22 (s,2H), 4.42(s,1H), 4.49(s,3H), 5.12(s,2H), 6.60(s,1H), 7.30–7.41(m,5H)

FAB(M+H): 349

Preparation 57

Synthesis of 1-(4-chlorobenzyl-5-chloromethyl-1H-imidazole hydrochloride 57-1) 1-(4-Chlorobenzyl)-5-hydroxymethyl-1H-imidazole The title compound was obtained in a yield of 50% according to the procedure described in J. M. Dener, L-H Zhang, H. Rapoport, *J.Org,Chem.*, 1993, 58, 1159 using dihydroxyacetone dimer and 4-chlorobenzylamine hydrochloride as starting materials.

¹H NMR(CDCl₃+CD₃OD) δ4.46(s,2H), 5.26(s,2H), 7.00 (s,1H), 7.07(d,2H), 7.50(d,2H), 7.65(s,1H)

57-2) 1-(4-Chlorobenzyl)-5-chloromethyl-1H-imidazole hydrochloride

The title compound was obtained in a yield of 96% according to the similar procedure as Preparation 56-4) except that the compound prepared in Preparation 57-1) was used as a starting material. This compound was directly used in the next reaction without purification.

Preparation 58

Synthesis of 4-[N-(2-methoxyethyl)N-methyl] carbamoyl-3-naphthalen-1-yl)-1H-pyrazole 58-1) N-t-Butyl-N'-(naphthalen-1-ylmethylenyl)-hydrazine 5.0 g(32 mmol) of 1-naphthaldehyde and 3.99 g(32 mmol) of t-butylhydrazine hydrochloride were dissolved in 100 ml of methanol, and then the mixture was reacted with 1 ml of acetic acid at room temperature for 24 hours After the solvent was removed by distillation under reduced pressure, 20 ml of ethyl acetate was added to the residue. The mixture was washed with saturated sodium hydrogen carbonate solution. Then, the separated organic layer was dried over anhydrous magnesium sulfate and distilled under reduced pressure to remove the solvent to obtain 6.3 g(28 mmol, Yield 86%) of the title compound.

¹H NMR(CDCl₃) δ1.70(s,9H), 7.23(s,1H), 7.32(m,1H), 7.42(m,2H), 7.80 (d1H), 7.90(d,2H), 8.60(d,1H), 9.91(s, 1H), 12.1(br,1H)

FAB(M+H): 227

58-2) 1-(t-Butyl)-3-(naphthalen-1-yl)-1H-pyrazole-4-carboxylic acid ethyl ester 6.3 g(28 mmol) of the compound prepared in Preparation 58-1) and 2.44 g(30.8 mmol) of ethylpropiolate were dissolved in a solvent mixture of 27 ml of acetic acid and 32 ml of acetonitrile, and the whole mixture was reacted in the air for 3 days. The solvent was removed, and the residue was subjected to silica gel column chromatography (eluent: ethyl acetate/n-hexane=9/1, v/v) to obtain 6.76 g(21 mmol, Yield 75%) of the title compound.

¹H NMR(CDCl₃) δ0.80(t,3H), 1.65(s,9H), 3.98(q,2H), 7.38(m,2H), 7.48 (m,1H), 7.55(m,1H), 7.74(m,1H), 7.85(m, 2H), 8.21(s, 1H), 11.31(br,1H)

FAB(M+H): 323

58-3) 3-(Naphthalen-1-yl)-1H-pyrazole-4-carboxylic acid ethylester 3.65 g(11.3 mmol) of the compound prepared in Preparation 58-2) was dissolved in 50 ml of formic acid, and the resulting solution was boiled for 12 hours under reflux. The solvent therein was removed by distillation under reduced pressure, and ethyl acetate was added thereto. The mixture was washed with saturated aqueous sodium hydrogen carbonate solution and dried over anhydrous magnesium sulfate. The solvent was removed by distillation under reduced pressure, and the residue was subjected to silica gel column chromatogropby(eluent: ethyl acetate/n-hexane=6/4, v/v) to obtain 1.1 g(4.1 mmol, Yield 37%) of the title compound (see, *J.Hetero.Chem.*, 31, 1447, 1944).

¹H NMR(CDCl₃) δ0.80(t,3H), 3.98(q,2H), 7.35–7.60(m, 5H), 7.90(m,2H), 7.94(s,1H)

FAB(M+H): 267

58-4) 3-(Naphthalen-1-yl)-1H-pyrazole-4-carboxylic acid 1.1 g(4.1 mmol) of the compound prepared in Preparation 58-3) and 2.1 g(12.4 mmol) of potassium hydroxide were dissolved in 50 ml of a solvent mixture of methanol/water (1:1, v/v). The mixture was reacted under reflux for 12 hours. The solvent was removed by distillation under reduced pressure. The residue was acidified with 1N aqueous hydrochloric acid solution, extracted with 50 ml of ethyl acetate and dried over anhydrous magnesium sulfate. The solvent was removed by distillation under reduced pressure to obtain 910 mg(3.8 mmol, Yield 92%) of the title compound.

¹H NMR(CD₃OD+CDCl₃) δ7.30(m,3H), 7.56(d,1H), 7.80–7.95 (m,3H), 8.07 (s,1H)

FAB(M+H): 239

58-5) 4-[N-(2-Methoxyethyl)-N-methyl]carbamoyl-3-(naphthalen-1-yl)-1H-pyrazole 238 mg(1 mmol) of the compound prepared in Preparation 58-4) was dissolved in 10 ml of dimethylformamide, and 230 mg(1.2 mmol) of EDC, 101 mg(1 mmol) of triethylamine and 162 mg(1.2 mmol) of HOBT(1-hydroxybenzotriazole) were added thereto, and then the mixture was stirred at 0° C. for 5 minutes. To the mixture was added 124 mg (1 mmol) of N-(2-methoxyethyl)-N-methylamine hydrochloride, which was then stirred at room temperature for 5 hours. The solvent was removed under reduced pressure, 10 ml of saturated aqueous potassium carbonate solution was added to the residue. The mixture was extracted with 20 ml of ethyl acetate, washed with 10 ml of 1N aqueous hydrochloric acid solution, washed with saturated sodium chloride solution and water, dried over anhydrous sodium sulfate, and concentrated to obtain 247 mg(0.8 mmol, Yield 80%) of the title compound.

¹H NMR(CDCl₃) δ2.40(s,2H), 2.81(s,1H), 2.84(s,1H), 2.96(s,1H), 3.02 (s,4H), 3.15(s,1.5H), 3.34(s,1.5H), 7.24–7.52(m,4H), 7.59(s,1H), 7.77(m,2H), 7.93(d,1H)

FAB(M+H): 310

Preparation 59

Synthesis of 4-(morpholin-4-yl)carbonyl-3-(naphthalen-1-yl)-1H-pyrazole 238 mg(1 mmol) of the compound prepared in Preparation 58-4) was dissolved in 10 ml of dimethylformamide, and 230 mg(1.2 mmol) of EDC and 162 mg(1.2 mmol) of HOBT were added thereto, and the mixture was stirred at 0° C. for 5 minutes. To the whole mixture was added 87 mg(1 mmol) of morpholine, which was then stirred at room temperature for 5 hours. The solvent was removed under reduced pressure and 10 ml of saturated aqueous potassium carbonate solution was added to the residue. The mixture was extracted with 20 ml of ethyl acetate, washed with 10 ml of 1N hydrochloric acid solution, washed with saturated aqueous sodium chloride solution and water, dried over anhydrous sodium sulfate, and concentrated to obtain 240 mg(0.8 mmol, Yield 80%) of the title compound.

$^1$H NMR(CDCl$_3$) δ2.5(br,2H), 2.95(br,2H), 3.15(br,2H), 3.40(br,2H), 7.50(m,4H), 7.95(m,4H), 9.73(br,1H)

FAB(M+H): 308

EXAMPLE 152

Synthesis of 1-[1-(1-benzyloxycarbonyl-piperidin-4-ylmethyl)-1H-imidazol-5-ylmethyl]-4-[N-(2-methoxyethyl)-N-methyl]carbamoyl-3-(naphthalen-1-yl)-1H-pyrazole(152)

616 mg(2.0 mmol) of the compound prepared in Preparation 56-4) was dissolved in 10 ml of dimethylformamide, 264 mg(6.6 mmol) of sodium hydride(60%) was added thereto at 0° C., and the whole mixture was stirred for 5 minutes. To the mixture was added 765 mg(2.2 mmol) of the compound prepared in Preparation 58-5) and the resulting mixture was stirred at room temperature for 5 hours. The solvent was removed by distillation under reduced pressure, and 10 ml of water was added to the residue. The mixture was then extracted twice with 20 ml of ethyl acetate, dried over magnesium sulfate, concentrated, and subjected to silica gel column chromatogrophy(eluent: dichloromethane/methanol=90/10, v/v) to obtain 930 mg(Yield 75%) of the title compound.

$^1$H NMR(CDCl$_3$) δ1.11(m,2H), 1.37(br,1H), 1.50(br,2H), 2.35(br,1H), 2.55 (br,2H), 2.71(br,1H), 2.90–3.21(m,7H), 3.35(br,1H), 3.90(br,2H), 3.98(d,1H), 4.50(d,1H), 5.02(s, 2H), 5.10(s,2H), 7.21–7.40(m,6H), 7.41–7.60(m,4H), 7.70 (s,1H), 7.80(s,1H), 7.95(m,2H), 8.13(d,1H)

FAB(M+H): 621

EXAMPLE 153

Synthesis of 1-[1-(1-methoxycarbonylpiperidin-4-ylmethyl)-1H-imidazole-5-ylmethyl]-4-[N-(2-methoxyethyl)-N-methyl]carbamoyl-3-(naphthalen-1-yl)-1H-pyrazole(153)

153-1) 1-[1-(Piperidin-4-ylmethyl)-1H-imidazole-5-ylmethyl]-4-[N-(2-methoxyethyl)-N-methyl]carbamoyl-3-(naphthalen-1-yl)-1H-pyrazole 227 mg(0.36 mmol) of the compound prepared in Example 152 was dissolved in methanol, 20 mg of palladium hydroxide carbon was added thereto, and then the mixture was reacted under 1 atm of hydrogen for 2 hours. After the reaction was completed, the mixture was filtered and the solvent was removed. The filtrate was subjected to silica gel column chromatogrophy(eluent: ammonia water/methanol=15/85, v/v) to, obtain 128 mg(0.26 mmol, Yield 74%) of the title compound.

$^1$H NMR(CDCl$_3$) δ1.08(s,2H), 1.53(m,4H), 2.33(s,2H), 2.64(br,4H), 3.20(m,6H), 3.31(s,1H), 3.75(d,2H), 4.13(m, 2H), 5.10(s,2H), 6.71(s, 1H), 7.11(s,1H), 7.30(m,9H), 7.74 (d,1H), 7.81(d,1H), 7.90(s,1H), 8.06(d,1H)

FAB(M+H): 486

153-2) 1-[1-(1-methoxycarbonylpiperidin-4-ylmethyl)-1H-imidazol-5-ylmethyl]-4-[N-(2-methoxyethyl)-N-methyl]carbamoyl-3-naphthalen-1-yl)-1H-pyrazole 30 mg(62 μmol) of the compound prepared in Example 153-1) was added to 2 ml of dichloromethane, 5.4 mg(6.9 μmol) of methylchloroformate was added thereto by an injector, and the mixture was stirred for 2 hours. The solvent was removed under reduced pressure, and the residue was subjected to silica gel column chromatograpby(eluent: dichloromethane/methanol=80/20, v/v) to obtain 27.8 mg(5.3 μmol, Yield 85%) of the title compound.

$^1$H NMR(CDCl$_3$) δ1.11(br,2H), 1.33(br,1H), 1.53(br,2H), 2.39(s,2H), 2.70 (br,4H), 2.90–3.20(br,6H), 3.32(s,1H), 3.62 (s,3H), 3.78(d,2H), 4.16(m,2H), 5.16(s,2H), 6.74(s, 1H), 7.10(s,1H), 7.21–750(m,14H), 7.76(d,1H), 7.84(d,1H), 7.91 (s,1H), 8.07(d,1H)

FAB(M+H): 545

EXAMPLE 154

Synthesis of 1-[1-(4-bromobenzyl)-1H-imidazol-5-ylmethyl]-4-[N-(2-methoxyethyl)-N-methyl]carbamoyl-3-(naphthalen-1-yl)-1H-pyrazole(154)

The title compound was obtained in a yield 81% according to the same procedure as Example 152 except that the compound prepared in Preparation 32-2) and the compound prepared in Preparation 58-5) were used.

$^1$H NMR(CDCl$_3$) δ2.41(s,2H), 2.82(s,1H), 2.85(s,1H), 2.98(s,1H), 3.04(s,4H), 3.17(s,1.5H), 3.36(s,1.5H), 5.11(s, 2H), 5.21(s,2H), 6.95(d,2H), 7.25(d,2H), 7.35–7.60(m,5H), 7.64(s,1H), 7.72(s,1H), 7.81(m,2H), 8.11(d,1H)

FAB(M+H): 558

EXAMPLE 155

Synthesis of 1-[1-(4-chlorobenzyl)-1H-imidazol-5-ylmethyl]-4-[N-(2-methoxyethyl)-N-methyl]carbamoyl-3-(naphthalen-1-yl)-1H-pyrazole(155)

The title compound was obtained in a yield 81% according to the same procedure as Example 152 except that the compound prepared in Preparation 57-2) and the compound prepared in Preparation 58-5) were used.

$^1$H NMR(CDCl$_3$) δ2.41(s,2H), 2.82(s,1H), 2.85(s,1H), 2.98(s,1H), 3.04 (s,4H), 3.17(s,1.5H), 3.36(s,1.5H), 5.20(s, 2H), 5.25(s,2H), 6.97(d,2H), 7.26(d,2H), 7.35–7.46(m,5H), 7.47(s,1H), 7.58(s,1H), 7.88(m,2H), 8.11(d,1H)

FAB(M+H): 514

EXAMPLE 156

Synthesis of 1-[1-(4-cyanobenzyl)-1H-imidazol-5-ylmethyl]-4-[N-(2-methoxyethyl)-N-methyl]carbamoyl-3-(naphthalen-1-yl)-1H-pyrazole(156)

The title compound was obtained in a yield 81% according to the same procedure as Example 152 except that the compound prepared in Preparation 29-5) and the compound prepared in Preparation 58-5) were used.

¹H NMR(CDCl₃) δ2.41(s,2H), 2.82(s,1H), 2.85(s,1H), 2.98(s,1H), 3.04 (s,4H), 3.17(s,1.5H), 3.36(s,1.5H), 5.20(s, 2H), 5.31(s,2H), 6.99(d,2H), 7.26 (d,2H), 7.35–7.46(m,5H), 7.48(s,1H), 7.57(s,1H), 7.89(m,2H), 8.12(d,1H)

FAB(M+H): 505

EXAMPLE 157

Synthesis of 1-[1-methyl-1H-imidazol-5-ylmethyl]-4-[N-(2-methoxyethyl)-N-methyl]carbamoyl-3-(naphthalen-1-yl)-1H-pyrazole (157)

The title compound was obtained in a yield 81% according to the same procedure as Example 152 except that 1-methyl-5-chloromethyl-1H-imidazole hydrochloride and the compound prepared in Preparation 58-5) were used.

¹H NMR(CDCl₃) δ2.42(br,2H), 2.71(br,1H), 3.10(br,5H), 3.30(br,1H), 3.50(s,3H), 5.17(s,2H), 6.69(s,1H), 7.09(s,1H), 7.41(m,9H), 7.74(d,1H), 7.83 (d,1H), 7.89(s,1H), 8.05(d, 1H)

FAB(M+H): 404

EXAMPLE 158

Synthesis of 1-[1-(1-benzyloxycarbonyl-piperidin-4-ylmethyl)-1H-imidazol-5-ylmethyl]-4-(morpholin-4-yl)carbonyl-3-(naphthalen-1-yl)1H-pyrazole(158)

612 mg(2.0 mmol) of the compound prepared in Preparation 59 was dissolved in 10 ml of dimethylformamide, 264 mg(6.6 mmol) of sodium hydride(60%) was added thereto at 0° C., and the whole mixture was studied for 5 minutes. To the mixture was added 765 mg(2.2 mmol) of the compound prepared in Preparation 56-4), which was then stirred at room temperature for 5 hours. The solvent was removed by distillation under reduced pressure and 10 ml of water was added to the residue. The resulting mixture was then extracted twice with 20 ml of ethyl acetate, dried over magnesium sulfate, concentrated, and subjected to silica gel column chromatography(eluent: dichloromethane/methanol=90/10, v/v) to obtain 930 mg(Yield 75%) of the title compound.

¹H NMR(CDCl₃) δ1.11(m,2H), 1.37(br,1H), 1.50(br,2H), 1.62(br, 1H), 2.35(br,1H), 2.55(br,2H), 2.71(br,1H), 3.14(br, 2H), 3.35(br,2H), 3.90(br,2H), 4.15(m,4H), 5.02(s,2H), 5.10 (s,2H), 7.21–7.40(m,6H), 7.41–7.60(m,4H), 7.70 (s,1H), 7.80(s,1H), 7.95(m,2H), 8.13(d,1H)

FAB(M+H): 619

EXAMPLE 159

Synthesis of 1-[1-(1-methoxycarbonylpiperidin-4-ylmethyl)-1H-imidazol-5-ylmethyl]-4-(morpholin-4-yl)carbonyl-3-(naphthalen-1-yl)-1H-pyrazole(159)

159-1) 1-[1-(Piperidin-4-ylmethyl)-1H-imidazol-5-ylmethyl]-4-(morpholin-4-yl)carbonyl-3-(naphthalen-1-yl)-1H-pyrazole 227 mg(0.36 mmol) of the compound prepared in Example 158 was dissolved in methanol, 20 mg of palladium hydroxide carbon was added thereto, and the mixture was reacted under 1 atm of hydrogen for 2 hours. After the reaction was completed, the mixture was flltered and the solvent therein was removed. The residue was subjected to silica gel column chromatography(eluent: ammonia water/methanol=15/85, v/v) to give 120 mg(0.26 mmol, Yield 74%) of the title compound.

¹H NMR(CDCl₃) δ1.06(m,2H), 1.43(m,3H), 2.36(br,5H), 2.41–3.79(br,13H), 3.78(d,2H), 5.22(s,2H), 6.88(s,1H), 7.12 (d,2H), 7.26(m,1H), 7.35(m,3H), 7.63(s,1H), 7.75(d,1H), 7.80(d,1H), 7.93(d,1H)

FAB(M+H): 484

159-2) 1-[1-(1-Methoxycarbonylpiperidin-4-ylmethyl)-1H-imidazol-5-ylmethyl]4-(morpholin-4-yl)carbonyl-3-(naphthalen-1-yl)-1H-pyrazole 30 mg(62 μmol) of the compound prepared in Example 159-1) was dissolved in 2 ml of dichloromethane, 5.4 mg(6.9 μmol) of methylchloroformate was added thereto by injector, and the whole mixture was stirred for 2 hours. The solvent was removed under reduced pressure, and the residue was subjected to silica gel column chromatography (eluent: dichloromethane/methanol=80/20, v/v) to give 27.8 mg(5.3 μmol, Yield 85%) of the title compound.

¹H NMR(CDCl₃) δ1.05(br,2H), 1.32(br,1H), 1.53(br,2H), 2.31–2.72(m,5H), 3.03~3.33(m,7H), 3.62(s,3H), 3.66(m, 2H), 4.13(br,2H), 5.12(s,2H), 6.71 (s,1H), 7.03(s,1H), 7.14 (s,1H), 7.24~7.43(m,5H), 7.74(d,1H), 7.82(d,1H), 8.10(d, 1H)

FAB(M+H): 543

EXAMPLE 160

Synthesis of 1-[1-(4-bromobenzyl)-1H-imidazol-5-ylmethyl]-4-(morpholin-4-yl)carbonyl-3-(naphthalen-1-yl)-1H-pyrazole(160)

The title compound was obtained in a yield 81% according to the same procedure as Example 152 except that the compound prepared in Preparation 32-2) and the compound prepared in Preparation 59 were used.

¹H NMR(CDCl₃) δ2.35(br,2H), 2.80(br,2H), 3.15(br,2H), 3.35(br,2H), 5.29(s,2H), 5.31(s,2H), 7.00(d,2H), 7.20–7.35 (m,3H), 7.40–7.60(m,4H), 7.72 (s,1H), 7.80(s,1H), 7.90(m, 2H), 8.01(d,1H)

FAB(M+H): 556

EXAMPLE 161

Synthesis of 1-[1-(4-chlorobenzyl)-1H-imidazol-5-ylmethyl]-4-(morpholin-4yl)carbonyl-3-(naphthalen-1-yl)-1H-pyrazole(161)

The title compound was obtained in a yield 81% according to the same procedure as Example 152 except that the compound prepared in Preparation 57-2) and the compound prepared in Preparation 59 were used.

¹H NMR(CDCl₃) δ2.35(br,2H), 2.80(br,2H), 3.15(br,2H), 3.35(br,2H), 5.29(s,2H), 5.31 (s,2H), 7.00(d,2H), 7.20–7.35 (m,3H), 7.40–7.60(m,4H), 7.72 (s,1H), 7.80(s,1H), 7.90(m, 2H), 8.01(d,1H)

FAB(M+H): 512

EXAMPLE 162

Synthesis of 1-[1-(4-cyanobenzyl)-1H-imidazol-5-ylmethyl]-4-(morpholinyl-4-yl)carbonyl-3-(naphthalen-1-yl)-1H-pyrazole(162)

The title compound was obtained in a yield 81% according to the same procedure as Example 152 except that the compound prepared in Preparation 29-5) and the compound prepared in Preparation 59 were used.

¹H NMR(CDCl₃) δ2.35(br,2H), 2.80(br,2H), 3.15(br,2H), 3.35(br,2H), 5.28(s,2H), 5.34(s,2H). 7.03(d,2H), 7.20–7.35

(m,3H), 7.40–7.60(m,4H), 7.72 (s,1H), 7.80(s,1H), 7.90(m, 2H), 8.01(d,1H)

FAB(M+H): 503

EXAMPLE 163

Synthesis of 1-(1-methyl-1H-imidazol-5-ylmethyl)-4-(morpholin-4-yl)carbonyl-3-naphthalen-1-yl)-1H-pyrazole(163)

The title compound was obtained in a yield 81% according to the same procedure as Example 152 except that 1-methyl-5-chloromethyl-1H-imidazole hydrochloride and the compound prepared in Preparation 59 were used.

$^1$H NMR(CDCl$_3$) δ2.35(br,2H), 2.80(br,2H), 3.15(br,2H), 3.35(br,2H), 3.62(s,3H), 5.29(s,2H), 7.20–7.35(m,3H), 7.40–7.60(m,2 H), 7.72(s,1H), 7.80 (s,1H), 7.90(m,2H), 8.01(d,1H)

FAB(M+H): 402

Experimental Example 1

Analysis of in vitro Inhibitory Activity for Ras Farnesyl Transferase

In the present experiment, Ras farnesyl transferase produced by genetic recombination techniques according to the improved Pompliano's method (Pompliano et al., Biochemistry, 1992, 31, 3800) was used, and Ras substrate (Ras-CVLS) protein described in Korean Patent Appln. No. 97-14409 was used after it has been purified according to the known method(see, Chung et al., Biochimica et Biophysica Acta, 1992, 278, 1129).

The enzyme reaction was performed in 50 μl of 50 mM Sodium HEPES buffer solution containing 25 mM of potassium chloride, 25 mM of magnesium chloride, 10 mM of DTT and 50 μM of zinc chloride. 1.5 μM of Ras substrate protein, 0.15 μM of tritium-farnesylpyrophosphate and 4.5 nM of farnesyl transferase were used.

More specifically, in the initial step, farnesyl transferase was added to the above buffer solution, reaction was maintained for 30 minutes at 37° C. and then the reaction was stopped by adding 1 ml of ethanol solution containing 1M HCl. The formed precipitates were adsorbed to GF/B filter using Hopper harvestor(Hopper #FH 225V) for filter-binding, washed with ethanol, and then radioactivity of the dried filter was measured using LKB β counter. Enzyme titer was measured in the unsaturated state of substrate where the concentrations of Ras substrate protein and farnesyl transferase have quantitative relationship. The compound according to the present invention dissolved in dimethyl sulfoxide (DMSO) was added to the reaction solution in an amount of less than 5% of the total reaction solution, and then the enzyme inhibitory activity thereof was measured. The enzyme inhibitory activity was represented by percentage of the amount of farnesyl incorporated into the Ras substrate protein in the presence of the test compound to that in the absence of the test compound. IC$_{50}$ of the test compound was defined as the concentration at which 50% of the enzyme activity was inhibited.

To evaluate the selective enzyme inhibitory activity of the compound according to the present invention, inhibitory activity on geranylgeranyl transferase was measured. Geranylgeranyl transferase was purified from bovine brain according to the method modified from Schaber's method (Schaber et al., J. Biol. Chem. 1990, 265, 14701), and substantially the same experimental procedure as that for farnesyl transferase was performed on geranylgeranyl pyrophosphate and Ras-CVIL substrate protein.

The test results are represented in the following Table 7.

Experimental Example 2

Analysis of in vivo Inhibitory Activity for Ras Farnesyl Transferase

In the present experiment, Rat2 cell line which expresses C-Harvey-Ras protein having transforming activity and Rat2 cell line(Korean patent application No. 97-14409) which is transformed with fused protein of H-Ras substituted with polybasic lysine domain at C-terminus of K-Ras were used. The experiment was performed by the modified Declue's method(Declue. J. E. et al., Cancer Research, 1991, 51, 712). Hereinafter, the experimental method will be described in more detail.

3×10$^5$ cells of tansformed Rat2 fibroblast cell line were sprayed on 60 mm cell cultivation dish and cultivated for 48 hours in a cell incubator at 37° C. and after 50% or more of density was reached, it was treated with the test compounds. The compound according to the present invention dissolved in dimethylsulfoxide(DMSO) was used. 1% concentration of dimethylsulfoxide was used in both control and test groups. After 4 hours from the treatment with the compound, methionine labeled with 150 μCi of radioactive isotope [$^{35}$S] per 1 ml of medium was added and after cultivating for 20 hours, the cells were. washed with physiological saline water. The cells were lysed using 1 ml of cold cell lysis buffer solution(50 mM of Sodium HEPES buffer solution containing 5 mM of magnesium chloride, 1 mM of DTT, 1% NP 40, 1 mM of EDTA, 1 mM of PMSF, 2 μM of leupeptin, 2 μM of pepstatin A and 2 μM of antipain) and the supernatant wherein the cells were lysed was obtained by high-velocity centrifugation of 12,000 g×5 minutes. The amount of radioisotope in the supernatant was measured and standardized to obtain a quantitative result in immunoprecipitation reaction and then, Y13-259, a monoclonal antiboby specifically binding to Ras protein(Furth, M. E. et al., J. Virol, 1982, 43, 294) was added and reacted for 15 hours at 4° C. Protein A(combined with goat anti-murine imunoglobulin antibody)-agarose suspension was added to the solution and reacted for 1 hour at 4° C. and then, to remove the unspecific binding product, immunoprecipitates were washed with a buffer solution (50 mM Tris chloride buffer solution containing 50 mM of sodium chloride, 0.5% of sodium dioxycolate, 0.5% of NP 40 and 0.1% of SDS). The precipitates were added to a buffer solution for electrophoresis and boiled and then, electrophoresis was performed using 13.5% of SDS polyacrylamide gel. After electrophoresis, the gel was fixed and dried. Then, the gel was exposed to X-ray film, developed and printed. From the result of the experiment, intensities of band of protein combined with or without farnesyl of Ras protein were measured, and the concentration of the test compound inhibiting 50% of farnesyl binding was defined as CIC$_{50}$, an in vivo Ras farnesyl tansferase inhibitory activity. The test results are shown in the following Table 7.

TABLE 7-1

| COM. NO. | H-Ras IC$_{50}$ (μM) | H-Ras CIC$_{50}$ (μM) | K-Ras IC$_{50}$ (μM) | K-Ras CIC$_{50}$ (μM) |
|---|---|---|---|---|
| 1 | 0.0011 | 0.025 | 0.0035 | 10 |
| 2 | 0.00085 | 0.025 | 0.002 | 10–50 |
| 3 | 0.001 | 0.025 | 0.0024 | 15 |
| 4 | 0.047 | 0.1–1 | 0.75 | 10–100 |
| 5 | 0.0037 | 0.025 | 0.0085 | 10–50 |
| 6 | 0.001 | 0.025 | 0.002 | 10–50 |
| 7 | 0.0006 | 0.025 | 0.0022 | 10–50 |
| 8 | 0.004 | 0.025 | 0.008 | 10–50 |
| 9 | 0.005 | 0.025 | 0.0066 | 10–50 |

TABLE 7-1-continued

| COM. NO. | H-Ras IC$_{50}$ ($\mu$M) | H-Ras CIC$_{50}$ ($\mu$M) | K-Ras IC$_{50}$ ($\mu$M) | K-Ras CIC$_{50}$ ($\mu$M) |
|---|---|---|---|---|
| 10 | 0.00085 | 0.0125 | 0.005 | 10–50 |
| 11 | 0.004 | 0.025 | 0.008 | 10–50 |
| 12 | 0.005 | 0.025 | 0.0066 | 10–50 |
| 13 | 0.00085 | 0.0125 | 0.005 | 10–50 |
| 14 | 0.002 | 0.0125 | 0.005 | 10–50 |
| 15 | 0.005 | 0.025 | 0.01 | 10–50 |
| 16 | 0.0012 | 0.0125 | 0.005 | 10–50 |
| 17 | 0.002 | 0.025 | 0.003 | 10–50 |
| 18 | 0.001 | 0.025 | 0.002 | 10–50 |

TABLE 7-2

| COM. NO. | H-Ras IC$_{50}$ ($\mu$M) | H-Ras CIC$_{50}$ ($\mu$M) | K-Ras IC$_{50}$ ($\mu$M) | K-Ras CIC$_{50}$ ($\mu$M) |
|---|---|---|---|---|
| 19 | 0.001 | 0.020 | 0.003 | 10–50 |
| 20 | 0.001 | 0.020 | 0.002 | 10–50 |
| 21 | 0.001 | 0.021 | 0.001 | 10–50 |
| 22 | 0.001 | 0.020 | 0.002 | 10–50 |
| 23 | 0.002 | 0.023 | 0.002 | 10–50 |
| 24 | 0.002 | 0.025 | 0.003 | 10–50 |
| 25 | 0.002 | 0.015 | 0.005 | 10–50 |
| 26 | 0.002 | 0.015 | 0.003 | 10–50 |
| 27 | 0.006 | 0.025 | 0.005 | 10–30 |
| 28 | 0.001 | 0.020 | 0.002 | 10–30 |
| 29 | 0.002 | 0.010 | 0.004 | 10–20 |
| 30 | 0.002 | 0.010 | 0.004 | 10–20 |
| 31 | 0.002 | 0.012 | 0.005 | 10–20 |
| 32 | 0.002 | 0.015 | 0.003 | 10–50 |
| 33 | 0.002 | 0.018 | 0.003 | 10–50 |
| 34 | 0.002 | 0.020 | 0.003 | 10–50 |
| 35 | 0.001 | 0.025 | 0.002 | 10–50 |
| 36 | 0.001 | 0.025 | 0.002 | 10–50 |
| 37 | 0.002 | 0.025 | 0.003 | 10–50 |
| 38 | 0.002 | 0.025 | 0.004 | 10–50 |
| 39 | 0.002 | 0.020 | 0.003 | 10–50 |
| 40 | 0.002 | 0.025 | 0.003 | 10–50 |
| 41 | 0.003 | 0.015 | 0.004 | 10–50 |

TABLE 7-3

| COM. NO. | H-Ras IC$_{50}$ ($\mu$M) | H-Ras CIC$_{50}$ ($\mu$M) | K-Ras IC$_{50}$ ($\mu$M) | K-Ras CIC$_{50}$ ($\mu$M) |
|---|---|---|---|---|
| 42 | 0.004 | 0.015 | 0.003 | 10–50 |
| 43 | 0.001 | 0.015 | 0.002 | 5–10 |
| 44 | 0.25 | 1–50 | 0.1–10 | 10–100 |
| 45 | 0.13 | 1–50 | 0.1–10 | 10–100 |
| 46 | 0.12 | 1–50 | 0.1–10 | 10–100 |
| 47 | 0.09 | 1–50 | 0.1–10 | 10–100 |
| 48 | 0.15 | 1–50 | 10 | 10–100 |
| 49 | 0.03 | 0.7 | 0.485 | <20 |
| 50 | 0.15 | 1–50 | 0.1–10 | 10–100 |
| 51 | 0.27 | 1–50 | 0.1–10 | 10–100 |
| 52 | 0.07 | 1–50 | 0.1–10 | 10–100 |
| 53 | 0.3 | 1–50 | 0.1–10 | 10–100 |
| 54 | 0.39 | 1–50 | 0.1–10 | 10–100 |
| 55 | 0.06 | 1–50 | 0.1–10 | 10–100 |
| 56 | 0.04 | 1–50 | 0.1–10 | 10–100 |
| 57 | 0.038 | 1–50 | 0.1–10 | 10–100 |
| 58 | 0.025 | 1–50 | 0.1–10 | 10–100 |
| 59 | 0.57 | 1–50 | 0.1–10 | 10–100 |
| 60 | 0.2 | 1–50 | 0.1–10 | 10–100 |
| 61 | 0.74 | 1–50 | 0.1–10 | 10–100 |
| 62 | 0.068 | 1–50 | 0.1–10 | 10–100 |
| 63 | 0.23 | 1–50 | 0.1–10 | 10–100 |

TABLE 7-4

| COM. NO. | H-Ras IC$_{50}$ ($\mu$M) | H-Ras CIC$_{50}$ ($\mu$M) | K-Ras IC$_{50}$ ($\mu$M) | K-Ras CIC$_{50}$ ($\mu$M) |
|---|---|---|---|---|
| 64 | 0.16 | 1–50 | 0.1–10 | 10–100 |
| 65 | 0.42 | 1–50 | 0.1–10 | 10–100 |
| 66 | 0.12 | 1–50 | 0.1–10 | 10–100 |
| 67 | 0.02 | 3 | 0.1–10 | >50 |
| 68 | 0.12 | 1–50 | 0.1–10 | 10–100 |
| 69 | 0.55 | 1–50 | 0.1–10 | 10–100 |
| 70 | 0.21 | 1–50 | 0.1–10 | 10–100 |
| 71 | 0.12 | 1–50 | 0.1–10 | 10–100 |
| 72 | 0.05 | 1–50 | 0.1–10 | 10–100 |
| 73 | 0.002 | 0.2 | 0.02 | >10 |
| 74 | 0.01 | 0.1–1 | 0.001–0.1 | 10–100 |
| 75 | 0.005 | 0.2 | 0.16 | 20 |
| 76 | 0.004 | 0.1–1 | 0.1–10 | 10–100 |
| 77 | 0.004 | 0.1 | 0.12 | 20 |
| 78 | 0.0045 | 0.1 | 0.2 | 10–100 |
| 79 | 0.005 | 0.1 | 0.1 | >50 |
| 80 | 8.21 | 1–50 | 0.1–10 | 10–100 |
| 81 | 0.68 | 1–50 | 0.1–10 | 10–100 |
| 82 | 0.4 | 1–50 | 0.1–10 | 10–100 |
| 83 | 0.26 | 1–50 | 18.5 | 10–100 |
| 84 | 0.72 | 1–50 | 1.83 | 10–100 |
| 85 | 0.03 | 4 | 0.1–10 | >50 |

TABLE 7-5

| COM. NO. | H-Ras IC$_{50}$ ($\mu$M) | H-Ras CIC$_{50}$ ($\mu$M) | K-Ras IC$_{50}$ ($\mu$M) | K-Ras CIC$_{50}$ ($\mu$M) |
|---|---|---|---|---|
| 86 | 0.03 | 2 | 0.1–10 | >50 |
| 87 | 0.06 | 1–50 | 0.1–10 | 10–100 |
| 88 | 0.6 | 1–50 | 0.1–10 | 10–100 |
| 89 | 0.014 | 1 | 0.1–10 | 10–100 |
| 90 | 0.0425 | 1–50 | 0.1–10 | 10–100 |
| 91 | 2.15 | 1–50 | 0.1–10 | 10–100 |
| 92 | 0.07 | 1–50 | 0.1–10 | 10–100 |
| 93 | 0.32 | 1–50 | 0.1–10 | 10–100 |
| 94 | 0.2 | 1–50 | 0.1–10 | 10–100 |
| 95 | 0.0007 | 0.01–0.1 | 0.1–1 | 10–50 |
| 96 | 0.23 | 1–50 | 1–10 | 10–100 |
| 97 | 12 | 10–100 | 10–100 | 10–100 |
| 98 | 0.90–0.9 | 1–50 | 0.1–10 | 10–100 |
| 99 | 0.0030 | 0.1 | 0.1 | >50 |
| 100 | 1.8 | >1 | 0.1–10 | >20 |
| 101 | 0.01 | >5 | 0.8 | >50 |
| 102 | 0.45 | 1–50 | 22 | >50 |
| 103 | 0.064 | 0.1–10 | 1.7 | 10–100 |
| 104 | 0.0005 | <0.05 | 0.006 | <10 |
| 105 | 0.0004 | 0.05 | 0.09 | >50 |
| 106 | 0.9 | 1–50 | 10–100 | 10–100 |
| 107 | 10 | 1–50 | 0.1–10 | 10–100 |

TABLE 7-6

| COM. No. | H-Ras IC$_{50}$ ($\mu$M) | H-Ras CIC$_{50}$ ($\mu$M) | K-Ras IC$_{50}$ ($\mu$M) | K-Ras CIC$_{50}$ ($\mu$M) |
|---|---|---|---|---|
| 108 | 0.26 | 1–50 | 0.1–10 | 10–100 |
| 109 | 8.6 | 1–50 | 1–50 | 10–100 |
| 110 | 0.0006 | 0.008 | 0.0015 | 10 |
| 111 | 0.002 | 0.03 | 0.002 | 4 |
| 112 | 0.004 | 0.015 | 0.006 | 10 |
| 113 | 0.004 | <0.1 | <0.1 | 10–100 |
| 114 | 0.001 | 0.015 | 0.100 | <100 |
| 115 | 0.002 | 0.025 | 0.035 | <50 |
| 116 | 0.004 | 0.030 | 0.062 | <50 |
| 117 | — | — | — | <50 |
| 118 | — | — | — | <40 |
| 119 | — | — | — | <30 |
| 120 | — | — | — | <20 |
| 121 | — | — | — | <40 |
| 122 | — | — | — | <30 |

TABLE 7-6-continued

| COM. No. | H-Ras IC$_{50}$ ($\mu$M) | H-Ras CIC$_{50}$ ($\mu$M) | K-Ras IC$_{50}$ ($\mu$M) | K-Ras CIC$_{50}$ ($\mu$M) |
|---|---|---|---|---|
| 123 | — | — | — | <40 |
| 124 | — | — | — | <20 |
| 125 | 0.002 | 0.006 | 0.004 | 4 |
| 126 | 0.001 | 0.012 | 0.004 | 5 |
| 127 | 0.002 | 0.015 | 0.005 | 5 |
| 128 | 0.002 | 0.010 | 0.010 | 5 |
| 129 | 0.003 | 0.025 | 0.004 | 10–50 |

TABLE 7-7

| COM. NO. | H-Ras IC$_{50}$ ($\mu$M) | H-Ras CIC($\mu$M) | K-Ras IC$_{50}$ ($\mu$M) | K-Ras CIC$_{50}$ ($\mu$M) |
|---|---|---|---|---|
| 130 | 0.002 | 0.025 | 0.003 | 10–50 |
| 131 | 0.001 | 0.0125 | 0.0023 | 10–50 |
| 132 | 0.0035 | 0.025 | 0.011 | 10–50 |
| 133 | 0.00065 | 0.025 | 0.002 | 10–50 |
| 134 | 0.0027 | 0.025 | 0.002 | 10–50 |
| 135 | 0.0024 | 0.03 | 0.004 | 10–50 |
| 136 | 0.0016 | 0.025 | 0.0024 | 10–50 |
| 137 | 0.0017 | 0.020 | 0.0021 | 10–20 |
| 138 | 0.0014 | 0.025 | 0.0035 | 10–50 |
| 139 | 0.005 | 0.07 | 37 | 7 |
| 140 | 0.09 | 1–10 | 10–50 | 10–50 |
| 141 | 0.23 | 1–10 | 10–100 | 10–50 |
| 142 | 12 | >50 | >50 | >50 |
| 143 | 1.2 | 20 | >50 | >50 |
| 144 | 0.38 | 5 | 50 | >50 |
| 145 | 0.007 | 0.1 | 0.07 | 25 |
| 146 | 0.09 | 1 | 10 | 50 |
| 147 | 0.002 | 0.05 | 0.03 | 10 |
| 148 | 1.7 | 30 | >50 | >50 |
| 149 | 5 | 50 | >50 | >50 |
| 150 | 8 | >50 | >50 | >50 |
| 151 | 4.6 | 50 | >50 | >50 |

TABLE 7-8

| COM. NO. | H-Ras IC$_{50}$ ($\mu$M) | H-Ras CIC$_{50}$ ($\mu$M) | K-Ras IC$_{50}$ ($\mu$M) | K-Ras CIC$_{50}$ ($\mu$M) |
|---|---|---|---|---|
| 152 | 0.023 | 0.1 | 0.07 | 10 |
| 153 | 0.03 | 0.15 | 0.1 | 20 |
| 154 | 0.03 | 0.15 | 0.2 | 10 |
| 155 | 0.02 | 0.1 | 0.2 | 15 |
| 156 | 0.02 | 0.1 | 0.2 | 40 |
| 157 | 0.01 | 0.1 | 5 | >50 |
| 158 | 0.25 | 1 | 2 | 30 |
| 159 | 0.3 | 1.2 | 4 | 50 |
| 160 | 0.3 | 1.5 | 3 | 40 |
| 161 | 0.2 | 1 | 2 | 50 |
| 162 | 0.25 | 1 | 2 | 50 |
| 163 | 0.15 | 1 | 10 | >50 |

What is claimed is:

1. An imidazole derivative represented by the following formula (1):

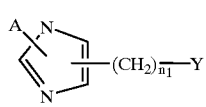

[Formula 1]

in which $n_1$ represents an integer of 1 to 4,

A represents hydrogen; straight-chain or branched $C_1$–$C_{10}$-alkyl which may be optionally substituted by $C_3$–$C_7$-cycloalkyl or lower alkoxy; or a radical selected from the following group:

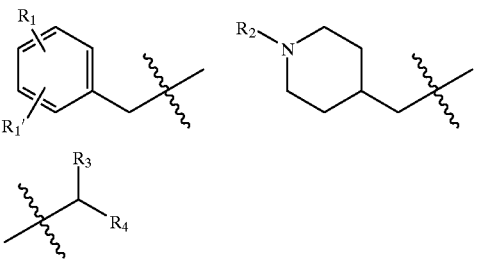

wherein $R_1$ and $R_1'$ independently of one another represent hydrogen, halogen, cyano, nitro, hydroxycarbonyl, aminocarbonyl, aminothiocarbonyl, lower alkoxy, phenoxy, phenyl, benzyloxy, or lower alkyl which may be optionally substituted by $C_3$–$C_6$-cycloalkyl, $R_2$ represents hydrogen or lower alkyl, or represents —E—F wherein E is —$CH_2$—, —C(O)— or —S(O)$_2$— and F is hydrogen; lower alkyl which may be optionally substituted by phenoxy or biphenyl; lower alkoxy which may be optionally substituted by aryl; phenyl; benzyl; benzyloxy; or amino which may be optionally substituted by lower alkyl, benzyl or $C_5$–$C_6$-cycloalkyl, $R_3$ represents hydrogen, lower alkyl or phenyl, $R_4$ represents a radical selected from the following group:

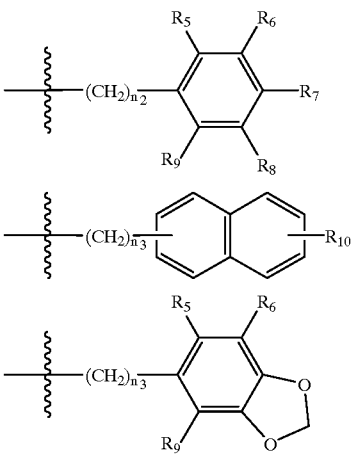

wherein $n_2$ and $n_3$ independently of one another denote 0, 1, 2, 3 or 4, $R_5$ and $R_9$ independently of one another represent hydrogen, lower alkyl, lower alkoxy, phenoxy, phenyl, hydroxy or halogen, $R_6$ and $R_8$ independently of one another represent hydrogen, lower alkyl, lower alkoxy, phenoxy, phenyl, cyano, hydroxy or halogen, $R_7$ represents hydrogen; lower alkyl which may be optionally substituted by $C_3$–$C_6$-cycloalkyl; lower alkoxy; hydroxy; $C_3$–$C_6$-cycloalkyl; di(lower alkyl) anino; phenyl; phenoxy; or halogen, $R_{10}$ represents hydrogen, lower alkyl or lower alkoxy, Y represents a radical selected from the following group:

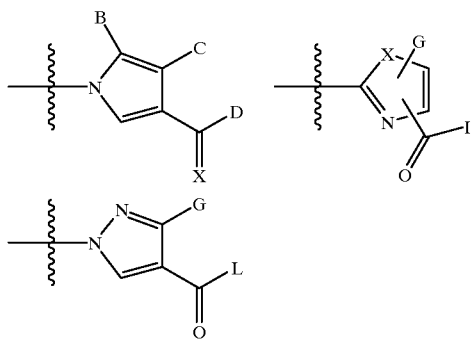

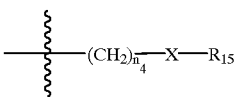

wherein

X represents O or S,

B represents hydrogen, or lower alkyl which may be optionally substituted by hydroxy, mercapto, lower alkoxy, lower alkylthio or aryl, C represents hydrogen, or lower alkyl which may be optionally substituted by aryl; or represents a radical selected from the following group:

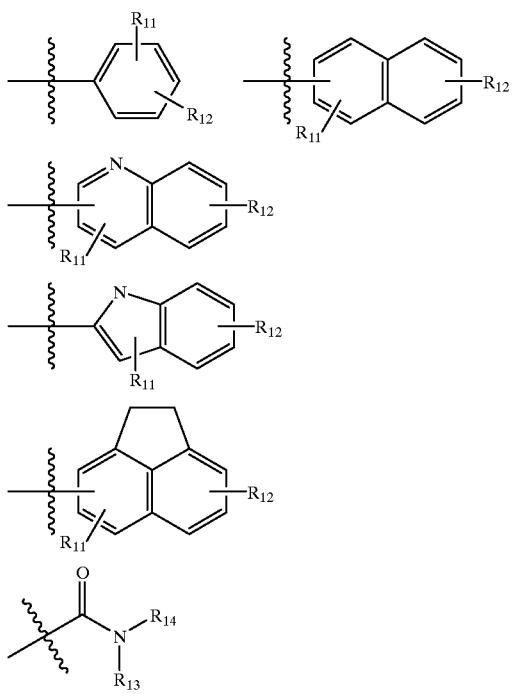

wherein $R_{11}$ and $R_{12}$ independently of one another represent hydrogen, lower alkyl, lower alkoxy, halogen, cyano, hydroxycarbonyl, aminocarbonyl, aminothiocarbonyl, hydroxy, phenyl or phenoxy, $R_{13}$ and $R_4$ independently of one another represent hydrogen, lower alkyl, aryl or wherein X is defined as previously described, $n_4$ is an integer of 2 to 4 and $R_{15}$ is lower alkyl, D represents amino acid residue or lower alkyl ester of amino acid residue; or represents a radical selected from the following group:

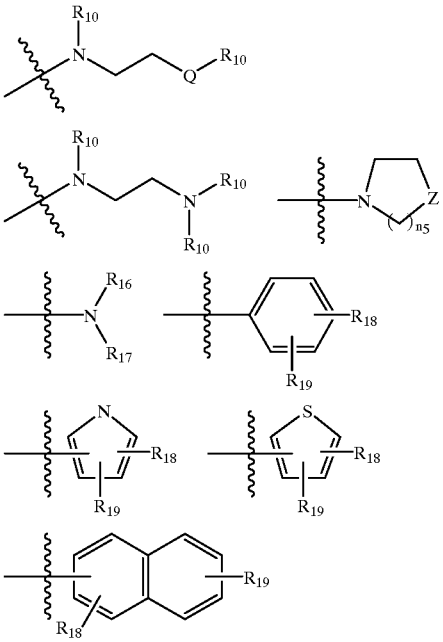

wherein $R_{10}$ is defined as previously described,

Q represents O, S, S=O or $SO_2$,

Z represents O, S, S=O, $SO_2$, C=O or C=S, or represents CH—$R_{20}$ or N—$R_{20}$ (wherein $R_{20}$ is hydrogen, lower alkyl or hydroxy), $n_5$ denotes an integer of 1 to 3, $R_{16}$ and $R_{17}$ independently of one another represents hydrogen; aryl; lower alkyl which may be optionally substituted by aryl or cyanoaryl; or

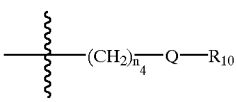

wherein $n_4$, Q and $R_{10}$ are defined as previously described, $R_{18}$ and $R_{19}$ independently of one another represents hydrogen; halogen; hydroxy; cyano; lower alkyl; lower alkoxy; alkoxyalkyl; alkylthio; hydroxycarbonyl; aminocarbonyl; aminothiocarbonyl; alkylsulfonyl; alkylthioalkyl; alkylthioalkyloxy; aryl; or oxy, thio, sulfonyl or lower alkyl substituted by aryl, G represents a radical selected by the following group:

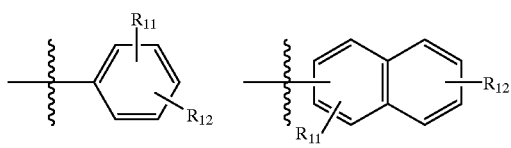

wherein
R$_{11}$ and R$_{12}$ are defied as previously described,
I represents lower alkoxy, or represents a radical selected from the following group:

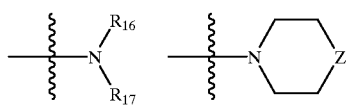

wherein
R$_{16}$, R$_{17}$ and Z are defined as previously described,
L represents a radical selected from the following group:

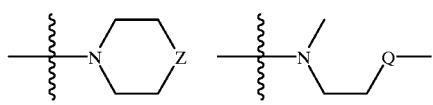

wherein Z and Q are defined as previously described, provided that
(1) n$_2$ is other than 0 when R$_3$ is hydrogen, and
(2) Y is other than

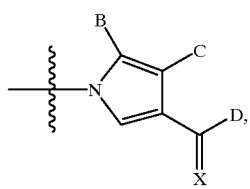

when A is

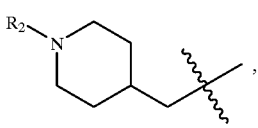

or a pharmaceutically acceptable salt or isomer thereof.

2. The compound of claim 1 wherein
n$_1$ represents an integer of 1 to 3,
A represents hydrogen; straight-chain or branched C$_1$–C$_{10}$-alkyl which may be optionally substituted by C$_3$–C$_7$-cycloalkyl or lower alkoxy; or a radical selected from the following group:

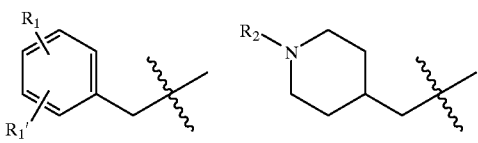

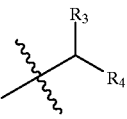

wherein
R$_1$ and R$_1$' independently of one another represent hydrogen, halogen, cyano, nitro, hydroxycarbonyl, aminocarbonyl, aminothiocarbonyl, lower alkoxy, phenoxy, phenyl, benzyloxy, or lower alkyl which may be optionally substituted by C$_3$–C$_6$-cycloalkyl,
R$_2$ represents hydrogen or lower alkyl, or represents —E—F wherein E is —CH$_2$—, —C(O)— or —S(O)$_2$— and F is hydrogen; lower alkyl which may be optionally substituted by phenoxy or biphenyl; lower alkoxy which may be optionally substituted by aryl; phenyl; benzyl; benzyloxy; or amino which may be optionally substituted by lower alkyl, benzl or C$_5$–C$_6$-cycloalkyl,
R$_3$ represents hydrogen or lower alkyl,
R$_4$ represents a radical selected from the following group:

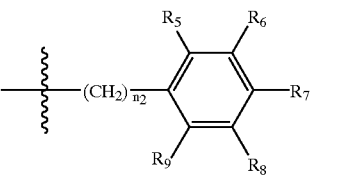

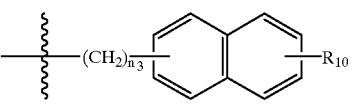

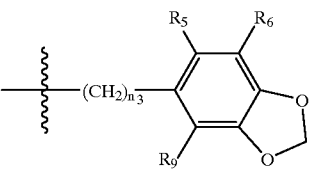

wherein
n$_2$ and n$_3$ independently of one another denote 0, 1, 2, 3 or 4,
R$_5$, R$_6$, R$_8$ and R$_9$ independently of one another represent hydrogen, lower alkyl, lower alkoxy, hydroxy or halogen,
R$_7$ represents hydrogen; lower alkyl which may be optionally substituted by C$_3$–C$_6$-cycloalkyl; lower alkoxy; hydroxy; C$_3$–C$_6$-cycloalkyl; or halogen,
R$_{10}$ represents hydrogen, methyl or methoxy,
Y represents a radical selected from the following group:

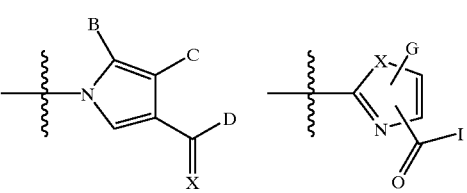

-continued

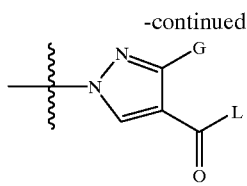

wherein

X represents O or S,

B represents hydrogen, or lower alkyl which may be optionally substituted by lower alkoxy or aryl, C represents hydrogen, or lower alkyl which may be optionally substituted by aryl; or represents a radical selected from the following group:

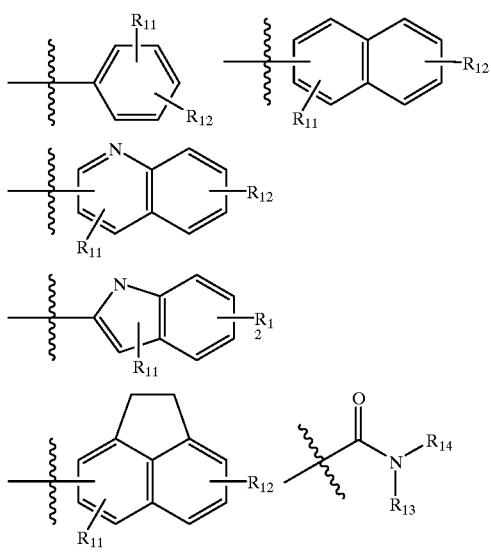

wherein $R_{11}$ and $R_{12}$ independently of one another represent hydrogen, lower alkyl, lower alkoxy, halogen, cyano, aminocarbonyl, phenyl or phenoxy, $R_{13}$ and $R_{14}$ independently of one another represent hydrogen, lower alkyl, aryl or

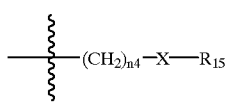

wherein X is defined as previously described, $n_4$ is 2 and $R_{15}$ is lower alkyl, D represents amino acid residue or lower alkyl ester of amino acid residue; or represents a radical selected from the following group:

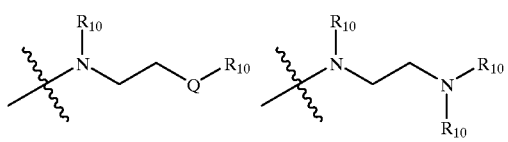

-continued

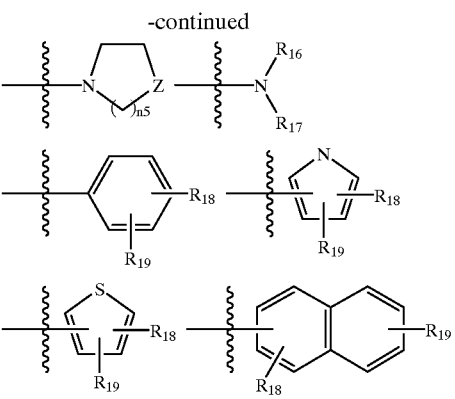

wherein $R_{10}$ is defined as previously described,

Q represents O, S, S=O or $SO_2$,

Z represents O, S, S=O, $SO_2$ or C=O, or represents CH—$R_{20}$ or N—$R_{20}$ (wherein $R_{20}$ is hydrogen, lower alkyl or hydroxy), $n_5$ denotes an integer of 1 to 3, $R_{16}$ and $R_{17}$ independently of one another represents hydrogen; aryl; lower alkyl which may be optionally substituted by aryl or cyanoaryl; or

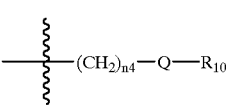

wherein $n_4$, Q and $R_{10}$ are defined as previously described, $R_{18}$ and $R_{19}$ independently of one another represents hydrogen; halogen; hydroxy; cyano; lower alkyl; lower alkoxy; alkoxyalkyl; alkylthio; hydroxycarbonyl; aminocarbonyl; aminothiocarbonyl; alkylsulfonyl; alkylthioalkyl; alkylthioalkyloxy; aryl; or oxy, thio, sulfonyl or lower alkyl substituted by aryl, G represents a radical selected by the following group:

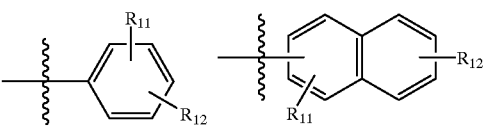

wherein $R_{11}$ and $R_{12}$ are defined as previously described,

I represents lower alkoxy, or represents a radical selected from the following group:

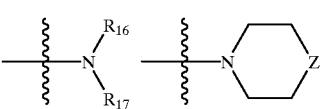

wherein $R_{16}$, $R_{17}$ and Z are defined as previously described,

L represents a radical selected from the following group:

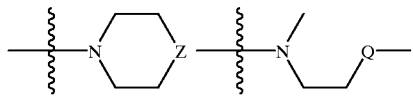

wherein Z and Q are defined as previously described, provided that
(1) $n_2$ is other than 0 when $R_3$ is hydrogen, and
(2) Y is other than

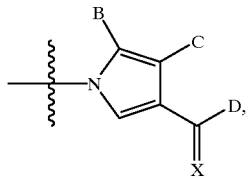

when A is

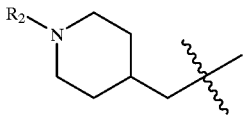

3. The compound of claim 1 wherein Y represents

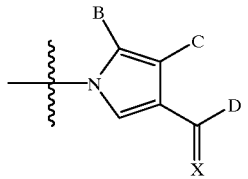

and C represents

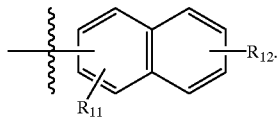

4. The compound of claim 1 which is selected from a group consisting of:

3-[N-(2-methoxyethyl)-N-methyl]carbamoyl-1-[1-(3,4methylenedioxybenzyl)-1H-imidazol-5-ylmethyl]-4-naphthalen-1-yl)-1H-pyrrole(1),
1-[1-(3,4-methylenedioxybenzyl)-1H-imidazol-5-ylmethyl]-3-(morpholin-4-yl)carbonyl-4-(naphthalen-1-yl)-1H-pyrrole(2),
1-[1-(3,4-methylenedioxybenzyl)-1H-imidazol-5-ylmethyl]-3-(4-methylpiperazin-1-yl)carbonyl4-(naphthalen-1-yl)-1H-pyrrole(3),
3-{N-[2-(N,N-dimethylamino)ethyl]-N-methyl}carbamoyl-1-[1-(3,4-methylendioxybenzyl)-1H-imidazol-5-ylmethyl]-4-(naphthalen-1-yl)-1H-pyrrole(4),
3-[N-(2-methoxyethyl)-N-methyl]carbamoyl-4-naphthalen-1-yl)-1-[1-naphthalen-1-ylmethyl)-1H-imidazol-5-ylmethyl]-1H-pyrrole(5),
3-(morpholin-4-yl)carbonyl-4-(naphthalen-1-yl)-1-[1-naphthalen-1-ylmethyl)-1H-imidazol-5-ylmethyl]-1H-pyrrole(6),
3-(4-methylpiperazin-1-yl)carbonyl-4-(naphthalen-1-yl)-1-[1-(naphthalen-1-ylmethyl)-1H-imidazol-5-ylmethyl]-1H-pyrrole(7),
3-[N-(2-methoxyethyl)-N-methyl]carbamoyl-1-[1-((R)-α-methylbenzyl)-1H-imidazol-5-ylmethyl]-4-(naphthalen-1-yl)-1H-pyrrole(8),
1-[1-((R)-α-methylbenzyl)-1H-imidazol-5-ylmethyl]-3-(morpholin-4-yl)carbonyl-4-(naphthalen-1-yl)-1H-pyrrole(9),
1-[1-((R)-α-methylbenzyl)-1H-imidazol-5-ylmethyl]-3-(4-methylpiperazin-1-yl)carbonyl-4-(naphthalen-1-yl)-1H-pyrrole(10),
3-[N-(2-methoxyethyl)-N-methyl]carbamoyl-1-[1-((S)-α-methylbenzyl)-1H-imidazol-5-ylmethyl]-4-(naphthalen-1-yl)-1H-pyrrole(11),
1-[1-((S)-α-methylbenzyl)-1H-imidazol-5-ylmethyl]-3-(morpholin-4-yl)carbonyl-4-(naphthalen-1-yl)-1H-pyrrole(12),
1-[1-((S)-α-methylbenzyl)-1H-imidazol-5-ylmethyl]-3-(4-methylpiperazin-1-yl)carbonyl4-(naphthalen-1-yl)-1H-pyrrole(13),
3-[N-(2-methoxyethyl)-N-methyl]carbamoyl-4-(naphthalen-1-yl)-1-[1-(phenethyl)-1H-imidazol-5-ylmethyl]-1H-pyrrole(14),
3-(morpholin-4-yl)carbonyl-4-(naphthalen-1-yl)-1-[1-(phenethyl)-1H-imidazol-5-ylmethyl]-1H-pyrrole(15),
3-(4-methylpiperazin-1-yl)carbonyl-4-(naphthalen-1-yl)-1-[1-(phenethyl)-1H-imidazol-5-ylmethyl]-1H-pyrrole(16),
3-[N-(2-methoxyethyl)-N-methyl]carbamoyl-1-[1-(2-methoxy)phenethy-1H-imidazol-5-yl]methyl-4-(naphthalen-1-yl)-1H-pyrrole(17),
1-[1-(2-methoxy)phenethyl-1H-imidazol-5-yl]methyl-3-[4-methylpiperazin-1-yl]carbonyl-4-(naphthalen-1-yl)-1H-pyrrole(18),
3-[N-(2-methoxyethyl)-N-methyl]carbamoyl-1-[1-(4-methoxy)phenethyl-1H-imidazol-5-yl]methyl-4-(naphthalen-1-yl)-1H-pyrrole(19),
1-[1-(4-methoxy)phenethyl-1H-imidazol-5-yl]methyl-3-[4-methylpiperazin-1-yl]carbonyl-4-naphthalen-1-yl)-1H-pyrrole(20),
1-[1-(2-fluoro)phenethyl-1H-imidazol-5-yl]methyl-3-[N-(2-methoxyethyl)-N-methyl]carbamoyl-4-(naphthalen-1-yl)-1H-pyrrole(21),
1-[1-(2-fluoro)phenethyl-1H-imidazol-5-yl]methyl-3-[4-methylpiperazin-1-yl]carbonyl-4-(naphthalen-1-yl)-1H-pyrrole(22),
1-[1-(2-chloro)phenethyl-1H-imidazol-5-yl]methyl-3-[N-(2-methoxyethyl)-N-methyl]carbamoyl-4-(naphthalen-1-yl)-1H-pyrrole(23),
1-[1-(2-chloro)phenethyl-1H-imidazol-5-yl]methyl-3-[4-methylpiperazin-1-yl]carbonyl-4-(naphthalen-1-yl)-1H-pyrrole(24),
1-[1-(3-chloro)phenethyl-1H-imidazol-5-yl]methyl-3-[N-(2-methoxyethyl)-N-methyl]carbamoyl-4-(naphthalen-1-yl)-1H-pyrrole(25),
1-[1-(3-chloro)phenethyl-1H-imidazol-5-yl]methyl-3-[4-methylpiperazin-1-yl]carbonyl-4-(naphthalen-1-yl)-1H-pyrrole(26),
3-[N-(2-methoxyethyl)-N-methyl]carbamoyl4-(naphthalen-1-yl)-1-[1-(3-phenyl)propyl-1H-imidazol-5-yl]methyl-1H-pyrrole(27),
3-[4-methylpiperazin-1-yl]carbonyl-4-(naphthalen-1-yl)-1-[1-(3-phenyl)propyl-1H-imidazol-5-yl]methyl-1H-pyrrole(28), 3-[N-(2-methoxyethyl)-N-methyl]carbamoyl-4-(naphthalen-1-yl)-1-[1-(naphthalen-2-yl)methyl-1H-imidazol-5-yl]methyl-1H-pyrrole(29),
3-[4-methylpiperazin-1-yl]carbonyl-4-(naphthalen-1-yl)-1-[1-naphthalen-2-yl)methyl-1H-imidazol-5-yl]methyl-1H-pyrrole(30),
3-[N-(2-methoxyethyl)-N-methyl]carbamoyl-4-(naphthalen-1-yl)-1-{1-[2-(naphthalen-1-yl)ethyl]-1H-imidazol-5-yl}methyl-1H-pyrrole(31),
3-[4-methylpiperazin-1-yl]carbonyl-4-(naphthalen-1-yl)-1-{1-[2-(naphthalen-1-yl)ethyl]-1H-imidazol-5-yl}methyl-1H-pyrrole(32),
1-[1-(4-bromo)phenethyl-1H-imidazol-5-yl]methyl-3-[N-(2-methoxyethyl)-N-methyl]carbamoyl-4-(naphthalen-1-yl)-1H-pyrrole(33),
1-[1-(4-bromo)phenethyl-1H-imidazol-5-yl]methyl-3-[4-methylpiperazin-1-yl]carbonyl-4-(naphthalen-1-yl)1H-pyrrole(34),
1-[1-(4-fluoro)phenethyl-1H-imidazol-5-yl]methyl-3-[N-(2-methoxyethyl)-N-methyl]carbamoyl-4-(naphthalen-1-yl)-1H-pyrrole(35),
1-[1-(4-fluoro)phenethyl-1H-imidazol-5-yl]methyl-3-[4-methylpiperazin-1-yl]carbonyl-4-(naphthalen-1-yl)-1H-pyrrole(36),
3-[N-(2-methoxyethyl)-N-methyl]carbamoyl-1-[1-(4-methyl)phenethyl-1H-imidazol-5-yl]methyl-4-(naphthalen-1-yl)-1H-pyrrole(37),
1-[1-(4-methyl)phenethyl-1H-imidazol-5-yl]methyl-3-[4-methylpiperazin-1-yl]carbonyl-4-(naphthalen-1-yl)-1H-pyrrole(38),
1-[1-(4-chloro)phenethyl-1H-imidazol-5-yl]methyl-3-[N-(2-methoxyethyl)-N-methyl]carbamoyl-4-(naphthalen-1-yl)-1H-pyrrole(39),
1-[1-(4-chloro)phenethyl-1H-imidazol-5-yl]methyl]-3-[4-methylpiperazin-1-yl]carbonyl-4-naphthalen-1-yl)-1H-pyrrole(40),
3-[N-(2-methoxyethyl)-N-methyl]carbamoyl-4-(naphthalen-1-yl)-1-{1-[2-naphthalen-2-yl)ethyl]-1H-imidazol-5-yl}methyl-1H-pyrrole(41),
3-[4-methypiperazin-1-yl]carbonyl-4-(naphthalen-1-yl)-1-{1-[2-naphthalen-2-yl)ethyl]-1H-imidazol-5-yl}methyl-1H-pyrrole(42),
1-[1-(4-hydroxy)phenethyl-1H-imidazol-5-yl]methyl-3-[4-methylpiperazin-1-yl]carbonyl-4-(naphthalen-1-yl)-1H-pyrrole(43),
1-(1H-imidazol-4-yl)methyl-4-(naphthalen-1-yl)-3-(thiophen-2-yl)carbonyl-1H-pyrrole(44),
1-(1H-imidazol-4-yl)methyl-4-(naphthalen-1-yl)-3-(thiophen-3-yl)carbonyl-1H-pyrrole(45),
3-benzoyl-1-(1H-imidazo-4-yl)methyl-4-(naphthalen-1-yl)-1H-pyirole(46),
3-(2-bromobenzoyl)-1-(1H-imidazol-4-yl)methyl-4-(naphthalen-1-yl)-1H-pyrrole(47),
3-(3-bromobenzoyl)-1-(1H-imidazol-4-yl)methyl-4-(naphthalen-1-yl)-1H-pyrrole(48),
3-(4-bromobenzoyl)-1-(1H-imidazol-4-yl)methyl-4-(naphthalen-1-yl)-1H-pyrrole(49),
1-(1H-imidazol-4-yl)methyl-3-(2-methylbenzoyl)-4-(naphthalen-1-yl)-1H-pyrrole(50),
1-(1H-imidazol-4-yl)methyl-3-(3-methylbenzoyl)-4-(naphthalen-1-yl)-1H-pyrrole(51),
1-(1H-imidazol-4-yl)methyl-3-(4-methylbenzoyl)-4-(naphthalen-1-yl)-1H-pyrrole(52),
1-(1H-imidazol-4-yl)methyl-3-(3-methoxybenzoyl)-4-(naphthalen-1-yl)-1H-pyrrole(53),
1-(1H-imidazol-4-yl)methyl-3-(4-methoxybenzoyl)-4-(naphthalen-1-yl)-1H-pyrrole(54),
3-(2-chlorobenzoyl)-1-(1H-imidazol-4-yl)methyl-4-(naphthalen-1-yl)-1H-pyrrole(55),
3-(4-chlorobenzoyl)-1-(1H-imidazol-4-yl)methyl-4-(naphthalen-1-yl)-1H-pyrrole(56),
3-(2,4-dichlorobenzoyl)-1-(1H-imidazol-4-yl)methyl-4-(naphthalen-1-yl)-1H-pyrrole(57),
3-(4-fluorobenzoyl)-1-(1H-imidazol-4-yl)methyl-4-(naphthalen-1-yl)-1H-pyrrole(58),
3-(2,4-difluorobenzoyl)-1-(1H-imidazol-4-yl)methyl-4-(naphthalen-1-yl)-1H-pyrrole(59),
3-(4-cyanobenzoyl)-1-(1H-imidazol-4-yl)methyl-4-(naphthalen-1-yl)-1H-pyrrole(60),
1-(1H-imidazol-4-yl)methyl-3-(4-methylthiomethyl-benzoyl)-4-(naphthalen-1-yl)-1H-pyrrole(61),
1-(1H-imidazol-4-yl)methyl-3-[4-(2-methylthioethyl)benzoyl]-4-(naphthalen-1-yl)-1H-pyrrole(62),
1-(1H-imidazol-4-yl)methyl-3-[4-(2-methylthioethoxy)benzoyl]-4-(naphthalen-1-yl)-1H-pyrrole(63),
1-(1H-imidazol-4-yl)methyl-3-(3-methylthiomethyl-benzoyl)-4-(naphthalen-1-yl)-1H-pyrrole(64),
1-(1H-imidazol-4-yl)methyl-4-(naphthalen-1-yl)-3-(3-phenylbenzoyl)-1H-pyrrole(65),
1-(1H-imidazol-4-yl)methyl-4-(naphthalen-1-yl)-3-(4-phenylbenzoyl)-1H-pyrrole(66),
1-(1H-imidazol-4-yl)methyl-4-(naphthalen-1-yl)-3-(4-phenoxybenzoyl)-1H-pyrrole(67),
3-(4-benzylbenzoyl)-1-(1H-imidazol-4-yl)methyl-4-(naphthalen-1-yl)-1H-pyrrole(68),
1-(1H-imidazol-4-yl)methyl-4-(naphthalen-1-yl)-3-(naphthalen-1-yl)carbonyl-1H-pyrrole(69),
1-(1H-imidazol-4-yl)methyl-3-(4-methylbenzoyl)-4-(N-methylindol-3-yl)-1H-pyrrole(70),
5-n-butyl-3-(2,4-dichlorobenzoyl)-1-(1H-imidazol-4-yl)methyl-4-(naphthalen-1-yl)-1H-pyrrole(71),
5-benzyl-3-(2,4dichlorobenzoyl)-1-(1H-imidazol-4-yl)methyl-4-(naphthalen-1-yl)-1H-pyrrole(72),
1-[1-(4-cyanobenzyl)-1H-imidazol-5-yl]methyl-4-(naphthalen-1-yl)-3-(thiophen-2-yl)carbonyl-1H-pyrrole(73),
1-[1-(4-cyanobenzyl)-1H-imidazol-5-yl]methyl-4-(naphthalen-1-yl)-3-(thiophen-3-yl)carbonyl-1H-pyrrole(74),
3-benzoyl-1-[1-(4-cyanobenzyl)-1H-imidazol-5-yl]methyl-4-(naphthalen-1-yl)-1H-pyrrole(75),
3-(3-bromobenzoyl)-1-[1-(4-cyanobenzyl)-1H-imidazol-5-yl]methyl-4-(naphthalen-1-yl)-1H-pyrrole(76),
3-(4-bromobenzoyl)-1-[1-(4-cyanobenzyl)-1H-imidazol-5-yl]methyl-4-(naphthalen-1-yl)-1H-pyrrole(77),
3-(4-fluorobenzoyl)-1-(1-methyl-1H-imidazol-4-yl)methyl-4-(naphthalen-1-yl)-1H-pyrrole(78),
1-(1-methyl-1H-imidazol-4-yl)methyl-4-(naphthalen-1-yl)-3-(4-phenoxybenzoyl)-1H-pyrrole(79),
(S)-1-(1H-imidazol-4-yl)methyl-3-[N-(1-methoxycarbonyl-3-methylthio)propyl]carbamoyl-4-(naphthalen-1-yl)-1H-pyrrole(80),
(S)-3-[N-(1-hydroxycarbonyl-3-methylthio)propyl]carbamoyl-1-(1H-imidazol-4-yl)methyl-4-(naphthalen-1-yl)-1H-pyrrole(81),
1-(1H-imidazol-4-yl)methyl-4-(naphthalen-1-yl)-3-(N-phenylcarbamoyl)-1H-pyrrole(82),
3-(N-benzylcarbanoyl)-1-(1H-imidazol-4-yl)methyl-4-(napbthalen-1-yl)-1H-pyrrole(83),
1-(1H-imidazol-4-yl)methyl-4-(naphthalen-1-yl)-3-(piperidin-1-yl)carbonyl-1H-pyrrole(84),
1-(1H-imidazol-4-yl)methyl-3-(morpholin-4-yl)carbonyl-4-(naphthalen-1-yl)-1H-pyrrole(85),
1-(1H-imidazol-4-yl)methyl-4-(naphthalen-1-yl)-3-(thiomorpholin-4-yl)carbonyl)-1H-pyrrole(86), 1-(1H-imidazol-4-yl)methyl-4-(naphthalen-1-yl)-3-(S,S-dioxotdiomorpholin-4-yl)carbonyl-1H-pyrrole(87), 1-(1H-imidazol-4-yl)methyl-4-(naphthalen-1-yl)-3-(piperazin-1-yl)carbonyl-1H-pyrrole(88), 1-(1H-imidazol-4-yl)methyl-3-(4-methylpiperazin-1-yl)carbonyl-4-(naphthalen-1-yl)-1H-pyrrole(89), 1-(1H-imidazol-4-yl)methyl-4-(naphthalen-1-yl)-3-(thiazolidin-3-yl)carbonyl-1H-pyrrole(90), 3-(4-hydroxypiperidin-1-yl)carbonyl-1-(1H-imidazol-4-yl)methyl-4-(naphthalen-1-yl)-1H-pyrrole(91), 1-(1H-imidazol-4-yl)methyl-4-(naphthalen-1-yl)-3-(4-oxopiperidin-1-yl)carbonyl-1H-pyrrole(92), 3-N-(2-hydroxyethyl)carbamoyl-1-(1H-imidazol-4-yl)methyl-4-(naphthalen-1-yl)-1H-pyrrole(93), 3-[N-(2-hydroxyethyl)-N-methyl]carbamoyl-1-(1H-imidazol-4-yl)methyl-4-(naphthalen-1-yl)-1H-pyrrole(94), 1-(1H-imidazo-4-yl)methyl-3-[N-(2-methoxyethyl)-N-methyl]carbamoyl-4-(naphthalen-1-yl)-1H-pyrrole(95), 1-(1H-imidazol-4-yl)methyl-3-(morpholin-4-yl)carbonyl-4-(quinolin-4-yl)-1H-pyrrole(96), 4-(1,2-dihydroacenaphthylen-5-yl)-1-(1H-imidazol-4-yl)methyl-3-(morpholin-4-yl)carbonyl-1H-pyrrole(97), 3-N-(4-cyanobenzyl)carbamoyl-1-(1H-imidazol-4-yl)methyl-4-(naphthalen-1-yl)-1H-pyrrole(98), 1-(1-methyl-1H-imidazol-5-yl)methyl-3-(morpholin-4-yl)carbonyl-4-(naphthalen-1-yl)-1H-pyrrole(99), (S)-1-[1-(4-cyanobenzyl)-1H-imidazol-5-yl]methyl-3-[N-(1-methoxycarbonyl-3-methylthio)propyl]carbamoyl-4-(naphthalen-1-yl)-1H-pyrrole(100), (S)-1-[1-(4-cyanobenzyl)-1H-imidazol-5-yl]methyl-3[-N-(1-hydroxycarbonyl-3-methylthio)propyl]carbamoyl-4-(naphthalen-1-yl)-1H-pyrrole(101), (S)-1-[1-(4-cyanobenzyl)-1H-imidazol-5-yl]methyl-3-[N-(1-methoxycarbonyl-3-methyl)butyl]carbamoyl-4-(naphthalen-1-yl)-1H-pyrrole(102), (S)-1-[1-(4-cyanobenzyl)-1H-imidazol-5-yl]methyl-3-[N-(1-hydroxycarbonyl-3-methyl)butyl]carbamoyl-4-(naphthalen-1-yl)-1H-pyrrole(103), 1-[1-(4-cyanobenzyl)-1H-imidazol-5-yl]methyl-3-(morpholin-4-yl)carbonyl-4-(naphthalen-1-yl)-1H-pyrrole(104), 1-[1-(4-cyanobenzyl)-1H-imidazol-5-yl]methyl-3-(4-methylpiperazin-1-yl)carbonyl-4-(naphthalen-1-yl)-1H-pyrrole(105), 1-[2-(1H-imidazol-1-yl)ethyl]-3-(morpholin-4-yl)carbonyl-4-(naphthalen-1-yl)-1H-pyrrole(106), (S)-1-[3-(1H-imidazolyl)propyl]-3-[N-(1-methoxycarbonyl-3-methylthio)propyl]carbamoyl-4-(naphthalen-1-yl)-1H-pyrrole(107), (S)-3-[N-(1-hydroxycarbonyl-3-methylthio)propyl]carbamoyl-1-[3-(1H-imnidazol-4-yl)propyl]-4-(naphthalen-1-yl)-1H-pyrrole(108), 1-[3-(1H-imidazol-4-yl)propyl]-3-(morpholin-4-yl)carbonyl-4-(naphthalen-1-yl)-1H-pyrrole(109), 1-[1-(4-cyanobenzyl)-1H-imidazol-5-yl]methyl-3-[N-(2-methoxyethyl)-N-methyl]carbamoyl-4-(naphthalen-1-yl)-1H-pyrrole(110), 1-[1-(4-bromobenzyl)-1H-imidazol-5-yl]methyl-3-[N-(2-methoxyethyl)-N-methyl]carbamoyl-4-(naphthalen-1-yl)-1H-pyrrole(111), 1-[1-(4-bromobenzyl)-1H-imidazol-5-yl]methyl-3-(morpholin-4-yl)carbonyl-4-(naphthalen-1-yl)-1H-pyrrole(112), 1-[1-(4-cyanobenzyl)-1H-imidazol-5-yl]methyl-3-(morpholin-4-yl)thiocarbonyl-4-(napbthalen-1-yl)-1H-pyrrole(113), 3-[N-(2-methoxyethyl)-N-methyl]carbamoyl-1-(1-methyl-1H-imidazol-5-yl)methyl-4-(naphthalen-1-yl)-1H-pyrrole(114), 1-(1-isobutyl-1H-imidazol-5-yl)methyl-3-[N-(2-methoxyethyl)-N-methyl]carbamoyl-4-(naphthalen-1-yl)-1H-pyrrole(115), 1-(1-cyclohexylmethyl-1H-imidazol-5-yl)methyl-3-[N-(2-methoxyethyl)-N-methyl]carbamoyl-4-(naphthalen-1-yl)-1H-pyrrole(116), 3-[N-(2-methoxyethyl)-N-methyl]carbamoyl-4-(naphthalen-1-yl)-1-(1-pentyl-1H-imidazol-5-yl)methyl-1H-pyrrole(117), 3-[N-(2-methoxyethyl)-N-methyl]carbamoyl-4-(naphthalen-1-yl)-1-(1-octyl-1H-imidazol-5-yl)methyl-1H-pyrrole(118), 1-(1-decyl-1H-imidazol-5-yl)methyl-3-[N-(2-methoxyethyl)-N-methyl]carbamoyl-4-(naphthalen-1-yl)-1H-pyrrole(119), 3-[N-(2-methoxyethyl)-N-methyl]carbomyl-1-[1-(3-methylbutyl)-1H-imidazol-5-yl]methyl-4-(naphthalen-1-yl)-1H-pyrrole(120), 1-[1-(2-methoxyethyl)-1H-imidazol-5-yl]methyl-3-[N-(2-methoxyethyl)-N-methyl]carbamoyl-4-(naphthalen-1-yl)-1H-pyrrole(121), 3-[N-(2-methoxyethyl)-N-methyl]carbamoyl-1-[1-(3-methoxypropyl)-1H-imidazol-5-yl]methyl-4-(naphthalen-1-yl)-1H-pyrrole(122), 1-[1-(3-ethoxypropyl)-1H-imidazol-5-yl]methyl-3-[N-(2-methoxyethyl)-N-methyl]carbamoyl-4-(naphthalen-1-yl)-1H-pyrrole(123), 1-[1-(3-isopropoxypropyl)-1H-imidazol-5-yl]methyl-3-[N-(2-methoxyethyl)-N-methyl]carbamoyl-4-(naphthalen-1-yl)-1H-pyrrole(124), 1-[1-(4-bromobenzyl)-1H-imidazol-5-yl]methyl-3-[4-methylpiperazin-1-yl]carbonyl-4-(naphthalen-1-yl)-1H-pyrrole(125), 1-[1-(4-chlorobenzyl)-1H-imidazol-5-yl]methyl-3-[4-methylpiperazin-1-yl]carbonyl-4-(naphthalen-1-yl)-1H-pyrrole(126), 1-[1-(4-fluorobenzyl)-1H-imidazol-5-yl]methyl-3-[N-(2-methoxyethyl)-N-methyl]carbamoyl-4-(naphthalen-1-yl)-1H-pyrrole(127), 1-[1-(4-fluorobenzyl)-1H-imidazol-5-yl]methyl-3-[4-methylpiperazin-1-yl]carbonyl-4-(naphthalen-1-yl)-1H-pyrrole(128), 1-[1-(4-methoxybenzyl)-1H-imidazol-5-yl]methyl-3-[N-(2-methoxyethyl)-N-methyl]carbamoyl-4-(naphthalen-1-yl)-1H-pyrrole(129), 1-[1-(4-methoxybenzyl)-1H-imidazol-5-yl]methyl-3-(4-methylpiperazin-1-yl)carbonyl-4-(naphthalen-1-yl)-1H-pyrrole(130), 1-[1-(3-chlorobenzyl)-1H-imidazol-5-yl]methyl-3-(4-methylpiperazin-1-yl)carbonyl-4-(naphthalen-1-yl)-1H-pyrrole(131), 1-[1-(3-chlorobenzyl)-1H-imidazol-5-yl]methyl-3-[N-(2-methoxyethyl)-N-methyl]carbamoyl-4-(naphthalen-1-yl)-1H-pyrrole(132), 1-[1-(2-chlorobenzyl)-1H-imidazol-5-yl]methyl-3-(4-methylpiperazin-1-yl)carbonyl-4-(naphthalen-1-yl)-1H-pyrrole(133), 1-[1-(2-chlorobenzyl)-1H-imidazol-5-yl]methyl-3-[N-(2-methoxyethyl)-N-methyl]carbamoyl-4-(naphthalen-1-yl)-1H-pyrrole(134), 1-[1-(2-fluorobenzyl)-1H-imidazol-5-yl]methyl-3-(4-methylpiperazin-1-yl)carbonyl-4-(naphthalen-1-yl)-1H-pyrrole(135), 1-[1-(4-methylbenzyl)-1H-imidazol-5-yl]methyl-3-(4-methylpiperazin-1-yl)carbonyl-4-(naphthalen-1-yl)-1H-pyrrole(136), 1-[1-(4-methylbenzyl)-1H-imidazol-5-yl]methyl-3-(morpholin-4-yl)carbonyl-4-(naphthalen-1-yl)-1H-pyrrole(137),
1-[1-(3-methylbenzyl)-1H-imidazol-5-yl]methyl-3-(4-methylpiperazin-1-yl)carbonyl-4-(naphthalen-1-yl)-1H-pyrrole(138),
1-[1-(4-cyanobenzyl)-1H-imidazol-5-yl]methyl-3-(naphthalen-1-yl)carbonyl-1H-pyrrole(139),
1-[1-(4-bromobenzyl)-1H-imidazol-5-yl]methyl-3-(naphthalen-1-yl)carbonyl-1H-pyrrole(140),
1-[1-(4-bromobenzyl)-1H-imidazol-5-yl]methyl-3-[N-(2-methoxyethyl)-N-methyl]carbamoyl-4-(naphthalen-1-yl)carbonyl-1H-pyrrole(141),
4-ethoxycarbonyl-2-(1H-imnidazol-5-ylmethyl)-5-(naphthalen-1-yl)oxazole(142),
2-(1H-imidazol-5-ylmethyl)-4-morpholin-4-yl)carbonyl-5-(naphthalen-1-yl)oxazole(143),
4-ethoxycarbonyl-2-(1H-imidazol-5-ylmethyl)-5-(naphthalen-1-yl)thiazole(144),
2-[1-(4-chlorobenzyl)-1H-imidazol-5-ylmethyl]-4-methoxycarbonyl-5-(naphthalen-1-yl)thiazole(145),
2-[1-(4-chlorobenzyl)-1H-imidazol-5-ylmethyl]-4-(morpholin-4-yl)calbonyl-5-(naphthalen-1-yl)thiazole(146),
2-[1-(4-chlorobenzyl)-1H-imidazol-5-ylmethyl]-4-[N-(2methoxy)ethyl-N-methylcarbamoyl]-5-(naphthalen-1-yl)thiazole(147),
2-[1-(4-chlorobenzyl)-1H-imidazol-5-ylmethyl]-5-methoxycarbonyl-4-(naphthalen-1-yl)thiazole(148),
2-[1-(4-chlorobenzyl)-1H-imidazol-5-ylmethyl]-5-(-morpholin4-yl)carbonyl-4-(naphthalen-1-yl)thiazole(149),
2-{1-[1-(benzyloxycarbonyl)piperidin-4-ylmethyl]-1H-imidazol-5-ylmethyl}-5-methoxycarbonyl-4-(naphthalen-1-yl)thiazole(150),
2-{1-[1-(benzyloxycarbonyl)piperidin-4-ylmethyl]-1H-imidazol-5-ylmethyl}-5-[N-(2-methoxy)ethyl-N-methylcarbamoyl]-4-(naphthalen-1-yl)thiazole(151),
1-[1-(1-benzyloxycarbonyl-piperidin-4-ylmethyl)-1H-imidazol-5-ylmethyl]-4-[N-(2-methoxyethyl)-N-methyl]carbamoyl-3-(naphthalen-1-yl)-1H-pyrazole(152),
1-[1-(1-methoxycarbonylpiperidin-4-ylmethyl)-1H-imidazole-5-ylmethyl]-4-[N-(2-methoxyethyl)-N-methyl]carbamoyl-3-(naphthalen-1-yl)-1H-pyrazole(153),
1-[1-(4-bromobenzyl)-1H-imidazol-5-ylmethyl]-4-[N-(2-methoxyethyl)-N-methyl]carbamoyl-3-(naphthalen-1-yl)-1H-pyrazole(154),
1-[1-(4-chlorobenzyl)-1H-imidazol-5-ylmethyl]-4-[N-(2-methoxyethyl)-N-methyl]carbamoyl-3-(naphthalen-1-yl)-1H-pyrazole(155),
1-[1-(4-cyanobenzyl)-1H-imidazol-5-ylmethyl]-4-[N-(2-methoxyethyl)-N-methyl]carbamoyl-3-(naphthalen-1-yl)-1H-pyrazole(156),
1-[1-methyl-1H-imidazol-5-ylmethyl]-4-[N-(2-methoxyethyl)-N-methyl]carbamoyl-3-(naphthalen-1-yl)-1H-pyrazole(157),
1-[1-(1-benzyloxycarbonyl-piperdin-4-ylmethyl)-1H-imidazol-5-ylmethyl]-4-(morpholin-4-yl)carbonyl-3-(naphthalen-1-yl)-1H-pyrazole(158),
1-[1-(1-methoxycarbonylpiperidin-4-ylmethyl)-1H-imidazol-5-ylmethyl]-4-(morpholin-4-yl)carbonyl-3-(naphthalen-1-yl)-1H-pyrazole(159),
1-[1-(4-bromobenzyl)-1H-imidazol-5-ylmethyl]-4-(morpholin-4-yl)carbonyl-3-(naphthalen-1-yl)-1H-pyrazole(160),
1-[1-(4-chlorobenzyl)-1H-imidazol-5-ylmethyl]-4-(morpholin-4-yl)carbonyl-3-(naphthalen-1-yl)-1H-pyrazole(161),
1-[1-(4-cyanobenzyl)-1H-imidazol-5-ylmethyl]-4-(morpholin-4-yl)carbonyl-3-(naphthalen-1-yl)-1H-pyrazole(162), and
1-(1-methyl-1H-imidazol-5-ylmethyl)-4-morpholin-4-yl)carbonyl-3-(naphthalen-1-yl)-1H-pyrazole(163).

5. A process for preparing an imidazole derivative of formula (1) as defined in claim 1 characterized in that (a) a compound represented by the following formula (2):

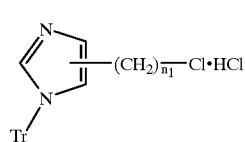

(2)

wherein $n_1$ is defined as claim 1 and Tr represents trityl, is reacted in a solvent in the presence of a base with a compound represented by the following formula (3):

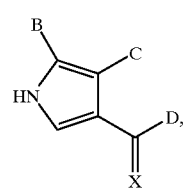

(3)

wherein B, C, D and X are defined as claim 1, then the trityl group in the product thus obtained is eliminated in the presence of trifluoroacetic acid to produce a compound represented by the following formula (1a):

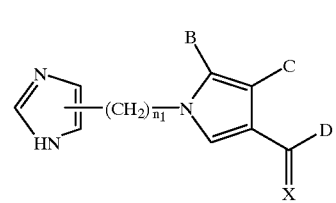

(Ia)

wherein $n_1$, B, C, D and X are defined as claim 1; or (b) a compound represented by the following formula (4):

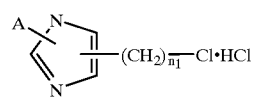

(4)

wherein $n_1$ and A are defined as claim 1, is reacted in a solvent in the presence of a base with the compound of formula (3) to produce a compound represented by the following formula (1b):

(Ib)

wherein $n_1$, A, B, C, D and X are defined as claim 1; or (c) a compound represented by the following formula (5):

(5)

is reacted in a solvent in the presence of a base with the compound of formula (3), the trityl group in the product thus obtained is eliminated in the presence of trifluoroacetic acid to produce a compound represented by the following formula (6):

(6)

wherein B, C, D and X are defined as claim 1, and then hydrogenation reaction is carried out to produce a compound represented by the following formula (1c):

(1c)

wherein B, C, D and X are defined as claim 1; or (d) a compound represented by the following formula (7):

(7)

wherein $n_1$, A, B and C are defined as claim 1, is hydrolyzed to produce a compound represented by the following formula (8)

(8)

wherein $n_1$, A, B and C are defined as claim 1, which is then reacted with a compound represented by the following formula (9):

$HNR_{16}R_{17}$ (9)

wherein $R_{16}$ and $R_{17}$ are defined as claim 1, in the presence of a coupling agent to produce a compound represented by the following formula (1d):

(1d)

wherein $n_1$, A, B, C, $R_{16}$ and $R_{17}$ are defined as claim 1; or (e) the carbonyl group in a compound represented by the following formula (1e):

(1e)

wherein $n_1$, A, B, C and D are defined as claim 1, is converted into the thiocarbonyl group in the presence of a sulfurizing agent to produce a compound represented by the following formula (1f):

(1f)

wherein $n_1$, A, B, C and D are defined as claim 1; or (f) a compound represented by the following formula (1g):

(1g)

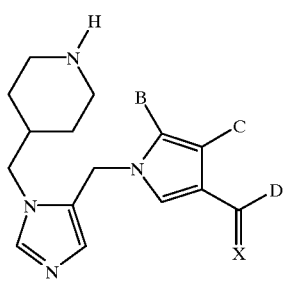

wherein B, C, D and X are defined as claim 1, is coupled in a solvent with a compound represented by the following formula (10):

R₂—T  (10)

wherein R₂ is defined as claim 1 and T represents hydroxy or reactive leaving group, to produce a compound represented by the following formula (1h):

(1h)

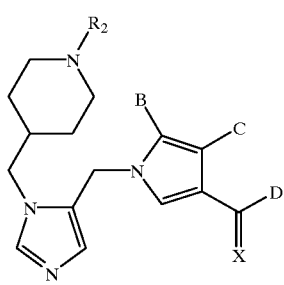

wherein R₂, B, C, D and X are defined as claim 1; or (g) a compound represented by the following formula (11):

(11)

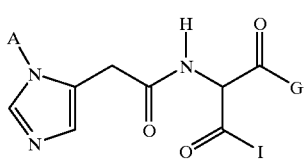

wherein A, G and I are defined as claim 1, is cyclized in an inert solvent to produce a compound represented by the following formula (1i):

(1i)

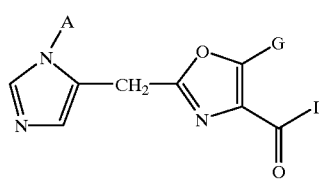

wherein A, G and I are defined as claim 1; or (h) the amide group in the compound of formula (11) is converted into the thioamide group to produce a compound represented by the following formula (12):

(12)

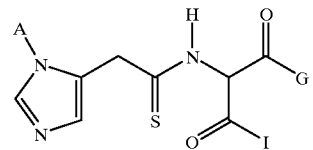

wherein A, G and I are defined as claim 1, which is then cyclized in an inert solvent to produce a compound represented by the following formula (1j):

(1j)

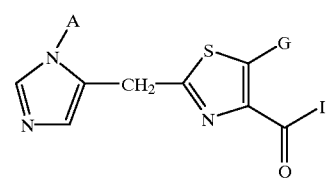

wherein A, G and I are defined as claim 1; or (i) a compound represented by the following formula (13):

(13)

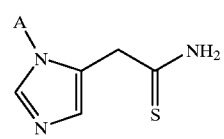

wherein A is defined as claim 1, is reacted in a solvent with a compound represented by the following formula (14a):

(14a)

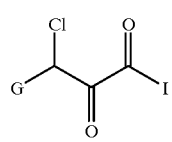

wherein G and I are defined as claim 1, to produce the compound of formula (1j); or (j) the compound of formula (13) is reacted in a solvent with a compound represented by the following formula (14b):

(14b)

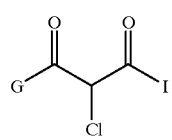

wherein G and I are defined as claim 1, to produce a compound represented by the following formula (1k):

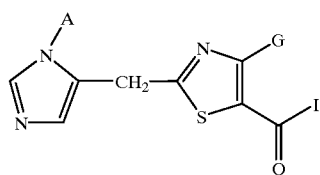
(1k)

wherein A, G and I are defined as claim 1; or (k) a compound represented by the following formula (1l).

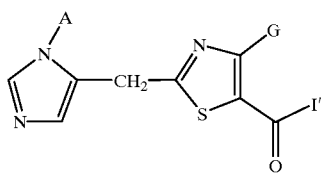
(1l)

wherein A and G are defined as claim 1 and I' represents lower alkoxy, is hydrolyzed in the presence of a base and the product thus obtained is reacted in a solvent in the presence of a coupling agent with a compound represented by the following formula (15):

I''     (15)

wherein I'' is identical with I except that lower alkoxy is not included, to produce a compound represented by the following formula (1m):

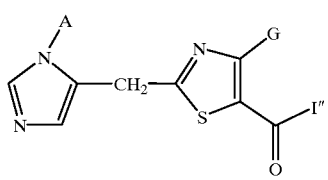
(1m)

wherein A and G are defined as claim 1 and I'' are defined as above; or (l) a compound represented by the following formula (16):

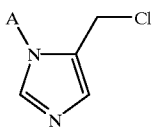
(16)

wherein A is defined as claim 1, is reacted in a solvent in the presence of a base with a compound represented by the following formula (17):

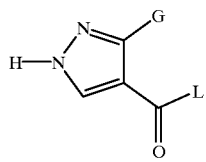
(17)

wherein G and L are defined as claim 1, to produce a compound represented by the following formula (1n):

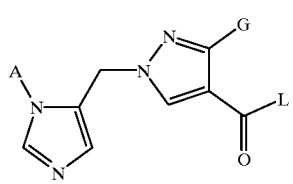
(1n)

wherein A, G and L are defined as claim 1; or (m) a compound represented by the following formula (18):

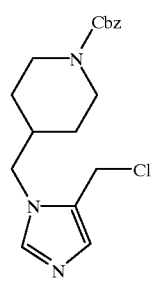
(18)

wherein Cbz represents benzyloxycarbonyl, is reacted in a solvent in the presence of a base with the compound of formula (17) and deprotected to produce a compound represented by the following formula (1o):

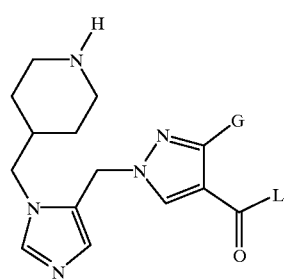
(1o)

wherein G and L are defined as claim 1, which is then coupled with a compound represented by the following formula (19):

T—E—F     (19)

wherein E and F are defined as claim 1, to produce a compound represented by the following formula (1p):

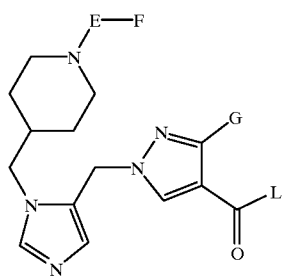 (1p)

wherein E, F, G and L are defined as claim 1.

6. A pharmaceutical composition comprising as active ingredient a therapeutically effective amount of a compound of formula (1) as defined in claim 1 or a pharmaceutically acceptable salt or isomer thereof together with a pharmaceutically acceptable carrier.

7. The pharmaceutical composition of claim 6 useful for treating cancer.

8. The pharmaceutical composition of claim 6 useful for treating restenosis.

9. The pharmaceutical composition of claim 6 useful for treating atherosclerosis.

10. The pharmaceutical composition of claim 6 useful for treating infections from hepatitis delta and related viruses.

* * * * *